(12) United States Patent
Hormann et al.

(10) Patent No.: US 8,076,517 B2
(45) Date of Patent: Dec. 13, 2011

(54) CHIRAL DIACYLHYDRAZINE LIGANDS FOR MODULATING THE EXPRESSION OF EXOGENOUS GENES VIA AN ECDYSONE RECEPTOR COMPLEX

(75) Inventors: Robert Eugene Hormann, Melrose Park, PA (US); Bing Li, Shrewsbury, MA (US)

(73) Assignee: Intrexon Corporation, Blacksburg, VA (US)

( * ) Notice: Subject to any disclaimer, the term of this patent is extended or adjusted under 35 U.S.C. 154(b) by 546 days.

(21) Appl. No.: 12/155,111

(22) Filed: May 29, 2008

(65) Prior Publication Data

US 2009/0163592 A1     Jun. 25, 2009

Related U.S. Application Data

(60) Provisional application No. 60/940,525, filed on May 29, 2007.

(51) Int. Cl.
*C07C 243/10*     (2006.01)
(52) U.S. Cl. ...................................... 564/310
(58) Field of Classification Search ........................ None
See application file for complete search history.

(56) References Cited

U.S. PATENT DOCUMENTS

| | | | | |
|---|---|---|---|---|
| 6,013,836 A * | 1/2000 | Hsu et al. | .................... | 564/149 |
| 6,326,403 B1 | 12/2001 | Hölzemann et al. | | |
| 6,649,613 B1 * | 11/2003 | Holzemann et al. | .......... | 514/247 |
| 7,456,315 B2 | 11/2008 | Hormann et al. | | |
| 7,563,928 B2 | 7/2009 | Hormann et al. | | |
| 2005/0209283 A1 | 9/2005 | Hormann et al. | | |
| 2006/0020146 A1 * | 1/2006 | Hormann et al. | ............. | 564/123 |

OTHER PUBLICATIONS

Gubitz et al., Molecular Biotechnology, 2006, 32: 159-179.*
International Search Report and Written Opinion for International Application No. PCT/US08/06757, mailed Sep. 22, 2008, International Searching Authority, United States.
Notice of Allowance and Fee(s) Due for U.S. Appl. No. 11/841,568, filed Aug. 20, 2007, U.S. Patent and Trademark Office, Alexandria, Virginia, United States, mailed May 8, 2009.
Non-final Office Action for U.S. Appl. No. 11/841,568, filed Aug. 20, 2007, U.S. Patent and Trademark Office, Alexandria, Virginia, United States, mailed Jan. 5, 2009.
Non-final Office Action for U.S. Appl. No. 11/841,568, filed Aug. 20, 2007, U.S. Patent and Trademark Office, Alexandria, Virginia, United States, mailed Sep. 12, 2008.
Office Action with Requirement for Restriction/Election, for U.S. Appl. No. 11/841,568, filed Aug. 20, 2007, U.S. Patent and Trademark Office, Alexandria, Virginia, United States, mailed Mar. 19, 2008.

* cited by examiner

*Primary Examiner* — Ileana Popa
(74) *Attorney, Agent, or Firm* — Sterne, Kessler, Goldstein & Fox P.L.L.C.

(57) ABSTRACT

The present invention provides diacylhydrazine ligands and chiral diacylhydrazine ligands for use with ecdysone receptor-based inducible gene expression systems. Thus, the present invention is useful for applications such as gene therapy, large scale production of proteins and antibodies, cell-based screening assays, functional genomics, proteomics, metabolomics, and regulation of traits in transgenic organisms, where control of gene expression levels is desirable. An advantage of the present invention is that it provides a means to regulate gene expression and to tailor expression levels to suit the user's requirements.

5 Claims, 25 Drawing Sheets

| Material | Lot # | Origin | Micronized | Analysis |
|---|---|---|---|---|
| R enantiomer | REH-28-4-2 | precipitated from $CH_3OH/H_2O$, dried in vac oven, then micronized | YES | All ADME analyses except mouse SEAP expression |
| Racemate | REH-28-9-1 (PYAP-2-8-2-2M) | micronized from PYAP 2-8-2-2 | YES | All ADME analyses except mouse PK and mouse SEAP expression |
| Racemate | PYAP 2-8-2-2 | Precipitation from CH3OH and dried in vac oven at ca. 50 °C | NO | Mouse PK |

FIG.4

| Particle size (μm) | Reading #1 | Reading #1 | Reading #1 | Average |
|---|---|---|---|---|
| D (V, 0.1) | 11.55 | 11.32 | 11.34 | 11.4 |
| D (V, 0.5) | 25.26 | 24.3 | 25.4 | 25.0 |
| D (V, 0.9) | 50.58 | 47.99 | 51.62 | 50.1 |

D (V, 0.1): distribution in volume, 10% of the particles is at or below this size.
D (V, 0.5): distribution in volume, 50% of the particles is at or below this size.
D (V, 0.9): distribution in volume, 90% of the particles is at or below this size.

FIG.5

| Particle size (μm) | Reading #1 | Reading #1 | Reading #1 | Average |
|---|---|---|---|---|
| D (V, 0.1) | 10.21 | 9.99 | 9.96 | 10.1 |
| D (V, 0.5) | 38.4 | 36.0 | 35.4 | 36.6 |
| D (V, 0.9) | 89.58 | 82.15 | 80.31 | 84.0 |

D (V, 0.1): distribution in volume, 10% of the particles is at or below this size.
D (V, 0.5): distribution in volume, 50% of the particles is at or below this size.
D (V, 0.9): distribution in volume, 90% of the particles is at or below this size.

FIG. 6

| Material | Bulk density (g/mL) | Tapped density (g/mL) | True density (g/mL) |
|---|---|---|---|
| R enantiomer | 0.149 | 0.175 | 1.1647 |
| racemate | 0.193 | 0.210 | 1.1522 |

FIG.7

| Excipient | Color/viscosity | Vendor | Ligand | Concentration | | | | | | |
|---|---|---|---|---|---|---|---|---|---|---|
| | | | | 2.5 mg/g | 5 mg/g | 10 mg/g | 15 mg/g | 20 mg/g | 30 mg/g | 50 mg/g |
| Labrasol | Clear/fluid | Gattefossé | R enantiomer | | soluble | soluble | soluble | | | |
| | | | Racemate | | soluble | mostly soluble, opaque | insoluble | | | |
| Lauroglycol 90 | Clear/fluid | Gattefossé | R enantiomer | | | soluble | soluble | soluble | | |
| | | | Racemate | | | soluble | soluble | soluble | partly soluble, suspension | insoluble |
| Phosal 53 MCT | Yellow/viscous | Phospholipid Gmbh | R enantiomer | | Mostly soluble | partly soluble | | | | |
| | | | Racemate | | insoluble | insoluble | | | | |
| Miglyol | Clear/fluid | Sasol | R enantiomer | | | soluble | soluble | | | |
| | | | Racemate | | | partly soluble | insoluble | | | |
| Cremophor EL | Clear/viscous | BASF | R enantiomer | Mostly soluble | Mostly soluble | partly soluble | | | | |
| | | | Racemate | insoluble | insoluble | insoluble | | | | |
| polysorbate 80 | Clear/fluid | Croda | R enantiomer | | partly soluble | insoluble | | | | |
| | | | Racemate | | partly soluble, suspension | insoluble | | | | |
| Crillet 1 HP | Yellow/viscous | Croda | R enantiomer | | mostly soluble | partly soluble | | | | |
| | | | Racemate | | partly soluble | insoluble | | | | |
| Isopropyl myristate | Clear/fluid | Croda | R enantiomer | | | soluble | soluble | | | |
| | | | Racemate | | | partly soluble, suspension | insoluble | | | |
| Oleic acid | Clear/fluid | TCI | R enantiomer | | | soluble | soluble | | | |
| | | | Racemate | | | partly soluble, suspension | partly soluble, suspension | | | |
| PEG 400 NF | Clear/fluid | Croda | R enantiomer | | | soluble | partly soluble | | | |
| | | | Racemate | | | partly soluble, suspension | insoluble | | | |

FIG.9

| Excipient | Vendor | Ligand | Conc. mg/g | Appearance | | Comments |
|---|---|---|---|---|---|---|
| | | | | Treatment 1 | Treatment 2 | |
| Labrasol (PEG-8 caprylic/ capric triglyceride) | Gattefossé | R enantiomer | 15 | transparent | Transparent (48 hour) | |
| | | Racemate | 15 | slight precipitate | precipitate (48 hr) | |
| Lauroglycol 90 (propylene glycol monolaurate) | Gattefossé | R enantiomer | 50 | transparent | transparent (48 hour) | |
| | | Racemate | 50 | precipitate | precipitate (48 hr) | |
| Phosal 53 MCT | Phospholipid Gmbh | R enantiomer | 10 | transparent | transparent | |
| | | Racemate | 10 | precipitate | precipitate | |
| Miglyol | Sasol | R enantiomer | 15 | transparent | transparent (24 and 48 hour) | |
| | | Racemate | 15 | precipitate | Precipitate (24 hour) | |
| Cremophor EL | BASF | R enantiomer | 2.5 | transparent | transparent (48 hour) | |
| | | Racemate | 2.5 | transparent | slight precipitate (48 hour) | (treatment 2) 90°C for 10 min |
| polysorbate 80 | Croda | R enantiomer | 10 | transparent | slight precipitate | (treatment 2) 90°C for 25 min |
| | | Racemate | 10 | precipitate | slight precipitate | (treatment 2) 90°C for 25 min |
| Crillet 1 HP (polysorbate 20) | Croda | R enantiomer | 10 | transparent | transparent | |
| | | Racemate | 10 | precipitate | precipitate | (treatment 2) 90°C for 15 min |
| Isopropyl myristate | Croda | R enantiomer | 15 | transparent | transparent | |
| | | Racemate | 15 | precipitate | precipitate | |
| Oleic acid | TCI | R enantiomer | 15 | Translucent/very slight precipitate | Translucent/very slight precipitate | |
| | | Racemate | 15 | precipitate | precipitate | |
| PEG 400 NF | Croda | R enantiomer | 10 | transparent | transparent | |
| | | Racemate | 10 | precipitate | precipitate | |

FIG.10

| Solubility (µM) 20% PEG 1000 in distilled water, pH 7.0 ||  |
|---|---|---|
|  | Filtration | Centrifugation |
| Racemate | <0.1 | 1.35 |
| R enantiomer | 0.32 | 7.53 |

FIG. 11

| Solvent | R enantiomer | | Racemate | |
|---|---|---|---|---|
| | Solubility (mg/g) | pH | Solubility (mg/g) | pH |
| Di-water | 0.03 | 6.70 | 0.1 | 4.03 |
| 0.5% polysorbate 80 | 2.9 | 6.33 | 2.8 | 4.23 |
| 1.0% polysorbate 80 | 12.3 | 5.84 | 4.7 | 4.39 |
| 1.5% polysorbate 80 | 9.3 | 5.41 | 4.5 | 4.41 |

FIG. 12

| Material | %Recovery | | Papp (X10-6 cm/s) | | Efflux | Permeability Classification[a] | Significant Efflux[b] |
|---|---|---|---|---|---|---|---|
| | A-B | B-A | A-B | B-A | | | |
| Racemate | 24 | 47 | 1.31 | 3.42 | 2.6 | High | No |
| R enantiomer | 19 | 48 | 12.4 | 19.1 | 1.5 | High | No |

Caco-2 Permeability

FIG.13

| Material | MDR1-MDCK Permeability | | | | | Brain Penetration Classification |
|---|---|---|---|---|---|---|
| | %Recovery | | Papp (X10-6 cm/s) | | Efflux | |
| | A-B | B-A | A-B | B-A | | |
| Racemate | 26 | 46 | 0.77 | 6.90 | 9.0 | Low |
| R enantiomer | 21 | 50 | 9.60 | 37.5 | 3.9 | Moderate |

| Material | Human Metabolic Stability % Remaining | | |
|---|---|---|---|
| | 0 Min | 15 min | 60 min |
| Racemate | 100 | -- | 21 |
| R enantiomer | 100 | -- | 28 |
| testosterone | 100 | 21 | -- |

| Group | Route | Test Article | Dose (mg/kg/day) | Dose volume (mL/kg/day) | Concentration (mg/mL) | Females[a] |
|---|---|---|---|---|---|---|
| 1 | Oral | R enantiomer | 3 | 2.5 | 1.2 | 36 + 2[b] |
| 2 | Oral | R enantiomer | 10 | 2.5 | 4 | 36 + 2[b] |
| 3 | Oral | R enantiomer | 30 | 2.5 | 12 | 36 + 2[b] |
| 4 | Oral | R enantiomer | 50 | 2.5 | 20 | 36 + 2[b] |
| 5 | Oral | Racemate | 3 | 2.5 | 1.2 | 36 + 2[b] |
| 6 | Oral | Racemate | 10 | 2.5 | 4 | 36 + 2[b] |
| 7 | Oral | Racemate | 30 | 2.5 | 12 | 36 + 2[b] |
| 8 | Oral | Racemate | 50 | 2.5 | 20 | 36 + 2[b] |

[a] Dose administration will occur for 9 days (first 18 females/group) or 12 days (second 18 females/group).
[b] Included as possible replacements

FIG. 16

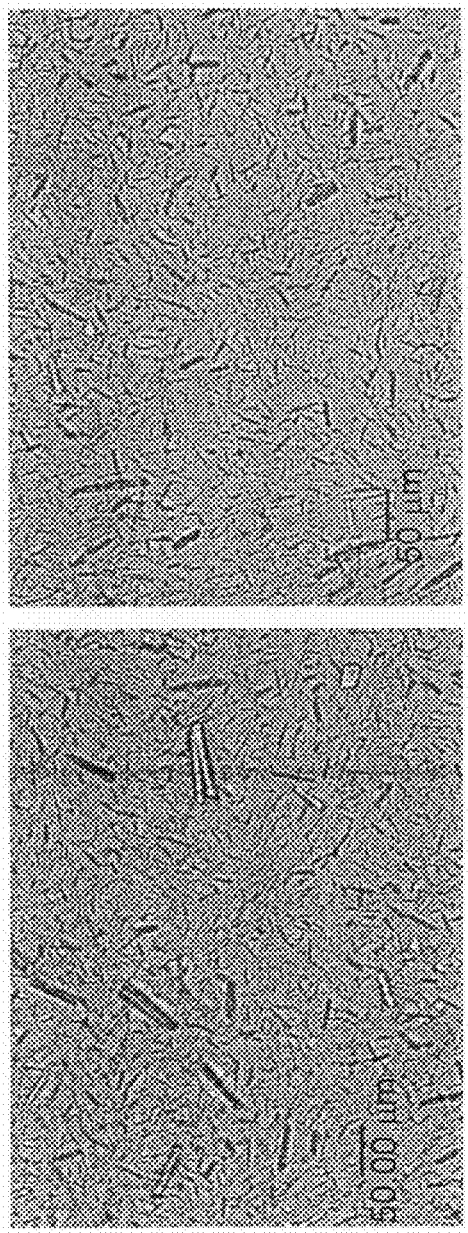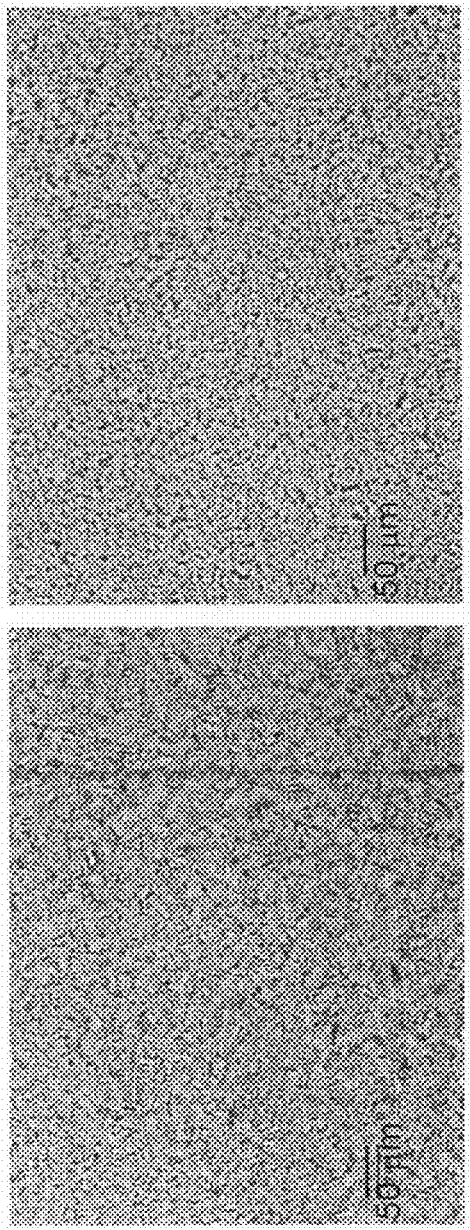
FIG. 17

CHIRAL DIACYLHYDRAZINE LIGANDS FOR MODULATING THE EXPRESSION OF EXOGENOUS GENES VIA AN ECDYSONE RECEPTOR COMPLEX

REFERENCE TO SEQUENCE LISTING SUBMITTED ELECTRONICALLY

The content of the electronically submitted sequence listing (Name "Substitute Sequence Listing.ST25.txt"; Size: 15.0 KB (15,408 bytes); and Date of Creation: Jan. 27, 2009) filed with the application is incorporated herein by reference in its entirety.

BACKGROUND OF THE INVENTION

1. Field of the Invention

This invention relates to the fields of biotechnology, genetic engineering and medicinal chemistry. In one embodiment, this invention relates to the field of gene expression. In another embodiment, this invention relates to diacylhydrazine ligands and chiral diacylhydrazine ligands for natural and mutated nuclear receptors and their use in a nuclear receptor-based inducible gene expression system and methods of modulating the expression of a gene within a host cell using these ligands and inducible gene expression system.

2. Background

Various publications are cited herein, the disclosures of which are incorporated by reference in their entireties. However, the citation of any reference herein should not be construed as an admission that such reference is available as "Prior Art" to the present application.

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., Proc. Natl. Acad. Sci. USA 83:5414-5418 (1986); Arnheiter et al., Cell 62:51-61 (1990); Filmus et al., Nucleic Acids Research 20:27550-27560 (1992)). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium Escherichia coli have been used in plants and animals to control gene expression. In the Tet system, tetracycline binds to the TetR repressor protein, resulting in a conformational change that releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., Science 262:1019-24 (1993); Belshaw et al., Proc Natl Acad Sci USA 93:4604-7 (1996)). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla et al., Annu. Rev. Entomol. 43: 545-569 (1998)). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al., Cell, 67:59-77 (1991)). EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see WO 96/27673 and U.S. Pat. No. 5,530, 028). Both analogs have exceptional safety profiles in other organisms.

The insect ecdysone receptor (EcR) heterodimerizes with Ultraspiracle (USP), the insect homologue of the mammalian retinoid X receptor (RXR), and binds ecdysteroids and ecdysone receptor response elements and activate transcription of ecdysone responsive genes. The EcR/USP/ligand complexes play important roles during insect development and reproduction. The EcR has five modular domains, A/B (transactivation), C (DNA binding, heterodimerization), D (Hinge, heterodimerization), E (ligand binding, heterodimerization and transactivation) and F (transactivation) domains. Some of these domains such as A/B, C and E retain their function when they are fused to other proteins.

Tightly regulated inducible gene expression systems or "gene switches" are useful for various applications such as gene therapy, large scale production of proteins in cells, cell based high throughput screening assays, functional genomics and regulation of traits in transgenic plants and animals.

The first version of an EcR-based gene switch used *Drosophila melanogaster* EcR (DmEcR) and *Mus musculus* RXR (MmRXR) and showed that these receptors in the presence of steroid, ponasteroneA, transactivate reporter genes in mammalian cell lines and transgenic mice (Christopherson et al., *Proc. Natl. Acad. Sci. USA*. 89:6314-6318 (1992); No et al., *Proc. Natl. Acad. Sci. USA*. 93:3346-3351 (1996)). Later, Suhr et al., *Proc. Natl. Acad. Sci*. 95:7999-8004 (1998) showed that non-steroidal ecdysone agonist, tebufenozide, induced high level of transactivation of reporter genes in mammalian cells through *Bombyx mori* EcR (BmEcR) in the absence of exogenous heterodimer partner.

WO 97/38117 and WO99/58155 disclose methods for modulating the expression of an exogenous gene in which a DNA construct comprising the exogenous gene and an ecdysone response element is activated by a second DNA construct comprising an ecdysone receptor that, in the presence of a ligand therefore, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. WO 99/02683 discloses that the ecdysone receptor isolated from the silk moth *Bombyx mori* is functional in mammalian systems without the need for an exogenous dimer partner.

U.S. Pat. No. 6,265,173 B1 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, these USP-based systems are constitutive in animal cells and therefore, are not effective for regulating reporter gene expression.

In each of these cases, the transactivation domain and the DNA binding domain (either as native EcR as in WO 99/02683 or as modified EcR as in WO 97/38117) were incorporated into a single molecule and the other heterodimeric partners, either USP or RXR, were used in their native state.

Drawbacks of the above described EcR-based gene regulation systems include a considerable background activity in the absence of ligands and non-applicability of these systems for use in both plants and animals (see U.S. Pat. No. 5,880, 333). Therefore, a need exists in the art for improved EcR-based systems to precisely modulate the expression of exogenous genes in both plants and animals. Such improved systems would be useful for applications such as gene therapy, large-scale production of proteins and antibodies, cell-based high throughput screening assays, functional genomics and regulation of traits in transgenic animals. For certain applications such as gene therapy, it may be desirable to have an inducible gene expression system that responds well to synthetic non-steroid ligands and at the same time is insensitive to the natural steroids. Thus, improved systems that are simple, compact, and dependent on ligands that are relatively inexpensive, readily available, and of low toxicity to the host would prove useful for regulating biological systems.

Recently, it has been shown that an ecdysone receptor-based inducible gene expression system in which the transactivation and DNA binding domains are separated from each other by placing them on two different proteins results in greatly reduced background activity in the absence of a ligand and significantly increased activity over background in the presence of a ligand (see WO 01/70816 A1, incorporated herein in its entirety by reference). This two-hybrid system is a significantly improved inducible gene expression modulation system compared to the two systems disclosed in applications WO 97/38117 and WO 99/02683. The two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283, 173). Briefly, the two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, the interaction of the first polypeptide with the second polypeptide effectively tethers the DNA binding domain to the transactivation domain. Since the DNA binding and transactivation domains reside on two different molecules, the background activity in the absence of ligand is greatly reduced.

A two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor gene switch systems to obtain maximum transactivation capability for each application. Furthermore, the two-hybrid system avoids some side effects due to overexpression of RXR that often occur when unmodified RXR is used as a heterodimer receptor partner. In one two-hybrid system, native DNA binding and transactivation domains of EcR or RXR are eliminated and as a result, these hybrid molecules have less chance of interacting with other steroid hormone receptors present in the cell resulting in reduced side effects. Additional gene switch systems include those described in the following, each of which is incorporated by reference: U.S. Pat. No. 7,091,038; WO2004078924; EP1266015; US20010044151; US20020110861; US20020119521; US20040033600; US20040197861; US20040235097; US20060020146; US20040049437; US20040096942; US20050228016; US20050266457; US20060100416; WO2001/70816; WO2002/29075; WO2002/066612; WO2002/066613; WO2002/066614; WO2002/066615; WO2005/108617; U.S. Pat. No. 6,258,603; US20050209283; US20050228016; US20060020146; EP0965644; U.S. Pat. No. 7,304,162; U.S. Pat. No. 7,304,161; MX234742; KR10-0563143; AU765306; AU2002-248500; and AU2002-306550.

With the improvement in ecdysone receptor-based gene regulation systems there is an increase in their use in various applications resulting in increased demand for ligands with higher activity than those currently in existence. U.S. Pat. No. 6,258,603 B1, US 2005/0209283 A1 and US 2006/0020146 A1 (and patents cited therein) disclose dibenzoylhydrazine ligands. However, a need exists for additional ligands with improved pharmacological properties. Applicants have discovered chiral diacylhydrazine ligands which have not previously been described that have surprising biological activities and the ability to modulate the expression of transgenes in unexpected ways.

SUMMARY OF THE INVENTION

The present invention provides diacylhydrazine ligands of Formula I and chiral diacylhydrazine ligands of Formula II or III for use with ecdysone receptor-based inducible gene expression systems useful for modulating expression of a target gene of interest in a host cell. Chiral diacylhydrazine ligands of the invention are enantiomerically enriched in either the R- or S-stereoisomer. Applicants have discovered these novel chiral diacylhydrazine ligands are surprisingly effective. Thus, the present invention is useful for applications such as gene therapy, large scale production of proteins and antibodies, cell-based screening assays, functional genomics, proteomics, metabolomics, and regulation of traits in transgenic organisms, where control of gene expression levels is desirable. An advantage of the present invention is that it provides a means to regulate gene expression and to tailor expression levels to suit the user's requirements.

The present invention pertains to compounds of Formula I

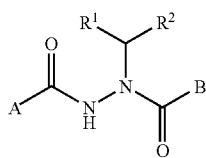

Formula I wherein

A is alkoxy, arylalkyloxy or aryloxy;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl;

or pharmaceutically acceptable salts, hydrates, crystalline forms or amorphous forms thereof.

In another embodiment, the present invention pertains to enantiomerically enriched compounds of Formula II

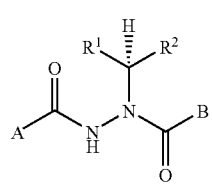

Formula II wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly S;

or pharmaceutically acceptable salts, hydrates, crystalline forms or amorphous forms thereof.

In another embodiment, the present invention pertains to enantiomerically enriched compounds of Formula III

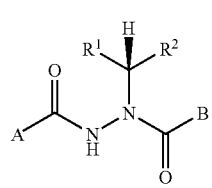

Formula III wherein

A is alkoxy, arylalkyloxy, aryloxy, arylalkyl, optionally substituted aryl or optionally substituted heteroaryl;

B is optionally substituted aryl or optionally substituted heteroaryl; and $R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl;

with the proviso that $R^1$ does not equal $R^2$;

wherein the absolute configuration at the asymmetric carbon atom bearing $R^1$ and $R^2$ is predominantly R;

or pharmaceutically acceptable salts, hydrates, crystalline forms or amorphous forms thereof.

In one embodiment, the present invention pertains to (R)-3,5-dimethyl-benzoic acid N-(1-tert-butyl-butyl)-N'-(2-ethyl-3-methoxy-benzoyl)-hydrazide having an enantiomeric excess of at least 95% or a pharmaceutically acceptable salt, hydrate, crystalline form or amorphous form thereof.

In another embodiment, the present invention pertains to a pharmaceutical composition comprising (R)-3,5-dimethyl-benzoic acid N-(1-tert-butyl-butyl)-N'-(2-ethyl-3-methoxy-benzoyl)-hydrazide having an enantiomeric excess of at least 95% or a pharmaceutically acceptable salt, hydrate, crystalline form or amorphous form thereof.

The present invention also pertains to a process for the preparation a compound of Formula IV

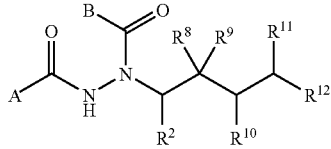

Formula IV wherein
A is arylalkyl, optionally substituted aryl or optionally substituted heteroaryl;
B is optionally substituted aryl or optionally substituted heteroaryl;
$R^2$ is optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl;
with the proviso that $R^2$ does not equal —$CR^8R^9CHR^{10}CR^{11}R^{12}$; and
$R^8$, $R^9$, $R^{10}$, $R^{11}$ and $R^{12}$ are independently selected from hydrogen, alkyl, cycloalkyl, heterocycle, aryl or heteroaryl;
wherein the asymmetric carbon atom to which $R^2$ is attached is enantiomerically enriched in either the R or S isomer;
comprising:
a) reacting a compound of Formula V

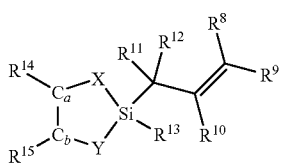

Formula V with a compound of Formula VI

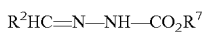 Formula VI wherein
X and Y are independently O or NR wherein R is alkyl or aryl;
$C_a$ and $C_b$ are independently an asymmetric carbon atom of the S configuration or an asymmetric carbon atom of the R configuration;
$R^{14}$ and $R^{15}$ are independently alkyl or aryl;
$R^{13}$ is halo, hydrogen, alkyl, alkoxy or $OSO_2CF_3$;
$R^7$ is alkyl, arylalkyl or aryl; and
$R^2$, $R^8$, $R^9$, $R^{10}$, $R^{11}$ and $R^{12}$ have the same meanings noted above;
to form a compound of Formula VII;

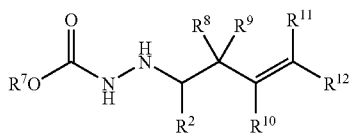

Formula VII b) reducing the compound of Formula VII to form a compound of Formula VIII;

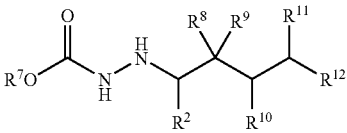

Formula VIII c) reacting the compound of Formula VIII with a compound of Formula B—CO-LG where LG is a leaving group to form a compound of Formula IX;

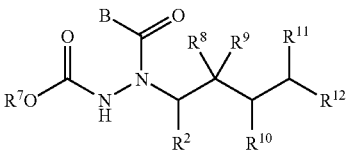

Formula IX d) removing the $R^7CO_2$— group of the compound of Formula IX to form a compound of Formula X; and

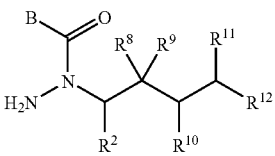

Formula X e) reacting the compound of Formula X with a compound of Formula A-CO-LG where LG is a leaving group to form a compound of Formula IV.

The present invention also pertains to methods of modulating gene expression in a host cell using a gene expression modulation system with a diacylhydrazine ligand of Formula I or chiral diacylhydrazine ligand of Formula II or III.

In one embodiment, the present invention relates to the use of a diacylhydrazine ligand of Formula I or chiral diacylhydrazine ligand of Formula II or III in an inducible gene expression system that has a reduced level of background gene expression and responds to submicromolar concentrations of the ligand.

In another embodiment, the invention relates to a method of modulating the expression of a target gene in a host cell, wherein the host cell comprises a first gene expression cassette comprising a first polynucleotide encoding a first polypeptide comprising:
i) a transactivation domain;
ii) a DNA-binding domain; and
iii) a Group H nuclear receptor ligand binding domain;
and a second gene expression cassette comprising:
i) a response element capable of binding to said DNA binding domain;
ii) a promoter that is activated by the transactivation domain; and
iii) said target gene;
the method comprising contacting said host cell with a diacylhydrazine ligand of Formula I or chiral diacylhydrazine ligand of Formula II or III; wherein the expression of the target gene is modulated.

In another embodiment, the invention relates to a method for regulating endogenous or heterologous gene expression in a transgenic subject comprising contacting a ligand with an ecdysone receptor complex within the cells of the subject, wherein the cells further contain a DNA binding sequence for the ecdysone receptor complex when in combination with the ligand and wherein formation of an ecdysone receptor complex-ligand-DNA binding sequence complex induces expression of the gene, and where the ligand is a diacylhydrazine ligand of Formula I or chiral diacylhydrazine ligand of Formula II or III; wherein endogenous or heterologous gene expression in a transgenic subject is regulated.

In another embodiment, the invention relates to a method of modulating the expression of a target gene in a host cell comprising the steps of:

a) introducing into the host cell a gene expression modulation system comprising:

i) a first gene expression cassette that is capable of being expressed in a host cell, said first gene expression cassette comprising a polynucleotide sequence that encodes a first hybrid polypeptide comprising:

(a) a DNA-binding domain that recognizes a response element associated with a gene whose expression is to be modulated; and (b) an ecdysone receptor ligand binding domain;

ii) a second gene expression cassette that is capable of being expressed in the host cell, said second gene expression cassette comprising a polynucleotide sequence that encodes a second hybrid polypeptide comprising:

(a) a transactivation domain; and (b) a chimeric retinoid X receptor ligand binding domain; and iii) a third gene expression cassette that is capable of being expressed in a host cell, said third gene expression cassette comprising a polynucleotide sequence comprising:

(a) a response element recognized by the DNA-binding domain of the first hybrid polypeptide;

(b) a promoter that is activated by the transactivation domain of the second hybrid polypeptide; and (c) a gene whose expression is to be modulated; and b) introducing into the host cell a diacylhydrazine ligand of Formula I or chiral diacylhydrazine ligand of Formula II or III; wherein the expression of a gene in a host cell is modulated.

In another embodiment, the present invention relates to a method for producing a polypeptide comprising the steps of:

a) selecting a cell which is substantially insensitive to exposure to a diacylhydrazine ligand of Formula I or chiral diacylhydrazine ligand of Formula II or III;

b) introducing into the cell:

i) a DNA construct comprising:

(a) an exogenous gene encoding the polypeptide; and (b) a response element;

wherein the gene is under the control of the response element; and ii) an ecdysone receptor complex comprising:

(a) a DNA binding domain that binds to the response element;

(b) a binding domain for said ligand; and (c) a transactivation domain; and c) exposing the cell to said ligand; wherein a polypeptide is produced.

This embodiment of the invention provides the advantage of temporally controlling polypeptide production by the cell. Moreover, in those cases when accumulation of such a polypeptide can damage the cell, the expression of the polypeptide may be limited to short periods by exposing said cell to compounds of the present invention. Such control is particularly important when the exogenous gene is a therapeutic gene. Therapeutic genes may be called upon to produce polypeptides which control needed functions, such as the production of insulin in diabetic patients. They may also be used to produce damaging or even lethal proteins, such as those lethal to cancer cells. Such control may also be important when the protein levels produced may constitute a metabolic drain on growth or reproduction, such as in transgenic plants.

BRIEF DESCRIPTION OF DRAWINGS

FIG. 4: Table of sample lots or the racemate and R enantiomer of 2-ethyl-3-methoxy-benzoic acid N'-(1-tert-butyl-butyl)-N'-(3,5-dimethyl-benzoyl)-hydrazide. Samples of the R enantiomer obtained by rapid crystallization/precipitation from either methanol/water or toluene/heptane yielded the same powder X-ray diffraction pattern (data not shown), and had essentially the same melting point ([toluene/heptane] 166.2-167.1° C., [$CH_3OH/H_2O$]166.5-167.4° C.) as compared to each other and as compared to a standard obtained from $CH_3OH$ crystallization (165.1-166.5° C.). Samples of two separate preparations of the racemate obtained by methanol evaporation gave the same melting point (170-171° C., 169-170° C.) within experimental error and slight variations in purity.

FIG. 5: Table showing particle size distribution of the micronized R enantiomer of 2-ethyl-3-methoxy-benzoic acid N'-(1-tert-butyl-butyl)-N'-(3,5-dimethyl-benzoyl)-hydrazide.

FIG. 6: Table showing particle size distribution of the micronized racemate of 2-ethyl-3-methoxy-benzoic acid N'-(1-tert-butyl-butyl)-N'-(3,5-dimethyl-benzoyl)-hydrazide.

FIG. 7: Table showing bulk and tapped density analysis of micronized racemate and R enantiomer of 2-ethyl-3-methoxy-benzoic acid N'-(1-tert-butyl-butyl)-N'-(3,5-dimethyl-benzoyl)-hydrazide.

FIG. 9: Table showing qualitative comparative solubility test of racemate and R enantiomer of 2-ethyl-3-methoxy-benzoic acid N'-(1-tert-butyl-butyl)-N'-(3,5-dimethyl-benzoyl)-hydrazide in pharmaceutical excipients.

FIG. 10: Table showing results of a thermodynamic equilibrium assay (90° C. for 5 minutes or indicated time; treatment 2) followed by cooling to room temperature and seeding of racemate and R enantiomer of 2-ethyl-3-methoxy-benzoic acid N'-(1-tert-butyl-butyl)-N'-(3,5-dimethyl-benzoyl)-hydrazide in pharmaceutical excipients. Treatment 1 is the result of stirring at room temperature for ≦2.5 hr.

FIG. 11: Table showing solubility (μM) of racemate and R enantiomer of 2-ethyl-3-methoxy-benzoic acid N'-(1-tert-butyl-butyl)-N'-(3,5-dimethyl-benzoyl)-hydrazide in 20% PEG 1000 in distilled water, pH 7.0.

FIG. 12: Table showing solubility of racemate and R enantiomer of 2-ethyl-3-methoxy-benzoic acid N'-(1-tert-butyl-butyl)-N'-(3,5-dimethyl-benzoyl)-hydrazide in aqueous polysorbate 80.

FIG. 13: Table showing bidirectional Permeability of racemate and R enantiomer of 2-ethyl-3-methoxy-benzoic acid N'-(1-tert-butyl-butyl)-N'-(3,5-dimethyl-benzoyl)-hydrazide Through Caco-2 Cell Monolayers. [a]Permeability Classification: (Papp A→B)<1.0×10-6 cm/s=LOW; (Papp A→B) >1.0×10-6 cm/s=HIGH; [b]Significant Efflux: Efflux>3.0 and (Papp B→A)>1.0×10-6 cm/s FIG. 14: Table showing permeability of racemate and R enantiomer of 2-ethyl-3-methoxy-benzoic acid N'-(1-tert-butyl-butyl)-N'-(3,5-dimethyl-benzoyl)-hydrazide in MDR1-MDCK cells. Classification: A-B Papp>3.0 and Efflux Ratio<3.0: High. A-B Papp>3.0 and 10>Efflux Ratio>3.0: Moderate. A-B Papp>3.0 and Efflux Ratio>10: Low A-B Papp<3.0: Low.

FIG. 15: Table showing stability of racemate and R enantiomer of 2-ethyl-3-methoxy-benzoic acid N'-(1-tert-butyl-butyl)-N'-(3,5-dimethyl-benzoyl)-hydrazide in human liver microsomes.

FIG. 16: Table showing dosing schedule of racemate and R enantiomer of 2-ethyl-3-methoxy-benzoic acid N'-(1-tert-butyl-butyl)-N'-(3,5-dimethyl-benzoyl)-hydrazide/Labrasol preparations in C57BL/6N:Crl mice. [a]Dose administration for 9 days (first 18 females/group) or 12 days (second 18 females/group); [b]Included as possible replacements.

FIG. 17: Micrographs of non-micronized and micronized samples of 2-ethyl-3-methoxy-benzoic acid N'-(1-tert-butyl-butyl)-N'-(3,5-dimethyl-benzoyl)-hydrazide racemate. Note the 50 micron reference scale.

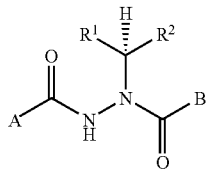

Figure 1:
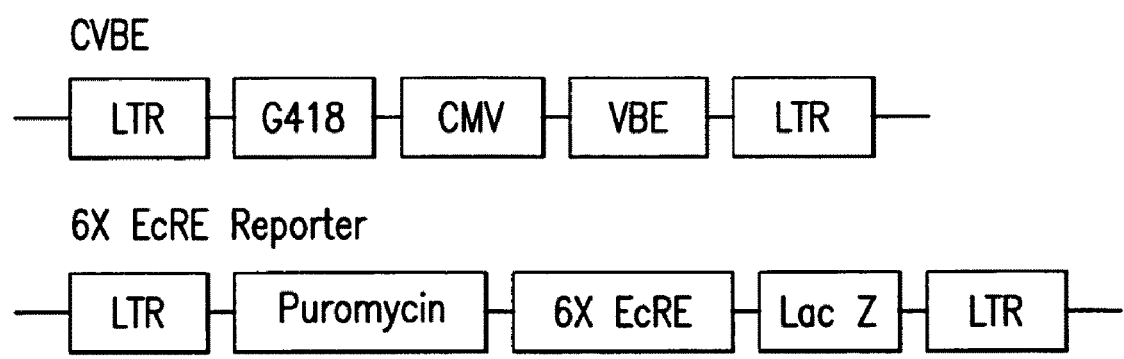
FIG. 1: Schematic of switch construct CVBE, and the reporter construct 6XEcRE Lac Z. Flanking both constructs are long terminal repeats, G418 and puromycin are selectable markers, CMV is the cytomegalovirus promoter, VBE is coding sequence for amino acids 26-546 from *Bombyx mori* EcR inserted downstream of the VP16 transactivation domain, 6× EcRE is six copies of the ecdysone response element, lacZ encodes for the reporter enzyme β-galactosidase.

Formula II wherein
A is alkoxy, arylalkyloxy, aryloxy, arylalkyl, optionally substituted aryl or optionally substituted heteroaryl;
B is optionally substituted aryl or optionally substituted heteroaryl; and
$R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl;
with the proviso that $R^1$ does not equal $R^2$;
wherein the absolute configuration at the asymmetric carbon atom bearing $R^1$ and $R^2$ is predominantly S;
or pharmaceutically acceptable salts, hydrates, crystalline forms or amorphous forms thereof.

In another embodiment, the present invention pertains to enantiomerically enriched compounds of Formula III

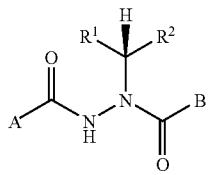

Formula III wherein
A is alkoxy, arylalkyloxy, aryloxy, arylalkyl, optionally substituted aryl or optionally substituted heteroaryl;
B is optionally substituted aryl or optionally substituted heteroaryl; and
$R^1$ and $R^2$ are independently optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl;
with the proviso that $R^1$ does not equal $R^2$;
wherein the absolute configuration at the asymmetric carbon atom bearing $R^1$ and $R^2$ is predominantly R;
or pharmaceutically acceptable salts, hydrates, crystalline forms or amorphous forms thereof.

In another embodiment, the present invention pertains to enantiomerically enriched compounds of Formula II or III wherein
A is $-OC(CH_3)_3$, $-OCH_2Ph$, optionally substituted aryl or optionally substituted heteroaryl;
B is optionally substituted aryl;
$R^1$ is optionally substituted $(C_1-C_6)$alkyl, hydroxy$(C_1-C_4)$alkyl or optionally substituted $(C_2-C_6)$alkenyl; and
$R^2$ is optionally substituted $(C_1-C_6)$alkyl, aryl$(C_1-C_4)$alkyl, optionally substituted $(C_3-C_7)$cycloalkyl or optionally substituted aryl;
with the proviso that $R^1$ does not equal $R^2$;
wherein
the absolute configuration at the asymmetric carbon atom bearing $R^1$ and $R^2$ is predominantly S in Formula II; and
the absolute configuration at the asymmetric carbon atom bearing $R^1$ and $R^2$ is predominantly R in Formula III;
or pharmaceutically acceptable salts, hydrates, crystalline forms or amorphous forms thereof.

In another embodiment, the present invention pertains to enantiomerically enriched compounds of Formula II or III wherein
A is optionally substituted aryl or optionally substituted heteroaryl;
B is optionally substituted aryl;
$R^1$ is optionally substituted $(C_1-C_6)$alkyl, hydroxy$(C_1-C_4)$alkyl or optionally substituted $(C_2-C_6)$alkenyl; and
$R^2$ is optionally substituted $(C_1-C_6)$alkyl, aryl$(C_1-C_4)$alkyl, optionally substituted $(C_3-C_7)$cycloalkyl or optionally substituted aryl;
with the proviso that $R^1$ does not equal $R^2$;
wherein
the absolute configuration at the asymmetric carbon atom bearing $R^1$ and $R^2$ is predominantly S in Formula II; and
the absolute configuration at the asymmetric carbon atom bearing $R^1$ and $R^2$ is predominantly R in Formula III;
or pharmaceutically acceptable salts, hydrates, crystalline forms or amorphous forms thereof.

In another embodiment, the present invention pertains to enantiomerically enriched compounds of Formula II or III wherein
A is

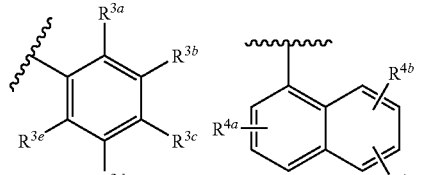

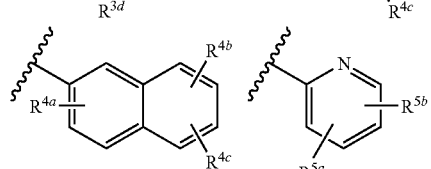

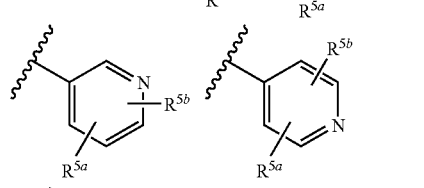

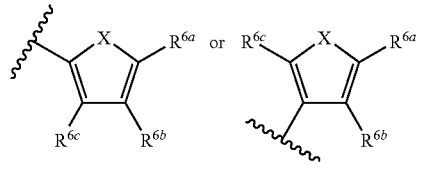

$R^{3a}$, $R^{3b}$, $R^{3c}$, $R^{3d}$ and $R^{3e}$ are independently selected from hydrogen, halo, nitro, cyano, hydroxy, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —COR$^c$, —SO$_2$R$^d$, —N(R$^e$COR$^f$, —N(R$^e$)SO$_2$R$^g$ or —N(R$^e$C=N(R$^h$)-amino; or R$^{3a}$ and R$^{3b}$ taken together with the carbon atoms to which they are attached form a five, six or seven membered fused cycloalkyl or heterocycle ring; or R$^{3b}$ and R$^{3c}$ taken together with the carbon atoms to which they are attached form a five, six or seven membered fused cycloalkyl or heterocycle ring;

R$^{4a}$, R$^{4b}$, R$^{4c}$, R$^{5a}$, R$^{5b}$, R$^{6a}$, R$^{6b}$ and R$^{6c}$ are independently selected from hydrogen, halo, nitro, cyano, hydroxy, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —COR$^c$, —SO$_2$R$^d$, —N(R$^e$)COR$^f$, —N(R$^e$)SO$_2$R$^g$ or —N(R$^e$)C=N(R$^h$)-amino;

X is O or S;

B is

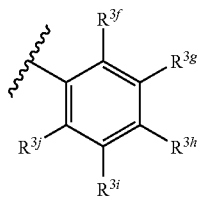

and;

R$^{3f}$, R$^{3g}$, R$^{3h}$, R$^{3i}$ and R$^{3j}$ are independently selected from hydrogen, halo, nitro, cyano, hydroxy, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —COR$^c$, —SO$_2$R$^d$, —N(R$^e$)COR$^f$, —N(R$^e$)SO$_2$R$^g$ or —N(R$^e$)C=N(R$^h$)-amino; or R$^{3f}$ and R$^{3g}$ taken together with the carbon atoms to which they are attached form a five, six or seven membered fused cycloalkyl or heterocycle ring; or R$^{3g}$ and R$^{3h}$ taken together with the carbon atoms to which they are attached form a five, six or seven membered fused cycloalkyl or heterocycle ring;

wherein

R$^c$ is hydrogen, hydroxy, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy or arylalkyloxy;

R$^d$ is haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl or optionally substituted heteroaryl;

R$^e$ is hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl or optionally substituted heteroaryl;

R$^f$ is hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy, arylalkyloxy or amino;

R$^g$ is haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl or amino;

R$^h$ is hydrogen, alkyl, aryl, cyano or nitro;

R$^1$ is optionally substituted (C$_1$-C$_6$)alkyl, hydroxy(C$_1$-C$_4$)alkyl or optionally substituted (C$_2$-C$_6$)alkenyl; and R$^2$ is optionally substituted (C$_1$-C$_6$)alkyl, aryl(C$_1$-C$_4$)alkyl, optionally substituted (C$_3$-C$_7$)cycloalkyl or optionally substituted aryl;

with the proviso that R$^1$ does not equal R$^2$;

wherein the absolute configuration at the asymmetric carbon atom bearing R$^1$ and R$^2$ is predominantly S in Formula II; and the absolute configuration at the asymmetric carbon atom bearing R$^1$ and R$^2$ is predominantly R in Formula III;

or pharmaceutically acceptable salts, hydrates, crystalline forms or amorphous forms thereof.

In another embodiment, the present invention pertains to enantiomerically enriched compounds of Formula II wherein A, B, R$^{3a}$, R$^{3b}$, R$^{3c}$, R$^{3d}$, R$^{3e}$, R$^{3f}$, R$^{3g}$, R$^{3h}$, R$^{3i}$, R$^{3j}$, R$^{4a}$, R$^{4b}$, R$^{4c}$, R$^{5a}$, R$^{5b}$, R$^{6a}$, R$^{6b}$, R$^{6c}$ and X have the same meanings as noted above;

R$^1$ is (C$_1$-C$_6$)alkyl, hydroxy(C$_1$-C$_4$)alkyl or (C$_2$-C$_4$)alkenyl; and R$^2$ is optionally substituted (C$_3$-C$_7$)cycloalkyl;

wherein the absolute configuration at the asymmetric carbon atom bearing R$^1$ and R$^2$ is predominantly S;

or pharmaceutically acceptable salts, hydrates, crystalline forms or amorphous forms thereof.

In another embodiment, the present invention pertains to enantiomerically enriched compounds of Formula III wherein A, B, R$^{3a}$, R$^{3b}$, R$^{3c}$, R$^{3d}$, R$^{3e}$, R$^{3f}$, R$^{3g}$, R$^{3h}$, R$^{3i}$, R$^{3j}$, R$^{4a}$, R$^{4b}$, R$^{4c}$, R$^{5a}$, R$^{5b}$, R$^{6a}$, R$^{6b}$, R$^{6c}$ and X have the same meanings as noted above;

R$^1$ is (C$_1$-C$_6$)alkyl, hydroxy(C$_1$-C$_4$)alkyl or (C$_2$-C$_4$)alkenyl; and R$^2$ is optionally substituted (C$_1$-C$_6$)alkyl;

with the proviso that R$^1$ does not equal R$^2$;

wherein the absolute configuration at the asymmetric carbon atom bearing R$^1$ and R$^2$ is predominantly R;

or pharmaceutically acceptable salts, hydrates, crystalline forms or amorphous forms thereof.

In one embodiment, the present invention pertains to enantiomerically enriched compounds of Formula II wherein A is

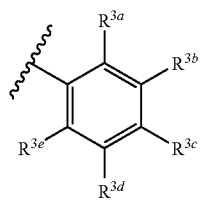

B is

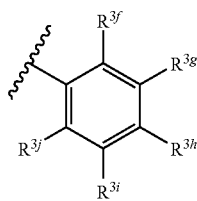

$R^{3a}$, $R^{3b}$, $R^{3c}$, $R^{3d}$, $R^{3e}$, $R^{3f}$, $R^{3g}$, $R^{3h}$, $R^{3i}$ and $R^{3j}$ are independently selected from hydrogen, halo, $(C_1-C_4)$alkyl or $(C_1-C_4)$alkoxy;

$R^1$ is $(C_1-C_6)$alkyl, hydroxy$(C_1-C_4)$alkyl or $(C_2-C_4)$alkenyl; and $R^2$ is optionally substituted $(C_3-C_7)$cycloalkyl wherein the absolute configuration at the asymmetric carbon atom bearing $R^1$ and $R^2$ is predominantly S;

or pharmaceutically acceptable salts, hydrates, crystalline forms or amorphous forms thereof.

In another embodiment, the present invention pertains to enantiomerically enriched compounds of Formula III wherein A is

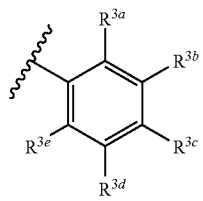

B is

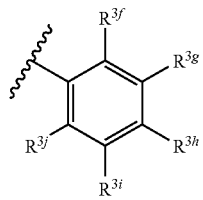

$R^{3a}$, $R^{3b}$, $R^{3c}$, $R^{3d}$, $R^{3e}$, $R^{3f}$, $R^{3g}$, $R^{3h}$, $R^{3i}$ and $R^{3j}$ are independently selected from hydrogen, halo, $(C_1-C_4)$alkyl or $(C_1-C_4)$alkoxy;

$R^1$ is $(C_1-C_6)$alkyl, hydroxy$(C_1-C_4)$alkyl or $(C_2-C_4)$alkenyl; and $R^2$ is optionally substituted $(C_1-C_6)$alkyl;

wherein the absolute configuration at the asymmetric carbon atom bearing $R^1$ and $R^2$ is predominantly R;

or pharmaceutically acceptable salts, hydrates, crystalline forms or amorphous forms thereof.

In another embodiment, the present invention pertains to enantiomerically enriched compounds of Formula II having an enantiomeric excess of at least 50%, 75%, 85%, 95% or >99% of the S-isomer. In one embodiment, the compound of Formula II consists essentially of the S-isomer.

In another embodiment, the present invention pertains to enantiomerically enriched compounds of Formula III having an enantiomeric excess of at least 50%, 75%, 85%, 95% or >99% of the R-isomer. In one embodiment, the compound of Formula III consists essentially of the R-isomer.

In another embodiment, the present invention pertains to a pharmaceutical composition comprising the compound of Formula I, II or III.

In one embodiment, the present invention pertains to (R)-3,5-dimethyl-benzoic acid N-(1-tert-butyl-butyl)-N'-(2-ethyl-3-methoxy-benzoyl)-hydrazide having an enantiomeric excess of at least 95% or of at least 99%, or a pharmaceutically acceptable salt, hydrate, crystalline form or amorphous form thereof. In one embodiment, the compound is enantiomerically pure.

In another embodiment, the present invention pertains to a pharmaceutical composition comprising (R)-3,5-dimethyl-benzoic acid N-(1-tert-butyl-butyl)-N'-(2-ethyl-3-methoxy-benzoyl)-hydrazide having an enantiomeric excess of at least 95% or of at least 99%, or a pharmaceutically acceptable salt, hydrate, crystalline form or amorphous form thereof. In one embodiment, the compound is enantiomerically pure.

It has been unexpectedly discovered that enantiomerically pure (R)-3,5-dimethyl-benzoic acid N-(1-tert-butyl-butyl)-N'-(2-ethyl-3-methoxy-benzoyl)-hydrazide has a combination of beneficial properties which make it uniquely suitable for in vivo pharmaceutical use. Such properties include a lower melting point and lower heat of fusion compared to the racemate (Example 68); better solubility in many liquid pharmaceutical excipients compared to the racemate (Example 68); better permeability in certain cells compared to the racemate (Example 69); is more likely to be able to cross the blood-brain barrier than the racemate (Example 69); better stability to hepatocyte metabolism compared to the racemate (Example 70); when administered orally as a Labrasol solution or suspension, achieves significantly higher plasma levels compared to the racemate (Example 71); and achieves much greater in vivo gene expression by activation of a EcR-based gene switch compared to the racemate (Example 72).

The present invention also pertains to a process for the preparation a compound of Formula IV

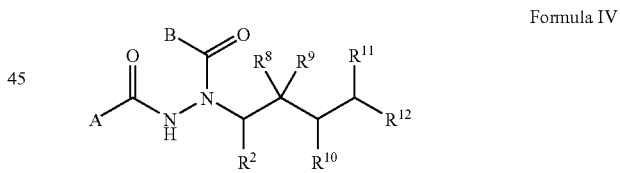

Formula IV wherein

A is arylalkyl, optionally substituted aryl or optionally substituted heteroaryl;

B is optionally substituted aryl or optionally substituted heteroaryl;

$R^2$ is optionally substituted alkyl, arylalkyl, hydroxyalkyl, haloalkyl, optionally substituted cycloalkyl, optionally substituted alkenyl, optionally substituted alkynyl, optionally substituted heterocycle, optionally substituted aryl or optionally substituted heteroaryl;

with the proviso that $R^2$ does not equal —$CR^8R^9CHR^{10}CR^{11}R^{12}$; and $R^8$, $R^9$, $R^{10}$, $R^{11}$ and $R^{12}$ are independently selected from hydrogen, alkyl, cycloalkyl, heterocycle, aryl or heteroaryl;

wherein the asymmetric carbon atom to which $R^2$ is attached is enantiomerically enriched in either the R or S isomer;

comprising:

a) reacting a compound of Formula V

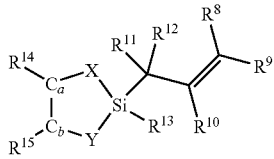

Formula V with a compound of Formula VI $R^2HC{=}N{-}NH{-}CO_2R^7$  Formula VI wherein X and Y are independently O or NR wherein R is alkyl or aryl;

$C_a$ and $C_b$ are independently an asymmetric carbon atom of the S configuration or a asymmetric carbon atom of the R configuration;

$R^{14}$ and $R^{15}$ are independently alkyl or aryl;

$R^{13}$ is halo, hydrogen, alkyl, alkoxy or $OSO_2CF_3$;

$R^7$ is alkyl, arylalkyl or aryl; and $R^2, R^8, R^9, R^{10}, R^{11}$ and $R^{12}$ have the same meanings noted above;

to form a compound of Formula VII;

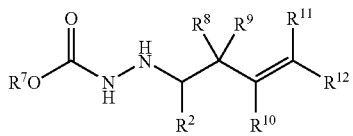

Formula VII b) reducing the compound of Formula VII to form a compound of Formula VIII;

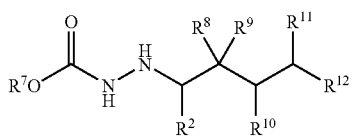

Formula VIII c) reacting the compound of Formula VIII with a compound of Formula B—CO-LG where LG is a leaving group to form a compound of Formula IX;

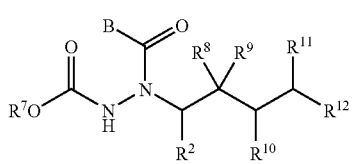

Formula IX d) removing the $R^7CO_2$— group of the compound of Formula IX to form a compound of Formula X; and

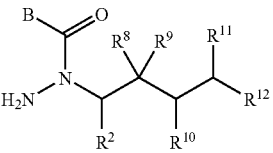

Formula X e) reacting the compound of Formula X with a compound of Formula A-CO-LG where LG is a leaving group, to form a compound of Formula IV.

In another embodiment, the present invention pertains to a process for the preparation a compound of Formula IV wherein $R^8, R^9, R^{10}, R^{11}$ and $R^{12}$ are hydrogen.

In another embodiment, the present invention pertains to a process for the preparation a compound of Formula IV wherein $R^8, R^9, R^{10}, R^{11}$ and $R^{12}$ are hydrogen;

X is NR and R is methyl;

Y is O;

$R^{14}$ is methyl;

$R^{15}$ is phenyl; and each of $C_a$ and $C_b$ is of the R configuration.

In another embodiment, the present invention pertains to a process for the preparation a compound of Formula IV wherein $R^8, R^9, R^{10}, R^{11}$ and $R^{12}$ are hydrogen;

X is NR and R is methyl;

Y is O;

$R^{14}$ is methyl;

$R^{15}$ is phenyl; and each of $C_a$ and $C_b$ is of the S configuration.

In another embodiment, the present invention pertains to a process for the preparation a compound of Formula IV wherein $R^8, R^9, R^{10}, R^{11}$ and $R^{12}$ are hydrogen;

X is NR and R is methyl;

Y is O;

$R^{14}$ is methyl;

$R^{15}$ is phenyl;

each of $C_a$ and $C_b$ is of the S configuration; and

B is 3,5-di-methylphenyl.

In another embodiment, the present invention pertains to a process for the preparation a compound of Formula IV wherein $R^8, R^9, R^{10}, R^{11}$ and $R^{12}$ are hydrogen;

X is NR and R is methyl;

Y is O;

$R^{14}$ is methyl;

$R^{15}$ is phenyl;

each of $C_a$ and $C_b$ is of the S configuration; and

A is 2-ethyl-3-methoxyphenyl.

In another embodiment, the present invention pertains to a process for the preparation a compound of Formula IV wherein $R^8, R^9, R^{10}, R^{11}$ and $R^{12}$ are hydrogen;

X is NR and R is methyl;

Y is O;

$R^{14}$ is methyl;

$R^{15}$ is phenyl;

each of $C_a$ and $C_b$ is of the S configuration; and $R^2$ is tert-butyl.

The present invention also pertains to a process for the preparation of a compound of Formula II or III comprising:
a) reacting an acyl hydrazine of formula XI

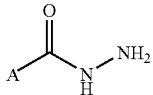
Formula XI with a ketone of Formula XII

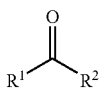
Formula XII to form a compound of Formula XIII;

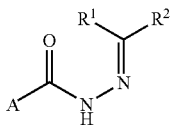
Formula XIII wherein $R^1$ does not equal $R^2$;
b) reducing the compound of Formula XIII in the presence of a chiral catalyst to form a compound of Formula S-XIV or R-XIV; and

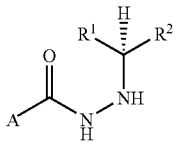
Formula S-XIV

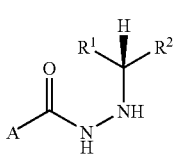
Formula R-XIV c) reacting the compound of Formula S-XIV or R-XIV with a compound of Formula B—CO-LG where LG is a leaving group to form a compound of Formula II or III.

Diacylhydrazines of Formula I of the invention include, but are not limited to:
rac-N'-(1-tert-Butyl-butyl)-N'-(3,5-dimethyl-benzoyl)-hydrazinecarboxylic acid benzyl ester; or rac-N'-(1-tert-Butyl-butyl)-N'-(3,5-dimethyl-benzoyl)-hydrazinecarboxylic acid tert-butyl ester.

Chiral diacylhydrazines of Formula II or III of the present invention include, but are not limited to:
(S)-3,5-Dimethyl-benzoic acid N-(1-cyclohexyl-butyl)-N'-(2-ethyl-3-methoxy-benzoyl)-hydrazide;
(S)-3,5-Dimethyl-benzoic acid N-(1-cyclohexyl-butyl)-N'-(3-methoxy-benzoyl)-hydrazide;
(S)-3,5-Dimethyl-benzoic acid N-(1-cyclohexyl-butyl)-N'-(4-methyl-benzoyl)-hydrazide.
(R)—N'-(1-tert-Butyl-butyl)-N'-(3,5-dimethyl-benzoyl)-hydrazinecarboxylic acid benzyl ester;
(R)—N'-(1-tert-Butyl-butyl)-N'-(3,5-dimethyl-benzoyl)-hydrazinecarboxylic acid tert-butyl ester;
(R)—N'-(1-tert-Butyl-4-hydroxy-butyl)-N'-(3,5-dimethyl-benzoyl)-hydrazinecarboxylic acid benzyl ester;
(R)—N'-(1-tert-Butyl-4-hydroxy-butyl)-N'-(3,5-dimethyl-benzoyl)-hydrazine carboxylic acid benzyl ester;
(R)-3,5-Dimethyl-benzoic acid N-(1-tert-butyl-butyl)-N'-(2-ethyl-3-methoxy-benzoyl)-hydrazide;
(R)-3,5-Dimethyl-benzoic acid N'-benzoyl-N-(1-tert-butyl-butyl)-hydrazide;
(R)-3,5-Dimethyl-benzoic acid N-(1-tert-butyl-butyl)-N'-(2-methyl-benzoyl)-hydrazide;
(R)-3,5-Dimethyl-benzoic acid N-(1-tert-butyl-butyl)-N'-(2-methoxy-benzoyl)-hydrazide;
(R)-3,5-Dimethyl-benzoic acid N-(1-tert-butyl-butyl)-N'-(2-fluoro-benzoyl)-hydrazide;
(R)-3,5-Dimethyl-benzoic acid N-(1-tert-butyl-butyl)-N'-(2-chloro-benzoyl)-hydrazide;
(R)-3,5-Dimethyl-benzoic acid N'-(2-bromo-benzoyl)-N-(1-tert-butyl-butyl)-hydrazide;
(R)-3,5-Dimethyl-benzoic acid N-(1-tert-butyl-butyl)-N'-(3-methyl-benzoyl)-hydrazide;
(R)-3,5-Dimethyl-benzoic acid N-(1-tert-butyl-butyl)-N'-(3-methoxy-benzoyl)-hydrazide;
(R)-3,5-Dimethyl-benzoic acid N-(1-tert-butyl-butyl)-N'-(3-chloro-benzoyl)-hydrazide;
(R)-3,5-Dimethyl-benzoic acid N-(1-tert-butyl-butyl)-N'-(4-methyl-benzoyl)-hydrazide;
(R)-3,5-Dimethyl-benzoic acid N-(1-tert-butyl-butyl)-N'-(4-ethyl-benzoyl)-hydrazide;
(R)-3,5-Dimethyl-benzoic acid N-(1-tert-butyl-butyl)-N'-(4-methoxy-benzoyl)-hydrazide;
(R)-3,5-Dimethyl-benzoic acid N-(1-tert-butyl-butyl)-N'-(4-chloro-benzoyl)-hydrazide;
(R)-3,5-Dimethyl-benzoic acid N-(1-tert-butyl-butyl)-N'-(2,6-difluoro-benzoyl)-hydrazide;
(R)-3,5-Dimethyl-benzoic acid N-(1-tert-butyl-butyl)-N'-(2,6-dichloro-benzoyl)-hydrazide;
(R)-3,5-Dimethyl-benzoic acid N-(1-tert-butyl-butyl)-N'-(3,4-dimethoxy-benzoyl)-hydrazide;
(R)-3,5-Dimethyl-benzoic acid N-(1-tert-butyl-butyl)-N'-(3,5-difluoro-benzoyl)-hydrazide;
(R)-3,5-Dimethyl-benzoic acid N-(1-tert-butyl-butyl)-N'-(3,5-dimethoxy-4-methyl-benzoyl)-hydrazide;
(R)-3,5-Dimethyl-benzoic acid N-(1-tert-butyl-butyl)-N'-(4-methyl-benzo[1,3]dioxole-5-carbonyl)-hydrazide;
(R)-3,5-Dimethyl-benzoic acid N-(1-tert-butyl-butyl)-N'-(5-methyl-2,3-dihydro-benzo[1,4]dioxine-6-carbonyl)-hydrazide;
(R)-3,5-Dimethyl-benzoic acid N-(1-tert-butyl-butyl)-N'-(5-ethyl-2,3-dihydro-benzo[1,4]dioxine-6-carbonyl)-hydrazide;
(R)-3,5-Dimethyl-benzoic acid N-(1-tert-butyl-butyl)-N'-(naphthalene-1-carbonyl)-hydrazide;
(R)-3,5-Dimethyl-benzoic acid N-(1-tert-butyl-butyl)-N'-(naphthalene-2-carbonyl)-hydrazide;
(R)-3,5-Dimethyl-benzoic acid N-(1-tert-butyl-butyl)-N'-(thiophene-2-carbonyl)-hydrazide;
(R)-3,5-Dimethyl-benzoic acid N-(1-tert-butyl-butyl)-N'-(2,5-dimethyl-furan-3-carbonyl)-hydrazide;
(R)-3,5-Dimethyl-benzoic acid N-(1-tert-butyl-butyl)-N'-(2-chloro-pyridine-3-carbonyl)-hydrazide;
(R)-3,5-Dimethyl-benzoic acid N-(1-tert-butyl-butyl)-N'-(6-chloro-pyridine-3-carbonyl)-hydrazide;
(R)-3,5-Dimethyl-benzoic acid N-(1-tert-butyl-butyl)-N'-(3-methoxy-2-methyl-benzoyl)-hydrazide;

(R)-3,5-Dimethoxy-4-methyl-benzoic acid N-(1-tert-butyl-butyl)-N'-(3-methoxy-2-methyl-benzoyl)-hydrazide; and
(R)-3,5-Dimethyl-benzoic acid N'-(4-ethyl-benzoyl)-N-(1-phenethyl-but-3-enyl)-hydrazide.

Chiral diacylhydrazines of Formula II and III may contain chirality centers in other portions of the molecule (i.e., not at the asymmetric carbon atom bearing $R^1$ and $R^2$). All possible enantiomers, diastereomers and stereoisomers are intended to be encompassed within the scope of the present invention.

The present invention also pertains to methods of modulating gene expression in a host cell using a gene expression modulation system with a diacylhydrazine ligand of Formula I or chiral diacylhydrazine ligand of Formula II or III.

In one embodiment, the present invention relates to the use of a diacylhydrazine ligand of Formula I or chiral diacylhydrazine ligand of Formula II or III in an inducible gene expression system that has a reduced level of background gene expression in the absence of ligand and responds to submicromolar concentrations of the ligand.

In another embodiment, the present invention relates to a method of modulating the expression of a target gene in a host cell, wherein the host cell comprises a first gene expression cassette comprising a first polynucleotide encoding a first polypeptide comprising:
  i) a transactivation domain;
  ii) a DNA-binding domain; and
  iii) a Group H nuclear receptor ligand binding domain;
  and a second gene expression cassette comprising:
  i) a response element capable of binding to said DNA binding domain;
  ii) a promoter that is activated by the transactivation domain; and
  iii) said target gene;
the method comprising contacting said host cell with a diacylhydrazine ligand of Formula I or chiral diacylhydrazine ligand of Formula II or III; wherein the expression of the target gene is modulated.

In another embodiment, the present invention relates to a method of modulating the expression of a gene of interest in a host cell, wherein the host cell comprises a first recombinant gene expression cassette comprising a first polynucleotide encoding a first polypeptide comprising:
  i) a DNA-binding domain; and
  ii) a Group H nuclear receptor ligand binding domain;
  and a second recombinant gene expression cassette comprising:
  i) a response element capable of binding to said DNA binding domain;
  ii) a promoter; and
  iii) said gene of interest;
the method comprising contacting said host cell with a diacylhydrazine ligand of Formula I or chiral diacylhydrazine ligand of Formula II or III; wherein the expression of the gene of interest is modulated.

In another embodiment, the invention relates to a method for regulating endogenous or heterologous gene expression in a transgenic subject comprising contacting a ligand with an ecdysone receptor complex within the cells of the subject, wherein the cells further contain a DNA binding sequence for the ecdysone receptor complex when in combination with the ligand and wherein formation of an ecdysone receptor complex-ligand-DNA binding sequence complex induces expression of the gene, and where the ligand is a diacylhydrazine ligand of Formula I or chiral diacylhydrazine ligand of Formula II or III, wherein endogenous or heterologous gene expression in a transgenic subject is regulated.

In one embodiment, the cells are autologous cells, i.e. the cells are obtained from the subject and transfected with the ecdysone receptor complex and DNA binding sequence. The transfected autologous cells are then implanted back into the subject which is then treated with the ligand. The autologous cells may be implanted in any of a number of ways, including by infusion or injection, e.g. direct injection. In one embodiment, the autologous cells are implanted by intra-tumoral injection.

In another embodiment, the invention relates to a method for regulating endogenous or heterologous gene expression in a transgenic subject comprising contacting a ligand with a chimeric ecdysone receptor complex within the cells of the subject, wherein the cells further contain a DNA binding sequence further comprising a promoter for the ecdysone receptor complex when in combination with the ligand and wherein formation of an ecdysone receptor complex-ligand-DNA binding sequence complex induces expression of the gene, and where the ligand is a diacylhydrazine ligand of Formula I or chiral diacylhydrazine ligand of Formula II or III, wherein endogenous or heterologous gene expression in a transgenic subject is regulated.

In another embodiment the transgenic subject is a plant, insect, animal or mammal, e.g human or veterinary animal such as a cow, pig, sheep, goat, horse, dog or cat.

In another embodiment, the invention relates to a method of regulating transgene expression in a transgenic subject, wherein said transgenic subject comprises a recombinant ecdysone receptor complex capable of regulating transgene expression; the method comprising administering to said subject an effective amount of a diacylhydrazine ligand of Formula I or chiral diacylhydrazine ligand of Formula II or III.

In another embodiment, the invention relates to a method of modulating the expression of a target gene in a host cell comprising the steps of:
  a) introducing into the host cell a gene expression modulation system comprising:
    i) a first gene expression cassette that is capable of being expressed in a host cell, said first gene expression cassette comprising a polynucleotide sequence that encodes a first hybrid polypeptide comprising:
      (a) a DNA-binding domain that recognizes a response element associated with a gene whose expression is to be modulated; and
      (b) an ecdysone receptor ligand binding domain;
    ii) a second gene expression cassette that is capable of being expressed in the host cell, said second gene expression cassette comprising a polynucleotide sequence that encodes a second hybrid polypeptide comprising:
      (a) a transactivation domain; and
      (b) a chimeric retinoid X receptor ligand binding domain; and
    iii) a third gene expression cassette that is capable of being expressed in a host cell, said third gene expression cassette comprising a polynucleotide sequence comprising:
      (a) a response element recognized by the DNA-binding domain of the first hybrid polypeptide;
      (b) a promoter that is activated by the transactivation domain of the second hybrid polypeptide; and
      (c) a gene whose expression is to be modulated; and
  b) introducing into the host cell a diacylhydrazine ligand of Formula I or chiral diacylhydrazine ligand of Formula II or III; wherein the expression of a gene in a host cell is modulated.

In another embodiment, the present invention relates to a method for producing a polypeptide comprising the steps of:

a) selecting a host cell which is substantially insensitive to exposure to a diacylhydrazine ligand of Formula I or chiral diacylhydrazine ligand of Formula II or III;

b) introducing into the host cell:
i) a DNA construct comprising:
(a) an exogenous gene encoding the polypeptide; and
(b) a response element;
wherein the gene is under the control of the response element; and
ii) an ecdysone receptor complex comprising:
a) a DNA binding domain that binds to the response element;
b) a binding domain for said compound; and
c) a transactivation domain; and
c) exposing the cell to said compound; wherein a polypeptide is produced.

In another embodiment, the invention pertains to a method wherein the ecdysone receptor complex or ecdysone receptor ligand binding domain comprises a mutation.

The abbreviations used herein have their conventional meaning within the chemical and biological arts, unless otherwise specified. For example: "h" means hour(s), "min" means minute(s), "sec" means second(s), "d" means day(s), "μL" means microliter(s), "mL" means milliliter(s), "L" means liter(s), "μM" means micromolar, "mM" means millimolar, "M" means molar, "mol" means moles, "mmol" means millimoles, "μg" means microgram(s), "mg" means milligram(s), "A" means adenine or adenosine, "T" means thymine or thymidine, "G" means guanine or guanosine, "C" means cytidine or cytosine, "xg" means times gravity, "nt" means nucleotide(s), "aa" means amino acid(s), "bp" means base pair(s), "kb" means kilobase(s), "k" means kilo, "μ" means micro, "° C." means degrees Celsius, "THF" means tetrahydrofuran, "DME" means dimethoxyethane, "DMF" means dimethylformamide, "NMR" means nuclear magnetic resonance, "psi" refers to pounds per square inch, and "TLC" means thin layer chromatography.

The term "alkyl" as used herein by itself or part of another group refers to a straight-chain or branched saturated aliphatic hydrocarbon having from one to ten carbons or the number of carbons designated ($C_1$-$C_{10}$ means 1 to 10 carbons). Exemplary alkyl groups include methyl, ethyl, n-propyl, isopropyl, n-butyl, sec-butyl, isobutyl, tert-butyl, n-pentyl, n-hexyl, isohexyl, n-heptyl, 4,4-dimethylpentyl, n-octyl, 2,2,4-trimethylpentyl, nonyl, decyl and the like.

The term "optionally substituted alkyl" as used herein by itself or part of another group refers to an alkyl as defined above that is optionally substituted with one to three substituents independently selected from nitro, cyano, amino, optionally substituted cycloalkyl, optionally substituted heteroaryl, optionally substituted heterocycle, alkoxy, aryloxy, arylalkyloxy, alkylthio, carboxamido, sulfonamido, —$COR^c$, —$SO_2R^d$, —$N(R^e)COR^f$, —$N(R^e)SO_2R^g$ or —$N(R^e)C{=}N(R^h)$-amino. Exemplary substituted alkyl groups include —$CH_2OCH_3$, —$CH_2CH_2NH_2$, —$CH_2CH_2CN$, —$CH_2SO_2CH_3$ and the like.

The term "haloalkyl" as used herein by itself or part of another group refers to an alkyl as defined above having one to six halo substitutents. Exemplary haloalkyl groups include, trifluoromethyl, —$CH_2CH_2F$ and the like.

The term "hydroxyalkyl" as used herein by itself or part of another group refers to an alkyl as defined above having one to three hydroxy substituents, typically one hydroxy substituent. Exemplary hydroxyalkyl groups include hydroxymethyl, hydroxyethyl, hydroxypropyl, and the like.

The term "arylalkyl" as used herein by itself or part of another group refers to an alkyl as defined above having one to three aryl substitutents (said aryl substituents may be optionally substituted as described below), typically one or two aryl substituents. Exemplary arylalkyl groups include, for example, benzyl, phenylethyl, 4-fluorophenylethyl, phenylpropyl, diphenylmethyl and the like.

The term "cycloalkyl" as used herein by itself or part of another group refers to saturated and partially unsaturated (containing one or two double bonds) cyclic hydrocarbon groups containing one to three rings having from three to twelve carbon atoms or the number of carbons designated. Exemplary cycloalkyl groups include cyclopropyl, cyclobutyl, cyclopentyl, cyclohexyl, cycloheptyl, cyclooctyl, norbornyl, decalin, adamantyl and the like.

The term "optionally substituted cycloalkyl" as used herein by itself or part of another group refers to a cycloalkyl as defined above that is optionally substituted with one to three substituents independently selected from halo, nitro, cyano, hydroxy, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —$COR^c$, —$SO_2R^d$, —$N(R^e)COR^f$, —$N(R^e)SO_2R^g$ or —$N(R^e)C{=}N(R^h)$-amino. Exemplary optionally substituted cycloalkyl groups include

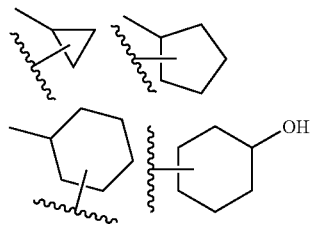

and the like. An optionally substituted cycloalkyl may be fused to an aryl group to provide an optionally substituted aryl as described below.

The term "alkenyl" as used herein by itself or part of another group refers to an alkyl group as defined above containing one to three carbon-to-carbon double bonds, typically one or two double bonds. Exemplary alkenyl groups include —CH=$CH_2$, —$CH_2$CH=$CH_2$, —$CH_2CH_2$CH=$CH_2$, —$CH_2CH_2$CH=CH$CH_3$ and the like.

The term "optionally substituted alkenyl" as used herein by itself or part of another group refers to an alkenyl as defined above that is optionally substituted with one to three substituents independently selected from halo, nitro, cyano, hydroxy, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —$COR^c$, —$SO_2R^d$, —$N(R^e)COR^f$, —$N(R^e)SO_2R^g$ or —$N(R^e)C{=}N(R^h)$-amino. Exemplary optionally substituted alkenyl groups include —CH=CHPh, —$CH_2$CH=CHPh and the like.

The term "alkynyl" as used herein by itself or part of another group refers to an alkyl group as defined above containing one to three carbon-to-carbon triple bonds, typically one or two triple bonds. Exemplary alkynyl groups include —C≡CH, —C≡C$CH_3$, —$CH_2$C≡CH, —$CH_2CH_2$C≡CH and —$CH_2CH_2$C≡C$CH_3$.

The term "optionally substituted alkynyl" as used herein by itself or part of another group refers to an alkynyl as defined above that is optionally substituted with one to three substituents independently selected from halo, nitro, cyano, hydroxy, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —COR$^c$, —SO$_2$R$^d$, —N(R$^e$)COR$^f$, —N(R$^e$)SO$_2$R$^g$ or —N(R$^e$)C=N(R$^h$)-amino. Exemplary optionally substituted alkenyl groups include —C≡CPh, —CH$_2$C≡CPh and the like.

The term "aryl" as used herein by itself or part of another group refers to monocyclic and bicyclic aromatic ring systems having from six to twelve carbon atoms such as phenyl (abbreviated as Ph), 1-naphthyl and 2-naphthyl.

The term "optionally substituted aryl" as used herein by itself or part of another group refers to an aryl as defined above that is optionally substituted with one to five substituents, typically one to three substitutents, independently selected from halo, nitro, cyano, hydroxy, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —COR$^c$, —SO$_2$R$^d$, —N(R$^e$COR$^f$, —N(R$^e$)SO$_2$R$^g$ or —N(R$^e$C=N(R$^h$)-amino. Exemplary optionally substituted aryl groups include 2-methylphenyl, 2-methoxyphenyl, 2-fluorophenyl, 2-chlorophenyl, 2-bromophenyl, 3-methylphenyl, 3-methoxyphenyl, 3-chlorophenyl, 4-methylphenyl, 4-ethylphenyl, 4-methoxyphenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl and 3,5-dimethoxy, 4-methylphenyl and the like. The term optionally substituted aryl is meant to include groups having fused optionally substituted cycloalkyl and fused optionally substituted heterocycle rings. Examples include

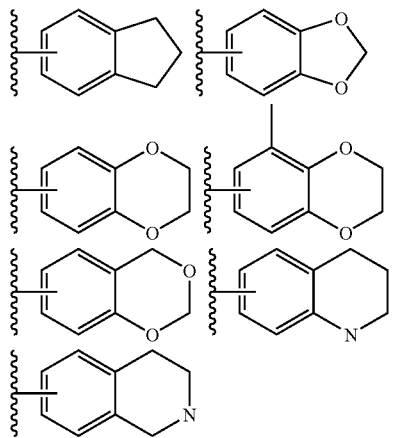

and the like.

The term "heteroaryl" as used herein by itself or part of another group refers to monocyclic and bicyclic aromatic ring systems having from five to fourteen carbon atoms and one, two, three or four heteroatoms independently selected from oxygen, nitrogen and sulfur. Exemplary heteroaryl groups include 1-pyrrolyl, 2-pyrrolyl, 3-pyrrolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 4-benzimidazolyl, 5-benzimidazolyl, 2-benzthiazolyl, 4-benzthiazolyl, 5-benzthiazolyl, 5-indolyl, 5-indolyl, 3-indazolyl, 4-indazolyl, 5-indazolyl, 1-isoquinolyl, 5-isoquinolyl, 2-quinoxalinyl, 5-quinoxalinyl, 2-quinolyl 3-quinolyl, 6-quinolyl and the like. The term heteroaryl is meant to include possible N-oxides. Exemplary N-oxides include pyridyl N-oxide and the like.

The term "optionally substituted heteroaryl" as used herein by itself or part of another group refers to a heteroaryl as defined above that is optionally substituted at any available carbon atom with one to four substituents, typically one or two substituents, independently selected from halo, nitro, cyano, hydroxy, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —COR$^c$, —SO$_2$R$^d$, —N(R$^e$)COR$^f$, —N(R$^e$)SO$_2$R$^g$ or —N(R$^e$C=N(R$^h$)-amino. Exemplary substituted heteroaryl groups include

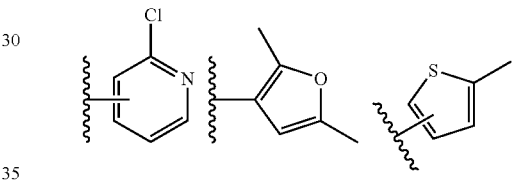

and the like.

The specific chemical nature of the optionally substituted aryl and optionally substituted heteroaryl groups for the terminal moieties A and B in the prior identified chiral diacylhydrazine ligands is not narrowly critical, and as noted, a wide variety of substituents are contemplated. Preferably, substituents for the optionally substituted aryl and optionally substituted heteroaryl are selected such that the total number of carbon and heteroatoms is no more than about twenty, more preferably no more than about fifteen.

The term "heterocycle" as used herein by itself or part of another group refers to saturated and partially unsaturated (containing one or two double bonds) cyclic groups containing one to three rings having from two to twelve carbon atoms and one or two oxygen, sulfur or nitrogen atoms. The heterocycle can be optionally linked to the rest of the molecule through a carbon atom or a nitrogen atom. Exemplary heterocycle groups include

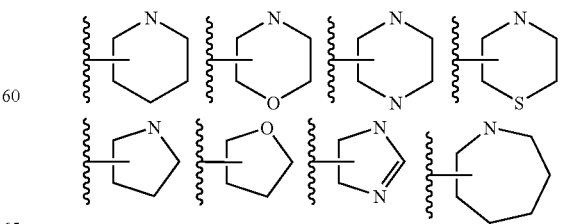

and the like.

The term "optionally substituted heterocycle" as used herein by itself or part of another group refers to a heterocycle as defined above that is optionally substituted with one to four substituents, typically one or two substituents independently selected from halo, nitro, cyano, hydroxy, amino, optionally substituted alkyl, haloalkyl, hydroxyalkyl, arylalkyl, optionally substituted cycloalkyl, optionally substituted alkenyl, optionally substituted alkynyl, optionally substituted aryl, optionally substituted heteroaryl, optionally substituted heterocycle, alkoxy, aryloxy, arylalkyloxy, alkylthio, carboxamido, sulfonamido, —$COR^c$, —$SO_2R^d$, —$N(R^e)COR^f$, —$N(R^e)SO_2R^g$ or —$N(R^e)C=N(R^h)$-amino. Exemplary optionally substituted heterocycle groups include

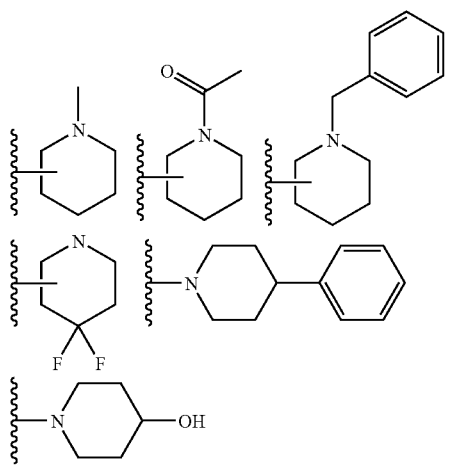

and the like. An optionally substituted heterocycle may be fused to an aryl group to provide an optionally substituted aryl as described above.

The term "alkoxy" as used herein by itself or part of another group refers to a hydroxyalkyl, haloalkyl, arylalkyl, optionally substituted alkyl, optionally substituted cycloalkyl, optionally substituted alkenyl or optionally substituted alkynyl attached to a terminal oxygen atom. Exemplary alkoxy groups include methoxy, tert-butoxy, —$OCH_2CH=CH_2$ and the like.

The term "aryloxy" as used herein by itself or part of another group refers to an optionally substituted aryl attached to a terminal oxygen atom. Exemplary aryloxy groups include phenoxy and the like.

The term "arylalkyloxy" as used herein by itself or part of another group refers to an arylalkyl attached to a terminal oxygen atom. Exemplary arylalkyloxy groups include benzyloxy and the like.

The term "alkylthio" as used herein by itself or part of another group refers to a hydroxyalkyl, haloalkyl, arylalkyl, optionally substituted alkyl, optionally substituted alkenyl or optionally substituted alkynyl attached to a terminal sulfur atom. Exemplary alkyl groups include —$SCH_3$ and the like.

The term "halo" or "halogen" as used herein by itself or part of another group refers to fluoro, chloro, bromo or iodo.

The term "amino" as used herein by itself or part of another group refers to a radical of formula —$NR^aR^b$ wherein $R^a$ and $R^b$ are independently hydrogen, haloalkyl, hydroxyalkyl, arylalkyl, optionally substituted alkyl, optionally substituted cycloalkyl, optionally substituted heterocycle, optionally substituted aryl or optionally substituted heteroaryl; or $R^a$ and $R^b$ taken together with the nitrogen atom to which they are attached form a four to seven membered heterocycle. Exemplary amino groups include —$NH_2$, —$N(H)CH_3$, —$N(CH_3)_2$, —$N(H)CH_2Ph$ and the like.

The term "carboxamido" as used herein by itself or part of another group refers to a radical of formula —CO-amino. Exemplary carboxamido groups include —$CONH_2$, —$CON(H)CH_3$, —$CON(H)Ph$ and the like.

The term "sulfonamido" as used herein by itself or part of another group refers to a radical of formula —$SO_2$-amino. Exemplary sulfonamido groups include —$SO_2NH_2$, —$SO_2N(H)CH_3$, —$SO_2N(H)Ph$ and the like.

In reference to the optionally substituted groups described above, $R^c$ is hydrogen, hydroxy, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy or arylalkyloxy; $R^d$ is haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl or optionally substituted heteroaryl; $R^e$ is hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl or optionally substituted heteroaryl; $R^f$ is hydrogen, haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl, alkoxy, aryloxy, arylalkyloxy or amino; $R^g$ is haloalkyl, hydroxyalkyl, arylalkyl, optionally substituted alkyl, optionally substituted cycloalkyl, optionally substituted alkenyl, optionally substituted alkynyl, optionally substituted heterocycle, optionally substituted aryl, optionally substituted heteroaryl or amino; and $R^h$ is hydrogen, alkyl, aryl, cyano or nitro.

Throughout the specification, groups and optional substituents thereof are chosen to provide stable moieties and compounds.

The compounds of the present invention may contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The compounds of the present invention may form salts which are also within the scope of this invention. Reference to a compound of the present invention herein is understood to include reference to salts thereof, unless otherwise indicated. The term "salt(s)" as used herein denotes acidic and/or basic salts formed with inorganic and/or organic acids and bases. In addition, when a compound of Formula I, II or III contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of Formula I, II or III may be formed, for example, by reacting a compound with an amount of acid or base, such as an equivalent amount, in a medium such as one in which the salt precipitates or in an aqueous medium followed by lyophilization.

The compounds of the present invention which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of the present invention which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

The stereochemical terms and conventions used in the specification are consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure.

The term "asymmetric carbon atom" refers to a carbon atom in a molecule of an organic compound that is attached to four different atoms or groups of atoms.

The term "predominantly" means in a ratio greater than 50:50.

The term "leaving group" or "LG" refers to an atom or group that becomes detached from an atom or group in what is considered to be the residual or main part of the substrate in a specified reaction. In amide coupling reactions, exemplary leaving groups include —F, —Cl, —Br, —OC$_6$F$_5$ and the like.

The term "isolated" for the purposes of the present invention designates a material (e.g. a chemical compound or biological material such as a nucleic acid or protein) that has been removed from its original environment (the environment in which it is naturally present). For example, a polynucleotide present in the natural state in a plant or an animal is not isolated, however the same polynucleotide separated from the adjacent nucleic acids in which it is naturally present, is considered "isolated".

The term "purified", as applied to biological materials does not require the material to be present in a form exhibiting absolute purity, exclusive of the presence of other compounds. It is rather a relative definition.

"Nucleic acid", "nucleic acid molecule", "oligonucleotide" and "polynucleotide" are used interchangeably and refer to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, supercoiled DNA and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. DNA includes but is not limited to cDNA, genomic DNA, plasmid DNA, synthetic DNA, and semi-synthetic DNA.

The term "fragment" refers to a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 6, 8, 9, 10, 12, 15, 18, 20, 21, 22, 23, 24, 25, 30, 39, 40, 42, 45, 48, 50, 51, 54, 57, 60, 63, 66, 70, 75, 78, 80, 90, 100, 105, 120, 135, 150, 200, 300, 500, 720, 900, 1000 or 1500 consecutive nucleotides of a nucleic acid according to the invention.

As used herein, an "isolated nucleic acid fragment" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to a polynucleotide comprising nucleotides that encode a functional molecule (e.g., a polypeptide or RNA), and includes cDNA and genomic DNA nucleic acids. "Gene" also refers to a nucleic acid fragment that expresses a specific RNA, protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook et al. in *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC.

Hybridization requires that the two nucleic acids contain complementary sequences, although depending on the stringency of the hybridization, mismatches between bases are possible. The term "complementary" is used to describe the relationship between nucleotide bases that are capable of hybridizing to one another. For example, with respect to DNA, adenosine is complementary to thymine and cytosine is complementary to guanine. Accordingly, the present invention also includes isolated nucleic acid fragments that are complementary to the complete sequences as disclosed or used herein as well as those substantially similar nucleic acid sequences.

In one embodiment of the invention, polynucleotides are detected by employing hybridization conditions comprising a hybridization step at $T_m$ of 55° C., and utilizing conditions as set forth above. In another embodiment, the $T_m$ is 60° C.; in one embodiment, the $T_m$ is 63° C.; in another embodiment, the $T_m$ is 65° C.

Post-hybridization washes also determine stringency conditions. One set of conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. One set of stringent conditions uses higher temperatures in which the washes are identical to those above except for the temperature of the final two 30 min washes in 0.2×SSC, 0.5% SDS is increased to 60° C. Another set of highly stringent conditions uses two final washes in 0.1×SSC, 0.1% SDS at 65° C.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA: RNA, DNA: RNA, DNA: DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8).

In one embodiment of the invention, polynucleotides are detected by employing hybridization conditions comprising a hybridization step in less than 500 mM salt and at least 37 degrees Celsius, and a washing step in 2×SSPE at least 63 degrees Celsius. In one embodiment, the hybridization conditions comprise less than 200 mM salt and at least 37 degrees Celsius for the hybridization step. In a another embodiment, the hybridization conditions comprise 2×SSPE and 63 degrees Celsius for both the hybridization and washing steps.

In another embodiment, the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a short nucleic acid that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" refers to an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and refers to an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and refers to an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" refers to a double-stranded DNA sequence that encodes a polypeptide and can be transcribed and translated into a polypeptide in a cell in vitro or in vivo when placed under the control of appropriate regulatory sequences. "Suitable regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and refers to a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←5').

The term "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" are used interchangeably and refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" includes both viral and nonviral vehicles for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as pBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra-chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" refers to a "replicon," which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

The term "expression vector" refers to a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); β-lactamase, lac, ara, tet, trp, lP$_L$, lP$_R$, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, a baculovirus IE1 promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In addition, these expression sequences may be modified by addition of enhancer or regulatory sequences and the like.

Vectors may be introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., *J. Biol. Chem.* 267:963-967 (1992); Wu et al., *J. Biol. Chem.* 263:14621-14624 (1988); and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker (Felgner et al., *Proc. Natl. Acad. Sci. USA.* 84:7413 (1987); Mackey et al., *Proc. Natl. Acad. Sci. USA* 85:8027-8031 (1988); and Ulmer et al., *Science* 259:1745-1748 (1993)). The use of cationic lipids may promote encapsulation of negatively charged nucleic acids, and also promote fusion with negatively charged cell membranes (Felgner et al., *Science* 337:387-388 (1989)). Particularly useful lipid compounds and compositions for transfer of nucleic acids are described in WO95/18863, WO96/17823 and U.S. Pat. No.

5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey et al. 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., *Hum. Gene Ther.* 3:147-154 (1992); and Wu et al., *J. Biol. Chem.* 262:4429-4432 (1987)).

The term "transfection" refers to the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

In addition, the recombinant vector comprising a polynucleotide according to the invention may include one or more origins for replication in the cellular hosts in which their amplification or their expression is sought, markers or selectable markers.

The term "selectable marker" refers to an identifying factor, usually an antibiotic or chemical resistance gene, that is able to be selected for based upon the marker gene's effect, i.e., resistance to an antibiotic, resistance to a herbicide, calorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" refers to a nucleic acid encoding an identifying factor that is able to be identified based upon the reporter gene's effect, wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter and "promoter sequence" are used interchangeably and refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths may have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" refer to DNA regulatory sequences, such as promoters, enhancers, terminators, and the like, that provide for the expression of a coding sequence in a host cell. In eukaryotic cells, polyadenylation signals are control sequences.

The term "response element" refers to one or more cis-acting DNA elements which confer responsiveness on a promoter mediated through interaction with the DNA-binding domains of a transcription factor, e.g., the DNA binding domain of the first hybrid protein. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (SEQ ID NO: 16) (see Cherbas et. al., *Genes Dev.* 5:120-131 (1991)); AGGT- CAN$_{(n)}$AGGTCA, where N$_{(n)}$ can be one or more spacer nucleotides (SEQ ID NO: 17) (see D'Avino et al., *Mol. Cell. Endocrinol.* 113:1-9 (1995)); and GGGTTGAATGAATTT (SEQ ID NO: 18) (see Antoniewski et al., *Mol. Cell Biol.* 14:4465-4474 (1994)).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein refers to the transcription and stable accumulation of sense (mRNA) or antisense RNA derived from a nucleic acid or polynucleotide. Expression may also refer to translation of mRNA into a protein or polypeptide.

The terms "cassette," "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR-based system which in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell.

Enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like.

Termination control regions, i.e., terminator or polyadenylation sequences, may also be derived from various genes native to the preferred hosts. Optionally, a termination site may be unnecessary, however, it is most preferred if included. In one embodiment of the invention, the termination control region may be comprised or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Regulatory region" refers to a nucleic acid sequence that regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" refers to a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

"Polypeptide," "peptide" and "protein" are used interchangeably and refer to a polymeric compound comprised of covalently linked amino acid residues. Amino acids have the following general structure:

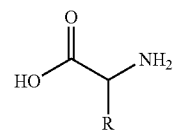

An "isolated polypeptide," "isolated peptide" or "isolated protein" refers to a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

A "substitution mutant polypeptide" or a "substitution mutant" will be understood to mean a mutant polypeptide comprising a substitution of at least one (1) wild-type or naturally occurring amino acid with a different amino acid relative to the wild-type or naturally occurring polypeptide. A substitution mutant polypeptide may comprise only one (1) wild-type or naturally occurring amino acid substitution and may be referred to as a "point mutant" or a "single point mutant" polypeptide. Alternatively, a substitution mutant polypeptide may comprise a substitution of two (2) or more wild-type or naturally occurring amino acids with 2 or more amino acids relative to the wild-type or naturally occurring polypeptide. According to the invention, a Group H nuclear receptor ligand binding domain polypeptide comprising a substitution mutation comprises a substitution of at least one (1) wild-type or naturally occurring amino acid with a different amino acid relative to the wild-type or naturally occurring Group H nuclear receptor ligand binding domain polypeptide.

Wherein the substitution mutant polypeptide comprises a substitution of two (2) or more wild-type or naturally occurring amino acids, this substitution may comprise either an equivalent number of wild-type or naturally occurring amino acids deleted for the substitution, i.e., 2 wild-type or naturally occurring amino acids replaced with 2 non-wild-type or non-naturally occurring amino acids, or a non-equivalent number of wild-type amino acids deleted for the substitution, i.e., 2 wild-type amino acids replaced with 1 non-wild-type amino acid (a substitution+deletion mutation), or 2 wild-type amino acids replaced with 3 non-wild-type amino acids (a substitution+insertion mutation).

Substitution mutants may be described using an abbreviated nomenclature system to indicate the amino acid residue and number replaced within the reference polypeptide sequence and the new substituted amino acid residue. For example, a substitution mutant in which the twentieth ($20^{th}$) amino acid residue of a polypeptide is substituted may be abbreviated as "x20z", wherein "x" is the amino acid to be replaced, "20" is the amino acid residue position or number within the polypeptide, and "z" is the new substituted amino acid. Therefore, a substitution mutant abbreviated interchangeably as "E20A" or "Glu20Ala" indicates that the mutant comprises an alanine residue (commonly abbreviated in the art as "A" or "Ala") in place of the glutamic acid (commonly abbreviated in the art as "E" or "Glu") at position 20 of the polypeptide.

A substitution mutation may be made by any technique for mutagenesis known in the art, including but not limited to, in vitro site-directed mutagenesis (Hutchinson et al., *J. Biol. Chem.* 253:6551 (1978); Zoller et al., *DNA* 3:479-488 (1984); Oliphant et al., *Gene* 44:177 (1986); Hutchinson et al., *Proc. Natl. Acad. Sci. USA* 83:710 (1986)), use of TAB® linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

"Fragment" of a polypeptide according to the invention refers to a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of at least 2, 3, 4, 5, 6, 8, 10, 13, 14, 15, 16, 17, 18, 19, 20, 21, 22, 25, 26, 30, 35, 40, 45, 50, 100, 200, 240, or 300 amino acids.

A "variant" of a polypeptide or protein refers to any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., *Cell* 50:667 (1987)). Such proteins (and their encoding genes) have sequence homology, as reflected by their high degree of sequence similarity. However, in common usage and in the present application, the term "homologous," when modified with an adverb such as "highly," may refer to sequence similarity and not a common evolutionary origin.

Accordingly, the term "sequence similarity" in all its grammatical forms refers to the degree of identity or correspondence between nucleic acid or amino acid sequences of proteins that may or may not share a common evolutionary origin (see Reeck et al., *Cell* 50:667 (1987)). In one embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see e.g., Sambrook et al., 1989, supra.).

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the present invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the present invention are those nucleic acid fragments whose DNA sequences are at least 70% identical to the DNA sequence of the nucleic acid fragments reported herein. Nucleic acid fragments of the present invention include those nucleic acid fragments whose DNA sequences are at least 80% identical to the DNA sequence of the nucleic acid fragments reported herein. Other nucleic acid fragments are at least 90% identical to the DNA sequence of the nucleic acid fragments reported herein. Other nucleic acid fragments are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215:403-410 (1993)); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences may be performed using the Clustal method of alignment (Higgins et al., *CABIOS.* 5:151-153 (1989)) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, two or more individually operable gene regulation systems are said to be "orthogonal" when; a) modulation of each of the given systems by its respective ligand, at a chosen concentration, results in a measurable change in the magnitude of expression of the gene of that system, and b) the change is statistically significantly different than the change in expression of all other systems simultaneously operable in the cell, tissue, or organism, regardless of the simultaneity or sequentially of the actual modulation. Preferably, modulation of each individually operable gene regulation system effects a change in gene expression at least 2-fold greater than all other operable systems in the cell, tissue, or organism. More preferably, the change is at least 5-fold greater. Even more preferably, the change is at least 10-fold greater. Still more preferably, the change is at least 100 fold greater. Even still more preferably, the change is at least 500-fold greater. Ideally, modulation of each of the given systems by its respective ligand at a chosen concentration results in a measurable change in the magnitude of expression of the gene of that system and no measurable change in expression of all other systems operable in the cell, tissue, or organism. In such cases the multiple inducible gene regulation system is said to be "fully orthogonal." The present invention is useful to search for orthogonal ligands and orthogonal receptor-based gene expression systems such as those described in US 2002/0110861 A1, which is incorporated herein by reference in its entirety.

The term "modulate" means the ability of a given ligand/receptor complex to induce or suppress the transactivation of an exogenous gene.

The term "exogenous gene" means a gene foreign to the subject, that is, a gene which is introduced into the subject through a transformation process, an unmutated version of an endogenous mutated gene or a mutated version of an endogenous unmutated gene. The method of transformation is not critical to this invention and may be any method suitable for the subject known to those in the art. For example, transgenic plants are obtained by regeneration from the transformed cells. Numerous transformation procedures are known from the literature such as agroinfection using *Agrobacterium tumefaciens* or its $T_1$ plasmid, electroporation, microinjection of plant cells and protoplasts, and microprojectile transformation. Complementary techniques are known for transformation of animal cells and regeneration of such transformed cells in transgenic animals. Exogenous genes can be either natural or synthetic genes and therapeutic genes which are introduced into the subject in the form of DNA or RNA which may function through a DNA intermediate such as by reverse transcriptase. Such genes can be introduced into target cells, directly introduced into the subject, or indirectly introduced by the transfer of transformed cells, e.g. autologous cells, into the subject. The term "therapeutic gene" means a gene which imparts a beneficial function to the host cell in which such gene is expressed.

The term "ecdysone receptor complex" generally refers to a heteromeric protein complex consisting of two members of the steroid receptor family, ecdysone receptor ("EcR") and ultraspiracle ("USP") proteins (see Yao et al., *Nature* 366: 476-479 (1993)); Yao et al., *Cell* 71:63-72 (1992)). The functional ecdysteroid receptor complex may also include additional protein(s) such as immunophilins. Additional members of the steroid receptor family of proteins, known as transcriptional factors (such as DHR38, betaFTZ-1 or other insect homologs), may also be ligand dependent or independent partners for EcR and/or USP. The ecdysone receptor complex can also be a heterodimer of ecdysone receptor protein and the vertebrate homolog of ultraspiracle protein, retinoic acid-X-receptor ("RXR") protein. Homodimer complexes of the ecdysone receptor protein or USP may also be functional under some circumstances.

An ecdysteroid receptor complex can be activated by an active ecdysteroid or non-steroidal ligand bound to one of the proteins of the complex, inclusive of EcR, but not excluding other proteins of the complex.

The ecdysone receptor complex includes proteins which are members of the steroid receptor superfamily wherein all members are characterized by the presence of an amino-terminal transactivation domain, a DNA binding domain ("DBD"), and a ligand binding domain ("LBD") separated by a hinge region. Some members of the family may also have another transactivation domain on the carboxy-terminal side of the LBD. The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins.

The DNA sequences making up the exogenous gene, the response element, and the ecdysone receptor complex may be incorporated into archaebacteria, procaryotic cells such as *Escherichia coli, Bacillus subtilis*, or other enterobacteria, or eucaryotic cells such as plant or animal cells. However, because many of the proteins expressed by the gene are processed incorrectly in bacteria, eucaryotic cells are preferred. The cells may be in the form of single cells or multicellular organisms. The nucleotide sequences for the exogenous gene, the response element, and the receptor complex can also be incorporated as RNA molecules, preferably in the form of functional viral RNAs such as tobacco mosaic virus. Of the eucaryotic cells, vertebrate cells are preferred because they naturally lack the molecules which confer responses to the ligands of this invention for the ecdysone receptor. As a result, they are "substantially insensitive" to the ligands of this invention. Thus, the ligands of this invention will have negligible physiological or other effects on transformed cells, or the whole organism. Therefore, cells can grow and express the desired product, substantially unaffected by the presence of the ligand itself.

The term "subject" means an intact insect, plant or animal or a cell from an insect, plant or animal. It is also anticipated that the ligands will work equally well when the subject is a fungus or yeast. When the subject is an intact animal, preferably the animal is a vertebrate, most preferably a mammal.

The diacylhydrazine ligands of Formula I and chiral diacylhydrazine ligands of Formula II or III of the present invention, when used with the ecdysone receptor complex which in turn is bound to the response element linked to an exogenous gene, provide the means for external temporal regulation of expression of the exogenous gene. The order in which the various components bind to each other, that is, ligand to receptor complex and receptor complex to response element, is not critical. Typically, modulation of expression of the exogenous gene is in response to the binding of the ecdysone receptor complex to a specific control, or regulatory, DNA element. The ecdysone receptor protein, like other members of the steroid receptor family, possesses at least three domains, a transactivation domain, a DNA binding domain, and a ligand binding domain. This receptor, like a subset of the steroid receptor family, also possesses less well-defined regions responsible for heterodimerization properties. Binding of the ligand to the ligand binding domain of ecdysone receptor protein, after heterodimerization with USP or RXR protein, enables the DNA binding domains of the heterodimeric proteins to bind to the response element in an activated form, thus resulting in expression or suppression of the exogenous gene. This mechanism does not exclude the potential for ligand binding to either EcR or USP, and the resulting formation of active homodimer complexes (e.g. EcR+EcR or USP+USP). Preferably, one or more of the receptor domains can be varied producing a chimeric gene switch. Typically, one or more of the three domains may be chosen from a source different than the source of the other domains so that the chimeric receptor is optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., *Nature* 335:563-564 (1988) or LexA protein from *E. coli* (see Brent et al., *Cell* 43:729-736 (1985)) to accommodate chimeric ecdysone receptor complexes. Another advantage of chimeric systems is that they allow choice of a promoter used to drive the exogenous gene according to a desired end result. Such double control can be particularly important in areas of gene therapy, especially when cytotoxic proteins are produced, because both the timing of expression as well as the cells wherein expression occurs can be controlled. When exogenous genes, operatively linked to a suitable promoter, are introduced into the cells of the subject, expression of the exogenous genes is controlled by the presence of the ligand of this invention. Promoters may be constitutively or inducibly regulated or may be tissue-specific (that is, expressed only in a particular type of cell) or specific to certain developmental stages of the organism.

Numerous genomic and cDNA nucleic acid sequences coding for a variety of polypeptides are well known in the art. Exogenous genetic material useful with the ligands of this invention include genes that encode biologically active proteins of interest, such as, for example, secretory proteins that can be released from a cell; enzymes that can metabolize a substrate from a toxic substance to a non-toxic substance, or from an inactive substance to an active substance; regulatory proteins; cell surface receptors; and the like. Useful genes also include genes that encode blood clotting factors, hormones such as insulin, parathyroid hormone, luteinizing hormone releasing factor, alpha and beta seminal inhibins, and human growth hormone; genes that encode proteins such as enzymes, the absence of which leads to the occurrence of an abnormal state; genes encoding cytokines or lymphokines such as interferons, granulocytic macrophage colony stimulating factor, colony stimulating factor-1, tumor necrosis factor, and erythropoietin; genes encoding inhibitor substances such as alpha$_1$-antitrypsin, genes encoding substances that function as drugs such as diphtheria and cholera toxins; and the like. Useful genes also include those useful for cancer therapies and to treat genetic disorders. Those skilled in the art have access to nucleic acid sequence information for virtually all known genes and can either obtain the nucleic acid molecule directly from a public depository, the institution that published the sequence, or employ routine methods to prepare the molecule.

In one embodiment, the exogenous gene is the hIL-12 gene under control of the RheoSwitch™ Therapeutic System (RTS), transfected ex vivo with an adenovirus into autologous dendritic cells.

For gene therapy use, the ligands described herein may be administered alone or as part of a pharmaceutical composition comprising a pharmaceutically acceptable carrier. In one embodiment, the pharmaceutical composition are in the form of solutions, suspensions, tablets, capsules, ointments, elixirs, or injectable compositions.

Pharmaceutically acceptable carriers include fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are flow-regulating agents and lubricants, for example, silica, talc, stearic acid or salts thereof, such as magnesium stearate or calcium stearate, and/or polyethylene glycol. In one embodiment, dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules or nanoparticles which may optionally be mixed with fillers such as lactose, binders such as starches, and/or lubricants such as talc or magnesium stearate and, optionally, stabilizers. In one embodiment, the is dissolved or suspended in suitable liquids, such as fatty oils, or liquid paraffin, optionally with stabilizers.

Fatty oils may comprise mono-, di- or triglycerides. Mono-, di- and triglycerides include those that are derived from $C_6$, $C_8$, $C_{10}$, $C_{12}$, $C_{14}$, $C_{16}$, $C_{18}$, $C_{20}$ and $C_{22}$ acids. Exemplary diglycerides include, in particular, diolein, dipalmitolein, and mixed caprylin-caprin diglycerides. Preferred triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof. Exemplary triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil;

hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

In one embodiment, the triglyceride is the medium chain triglyceride available under the trade name LABRAFAC CC. Other triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX 355. Other triglycerides are caprylic-capric acid triglycerides such as known and commercially available under the trade name MYRITOL, including the product MYRITOL 813. Further triglycerides of this class are CAPMUL MCT, CAPTEX 200, CAPTEX 300, CAPTEX 800, NEOBEE M5 and MAZOL 1400.

Pharmaceutical compositions comprising triglycerides may further comprise lipophilic and/or hydrophilic surfactants which may form clear solutions upon dissolution with an aqueous solvent. One such surfactant is tocopheryl polyethylene glycol 1000 succinate (vitamin E TPGS). Examples of such compositions are described in U.S. Pat. No. 6,267,985.

In another embodiment, the pharmaceutically acceptable carrier comprises LABRASOL (Gattefosse SA), which is PEG-8 caprylic/capric glycerides. In another embodiment, the pharmaceutically acceptable carrier comprises PL90G, vitamin E TPGS, and Miglyol 812N. The components of such a formulation are shown in Table 1.

TABLE 1

| Ingredient | Concentration (mg/ml) | |
|---|---|---|
| | Placebo | 30 mg/ml |
| 3,5-Dimethyl-benzoic acid (R)—N-(1-tert-butyl-butyl)-N'-(2-ethyl-3-methoxy-benzoyl)-hydrazide | 0 mg | 30 mg |
| PL90G [Phospholipon 90G] | 100 mg | 100 mg |
| Vitamin E TPGS | 100 mg | 100 mg |
| BHT [butylated hydroxytoluene] | 0.1 mg | 0.1 mg |
| Miglyol 812N [Medium chain triglycerides] | QS to 1 ml | QS to 1 ml |
| Li-caps [hard gelatine capsules] | 1 per dose | 1 per dose |

Possible pharmaceutical preparations which can be used rectally include, for example, suppositories, which consist of a combination of one or more of the ligands with a suppository base. Suitable suppository bases are, for example, natural or synthetic triglycerides, or paraffin hydrocarbons. In addition, it is also possible to use gelatin rectal capsules which consist of a combination of the ligand with a base. Possible base materials include, for example, liquid triglycerides, polyethylene glycols, or paraffin hydrocarbons.

Suitable formulations for parenteral administration include aqueous solutions of the ligand in water-soluble form, for example, water-soluble salts and alkaline solutions. In addition, suspensions of the ligand as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions may be formulated as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams may be formulated from a mixture of mineral oil, self-emulsifying beeswax and water in which ligand, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a suspension of the ligand in a vegetable oil such as almond oil with warm soft paraffin and allowing the mixture to cool. A typical example of such an ointment is one which includes about 30% almond oil and about 70% white soft paraffin by weight.

Lotions may be conveniently prepared by preparing a suspension of the ligand in a suitable high molecular weight alcohol such as propylene glycol or polyethylene glycol.

Examples of antioxidants which may be added to the pharmaceutical compositions include BHA and BHT.

In one embodiment, the pharmaceutical composition comprises 30 mg ligand per mL LABRASOL in a solid gelatin capsule. In another embodiment, the capsule contains 1, 2, 3, 4, 5, 6, 7, 8, 9, 10, 15, 20, 25, 30, 35, 40, 45, 50, 55, 60, 65, 70, 75, 80, 85, 90, 95 or 100 mg ligand.

Pharmaceutical compositions may contain from 0.01% to 99% by weight of the ligand. Compositions may be either in single or multiple dose forms. The amount of ligand in any particular pharmaceutical composition will depend upon the effective dose, that is, the dose required to elicit the desired gene expression or suppression. In one embodiment, 0.1 to 7.5 mg/kg is administered to the subject. In another embodiment, 0.1 to 3 mg/kg is administered to the subject. In another embodiment, 0.1 to 3 mg/kg is administered.

Suitable routes of administering the pharmaceutical compositions include oral, rectal, topical (including dermal, buccal and sublingual), vaginal, parenteral (including subcutaneous, intramuscular, intravenous, intradermal, intrathecal, intra-tumoral and epidural) and by naso-gastric tube. It will be understood by those skilled in the art that the preferred route of administration will depend upon the condition being treated and may vary with factors such as the condition of the recipient. The pharmaceutical compositions may be administered one or more times daily. In one embodiment, the pharmaceutical composition is administered daily beginning 24 hours prior to the administration of cells containing the ecdysone receptor complex and DNA binding sequence.

The diacylhydrazine ligands of Formula I and chiral diacylhydrazine ligands of Formula II or III of the present invention described herein may also be administered in conjunction with other pharmaceutically active compounds. It will be understood by those skilled in the art that pharmaceutically active compounds to be used in combination with the ligands described herein will be selected in order to avoid adverse effects on the recipient or undesirable interactions between the compounds. Examples of other pharmaceutically active compounds which may be used in combination with the ligands include, for example, AIDS chemotherapeutic agents, amino acid derivatives, analgesics, anesthetics, anorectal products, antacids and antiflatulents, antibiotics, anticoagulants, antidotes, antifibrinolytic agents, antihistamines, anti-inflamatory agents, antineoplastics, antiparasitics, antiprotozoals, antipyretics, antiseptics, antispasmodics and anticholinergics, antivirals, appetite suppressants, arthritis medications, biological response modifiers, bone metabolism regulators, bowel evacuants, cardiovascular agents, central nervous system stimulants, cerebral metabolic enhancers, cerumenolytics, cholinesterase inhibitors, cold and cough preparations, colony stimulating factors, contraceptives, cytoprotective agents, dental preparations, deodorants, dermatologicals, detoxifying agents, diabetes agents, diagnostics, diarrhea medications, dopamine receptor agonists, electrolytes, enzymes and digestants, ergot preparations, fertility agents, fiber supplements, antifungal agents, galactorrhea inhibitors, gastric acid secretion inhibitors, gastrointestinal prokinetic agents, gonadotropin inhibitors, hair growth stimulants, hematinics, hemorrheologic agents, hemostatics, histamine $H_2$ receptor antagonists, hormones, hyperglycemic agents, hypolipidemics, immunosuppressants, laxatives, leprostatics, leukapheresis adjuncts, lung surfactants, migraine preparations, mucolytics, muscle relaxant antagonists, muscle relaxants, narcotic antagonists, nasal sprays, nausea medications nucleoside analogues, nutritional supplements, osteoporosis preparations, oxytocics, parasympatholytics, parasympathomimetics, Parkinsonism drugs, Penicillin adjuvants, phospholipids, platelet inhibitors, porphyria agents, prostaglandin analogues, prostaglandins, proton pump inhibitors, pruritus medications psychotropics, quinolones, respiratory stimulants, saliva stimulants, salt substitutes, sclerosing agents, skin wound preparations, smoking cessation aids, sulfonamides, sympatholytics, thrombolytics, Tourette's syndrome agents, tremor preparations, tuberculosis preparations, uricosuric agents, urinary tract agents, uterine contractants, uterine relaxants, vaginal preparations, vertigo agents, vitamin D analogs, vitamins, and medical imaging contrast media. In some cases the ligands may be useful as an adjunct to drug therapy, for example, to "turn off" a gene that produces an enzyme that metabolizes a particular drug.

For agricultural applications, in addition to the applications described above, the ligands of this invention may also be used to control the expression of pesticidal proteins such as *Bacillus thuringiensis* (Bt) toxin. Such expression may be tissue or plant specific. In addition, particularly when control of plant pests is also needed, one or more pesticides may be combined with the ligands described herein, thereby providing additional advantages and effectiveness, including fewer total applications, than if the pesticides are applied separately. When mixtures with pesticides are employed, the relative proportions of each component in the composition will depend upon the relative efficacy and the desired application rate of each pesticide with respect to the crops, pests, and/or weeds to be treated. Those skilled in the art will recognize that mixtures of pesticides may provide advantages such as a broader spectrum of activity than one pesticide used alone. Examples of pesticides which can be combined in compositions with the ligands described herein include fungicides, herbicides, insecticides, miticides, and microbicides.

The diacylhydrazine ligands of Formula I and chiral diacylhydrazine ligands of Formula II or III of the present invention described herein can be applied to plant foliage as aqueous sprays by methods commonly employed, such as conventional high-liter hydraulic sprays, low-liter sprays, airblast, and aerial sprays. The dilution and rate of application will depend upon the type of equipment employed, the method and frequency of application desired, and the ligand application rate. It may be desirable to include additional adjuvants in the spray tank. Such adjuvants include surfactants, dispersants, spreaders, stickers, antifoam agents, emulsifiers, and other similar materials described in *McCutcheon's Emulsifiers and Detergents, McCutcheon's Emulsifiers and Detergents/Functional Materials*, and *McCutcheon's Functional Materials*, all published annually by McCutcheon Division of MC Publishing Company (New Jersey). These ligands can also be mixed with fertilizers or fertilizing materials before their application. These ligands and solid fertilizing material can also be admixed in mixing or blending equipment, or they can be incorporated with fertilizers in granular formulations. Any relative proportion of fertilizer can be used which is suitable for the crops and weeds to be treated. The ligands described herein will commonly comprise from 5% to 50% of the fertilizing composition. These compositions provide fertilizing materials which promote the rapid growth of desired plants, and at the same time control gene expression.

Host Cells and Non-Human Organisms

As described above, diacylhydrazine ligands of Formula I and chiral diacylhydrazine ligands of Formula II or III may be used to modulate gene expression in a host cell. Expression in transgenic host cells may be useful for the expression of various genes of interest. The present invention provides ligands for modulation of gene expression in prokaryotic and eukaryotic host cells.

Expression in transgenic host cells is useful for the expression of various polypeptides of interest including, but not limited to, antigens produced in plants as vaccines; enzymes like alpha-amylase, phytase, glucanes, and xylanase; genes for resistance against insects, nematodes, fungi, bacteria, viruses, and abiotic stresses in plants; antigens; nutraceuticals; pharmaceuticals; vitamins; genes for modifying amino acid content, herbicide resistance, cold, drought, and heat tolerance; industrial products; oils, protein, carbohydrates; antioxidants; male sterile plants; flowers; fuels; other output traits; therapeutic polypeptides or products that may be used to treat a condition, a disease, a disorder, a dysfunction, or a genetic defect, such as monoclonal antibodies, enzymes, proteases, cytokines, interferons, insulin, erythropoietin, clotting factors, other blood factors or components; viral vectors for gene therapy; virus for vaccines; targets for drug discovery, functional genomics, and proteomics analyses and applications: pathway intermediates for the modulation of pathways already existing in the host; pathway intermediates for the synthesis of new products heretofore not possible using the host; cell based assays; functional genomics assays; proteomics assays, and the like. Additionally the gene products may be useful for conferring higher growth yields of the host or for enabling an alternative growth mode to be utilized.

Thus, the present invention provides diacylhydrazine ligands of Formula I and chiral diacylhydrazine ligands of Formula II or III for modulating gene expression in an isolated host cell. In one embodiment, the isolated host cell is a prokaryotic host cell or a eukaryotic host cell. In another embodiment, the isolated host cell is an invertebrate host cell or a vertebrate host cell. Preferably, the host cell is selected from the group consisting of a bacterial cell, a fungal cell, a yeast cell, a nematode cell, an insect cell, a fish cell, a plant cell, an avian cell, an animal cell, and a mammalian cell. More preferably, the host cell is a yeast cell, a nematode cell, an insect cell, a plant cell, a zebrafish cell, a chicken cell, a hamster cell, a mouse cell, a rat cell, a rabbit cell, a cat cell, a dog cell, a bovine cell, a goat cell, a cow cell, a pig cell, a horse cell, a sheep cell, a simian cell, a monkey cell, a chimpanzee cell, or a human cell. Examples of host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Anabaena, Thiobacillus, Methanobacterium* and *Klebsiella*; plant species selected from the group consisting of apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat; animal; and mammalian host cells.

In another embodiment, the host cell is a yeast cell selected from the group consisting of a *Saccharomyces*, a *Pichia*, and a *Candida* host cell.

In another embodiment, the host cell is a *Caenorhabditis elegans* nematode cell.

In another embodiment, the host cell is an insect cell.

In another embodiment, the host cell is a plant cell selected from the group consisting of an apple, *Arabidopsis*, bajra, banana, barley, beans, beet, blackgrum, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat cell.

In another embodiment, the host cell is a zebrafish cell.

In another embodiment, the host cell is a chicken cell.

In another embodiment, the host cell is a mammalian cell selected from the group consisting of a hamster cell, a mouse cell, a rat cell, a rabbit cell, a cat cell, a dog cell, a bovine cell, a goat cell, a cow cell, a pig cell, a horse cell, a sheep cell, a monkey cell, a chimpanzee cell, and a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art. Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification (e.g., glycosylation, cleavage (e.g., of signal sequence)) of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent. The diacylhydrazine ligands of Formula I and chiral diacylhydrazine ligands of Formula II or III of the present invention may be used in a non-human organism comprising an isolated host cell. In one embodiment, the non-human organism is a prokaryotic organism or a eukaryotic organism. In another embodiment, the non-human organism is an invertebrate organism or a vertebrate organism.

Preferably, the non-human organism is selected from the group consisting of a bacterium, a fungus, a yeast, a nematode, an insect, a fish, a plant, a bird, an animal, and a mammal. More preferably, the non-human organism is a yeast, a nematode, an insect, a plant, a zebrafish, a chicken, a hamster, a mouse, a rat, a rabbit, a cat, a dog, a bovine, a goat, a cow, a pig, a horse, a sheep, a simian, a monkey, or a chimpanzee.

In another embodiment, the non-human organism is a yeast selected from the group consisting of *Saccharomyces, Pichia*, and *Candida*.

In another embodiment, the non-human organism is a *Caenorhabditis elegans* nematode.

In another embodiment, the non-human organism is a plant selected from the group consisting of apple, *Arabidopsis*, bajra, banana, barley, beans, beet, blackgum, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, sorghum, soybean, squash, sugarcane, sugarbeet, sunflower, sweet potato, tea, tomato, tobacco, watermelon, and wheat.

In another embodiment, the non-human organism is a *Mus musculus* mouse.

Gene Expression Modulation Systems

The present invention pertains to diacylhydrazine ligands of Formula I and chiral diacylhydrazine ligands of Formula II or III that are useful in an ecdysone receptor-based inducible gene expression system. These diacylhydrazine ligands provide an improved inducible gene expression system in both prokaryotic and eukaryotic host cells. Thus, the present invention pertains to diacylhydrazine ligands of Formula I and chiral diacylhydrazine ligands of Formula II or III that are useful to modulate expression of genes. In particular, the present invention pertains to diacylhydrazine ligands of Formula I and chiral diacylhydrazine ligands of Formula II or III having the ability to transactivate a gene expression modulation system comprising at least one gene expression cassette that is capable of being expressed in a host cell comprising a polynucleotide that encodes a polypeptide comprising a Group H nuclear receptor ligand binding domain. In one embodiment, the Group H nuclear receptor ligand binding is from an ecdysone receptor, a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, or a farnesol receptor. In another embodiment, the Group H nuclear receptor ligand binding domain is from an ecdysone receptor.

In another embodiment, the gene expression modulation system comprises a gene expression cassette comprising a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another embodiment, the gene expression modulation system comprises a gene expression cassette comprising a) a polynucleotide that encodes a polypeptide comprising a transactivation domain, a DNA-binding domain that recognizes a response element associated with a gene whose expression is to be modulated; and a Group H nuclear receptor ligand binding domain comprising a substitution mutation, and b) a second nuclear receptor ligand binding domain selected from the group consisting of a vertebrate retinoid X receptor ligand binding domain, an invertebrate retinoid X receptor ligand binding domain, an ultraspiracle protein ligand binding domain, and a chimeric ligand binding domain comprising two polypeptide fragments, wherein the first polypeptide fragment is from a vertebrate retinoid X receptor ligand binding domain, an invertebrate retinoid X receptor ligand binding domain, or an ultraspiracle protein ligand binding domain, and the second polypeptide fragment is from a different vertebrate retinoid X receptor ligand binding domain, invertebrate retinoid X receptor ligand binding domain, or ultraspiracle protein ligand binding domain. The gene expression modulation system may further comprise a second gene expression cassette comprising: i) a response element recognized by the DNA-binding domain of the encoded polypeptide of the first gene expression cassette; ii) a promoter that is activated by the transactivation domain of the encoded polypeptide of the first gene expression cassette; and iii) a gene whose expression is to be modulated.

In another embodiment, the gene expression modulation system comprises a first gene expression cassette comprising a polynucleotide that encodes a first polypeptide comprising a DNA-binding domain that recognizes a response element associated with a gene whose expression is to be modulated and a nuclear receptor ligand binding domain, and a second gene expression cassette comprising a polynucleotide that encodes a second polypeptide comprising a transactivation domain and a nuclear receptor ligand binding domain, wherein one of the nuclear receptor ligand binding domains is a Group H nuclear receptor ligand binding domain comprising a substitution mutation. In one embodiment, the first polypeptide is substantially free of a transactivation domain and the second polypeptide is substantially free of a DNA binding domain. For purposes of the invention, "substantially free" means that the protein in question does not contain a sufficient sequence of the domain in question to provide activation or binding activity. The gene expression modulation system may further comprise a third gene expression cassette comprising: i) a response element recognized by the DNA-binding domain of the first polypeptide of the first gene expression cassette; ii) a promoter that is activated by the transactivation domain of the second polypeptide of the second gene expression cassette; and iii) a gene whose expression is to be modulated.

Wherein when only one nuclear receptor ligand binding domain is a Group H ligand binding domain comprising a substitution mutation, the other nuclear receptor ligand binding domain may be from any other nuclear receptor that forms a dimer with the Group H ligand binding domain comprising the substitution mutation. For example, when the Group H nuclear receptor ligand binding domain comprising a substitution mutation is an ecdysone receptor ligand binding domain comprising a substitution mutation, the other nuclear receptor ligand binding domain ("partner") may be from an ecdysone receptor, a vertebrate retinoid X receptor (RXR), an invertebrate RXR, an ultraspiracle protein (USP), or a chimeric nuclear receptor comprising at least two different nuclear receptor ligand binding domain polypeptide fragments selected from the group consisting of a vertebrate RXR, an invertebrate RXR, and a USP (see WO 01/70816 A2, International Patent Application No. PCT/US02/05235 and US 2004/0096942 A1, incorporated herein by reference in their entirety). The "partner" nuclear receptor ligand binding domain may further comprise a truncation mutation, a deletion mutation, a substitution mutation, or another modification.

In one embodiment, the vertebrate RXR ligand binding domain is from a human *Homo sapiens*, mouse *Mus musculus*, rat *Rattus norvegicus*, chicken *Gallus gallus*, pig *Sus scrofa domestica*, frog *Xenopus laevis*, zebrafish *Danio rerio*, tunicate *Polyandrocarpa misakiensis*, or jellyfish *Tripedalia cysophora* RXR.

In one embodiment, the invertebrate RXR ligand binding domain is from a locust *Locusta migratoria* ultraspiracle polypeptide ("LmUSP"), an ixodid tick *Amblyomma americanum* RXR homolog 1 ("AmaRXR1"), an ixodid tick *Amblyomma americanum* RXR homolog 2 ("AmaRXR2"), a fiddler crab *Celuca pugilator* RXR homolog ("CpRXR"), a beetle *Tenebrio molitor* RXR homolog ("TmRXR"), a honeybee *Apis mellifera* RXR homolog ("AmRXR"), an aphid *Myzus persicae* RXR homolog ("MpRXR"), or a non-Dipteran/non-Lepidopteran RXR homolog.

In one embodiment, the chimeric RXR ligand binding domain comprises at least two polypeptide fragments selected from the group consisting of a vertebrate species RXR polypeptide fragment, an invertebrate species RXR polypeptide fragment, and a non-Dipteran/non-Lepidopteran invertebrate species RXR homolog polypeptide fragment. A chimeric RXR ligand binding domain for use in the present invention may comprise at least two different species RXR polypeptide fragments, or when the species is the same, the two or more polypeptide fragments may be from two or more different isoforms of the species RXR polypeptide fragment.

In one embodiment, the chimeric RXR ligand binding domain comprises at least one vertebrate species RXR polypeptide fragment and one invertebrate species RXR polypeptide fragment.

In another embodiment, the chimeric RXR ligand binding domain comprises at least one vertebrate species RXR polypeptide fragment and one non-Dipteran/non-Lepidopteran invertebrate species RXR homolog polypeptide fragment.

In another embodiment, the gene whose expression is to be modulated is a homologous gene with respect to the host cell. In another embodiment, the gene whose expression is to be modulated is a heterologous gene with respect to the host cell.

The diacylhydrazine ligands of Formula I and chiral diacylhydrazine ligands of Formula II or III for use in the present invention as described below, when combined with the ligand binding domain of the nuclear receptor(s), which in turn are bound to the response element linked to a gene, provide the means for external temporal regulation of expression of the gene. The binding mechanism or the order in which the various components of this invention bind to each other, that is, for example, ligand to ligand binding domain, DNA-binding domain to response element, transactivation domain to promoter, etc., is not critical.

The ecdysone receptor is a member of the nuclear receptor superfamily and classified into subfamily 1, group H (referred to herein as "Group H nuclear receptors"). The members of each group share 40-60% amino acid identity in the E (ligand binding) domain (Laudet et al., *Cell* 97:161-163 (1999)). In addition to the ecdysone receptor, other members of this nuclear receptor subfamily 1, group H include: ubiquitous receptor (UR), orphan receptor 1 (OR-1), steroid hormone nuclear receptor 1 (NER-1), retinoid X receptor interacting protein-15 (RIP-15), liver X receptor β (LXRβ), steroid hormone receptor like protein (RLD-1), liver X receptor (LXR), liver X receptor α (LXRα), farnesoid X receptor (FXR), receptor interacting protein 14 (RIP-14), and farnesol receptor (HRR-1).

In a specific example, binding of the ligand to the ligand binding domain of a Group H nuclear receptor and its nuclear receptor ligand binding domain partner enables expression or suppression of the gene. This mechanism does not exclude the potential for ligand binding to the Group H nuclear receptor (GHNR) or its partner, and the resulting formation of active homodimer complexes (e.g. GHNR+GHNR or partner+partner). Preferably, one or more of the receptor domains is varied producing a hybrid gene switch. Typically, one or more of the three domains, DBD, LBD, and transactivation domain, may be chosen from a source different than the source of the other domains so that the hybrid genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski et al., Nature 335:563-564 (1988)) or LexA protein from Escherichia coli (see Brent et al., Cell 43:729-736 (1985)), or synthetic response elements specific for targeted interactions with proteins designed, modified, and selected for such specific interactions (see, for example, Kim et al., Proc. Natl. Acad. Sci. USA, 94:3616-3620 (1997)) to accommodate hybrid receptors. Another advantage of two-hybrid systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operably linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism.

In particular, described herein are diacylhydrazine ligands of Formula I and chiral diacylhydrazine ligands of Formula II or III useful in a gene expression modulation system comprising a Group H nuclear receptor ligand binding domain comprising a substitution mutation. This gene expression system may be a "single switch"-based gene expression system in which the transactivation domain, DNA-binding domain and ligand binding domain are on one encoded polypeptide. Alternatively, the gene expression modulation system may be a "dual switch"- or "two-hybrid"-based gene expression modulation system in which the transactivation domain and DNA-binding domain are located on two different encoded polypeptides.

An ecdysone receptor-based gene expression modulation system for use in the present invention may be either heterodimeric or homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao et al., Nature 366:476-479 (1993) and Yao et al., Cell 71:63-72 (1992)). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al., Curr. Opin. Cell Biol. 9:222-232 (1997)). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that the binding of ligand changes the conformation of the receptor, which results in release of the corepressor and recruitment of the above described coactivators, thereby abolishing their silencing activity. Examples of corepressors include N—CoR and SMRT (for review, see Horwitz et al., Mol. Endocrinol. 10: 1167-1177 (1996)). These cofactors may either be endogenous within the cell or organism, or may be added-exogenously as transgenes to be expressed in either a regulated or unregulated fashion. Homodimer complexes of the ecdysone receptor protein, USP, or RXR may also be functional under some circumstances.

The ecdysone receptor complex typically includes proteins that are members of the nuclear receptor superfamily wherein all members are generally characterized by the presence of an amino-terminal transactivation domain, a DNA binding domain ("DBD"), and a ligand binding domain ("LBD") separated from the DBD by a hinge region. As used herein, the term "DNA binding domain" comprises a minimal polypeptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see U.S. Pat. No. 4,981,784 and Evans, Science 240:889-895 (1988)). The "A/B" domain corresponds to the transactivation domain, "C" corresponds to the DNA binding domain, "D" corresponds to the hinge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. The EcR receptor, like a subset of the steroid receptor family, also possesses less well-defined regions responsible for heterodimerization properties. Because the domains of nuclear receptors are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. It has previously been shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex (see PCT/US01/09050).

Method of Modulating Gene Expression

The present invention also relates to methods of modulating gene expression in a host cell using a gene expression modulation system and the ligands of the present invention. Specifically, the present invention provides a method of modulating the expression of a gene in a host cell comprising the steps of: a) introducing into the host cell a gene expression modulation system; and b) introducing into the host cell a diacylhydrazine ligand of Formula I or chiral diacylhydrazine ligand of Formula II or III; wherein the gene to be modulated is a component of a gene expression cassette comprising: i) a response element comprising a domain recognized by the DNA binding domain of the gene expression system; ii) a promoter that is activated by the transactivation domain of the gene expression system; and iii) a gene whose expression is to be modulated, whereby upon introduction of the diacylhydrazine ligand of Formula I or chiral diacylhydrazine ligand of Formula II or III into the host cell, expression of the gene is modulated.

The present invention also provides a method of modulating the expression of a gene in a host cell comprising the steps of: a) introducing into the host cell a gene expression modulation system; b) introducing into the host cell a gene expression cassette, wherein the gene expression cassette comprises i) a response element comprising a domain recognized by the DNA binding domain from the gene expression system; ii) a promoter that is activated by the transactivation domain of the gene expression system; and iii) a gene whose expression is to be modulated; and c) introducing into the host cell a diacylhydrazine ligand of Formula I or chiral diacylhydrazine ligand of Formula II or III; whereby upon introduction of the diacylhydrazine ligand of Formula I or chiral diacylhydrazine ligand of Formula II or III into the host cell, expression of the gene is modulated.

The present invention also provides a method of modulating the expression of a gene in a host cell comprising a gene expression cassette comprising a response element comprising a domain to which the DNA binding domain from the first hybrid polypeptide of the gene expression modulation system binds; a promoter that is activated by the transactivation domain of the second hybrid polypeptide of the gene expression modulation system; and a gene whose expression is to be modulated; wherein the method comprises the steps of: a) introducing into the host cell a gene expression modulation system; and b) introducing into the host cell a diacylhydrazine ligand of Formula I or chiral diacylhydrazine ligand of Formula II or III; whereby upon introduction of the ligand into the host, expression of the gene is modulated.

Genes of interest for expression in a host cell using methods disclosed herein may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in the methods described herein.

Measuring Gene Expression/Transcription

One useful measurement of the methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can be used for analysis of up to 1700 genes. DNA microarrays are arrays of DNA samples, typically PCR products, that are robotically printed onto a microscope slide. Each gene is analyzed by a full or partial-length target DNA sequence. Microarrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of the methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using the present invention.

Other methods to detect the products of gene expression are well known in the art and include Southern blots (DNA detection), dot or slot blots (DNA, RNA), northern blots (RNA), RT-PCR (RNA), western blots (polypeptide detection), and ELISA (polypeptide) analyses. Although less preferred, labeled proteins can be used to detect a particular nucleic acid sequence to which it hybridizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one pair of oligonucleotide primers, with one primer hybridizing to one strand (template) of the specific sequence to be detected. The primers are sufficiently complementary to each template strand of the specific sequence to hybridize therewith. An extension product of each primer is synthesized and is complementary to the nucleic acid template strand to which it hybridized. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel et al., *Current Protocols in Molecular Biology*, Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" program is used the default gap creation penalty of 50 and the default gap extension penalty of 3 may be used. In any case where GCG program parameters are not prompted for, in these or any other GCG program, default values may be used.

Melting points were measured in glass capillary tubes with an Electrothermal® apparatus and are uncorrected. Optical rotations ($[\alpha]^{25}_{589}$) were measured at room temperature in a 10 cm long quartz cell using a Perkin Elmer Model 341 Polarimeter. Concentrations are given in g/100 mL. $^1$H NMR spectra were recorded at 300 MHz or 400.13 MHz using a Bruker NMR. Unless otherwise stated, the internal reference was solvent. $^{13}$C NMR spectra were recorded at 100.6 MHz with a Bruker NMR. Unless otherwise stated, the internal reference was solvent. LC-MS analysis was performed using an Agilent 1100 LC stack coupled with an Agilent single quad mass spectrometer. Solvents were (A) $H_2O/0.1\%$ formic acid and (B) ACN/0.1% formic acid in a gradient of T=0 15% B to T=10 98% B and a stop time of 20 min on a 75 mm×2.1 mm C18 column with a flow rate=0.2 mL/min. Exact mass analysis were performed by direct infusion into an Agilent ESI/TOF mass spectrometer. X-Ray crystal structure determinations were performed using a Bruker SMART6000. Elemental analyses were performed on a Perkin Elmer 2400 CHN analyzer. Analytical thin layer chromatography or TLC was performed using Macherey-Nagel Polygram® Sil G/UV$_{254}$ 0.2 mm plates. Most plates were visualized by UV light. Some were developed using iodine or phosphomolybdic acid. Silica gel chromatography was performed using Aldrich silica gel (230-400 mesh, 60 Å) in glass columns under a $N_2$ or argon head pressure of ca. 30 psi. Analytical HPLC was performed using a Gilson HPLC system equipped with a 811C dynamic mixer, 306 UV/VIS 155 detector, and 215 liquid handler. UV absorbance was measured at 220 nm and 254 nm and integrations were performed at 254 nm. Flow rates were typically held at 1 mL/min. Normal phase chromatography was performed with a 4.6 mm×25 cm DuPont Zorbax ODS column. Reverse phase chromatography was performed using an Alltech Adsorbosphere 5 micron, 4.6 mm×25 cm C18 column. Chiral HPLC was performed using a CHIRALCEL® 5 micron, 4.6 mm×25 cm OD-H column, a CHIRAKPAK® 5 micron, 4.6 mm×25 cm AD-H column, or a 5 micron, 100 Å, 4.6 mm×25 cm Regis Rexchrom (S,S) ULMO column. Solvents were reagent grade unless otherwise stated. Anhydrous solvents were used as purchased.

General Synthetic Methods

Enantiomerically enriched compounds of Formula II or III where A, B and $R^2$ are defined as above and $R^1$ is alkenyl may be prepared via asymmetric synthesis as described in General Scheme 1.

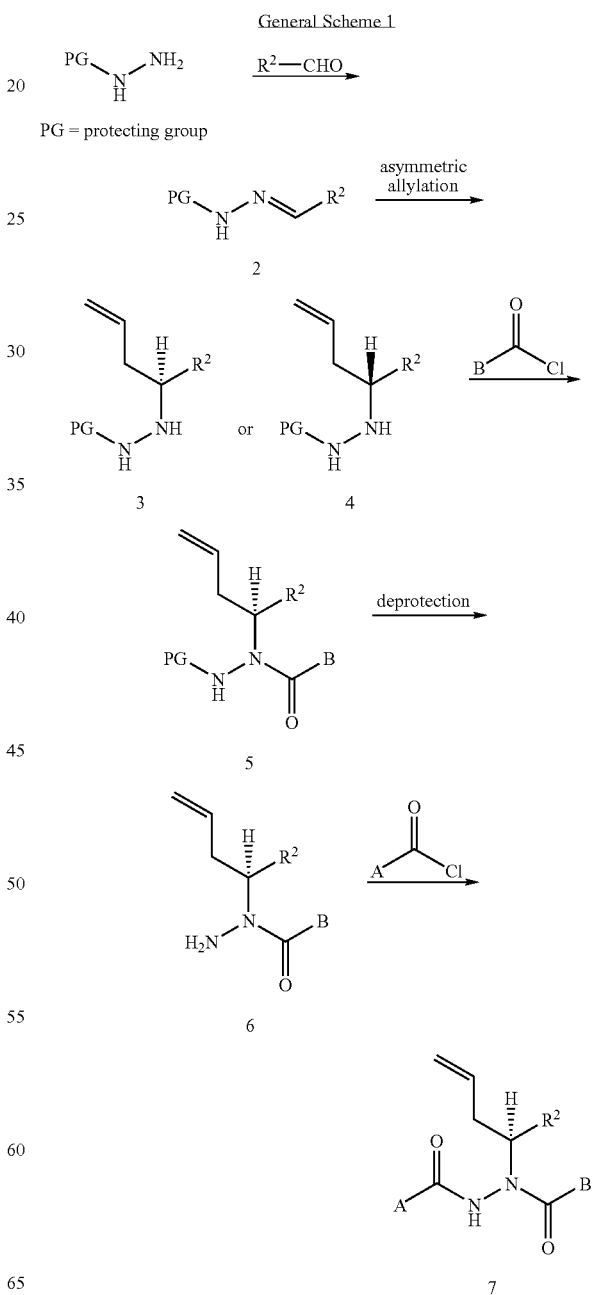

Reaction of protected hydrazine 1 (e.g.; benzyl carbazate or t-butyl carbazate) with aldehyde $R^2$CHO affords 2. Asymmetric allylation of 2 provides either 3 or 4 in enantiomerically enriched form, depending inter alia on the choice of chiral reagent and $R^2$. Methods to perform asymmetric allylation reactions are known in the art and may be utilized to prepare compounds of the invention. The synthesis of chiral reagents particularly useful in asymmetric allylation reactions is described in Leighton et al., *J. Am. Chem. Soc.* 125: 9596 (2003) and WO 03/074534. Reaction of 3 with carboxylic acid chloride B—COCl gives 5. Carboxylic acid B—CO$_2$H may also be coupled with 3 to provide 5. Removal of the protecting group of 5 gives 6. One skilled in the art recognizes there are a variety of methods to deprotect a hydrazine, depending on the nature of the protecting group. Suitable protection/deprotection strategies are discussed in "Protective Groups in Organic Synthesis", T. W. Green and P. G. M. Wuts (1999). Reaction of 7 with carboxylic acid chloride A-COCl or carboxylic acid A-CO$_2$H gives 8, a compound of Formula II. Similarly, reaction of 4 leads to a compound of Formula III.

Enantiomerically enriched compounds of Formula II or III where A, B, $R^1$ and $R^2$ are defined as above may also be prepared via asymmetric reduction as described in General Scheme 2.

Reaction of acyl hydrazine 1 with ketone $R^1$COR$^2$ provides hydrazone 2. Asymmetric reduction of 2 provides 3 or 4 in enantiomerically enriched form, depending inter alia on the choice of reducing agent, $R^1$ and $R^2$. U.S. Pat. No. 5,250,731 describes the asymmetric catalytic hydrogenation of acyl hydrazones to give optically active acyl hydrazines in the presence of a chiral phospholane catalyst complex. One skilled in the art will recognize other chiral ligands may also be used. Moreover, one skilled in the art will recognize additional asymmetric reduction methods may employed. In this example, reaction of 3 with BCOCl gives 5, a compound of Formula II. Similarly, reaction of 4 leads to a compound of Formula III.

In addition, enantiomerically enriched compounds of Formula II or III may be prepared via chiral resolution, or a combination of asymmetric synthesis and chiral resolution or a combination of asymmetric hydrogenation and chiral resolution. As described in General Scheme 3, subjecting racemic diacylhydrazines to chiral HPLC chromatography provides enantiomerically enriched compounds of Formula II or III. Suitable chiral columns for use in chiral resolutions include, for example, Daicel CHIRALCEL® OD-H, Daicel CHIRAKPAK® AD-H and Regis Technologies ULMO chiral columns. Other chiral resolution methods are also possible. Racemic diacylhydrazines for use in chiral resolution processes may be prepared using methodology described in US 2005/0209283 A1 and US 2006/0020146 A1.

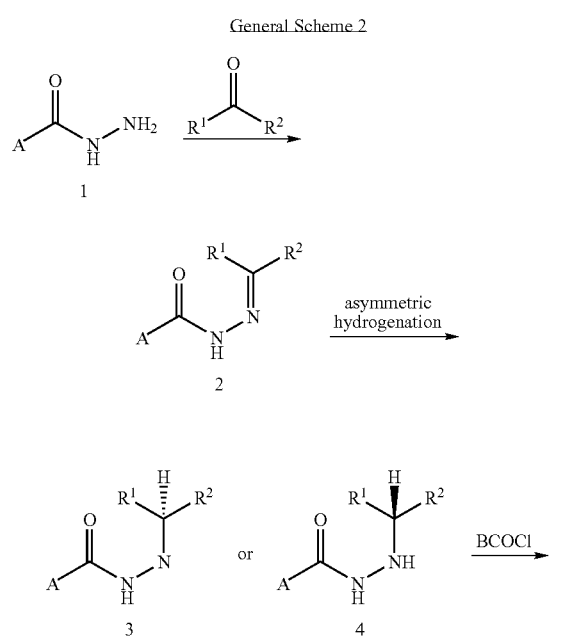

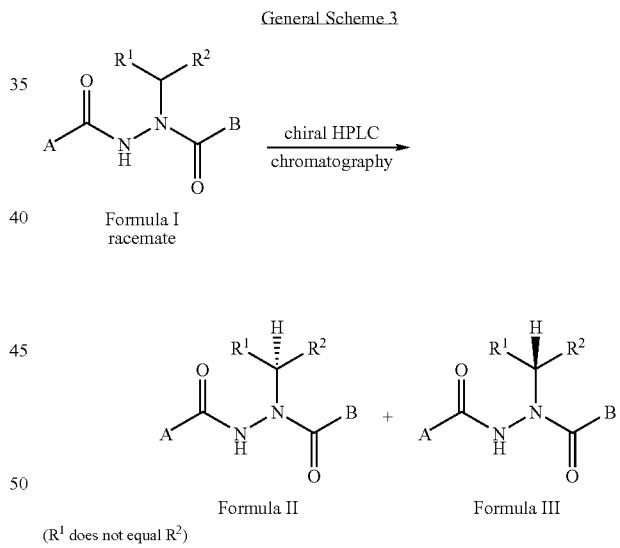

Enantiomerically enriched compounds of Formula II or III where $R^1$ is alkenyl may be further elaborated using standard chemical transformations. As described in General Scheme 4 for an enantiomerically enriched compound of Formula III, the alkenyl may be converted to an alkyl, a hydroxyalkyl, an alkyl optionally substituted with a cycloalkyl, an alkyl optionally substituted with a heterocycle, an alkyl substituted with an alkoxy, a haloalkyl and other optionally substituted alkyl groups. One skilled in the art will recognize an assortment of single or multi-step chemical transformations that may be used to convert an alkene to other groups of the invention.

General Scheme 4
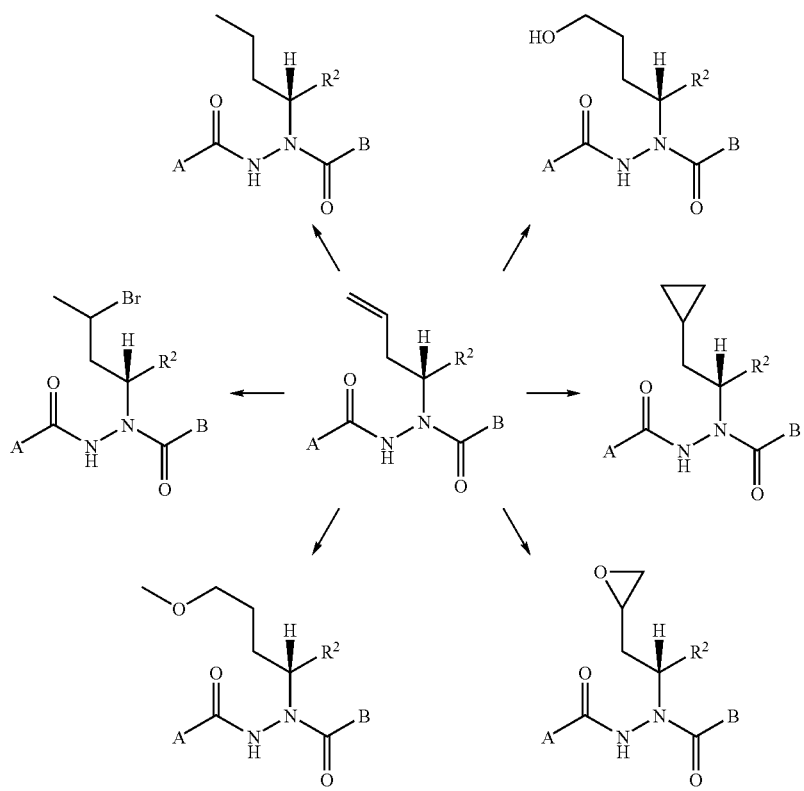
EXAMPLES
The present invention may be better understood by reference to the following general synthetic methods provided above and non-limiting examples provided below, which are provided as exemplary of the invention.
Example 1
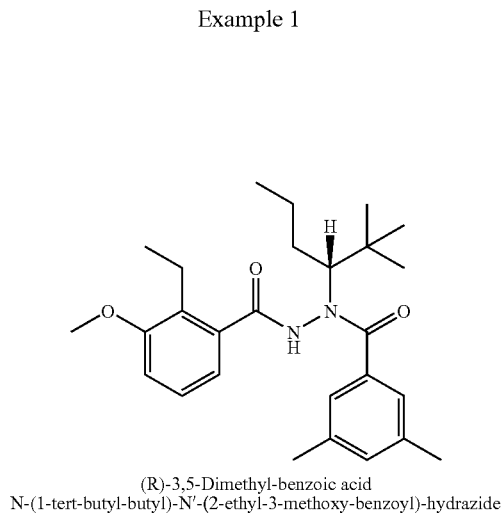
(R)-3,5-Dimethyl-benzoic acid
N-(1-tert-butyl-butyl)-N'-(2-ethyl-3-methoxy-benzoyl)-hydrazide
Synthesis
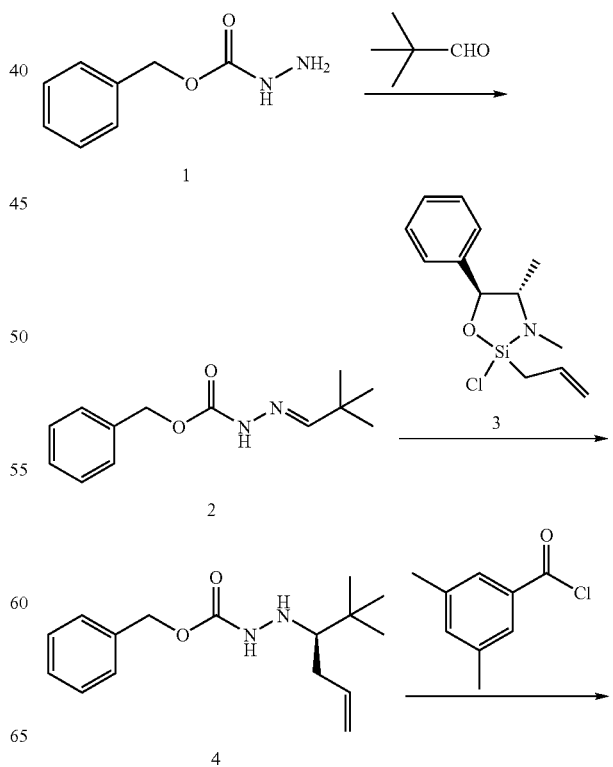

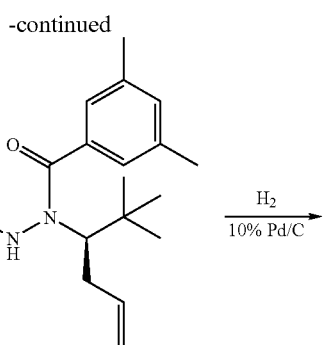

Compound 1: Benzyl carbazate is commercially available.

Compound 2: Benzyl carbazate (300 g, 1.81 moles) was dissolved in 1.2 L of methyl alcohol in a 3 L 4-neck flask equipped with reflux condenser, thermometer, magnetic stirring, and a 500 mL addition funnel. Glacial acetic acid (5 mL) was added to the mixture that was then brought to 45° C. Pivaldehyde (248.8 g of solution, 2.17 moles, ca. 75% in t-butanol) was added portionwise over 30 minutes. The reaction was heated at reflux for 30 minutes, while monitoring by TLC. The mixture was allowed to cool to nearly room temperature and was concentrated on a rotary evaporator to a total volume of ca. 700 mL. Ca. 7 g activated charcoal was added at ca. 30° C. The mixture was stirred overnight and filtered through a pad of Celite in a pore size "C" glass fritted Büchner funnel. The solvent was removed in vacuo to leave a light yellow oil that was poured into a crystallizing dish and induced to crystallize by manipulation with a spatula. The material was granulated and residual solvent was allowed to evaporate in air at room temperature for several days, leaving 420.4 g crude product. Recrystallization at room temperature from an initially boiling mixture of 300 mL ethyl acetate and 1 L hexanes produced 363.2 g of (E)-N'-(2,2-dimethyl-propylidene)-hydrazinecarboxylic acid benzyl ester as an off-white solid. A second crop of 43.1 g and identical melting point was obtained from a mixture of ca. 150 mL hexanes and 45 mL ethyl acetate. Total yield: 96.1%. $R_f$=0.32 (2:1 hexanes:ethyl acetate); mp=74-74.5° C.; $^1$H NMR (400 MHz, CDCl$_3$) δ 8.0 (1H, br s), 7.4-7.3 (5H, m), 7.1 (1H, s), 5.20 (2H, s), 1.1 (9H, s).

Compound 3: (S,S)-2-Allyl-2-chloro-3,4-dimethyl-5-phenyl-[1,3,2]oxazasilolidine was prepared using a modified procedure of Leighton et al., *J. Am. Chem. Soc.* 125:9596 (2003) and WO 03/074534. The entire procedure was performed under an anhydrous closed system with minimized and brief moments of exposure to the atmosphere. An oven-dried 5 L 4-neck flask with gas inlet, overhead stirring, and addition funnel was charged first with allyltrichlorosilane (419.5 g, 2.39 moles) and then with 2 L anhydrous CH$_2$Cl$_2$. The solution was cooled under argon to 0° C. in an ice/salt bath. Triethylamine (485 g, 4.79 moles) was added via addition funnel, maintaining the temperature at 0° C. At this point the reaction was a transparent amber color. S,S-pseudoephedrine (359 g, 2.17 moles) was added portionwise using a solid addition funnel over a period of 2 h, maintaining an internal temperature <15° C. The addition funnel was flushed with 200 mL CH$_2$Cl$_2$ into the reaction. Over time, paste-like semi-granular solids formed (Et$_3$NCl). The light brown viscous slurry was stirred for ca. 2 h on ice, then the ice bath was removed, thereby allowing the reaction to reach room temperature over a period of several hours. Approximately 12 h later, most of the CH$_2$Cl$_2$ was removed by distillation while maintaining the system under argon. 1 L anhydrous hexane was added, and solvent was distilled again. 1 L anhydrous pentane was then added and the mixture was stirred at room temperature for ca. 1 h under argon. The previously paste-like sludge that originally formed in CH$_2$Cl$_2$ became more granular, first upon hexane addition, and then especially after pentane addition. The solution was light amber brown in color. In portions, and by use of gentle argon pressure, pentane and soluble product were transferred out of the reaction flask through a glass wool filter and PFA tube into second dry 1 L, 3-necked round bottom flask equipped with a distillation head and magnetic stirring. In alternation with solution transfer, pentane was distilled out of this second flask leaving behind the concentrated oily product. This process was repeated, washing the Et$_3$NCl residue two times each with 500 mL pentane, and transferring the washes to the second flask under an argon atmosphere. The product was collected by distillation in fractions under a vacuum of ca. 10 torr. Ca. 56.3 g (9.7%) was collected in a forerun that possibly contained up to ca. 3% allyltrichlorosilane. The main fraction, purified (S,S)-2-allyl-2-chloro-3,4-dimethyl-5-phenyl-[1,3,2]oxazasilolidine, was obtained in a quantity of 413.3 g (71%), bp=140-144 @ ca. 10 torr, as a mildly viscous liquid light yellow at the time of collection, but which became orange over several days under refrigeration and tight septum/parafilm sealing. The material was stored under refrigeration, was not characterized, and was used without further purification in the subsequent allylation reaction.

Compound 4: A 5 L, 4-neck flask equipped with thermometer and magnetic stirring, was dried in an oven and maintained under argon while 2 L anhydrous CH$_2$Cl$_2$ was added, followed by N'-(2,2-dimethyl-propylidene)-hydrazinecarboxylic acid benzyl ester (220 g, 939 mmoles). The mixture was chilled and stirred in large, ca. 10 gal ice/brine bath at 2-3° C. (S,S)-2-allyl-2-chloro-3,4-dimethyl-5-phenyl-[1,3,2] oxazasilolidine (363 g, 1.355 moles) was added to the flask over ca. 30 min using a cannula and assistance with gentle argon pressure. The originally pale yellow solution became a transparent light orange, while the temperature remained at 2-3° C. The reaction was allowed to warm to room temperature on its own accord and was monitored by quenching a small aliquot in CH$_3$OH and analyzing by TLC (2:1 hexanes:EtOAc). 36 hours after initiation, TLC analysis indicated ca. 90% completion. The mixture was chilled to 5° C., an additional 48 g (0.179 mmoles) oxazasilolidine were added, and the mixture was allowed to warm to room temperature. Ca. 8 hours later, the reaction was again cooled to 5° C. and quenched with a pre-chilled solution of 100 g K$_2$CO$_3$ in 100 mL deionized water over a period of ca. 1 h. During the quench, an exotherm raised the temperature to as high as 17° C. Approximately 100 mL additional deionized water was added. The solution became a transparent blue-green in appearance. At no time during the reaction or quench was there any apparent evolution of gas. After 4 days of stirring at room temperature, the solution was light yellow in color, and after 5 days, the organic phase had gelled but remained light yellow in color. The mixture was chilled to ca 15° C. (later apparent that this is not necessary), ca. 1.25 L hexanes was added, and the gel was partially collapsed and broken up with overhead stirring. The supernatant was siphoned off and filtered through glass wool while alternately adding ca. 1 L portions to the white gel remaining in the flask. Additional hexanes were also added to the supernatant to precipitate pseudoephedrine as a white solid and to collapse any remaining gel. The hexane extracts were combined and solvent was removed in vacuo. Overall, through extractions of gel, hexanes-induced precipitation of pseudoephedrine, and filtrations through glass wool and a glass-fritted Büchner funnel, approximately 5-6 L hexanes was used to obtain the crude allyl hydrazide as a yellow oil. In batches, this crude material was treated with ca. three volumes of hexanes, allowed to stand at room temp, decanted from precipitated pseudoephedrine, and transferred to a separatory funnel. The product solution was isolated from residual pseudoephedrine by washing thrice with ca. 25 mL each 1.4 N HCl (much color also removed), followed by washes with 10% K$_2$CO$_3$ and brine. The hexanes solution of crude product was dried over solid anhydrous Na$_2$SO$_4$, and solvent was removed in vacuo to give a light-yellow colored viscous oil. TLC (2:1 hexanes:EtOAc) showed desired product R$_f$=0.4; two impurities at 0.25 and 0.31 (5-10% each, one of them probably starting material), and a few less prominent impurities above R$_f$=0.4. Pseudoephedrine previously detected at the baseline was now absent. A total of 196.8 g (75.8%) (R)—N'-(1-tert-butyl-but-3-enyl)-hydrazinecarboxylic acid benzyl ester was isolated as an amber oil after removing trace solvent on a vacuum pump. The original gel, now somewhat condensed and granular, was extracted with ca. 2 L boiling hexanes. Solids were filtered, hexanes were stripped, and the oil was decanted from precipitated pseudoephedrine, yielding ca. 18 g. This material was combined with residues from the primary product batch above (ca. 3-4 g), and washed with 1.4 N HCl, aq. K$_2$CO$_3$, and brine as before. The hexanes were stripped to yield 20.6 grams additional product, as an amber oil which by TLC appears identical to the first batch. A 10.1 g portion of (R)—N'-(1-tert-butyl-but-3-enyl)-hydrazinecarboxylic acid benzyl ester was chromatographed quantitatively on silica gel to yield 8.88 g (88% yield for chromatography) pure product as a clear, off-white oil. R$_f$=0.43 (2:1 hexanes:ethyl acetate); $^1$H NMR (400 MHz, CDCl$_3$) δ 7.4 (5H, br s), 6.2 (1H, br s), 6.0 (1H, br s), 5.15 (2H, s), 5.1 (2H, s), 4.1 (1H, br), 2.7 (1H, m), 2.4 (1H, br d), 2.0 (1H, m), 0.95 (9H, s); ee=98.1%, AD-H column; $[\alpha]^{25}_{589}$ −42.5° (c 2.18, CH$_3$OH).

Compound 5: (R)—N'-(1-tert-butyl-but-3-enyl)-hydrazinecarboxylic acid benzyl ester (110 g, 398 mmoles) and 500 mL of methylene chloride were added to a 2 L round bottom flask with a thermometer and magnetic stirrer. A solution of K$_2$CO$_3$ (82.51 g, 597 mmol in 200 mL deionized water) was subsequently added, and the flask was cooled to ca. 10° C. Neat 3,5-dimethyl benzoyl chloride (73.82 g, 437.8 mmol) was then added slowly over a period of 20 min. 1 L methylene chloride was used to rinse residual acid chloride into the flask and to dilute the reaction mixture. The temperature was not allowed to exceed 15° C. during the addition. The reaction was stirred overnight, first in an ice bath and then at room temperature. TLC analysis at ca. 16 hours indicated that the reaction was complete with residual acid chloride; the mixture was stirred for a total of ca. 40 hours. The reaction mixture was poured into a 2 L separatory funnel. The organic layer was collected and combined with a small CH$_2$Cl$_2$ backwash of the aqueous layer. The organic phase was washed once more with 10% K$_2$CO$_3$, washed with brine, and then dried over solid MgSO$_4$/Na$_2$SO$_4$. The mixture was filtered from salts, and solvent was removed in vacuo to obtain a granular light beige solid. The crude product was suspended and stirred in 300 mL of 2:1 hexanes:ether and filtered on a Büchner funnel to substantially remove residual 3,5-dimethylbenzoyl chloride. The collected solids were washed four times more with a combined total of ca. 1200 mL 2:1 hexanes:ether, thereby providing a white granular solid. The product was collected and allowed to dry in the air to yield 144.55 g (R)—N'-(1-tert-butyl-but-3-enyl)-N'-(3,5-dimethyl-benzoyl)-hydrazinecarboxylic acid benzyl ester, yield=88.9%. A 30 g sample of was dissolved in 205 mL boiling methanol and allowed to crystallize at room temperature. The resultant flocculant material was washed in a Büchner with 50 mL CH$_3$OH to give 22.2 g, mp=146° C., (ee>99.9%). An analytical sample of (R)—N'-(1-tert-butyl-but-3-enyl)-N'-(3,5-dimethyl-benzoyl)-hydrazinecarboxylic acid benzyl ester was obtained by twice-recrystallizing this material from boiling CH$_3$OH followed by Kugelrohr short-path distillation and collection as a solid to give a pure white material: mp=145.5-147° C. R$_f$=0.12 (10:1 hexanes:ethyl acetate); $^1$H NMR (400 MHz, CDCl$_3$): δ7.5-7.2 (m, 9H, φ+NH), 7.2-6.8 (m), 6.4 (S), 6.3 (S), 5.95 (br, 5H, benzylic+C=C), 5.4-4.6 (m, 9H, allylic N—CH, φ-CH3), 3.65 (br), 2.5 (m), 2.35 (S), 2.3 (S), 1.2-0.8 (m, 9H, —C(CH$_3$)$_3$); $[\alpha]^{25}_{589}$ −12.8° (c 2.01, CHCl$_3$).

Compound 6 (R)—N'-(1-tert-butyl-but-3-enyl)-N'-(3,5-dimethyl-benzoyl)-hydrazine carboxylic acid benzyl ester (13.5 g, 33 mmoles) was suspended in 100 mL glacial acetic acid at room temperature. 10% Palladium on charcoal (0.24 g) were added as a slurry in 4.4 g acetic acid. The gray suspension was shaken for 90 minutes at 10-30 psi on a Parr hydrogenator, monitoring the reaction by TLC. The catalyst was allowed to settle, and the reaction solution was removed with a pipette and passed through fluted filter paper (Schleicher & Schuell 597½, 125 mm dia). The catalyst residue was washed with acetic acid and washes were passed through filter paper to give a combined total mass of 156 g acetic acid and product. The mixture was chilled on ice and ca. 600 mL deionized water was added. Over a period of 30 minutes, product oiled out and then crystallized. This was filter through paper, dried in air, and collect on paper to yield 7.9 g of a light yellow solid. Over several hours, 0.52 g additional product precipitated out of the filtrate to give a total yield of 8.42 g (92.2%) of (R)-3,5-dimethyl-benzoic acid N-(1-tert-butyl-butyl)-hydrazide; R$_f$=0.5 (1:1 hexanes:ethyl acetate); $[\alpha]^{25}_{589}$ +7.63 (c 1.98, CH$_3$OH), $^1$H NMR (400 MHz, CDCl$_3$) δ 7.05 (1H, s), 7.02 (2H, s), 4.6+3.5 (1H, 2 d), 4.1 (2H, s, NH$_2$), 2.38+2.37 (6H, 2 s), 1.1-2.1 (4H, m), 1.0+0.9 (9H, 2 s), 1.0+0.98 (3H, 2 t), 2 distinct conformers.

Compound 7 (title compound): (R)-3,5-dimethyl-benzoic acid N-(1-tert-butyl-butyl)-hydrazide (35 g, 126.6 mmoles) was dissolved in 100 mL methylene chloride in a 500 mL round bottom flask with magnetic stirring. Aqueous $K_2CO_3$ (26.25 g, 189.9 mmoles, solution in 75 mL deionized water) was added and the mixture was stirred on ice. Solid 2-ethyl-3-methoxybenzoyl chloride (27.67 g, 139.3 mmoles) was added and rinsed into the flask using 25 mL $CH_2Cl_2$. The mixture was stirred on ice for ca. 40 h, allowing the bath to warm to room temperature. Additional methylene chloride and water were added as needed to aid manipulation. The organic layer was separated and dried over $MgSO_4$. Ca. 5 g activated charcoal was added and the salt and carbon were removed by filtration through paper. The solvent was evaporated in vacuo, first on a rotary evaporator and then under high vacuum, providing 57.8 g crude product, containing traces of $CH_2Cl_2$. The crude material was triturated first with 3×100 mL portions of ether (2% ethanol) and then with 1×100 mL portion of 1:1 hexanes:ether in a fritted glass Büchner funnel (pore size ASTM 40-60 C, Pyrex). The product was then washed with 2×200 mL deionized water with thorough mixing and allowed to dry in air. (R)-3,5-Dimethyl-benzoic acid N-(1-tert-butyl-butyl)-N'-(2-ethyl-3-methoxy-benzoyl)-hydrazide (also referred to as (R)-2-ethyl-3-methoxy-benzoic acid N'-(1-tert-butyl-butyl)-N'-(3,5-dimethyl-benzoyl)-hydrazide) was collected as a bright white powdery solid (36.51 g, 65.7% yield, quite pure and very high ee by HPLC and chiral HPLC, one spot by TLC, 1:1 hexanes:ether). Evaporation of the combined organic washes yielded ca. 20 g material, which was triturated first with 200 mL 2:1 hexanes:ether and then with 2×100 mL 2:1 hexanes:ether in a fritted glass Büchner, pore size ASTM 40-60 C. The material was washed with 3×100 mL deionized water with thorough mixing and allowed to air dry. A second crop was collected as a white powder (12.98 g, 23.4% yield, quite pure and high ee by HPLC and chiral HPLC). A third crop was obtained in a similar manner as an off-white solid (1.52 g, 2.7%, 98% pure, >99% ee). A final sample was prepared by dissolving in warm methanol and filtering through a 0.45 micron syringe filter into a large crystallization dish. The material was collected, pulverized with a spatula, and heated at 50-58° C. in a vacuum oven virtually until constant weight. HPLC analysis indicated 99.3% chemical purity and >99.9% ee $R_f$=0.28 (1:1 hexanes:ethyl acetate); mp=162.2-162.8° C.; $[\alpha]^{25}_{589}$ +12.9 (c 2.04, $CH_3OH$); $^1H$ NMR (400 MHz, $CD_3OD$) δ 7.0-7.1 (4H, m), 6.9 (1H, d), 6.1-6.4 (1H, 2 d), 4.5-4.7 (1H, 2 d), 3.78 (3H, s), 2.3 (6H, s), 2.3 (1H, m), 1.9 (2H, m), 1.55 (3H, m), 1.1-1.15 (9H, 2 s), 0.9-1.0 (6H, m).

Examples 2 to 29 were prepared using methodology described in Example 1. The percent enantiomeric excess (ee) was determined by chiral HPLC. Table 2 provides analytical data for examples 2 to 29.

| Example | Structure | ee; % | Name |
|---|---|---|---|
| 2 | 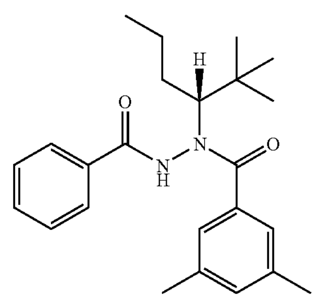 | >99 | (R)-3,5-Dimethyl-benzoic acid N'-benzoyl-N-(1-tert-butyl-butyl)-hydrazide |
| 3 | 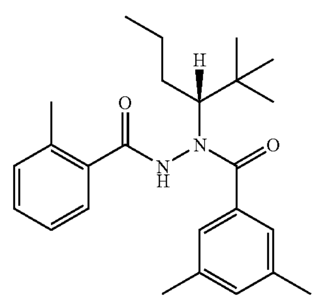 | >99 | (R)-3,5-Dimethyl-benzoic acid N-(1-tert-butyl-butyl)-N'-(2-methyl-benzoyl)-hydrazide |
| 4 | 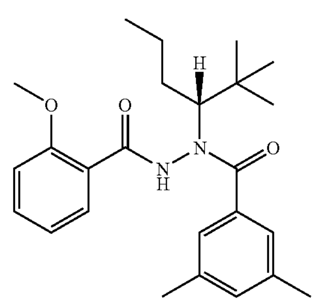 | >99 | (R)-3,5-Dimethyl-benzoic acid N-(1-tert-butyl-butyl)-N'-(2-methoxy-benzoyl)-hydrazide |

-continued

| Example | Structure | ee; % | Name |
|---|---|---|---|
| 5 | 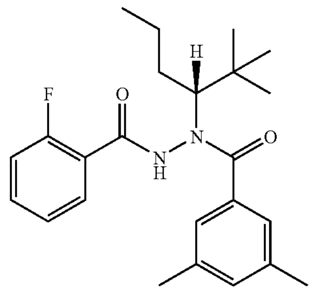 | >98 | (R)-3,5-Dimethyl-benzoic acid N-(1-tert-butyl-butyl)-N'-(2-fluoro-benzoyl)-hydrazide |
| 6 | 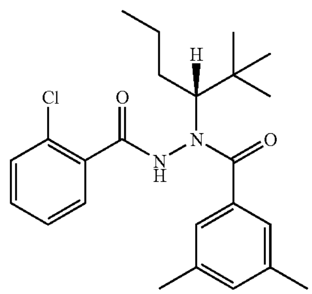 | >99 | (R)-3,5-Dimethyl-benzoic acid N-(1-tert-butyl-butyl)-N'-(2-chloro-benzoyl)-hydrazide |
| 7 | 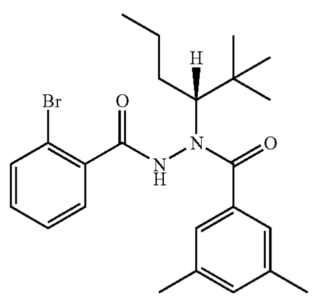 | >99 | (R)-3,5-Dimethyl-benzoic acid N'-(2-bromo-benzoyl)-N-(1-tert-butyl-butyl)-hydrazide |
| 8 | 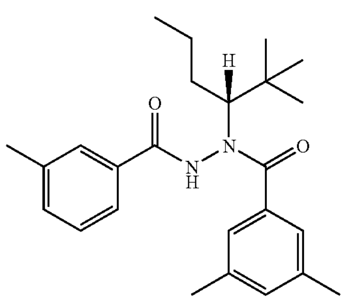 | >99 | (R)-3,5-Dimethyl-benzoic acid N-(1-tert-butyl-butyl)-N'-(3-methyl-benzoyl)-hydrazide |
| 9 | 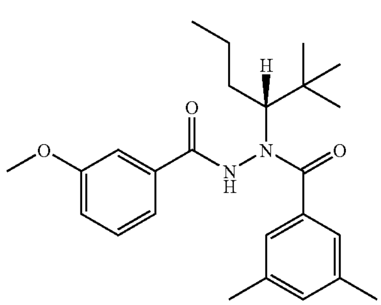 | >99 | (R)-3,5-Dimethyl-benzoic acid N-(1-tert-butyl-butyl)-N'-(3-methoxy-benzoyl)-hydrazide |

-continued

| Example | Structure | ee; % | Name |
|---|---|---|---|
| 10 | 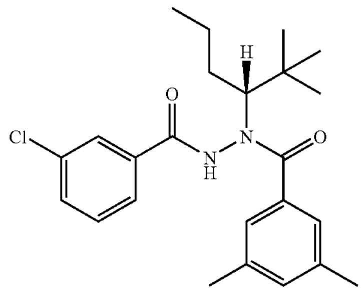 | >99 | (R)-3,5-Dimethyl-benzoic acid N-(1-tert-butyl-butyl)-N'-(3-chloro-benzoyl)-hydrazide |
| 11 | 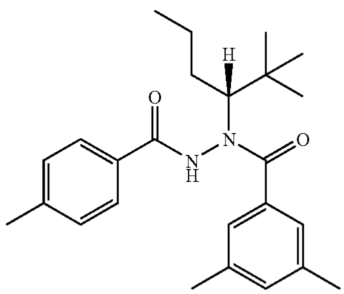 | >99 | (R)-3,5-Dimethyl-benzoic acid N-(1-tert-butyl-butyl)-N'-(4-methyl-benzoyl)-hydrazide |
| 12 | 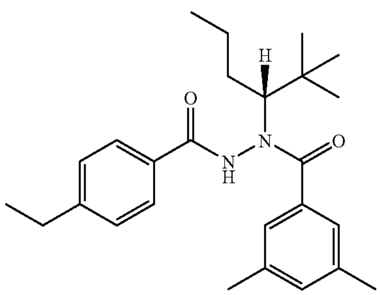 | >99 | (R)-3,5-Dimethyl-benzoic acid N-(1-tert-butyl-butyl)-N'-(4-ethyl-benzoyl)-hydrazide |
| 13 | 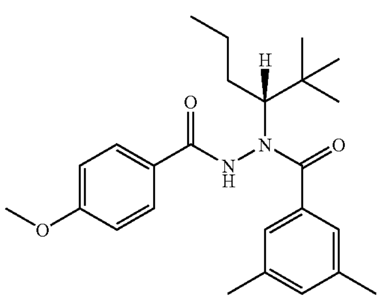 | >99 | (R)-3,5-Dimethyl-benzoic acid N-(1-tert-butyl-butyl)-N'-(4-methoxy-benzoyl)-hydrazide |
| 14 | 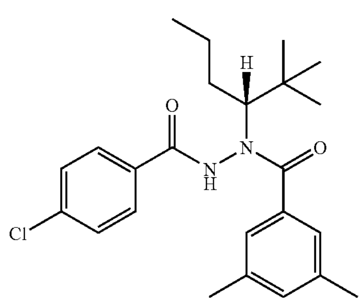 | >99 | (R)-3,5-Dimethyl-benzoic acid N-(1-tert-butyl-butyl)-N'-(4-chloro-benzoyl)-hydrazide |

-continued

| Example | Structure | ee; % | Name |
|---|---|---|---|
| 15 | 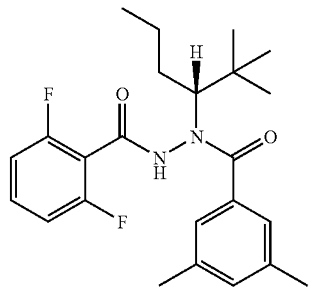 | >99 | (R)-3,5-Dimethyl-benzoic acid N-(1-tert-butyl-butyl)-N'-(2,6-difluoro-benzoyl)-hydrazide |
| 16 | 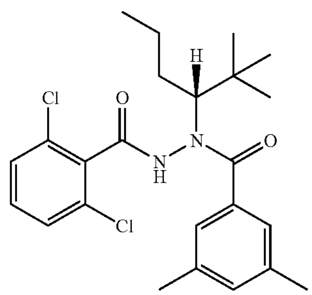 | >99 | (R)-3,5-Dimethyl-benzoic acid N-(1-tert-butyl-butyl)-N'-(2,6-dichloro-benzoyl)-hydrazide |
| 17 | 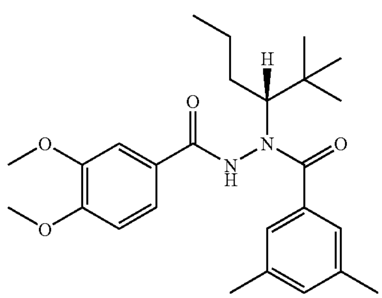 | >99 | (R)-3,5-Dimethyl-benzoic acid N-(1-tert-butyl-butyl)-N'-(3,4-dimethoxy-benzoyl)-hydrazide |
| 18 | 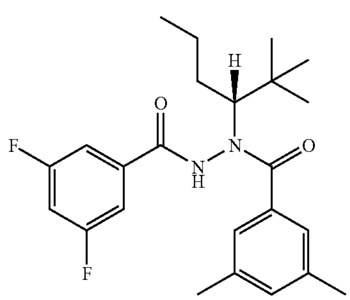 | >98 | (R)-3,5-Dimethyl-benzoic acid N-(1-tert-butyl-butyl)-N'-(3,5-difluoro-benzoyl)-hydrazide |
| 19 | 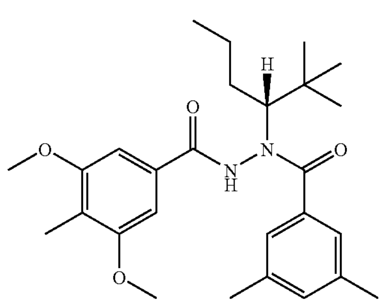 | >99 | (R)-3,5-Dimethyl-benzoic acid N-(1-tert-butyl-butyl)-N'-(3,5-dimethoxy-4-methyl-benzoyl)-hydrazide |

-continued

| Example | Structure | ee; % | Name |
|---|---|---|---|
| 20 | 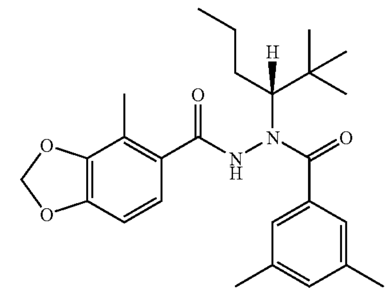 | 97 | (R)-3,5-Dimethyl-benzoic acid N-(1-tert-butyl-butyl)-N'-(4-methyl-benzo[1,3]dioxole-5-carbonyl)-hydrazide |
| 21 | 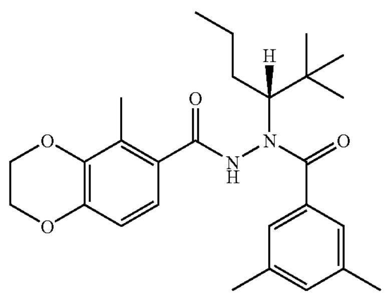 | >99 | (R)-3,5-Dimethyl-benzoic acid N-(1-tert-butyl-butyl)-N'-(5-methyl-2,3-dihydro-benzo[1,4]dioxine-6-carbonyl)-hydrazide |
| 22 | 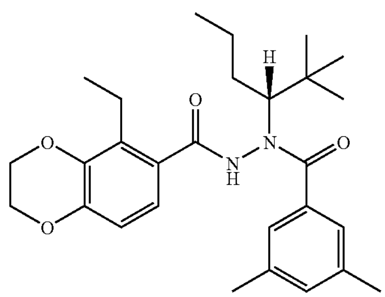 | >99 | (R)-3,5-Dimethyl-benzoic acid N-(1-tert-butyl-butyl)-N'-(5-ethyl-2,3-dihydro-benzo[1,4]dioxine-6-carbonyl)-hydrazide |
| 23 | 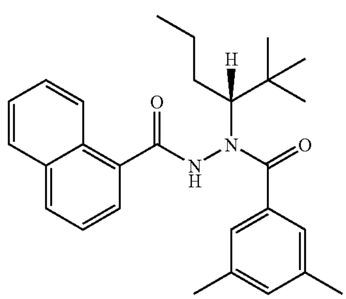 | >99 | (R)-3,5-Dimethyl-benzoic acid N-(1-tert-butyl-butyl)-N'-(naphthalene-1-carbonyl)-hydrazide |
| 24 | 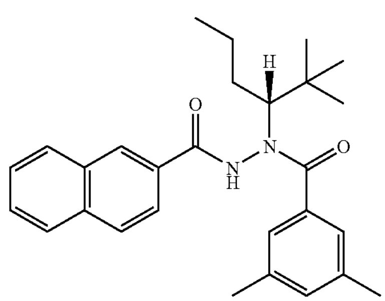 | >99 | (R)-3,5-Dimethyl-benzoic acid N-(1-tert-butyl-butyl)-N'-(naphthalene-2-carbonyl)-hydrazide |

-continued

| Example | Structure | ee; % | Name |
|---|---|---|---|
| 25 | 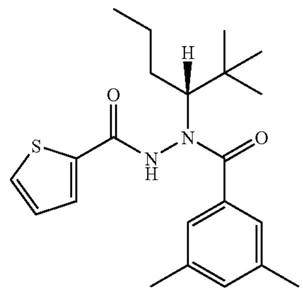 | >99 | (R)-3,5-Dimethyl-benzoic acid N-(1-tert-butyl-butyl)-N'-(thiophene-2-carbonyl)-hydrazide |
| 26 | 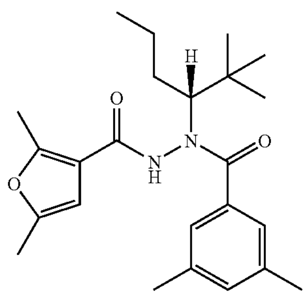 | >99 | (R)-3,5-Dimethyl-benzoic acid N-(1-tert-butyl-butyl)-N'-(2,5-dimethyl-furan-3-carbonyl)-hydrazide |
| 27 | 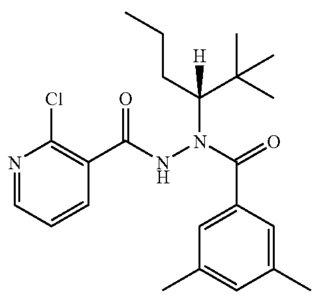 | >99 | (R)-3,5-Dimethyl-benzoic acid N-(1-tert-butyl-butyl)-N'-(2-chloro-pyridine-3-carbonyl)-hydrazide |
| 28 | 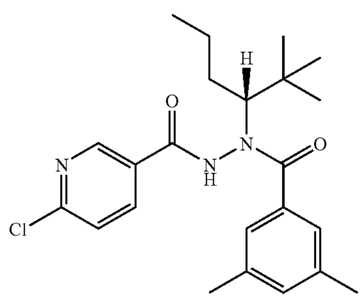 | >99 | (R)-3,5-Dimethyl-benzoic acid N-(1-tert-butyl-butyl)-N'-(6-chloro-pyridine-3-carbonyl)-hydrazide |
| 29 | 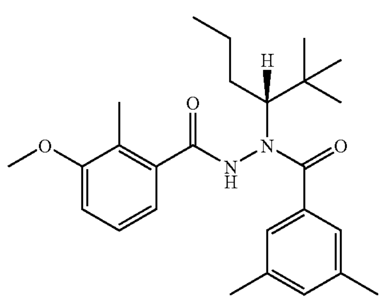 | >99 | (R)-3,5-Dimethyl-benzoic acid N-(1-tert-butyl-butyl)-N'-(3-methoxy-2-methyl-benzoyl)-hydrazide |

TABLE 2

| | Analytical Data | | |
|---|---|---|---|
| Example | $^1$H NMR (solvent) | MS | MP; °C |
| 2 | (CDCl$_3$) δ 7.88-7.0 (m, 8H), 4.75 + 3.69 (2d, 1H), 2.4 + 2.28 (2s, 6H), 2.0-1.3 (mm, 4H), 1.15 + 1.02 (2s, 9H), 0.94 (m, 3H) ppm | [M + H]$^+$ 381.2533, [M + Na]$^+$ 403.2351 | 66-68 |
| 3 | (CDCl$_3$) δ 7.62-6.77 (m, 7H), 4.75 + 3.72 (2d, 1H), 2.34 + 2.33 (2s, 6H), 2.02 (s, 3H), 1.85-1.42 (mm, 4H), 1.19 + 1.14 (2s, 9H), 1.01 (m, 3H) ppm | [M + H]$^+$ 395.2685, [M + Na]$^+$ 417.2507 | 137-138 |
| 4 | (DMSO-d$_6$) δ 10.07 + 9.98 (2s, NH), 7.73-6.63 (m, 7H), 4.54 + 4.39 (2d, 1H), 3.91 + 3.77 (2s, 3H), 2.36 + 2.28 (2s, 6H), 1.77-1.25 (mm, 4H), 1.1 + 0.98 (2s, 9H), 0.87 (m, 3H) ppm | [M + H]$^+$ 411.2637, [M + Na]$^+$ 433.2459 | |
| 5 | (DMSO-d$_6$) δ 10.48 + 10.35 (2s, NH), 7.61-6.68 (m, 7H), 4.52 + 4.37 (2d, 1H), 2.25 (s, 6H), 1.76-1.19 (mm, 4H), 1.02 + 0.83 (m, 12H) ppm | [M + H]$^+$ 399.2436, [M + Na]$^+$ 421.2253 | 114-116 |
| 6 | (CDCl$_3$) δ 7.84-6.6 (m, 7H), 4.74 + 3.72 (2d, 1H), 2.4 + 2.34 (2s, 6H), 1.97-1.44 (mm, 4H), 1.18 + 1.13 (2s, 9H), 0.99 (m, 3H) ppm | [M + H]$^+$ 415.2146, [M + Na]$^+$ 437.1962 | 138-140 |
| 7 | (DMSO-d$_6$) δ 10.47 + 10.37 (2s, NH), 7.62-6.13 (m, 7H), 4.52 + 4.35 (2d, 1H), 2.28 + 2.26 (2s, 6H), 1.79-1.38 (mm, 4H), 1.07 + 0.85 (m, 12H) ppm | [M + H]$^+$ 459.1637, [M + Na]$^+$ 481.1453 | 145-147 |
| 8 | (CDCl$_3$) δ 7.72-7.09 (m, 7H), 4.74 + 3.68 (2d, 1H), 2.4 + 2.38 (2s, 6H), 2.29 (s, 3H), 2.0-1.45 (mm, 4H), 1.31 + 1.15 (2s, 9H), 1.02 (m, 3H) ppm | [M + H]$^+$ 395.2685, [M + Na]$^+$ 417.2503 | 158-159 |
| 9 | (DMSO-d$_6$) δ 10.3 + 10.12 (2s, NH), 7.48-6.8 (m, 7H), 4.57 + 4.41 (2d, 1H), 3.86 + 3.77 (2s, 3H), 2.35 + 2.25 (2s, 6H), 1.78-1.29 (mm, 4H), 1.08 + 1.04 (2s, 9H), 0.98-0.88 (m, 3H) ppm | [M + H]$^+$ 411.2637, [M + Na]$^+$ 433.2456 | 110-111 |
| 10 | (CDCl$_3$) δ 7.83-7.07 (m, 7H), 4.74 + 3.69 (2d, 1H), 2.4 + 2.31 (2s, 6H), 2.0-1.45 (mm, 4H), 1.15 + 1.09 (2s, 9H), 1.02-0.94 (m, 3H) ppm | [M + H]$^+$ 415.2148, [M + Na]$^+$ 437.1963 | 163-164 |
| 11 | (CDCl$_3$) δ 8.08-7.08 (m, 7H), 4.74 + 3.68 (2d, 1H), 2.46 + 2.40 (2s, 6H), 2.34 + 2.28 (2s, 3H), 1.74-1.31 (mm, 4H), 1.15 + 1.02 (2s, 9H), 0.95 (m, 3H) ppm | [M + H]$^+$ 395.2687, [M + Na]$^+$ 417.2511 | 60-62 |
| 12 | (DMSO-d$_6$) δ 10.21 + 10.04 (NH, 2s) d 7.78-6.93 (m, 7H), 4.54 + 4.39 (2d, 1H), 2.60 (m, 2H), 2.32 + 2.21 (2s, 6H), 1.84-1.21 (mm, 4H), 1.15 (t, 3H), 1.05-0.84 (m, 12H) ppm | [M + H]$^+$ 409.2844, [M + Na]$^+$ 431.2670 | 111-112 |
| 13 | (DMSO-d$_6$) δ 10.16 + 9.98 (2s, NH), 7.88-6.97 (m, 7H), 4.57 + 4.41 (2d, 1H), 3.87 + 3.8 (2s, 3H), 2.35 + 2.24 (2s, 6H), 2.02-1.21 (mm, 4H), 1.08 + 1.02 (2s, 9H), 0.93-0.86 (m, 3H) ppm | [M + H]$^+$ 411.2640, [M + Na]$^+$ 433.2458 | 65-67 |
| 14 | (CDCl$_3$) δ 8.38-7.06 (m, 7H), 4.74 + 3.7 (2d, 1H), 2.41 + 2.28 (2s, 6H), 1.65-1.31 (mm, 4H), 1.14 + 1.02 (2s, 9H), 0.93 (m, 3H) ppm | [M + H]$^+$ 415.2136, [M + Na]$^+$ 437.1961 | 87-89 |
| 15 | (DMSO-d$_6$) δ 10.62 + 10.54 (NH, 2s) d 7.45-6.96 (m, 6H), 4.50 + 4.35 (2d, 1H), 2.29 + 2.22 (2s, 6H), 1.70-1.15 (mm, 4H), 1.0-0.80 (m, 12H) ppm | [M + H]$^+$ 417.2335, [M + Na]$^+$ 439.2160 | 180-182 |
| 16 | (DMSO-d$_6$) δ 10.53 (s, 1H), 7.53-7.35 (m, 3H), 7.08 (s, 2H), 7.03 (s, 1H), 4.64 (d, 1H), 2.31 + 2.28 (2s, 6H), 1.89-1.42 (mm, 4H), 1.06 (s, 9H), 0.93-0.86 (m, 3H) ppm | [M + H]$^+$ 449.1730, [M + Na]$^+$ 471.1546 | 185-187 |
| 17 | (DMSO-d$_6$) δ 10.08 + 9.89 (NH, 2s) d 7.75-6.87 (m, 6H), 4.53 + 4.38 (2d, 1H), 3.88 + 3.72 (m, 6H), 2.32-2.21 (m, 6H), 1.81-1.21 (mm, 4H), 1.05-0.82 (m, 12H) ppm | [M + H]$^+$ 441.2732, [M + Na]$^+$ 463.2545 | 121-123 |
| 18 | (DMSO-d$_6$) δ 10.40 + 10.21 (NH, 2s) d 7.57-6.97 (m, 6H), 4.53 + 4.38 (2d, 1H), 2.31 + 2.22 (2s, 6H), 1.71-1.24 (mm, 4H), 1.03 + 0.99 (2s, 9H), 0.88-0.76 (m, 3H) ppm | [M + H]$^+$ 417.2337, [M + Na]$^+$ 439.2155 | 192-194 |

TABLE 2-continued

| | Analytical Data | | |
|---|---|---|---|
| Example | $^1$H NMR (solvent) | MS | MP; ° C. |
| 19 | (DMSO-d$_6$) δ 10.16 + 9.98 (2s, 1H), 7.37-6.51 (m, 5H), 4.58 + 4.41 (2d, 1H), 3.91 + 3.86 (2s, 3H), 3.78 (s, 3H), 2.36 + 2.26 + 2.13 + 2.10 (4s, 6H), 2.00 (s, 3H), 1.80 + 1.30 (m, 4H), 1.09 + 1.06 (2s, 9H), 0.99 + 0.89 (2t, 3H) ppm | [M + H]$^+$ 455.2913, [M + Na]$^+$ 477.2728 | |
| 20 | (CDCl3) δ 7.26-6.43 (m, 5H), 6.06 + 5.99 (2s, 2H), 4.72 + 4.60 (2d, 1H), 2.45-2.32 (m, 6H), 1.88 (s, 3H), 1.99-1.44 (m, 4H), 1.17-0.97 (m, 12H) ppm | [M + H]$^+$ 439.2609, [M + Na]$^+$ 461.2407 | |
| 21 | (DMSO-d$_6$) δ 10.25 + 10.10 (s, 1H), 7.13 (s, 2H), 7.05 (s, 1H), 6.70 (d, 1H), 6.45 + 6.36 (2d, 1H), 4.56 + 4.36 (2d, 1H), 4.22-3.53 (mm, 4H), 2.28 (s, 6H), 1.80-1.37 (mm, 4H), 1.65 + 1.58 (2s, 3H), 1.06 (s, 9H), 0.96 + 0.88 (2t, 3H) ppm | | 70 |
| 22 | (CDCl$_3$) δ 7.08-6.22 (m, 5H), 4.74 + 3.69 (2d, 1H), 4.3-4.13 (m, 4H), 2.39 + 2.34 (2s, 6H), 2.14-1.95 (m, 2H), 1.44-1.29 (mm, 4H), 1.18 + 1.12 (2s, 9H), 1.0 (m, 6H) ppm | [M + H]$^+$ 467.2905, [M + Na]$^+$ 489.2721 | 128-129 |
| 23 | (CDCl$_3$) δ 9.2-7.08 (m, 10H), 4.81 + 3.76 (2d, 1H), 2.42 + 2.32 (2s, 6H), 2.08-1.45 (mm, 4H), 1.25-1.02 (m, 12H) ppm | [M + H]$^+$ 431.2691, [M + Na]$^+$ 453.2512 | 173-174 |
| 24 | (CDCl$_3$) δ 8.43-6.94 (m, 10H), 4.78 + 3.73 (2d, 1H), 2.41 + 2.29 (2s, 6H), 2.03-1.31 (mm, 4H), 1.18-0.94 (m, 12H) ppm | [M + H]$^+$ 431.2752, [M + Na]$^+$ 453.2512 | 91(glass)-134 |
| 25 | (DMSO-d$_6$) δ 10.25 + 10.08 (2s, 1H), 7.95-6.91 (m, 6H), 4.58 + 4.39 (2dd, 1H), 2.31 + 2.24 (2s, 6H), 1.90-1.25 (m, 4H), 1.08 + 1.01 (2s, 9H), 0.96-0.84 (m, 3H) ppm | [M + H]$^+$ 387.2104, [M + Na]$^+$ 409.1923 | |
| 26 | (DMSO-d$_6$) δ 9.78 + 9.56, 7.14 + 7.08 (2s, 1H), 7.03 + 6.98 (2s, 1H), 6.29 + 2.24 (2s, 1H), 4.53 + 4.37 (2d, 1H), 2.25 (s, 6H), 2.21 + 2.17 (2s, 6H), 1.78-1.23 (m, 4H), 1.05 + 1.00 (2s, 9H), 0.98 + 0.86 (2t, 3H) ppm | [M + H]$^+$ 399.2644 | |
| 27 | (DMSO-d$_6$) δ 10.59 + 10.51 (2s, 1H), 8.48 (dd, 1H), 7.45 (dd, 1H), 7.13 (s, 2H), 7.04 (s, 1H), 6.73 (dd, 1H), 6.62 (dd, 1H), 4.56 + 4.41 (2d, 1H), 2.30 (s, 6H), 1.79-1.27 (m, 4H), 1.09 + 1.05 (2s, 9H), 0.97 + 0.91 (2t, 3H) ppm | [M + H]$^+$ 416.2103, [M + Na]$^+$ 438.1922 | |
| 28 | (DMSO-d$_6$) δ 10.54 + 10.38 (2s, 1H), 8.39-7.00 (m, 6H), 4.58 + 4.42 (2d, 1H), 2.25 (s, 6H), 1.86-1.30 (m, 4H), 1.08 + 1.04 (2s, 9H), 1.00 + 0.89 (2t, 3H) ppm | [M + H]$^+$ 416.2102, [M + Na]$^+$ 438.1924 | |
| 29 | (DMSO-d$_6$) δ 10.39 + 10.22 (2s, NH), 7.16-7.0 (m, 5H), 6.45 + 6.33 (2d, 1H), 4.57 + 4.39 (2d, 1H), 3.85 + 3.78 (2s, 3H), 2.36 + 2.29 (2s, 6H), 1.80-1.46 (mm, 4H), 1.09 + 1.06 (2s, 9H), 0.96-0.89 (m, 3H) ppm | [M + H]$^+$ 425.2804, [M + Na]$^+$ 447.2616 | 141-143 |

Example 30

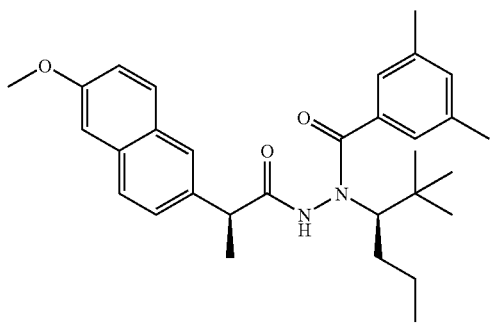

(R)-3,5-Dimethyl-benzoic acid N-(1-tert-butyl-butyl)-N'-(S)-[2-(6-methoxy-naphthalen-2-yl)-propionyl]-hydrazide Synthesis

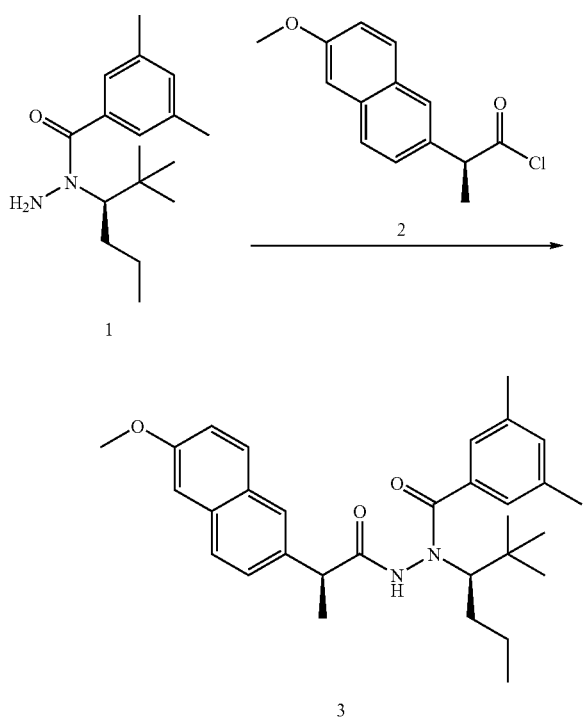

Compound 1: (R)-3,5-dimethyl-benzoic acid N-(1-tert-butyl-butyl)-hydrazide was prepared as described in Example 1.

Compound 2: Compound 2 was prepared from the corresponding carboxylic acid. Thionyl chloride (1.24 g, 10.42 mmoles) was added to a solution of (S)-(+)-2-(6-methoxy-naphthalen-2-yl)-propionic acid (Naproxen, 2 g, 8.69 mmoles) in 8.2 mL chloroform in a round bottom flask equipped with magnetic stirring. A drop of DMF was added and the mixture was refluxed for 3 hours. Chloroform and excess thionyl chloride were distilled from the reaction mixture while methylene chloride was added. Evaporation of residual solvent yielded (S)-2-(6-methoxy-naphthalen-2-yl)-propionyl chloride (1.918 g, 88.8% yield). $R_f$=0.2 (1:1 hexanes:ethyl ether). $^1$H NMR (400 MHz, CDCl$_3$) δ 9.98 (br, 1H), 7.78 (t, 2H), 7.36 (d, 1H), 7.18 (d, 1H), 7.14 (m, 2H), 4.25 (q, 1H), 3.93 (s, 3H), 1.68 (d, 3H).

Compound 3 (title compound): (R)-3,5-Dimethyl-benzoic acid N-(1-tert-butyl-butyl)-hydrazide (e.e estimated at >99% based on precursor, 1.1 g, 3.98 mmoles) was dissolved in 10 mL methylene chloride. Aqueous K$_2$CO$_3$ solution (0.907 g, 6.57 mmoles in 2.5 mL) was added to the reaction mixture. (S)-2-(6-methoxy-naphthalen-2-yl)-propionyl chloride (1.09 g, 4.38 mmoles) was added and the reaction was stirred for 24 hours and monitored by TLC. Additional methylene chloride and water were added as needed to aid manipulation. The organic layer was separated, dried over Na$_2$SO$_4$, filtered, and solvent was removed in vacuo to provide crude product: mp=98° C. (glass)-123° C. The crude material was triturated thrice with 2:1 hexanes:ether to provide 1.554 g, 80.1% yield of (R)-3,5-dimethyl-benzoic acid N-(1-tert-butyl-butyl)-N'-(S)-[2-(6-methoxy-naphthalen-2-yl)-propionyl]-hydrazide, mp=98° C. (glass)-122° C. The triturated material was crystallized from isopropanol at 35° C. to give crystalline product. $^1$H NMR spectra of all three lots were identical. $R_f$=0.15 (1:1 hexanes:ethyl ether); mp=158-160° C. (heating commenced at 150° C.); mp=156-164° C. (heating commenced at 25° C.); $[\alpha]^{25}_{589}$ +95.8° (c 2.02, CH$_3$OH); $^1$H NMR (400 MHz, DMSO-d$_6$) δ 9.96+9.82 (NH, 2 s), 7.71+7.58 (2H, 2 d), 7.63 (1H, s), 7.49+7.31 (1H, 2 d), 7.26 (1H, s), 7.13+6.77 (1H, 2 d), 7.06 (2H, s), 6.68+6.30 (1H, 2 s), 4.31 (m, 1H), 3.88+3.85 (3H, 2 s), 3.58 (1H, m), 2.30+1.83 (6H, 2 s), 1.64-1.03 (4H, m), 1.00 (3H, m), 0.87+0.84 (9H, 2 s), 0.63 (3H, t); $^{13}$C NMR (100 MHz, CDCl$_3$) δ 173.9, 172.2, 157.8, 137.3, 133.7, 130.8, 129.1, 128.8, 127.4, 125.9, 125.8, 123.7, 123.3, 119.2, 119.1, 105.5, 62.7, 55.3, 45.1, 35.0, 28.5, 27.6, 26.9, 21.2, 17.5, 14.2; HRMS (ESI) m/z calcd for C$_{31}$H$_{39}$N$_2$O$_3$ [M−H]$^−$ 487.2966, found 487.2949, calcd for C$_{31}$H$_{40}$ClN$_2$O$_3$ [M+Cl]$^−$ 523.2733, found 523.2718, Anal. Calcd for C$_{31}$H$_{40}$N$_2$O$_3$: C, 76.19; H, 8.25; N, 5.73; 0, 9.8. Found: C, 76.01; H, 8.35; N, 5.70.

In order to determine the stereochemical course of the asymmetric allylation reaction in Example 1, the x-ray crystal structure of (R)-3,5-dimethyl-benzoic acid N-(1-tert-butyl-butyl)-N'-(S)-[2-(6-methoxy-naphthalen-2-yl)-propionyl]-hydrazide was determined. This experiment established the absolute configuration of the carbon bearing the tert-butyl group and n-propyl group is R.

Example 31

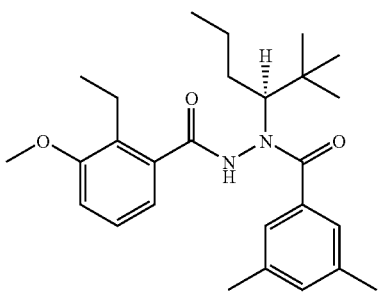

(S)-3,5-Dimethyl-benzoic acid N-(1-tert-butyl-butyl)-N'-(2-ethyl-3-methoxy-benzoyl)-hydrazide Synthesis

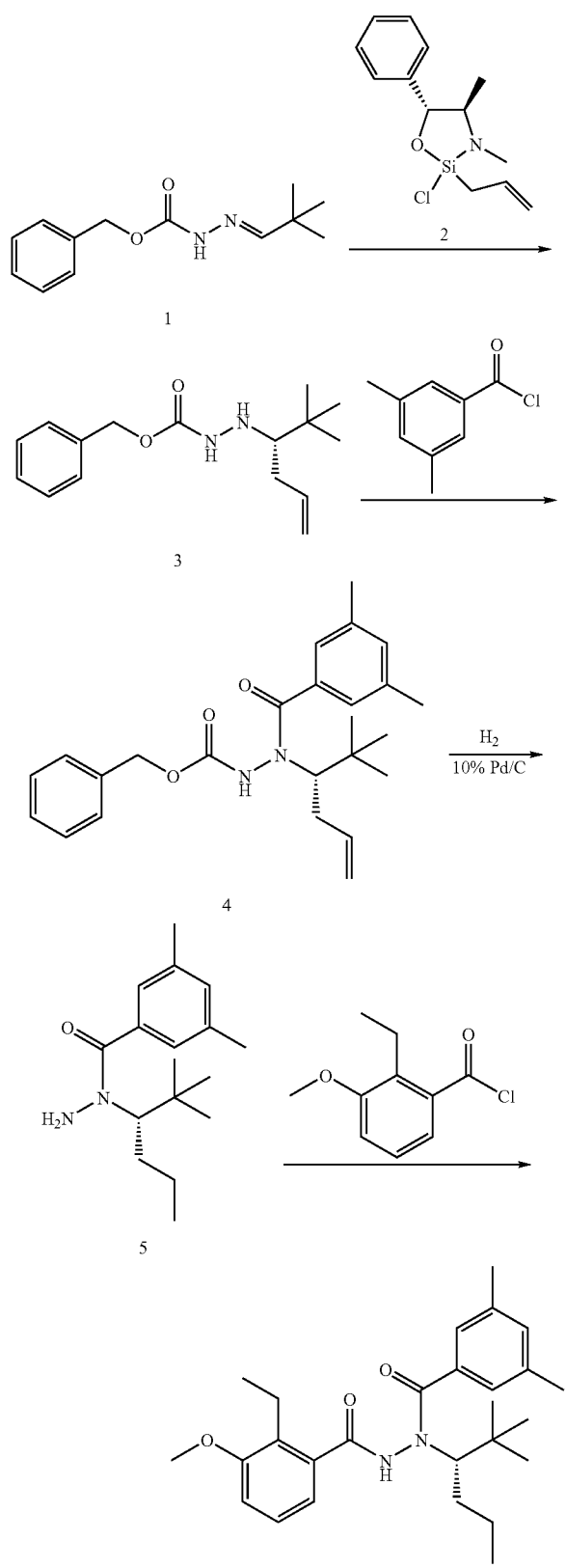

Compound 1: (E)-N'-(2,2-dimethyl-propylidene)-hydrazinecarboxylic acid benzyl ester was prepared as described in Example 1.

Compound 2: (R,R)-2-allyl-2-chloro-3,4-dimethyl-5-phenyl-[1,3,2]oxazasilolidine was prepared using methodology described in Example 1 using R,R-pseudephedrine.

Compound 3: (S)—N'-(1-tert-butyl-but-3-enyl)-hydrazinecarboxylic acid benzyl ester was prepared using methodology described in Example 1. Analytical data: $R_f$=0.46 (2:1 hexanes:ethyl acetate); mp=69-71° C.; $^1$H NMR (400 MHz, CDCl$_3$) δ 7.4 (br s, 5H), 6.2 (br s, 1H), 6.0 (br s, 1H), 5.15 (s, 2H), 5.1 (s, 2H), 4.1 (br, 1H), 2.7 (m, 1H), 2.4 (br d, 1H), 2.0 (m, 1H), 0.95 (s, 9H); ee=98.2%, ADH column; $[\alpha]^{25}_{589}$ +39.30 (c=2.03, CHCl$_3$).

Compound 4: (S)—N'-(1-tert-butyl-but-3-enyl)-N'-(3,5-dimethyl-benzoyl)-hydrazine carboxylic acid benzyl ester was prepared using methodology described in Example 1. Analytical data: $R_f$=0.43 (2:1 hexane:ethyl acetate); mp=150-151.5° C.; $^1$H NMR (400 MHz, CDCl$_3$) δ 7.45-6.88 (m, 7H), 6.44+6.28 (2 s, 1H), 5.96 (br, 1H), 5.38-4.68 (m, 5H), 3.69 (br, 1H), 2.68-2.43 (m, 2H), 2.36+2.29 (2 s, 6H), 1.13+1.02+0.94 (3 s, 9H); $[\alpha]^{25}_{589}$ +12.5° (c=2.01, CHCl$_3$).

Compound 5: (S)-3,5-dimethyl-benzoic acid N-(1-tert-butyl-butyl)-hydrazide was prepared using methodology described in Example 1. Analytical data: $R_f$=0.5 (1:1 hexanes:ethyl acetate); mp=112-112.8° C.; $^1$H NMR (400 MHz, CDCl$_3$) δ 7.05 (s, 1H), 7.02 (s, 2H), 4.6+3.5 (2d, 1H), 2.38+2.37 (2 s, 6H), 1.2-2.1 (m, 4H), 1.1+1.0 (2 s, 9H), 1.05+0.98 (2 t, 3H) 2 distinct conformers; $[\alpha]^{25}_{589}$ −7.97 (c 2.14, CH$_3$OH).

Compound 6 (title compound): (S)-3,5-Dimethyl-benzoic acid N-(1-tert-butyl-butyl)-N'-(2-ethyl-3-methoxy-benzoyl)-hydrazide was prepared using methodology described in Example 1. Analytical data: $R_f$=0.28 (1:1 hexanes:ethyl acetate); mp=156.5-157.5° C.; $[\alpha]^{25}_{589}$ −13.39° (c 2.05, CH$_3$OH); $^1$H NMR (400 MHz, DMSO-d$_6$) δ 10.4+10.26 (s, 1H), 7.18-7.14 (m, 3H), 7.08 (d, J=7.2 Hz, 1H), 7.03 (t, J=8.4 Hz, 1H), 6.34+6.21 (d, J=6.8 Hz, 1H), 4.57+4.38 (d, J=8.4 Hz, 1H), 3.78 (s, 3H), 2.29 (s, 6H), 2.27-2.23 (m, 1H), 1.89-1.79 (m, 2H), 1.59-1.38 (m, 3H), 1.09+1.06 (s, 9H), 0.95+0.87 (t, J=6.8 Hz, 6H); $^{13}$C NMR (100 MHz, DMSO-d$_6$) δ 173.40, 168.24, 157.64, 137.18, 136.98, 136.50, 130.89, 130.73, 130.20, 126.96, 125.28, 124.83, 119.37, 118.95, 112.41, 62.29, 56.11, 35.45, 28.71, 27.56, 21.24, 20.15, 15.15, 14.68; HRMS (ESI) m/z, calcd for C$_{27}$H$_{39}$N$_2$O$_3$ [M+H]$^+$ 439.2955, found 439.295, calcd for C$_{27}$H$_{38}$NaN$_2$O$_3$ [M+Na]$^+$ 461.2774, found 461.2765; Anal. Calcd for C$_{27}$H$_{38}$N$_2$O$_3$: C, 73.94; H, 8.73; N, 6.39; O, 10.94. Found: C, 73.87; H, 8.94; N, 6.38; ee: >99.9%; Regis (S,S) ULMO, 98:2 mixture of hexanes:methanol at a flow rate of 1 mL/min.

Examples 32 to 47 were prepared using methodology described in Example 31. The percent enantiomeric excess (ee) was determined by chiral HPLC.

| Example | Structure | % ee | Name |
|---|---|---|---|
| 32 | 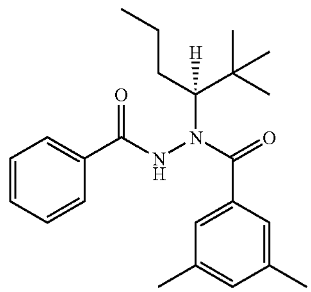 | >99 | (S)-(3,5-Dimethyl-benzoic acid N'-benzoyl-N-(1-tert-butyl-butyl)-hydrazide |
| 33 | 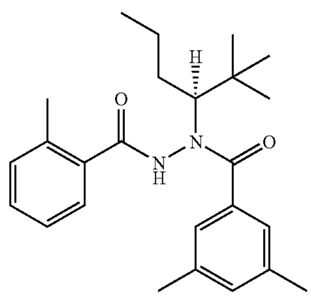 | >99 | (S)-3,5-Dimethyl-benzoic acid N-(1-tert-butyl-butyl)-N'-(2-methyl-benzoyl)-hydrazide |
| 34 | | >99 | (S)-3,5-Dimethyl-benzoic acid N-(1-tert-butyl-butyl)-N'-(2-fluoro-benzoyl)-hydrazide |
| 34 | | >99 | (S)-3,5-Dimethyl-benzoic acid N-(1-tert-butyl-butyl)-N'-(2-chloro-benzoyl)-hydrazide |
| 36 | 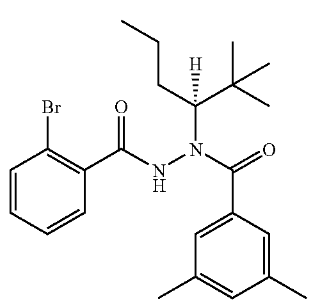 | >99 | (S)-3,5-Dimethyl-benzoic acid N'-(2-bromo-benzoyl)-N-(1-tert-butyl-butyl)-hydrazide |

| 37 | 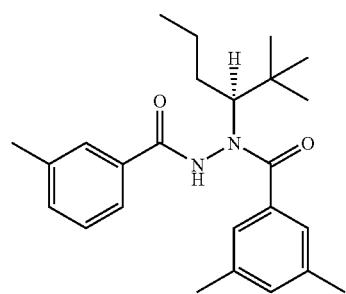 | >99 | (S)-3,5-Dimethyl-benzoic acid N-(1-tert-butyl-butyl)-N'-(3-methyl-benzoyl)-hydrazide |
| --- | --- | --- | --- |
| 38 | 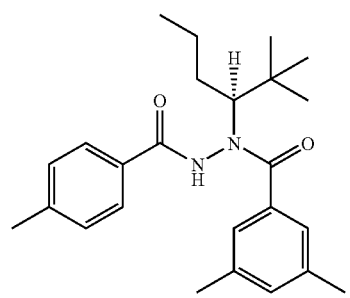 | >99 | (S)-3,5-Dimethyl-benzoic acid N-(1-tert-butyl-butyl)-N'-(4-methyl-benzoyl)-hydrazide |
| 39 | 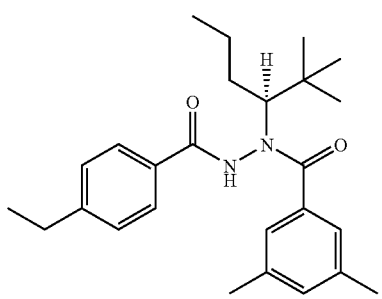 | >99 | (S)-3,5-Dimethyl-benzoic acid N-(1-tert-butyl-butyl)-N'-(4-ethyl-benzoyl)-hydrazide |
| 40 | 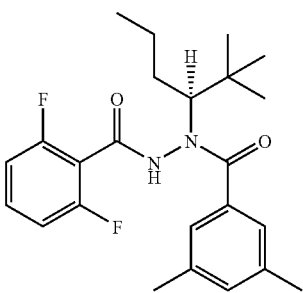 | >99 | (S)-3,5-Dimethyl-benzoic acid N-(1-tert-butyl-butyl)-N'-(2,6-difluoro-benzoyl)-hydrazide |
| 41 | 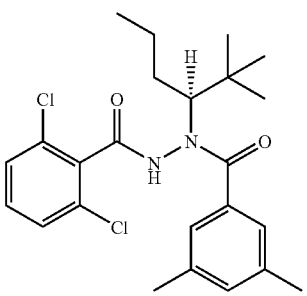 | >99 | (S)-3,5-Dimethyl-benzoic acid N-(1-tert-butyl-butyl)-N'-(2,6-dichloro-benzoyl)-hydrazide |

| 42 | 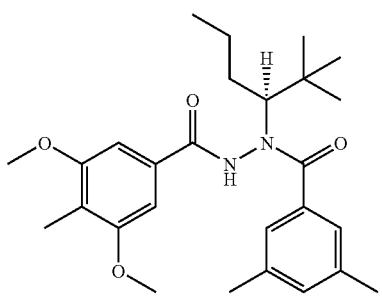 | >99 | (S)-3,5-Dimethyl-benzoic acid N-(1-tert-butyl-butyl)-N'-(3,5-dimethoxy-4-methyl-benzoyl)-hydrazide |
| 43 | 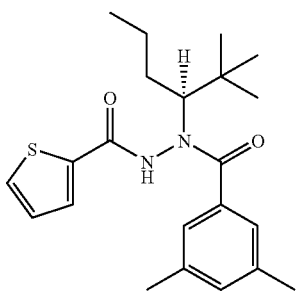 | >99 | (S)-3,5-Dimethyl-benzoic acid N-(1-tert-butyl-butyl)-N'-(thiophene-2-carbonyl)-hydrazide |
| 44 | 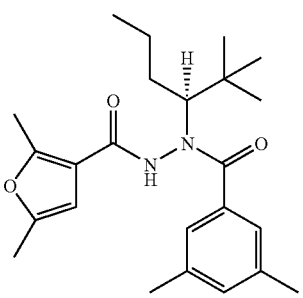 | >99 | (S)-3,5-Dimethyl-benzoic acid N-(1-tert-butyl-butyl)-N'-(2,5-dimethyl-furan-3-carbonyl)-hydrazide |
| 45 | 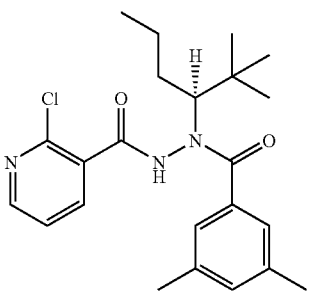 | >99 | (S)-3,5-Dimethyl-benzoic acid N-(1-tert-butyl-butyl)-N'-(2-chloro-pyridine-3-carbonyl)-hydrazide |
| 46 | 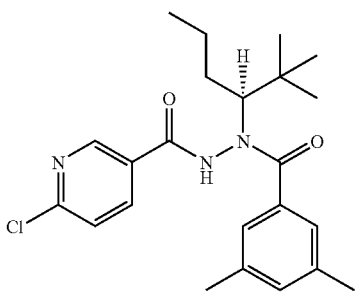 | >99 | (S)-3,5-Dimethyl-benzoic acid N-(1-tert-butyl-butyl)-N'-(6-chloro-pyridine-3-carbonyl)-hydrazide |

| 47 | 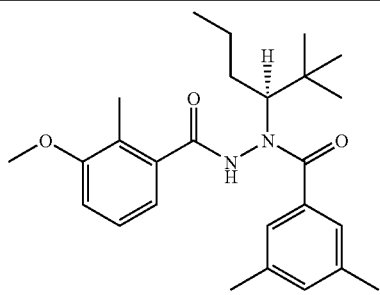 | >99 | (S)-3,5-Dimethyl-benzoic acid N-(1-tert-butyl-butyl)-N'-(3-methoxy-2-methyl-benzoyl)-hydrazide |

Example 48

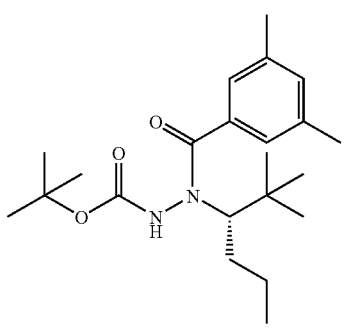

(S)-N'-(1-tert-Butyl-butyl)-N'-(3,5-dimethyl-benzoyl)-hydrazinecarboxylic acid tert-butyl ester Synthesis

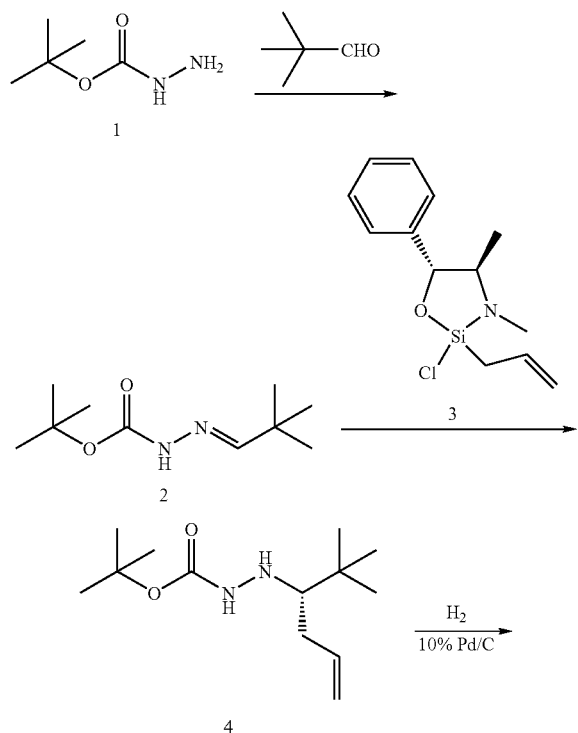

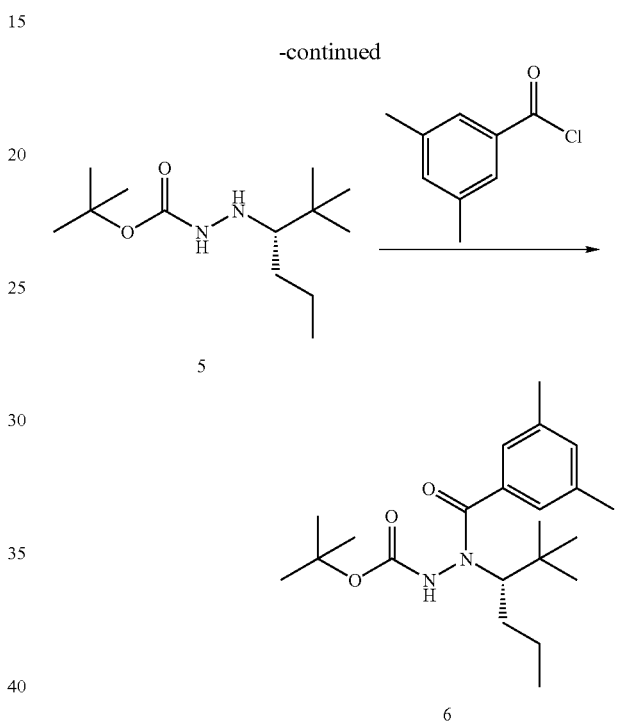

Compound 1: t-Butyl carbazate is commercially available.

Compound 2: Pivaldehyde (52.1 g, 454 mmoles, ca. 75% solution in t-butanol) was dissolved in 120 mL methanol in a 1 L, 3-necked round bottom flask with reflux condenser, thermometer, and addition funnel. Glacial acetic acid (1 mL) was added followed by controlled addition of t-butyl carbazate (50 g, 378 mmoles), without removal of heat of the reaction. The mixture was stirred for 4 hours, while monitoring by TLC. Upon completion of the reaction, the solvent was removed in vacuo, the residue was taken up in pentane, and the pentane was evaporated. The resultant oil crystallized upon standing to provide N'-(2,2-dimethyl-propylidene)-hydrazinecarboxylic acid tert-butyl ester (75.7 g, 93%). $R_f$=0.42 (2:1 hexanes:ethyl acetate, 1% acetic acid); $^1$H NMR (400 MHz, CDCl$_3$) δ 7.6 (br s, 1H), 7.1 (s, 1H), 1.5 (s, 9H), 1.1 (s, 9H) ppm.

Compound 3: (R,R)-2-Allyl-2-chloro-3,4-dimethyl-5-phenyl-[1,3,2]oxazasilolidine was prepared using methodology described in Example 1 using R,R-pseudephedrine.

Compound 4: N'-(2,2-Dimethyl-propylidene)-hydrazinecarboxylic acid tert-butyl ester (12 g, 59.9 mmoles) was charged to a dried, 3-neck, 1 L round bottom flask with thermometer, magnetic stirrer, and nitrogen atmosphere. Anhydrous methylene chloride (200 mL) was charged to the flask using a catheter. The mixture was chilled to 0° C. with an ice bath. (R,R)-2-Allyl-2-chloro-3,4-dimethyl-5-phenyl-[1,3,2]oxazasilolidine (24.07 g, 89.87 mmoles) was subsequently added to the flask under inert conditions. Within minutes, the originally light yellow solution turned transparent dark yellow. The reaction was stirred for 6 hr at 0° C., then allowed to warm to room temperature, and stirred overnight, while being monitored by TLC. The reaction was quenched by adding ca. 25 mL methanol, resulting in a lightening of color. The solution was concentrated and the residue was diluted with 100 mL of ethyl acetate and 100 mL of water. The phases were separated and the aqueous layer was extracted with ethyl acetate twice. The organic phases were combined, washed with brine, dried over $Na_2SO_4$ and concentrated. The resulting oil was purified by column chromatography using 10% ethyl acetate in hexanes. Purified (S)—N'-(1-tert-butyl-but-3-enyl)-hydrazinecarboxylic acid tert-butyl ester was obtained as an oil (2.87 g, 24.4% yield). An impure fraction was also collected (3.17 g). $R_f$=0.44 (5:1 hexanes:ethyl acetate, 12 visualization); $^1$H NMR (400 MHz, $CDCl_3$) δ 6.07 (br, 1H, NH), 5.85 (m, 1H), 5.0 (dd, 2H), 2.6 (m, 1H), 2.33 (m, 1H), 2.3 (m, 1H), 1.4 (s, 9H), 0.9 (s, 9H).

Compound 5: (S)—N'-(1-tert-Butyl-but-3-enyl)-hydrazinecarboxylic acid tert-butyl ester (2.34 g, 9.65 mmoles) was dissolved in methanol (50 mL) in a Parr bottle. 10% Pd/C (70 mg) was added as a slurry in water (1.6 mL), and the mixture was shaken on a Parr hydrogenator for 4.5 h with a starting pressure of 55 psi. The pressure decrease was monitored as a measure of the reaction progress, indicating that the reaction was likely complete after 30 minutes. The catalyst was allowed to substantially settle, and the supernatant was removed with a pipette, passed through a 0.45 micron syringe filter, and analyzed by TLC. Solvent was removed in vacuo to yield 2.19 g (92.7%) of (S)—N'-(1-tert-butyl-butyl)-hydrazinecarboxylic acid tert-butyl ester as a faintly pale yellow oil. $R_f$=0.48 (5:1 hexanes:ethyl acetate, 12 visualization), $^1$H NMR (400 MHz, $CDCl_3$) □ 6.0 (br, 1H), 4.0 (br, 1H), 2.5 (d, 1H), 1.5 (s, 9H), 1.1 (m, 2H), 1.6 (br, 2H), 0.94 (s, 9H), 0.94 (t, 3H).

Compound 6 (title compound): (S)—N'-(1-tert-Butyl-butyl)-hydrazinecarboxylic acid tert-butyl ester (1 g, 4.09 mmoles) was dissolved in ca. 3 mL methylene chloride in a vial with a magnetic stir bar. A solution of 0.8 g $K_2CO_3$ (5.79 mmoles) in ca. 2 mL water was added, followed by 0.81 g (4.80 mmoles) 3,5-dimethylbenzoyl chloride. The reaction was stirred overnight, first on ice, and then allowed to warm to room temperature. Several mL each water and methylene chloride were then added to dissolve all solids. The aqueous layer was removed and the organic layer was dried over solid $MgSO_4$. TLC indicated that the reaction was ca. 95% complete. The mixture was filtered through some glass wool into a vial. Solvent was evaporated with a stream of $N_2$, chasing with 3:1 hexanes:ether and pentane. The residue was manipulated with a spatula to initiate crystallization, and after complete solidification, was triturated thrice with 2-3 mL pentane in a small fritted glass funnel. After drying in air, 300 mg (19.5%) (S)—N'-(1-tert-Butyl-butyl)-N'-(3,5-dimethyl-benzoyl)-hydrazinecarboxylic acid tert-butyl ester was obtained, indicated by TLC to be quite pure, chiral HPLC indicated e.e=93.3%. The product was dried in a vacuum oven at 50° C. for melting point determination. $R_f$=0.42 (4:1 hexanes:ethyl acetate, UV (strong), 12 (weak) visualization); mp=115.5-117.5° C.; $[\alpha]^{25}_{589}$ −30.18 (c 2.02, $CH_3OH$), $^1$H NMR (400 MHz, $CDCl_3$) δ 7.15-7.03 (m, 3H), 6.07+6.00 (s+d, 1H), 4.52+4.40 (2 dd, 1H), 2.32+2.28+2.23 (3 s, 6H), 1.85-0.89 (m, 25H).

Example 49

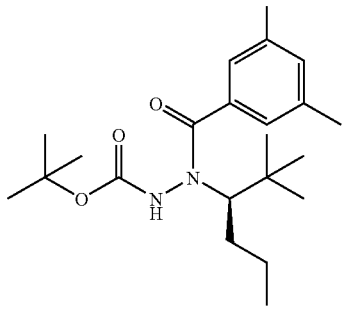

(R)-N'-(1-tert-Butyl-butyl)-N'-(3,5-dimethyl-benzoyl)-hydrazinecarboxylic acid tert-butyl ester

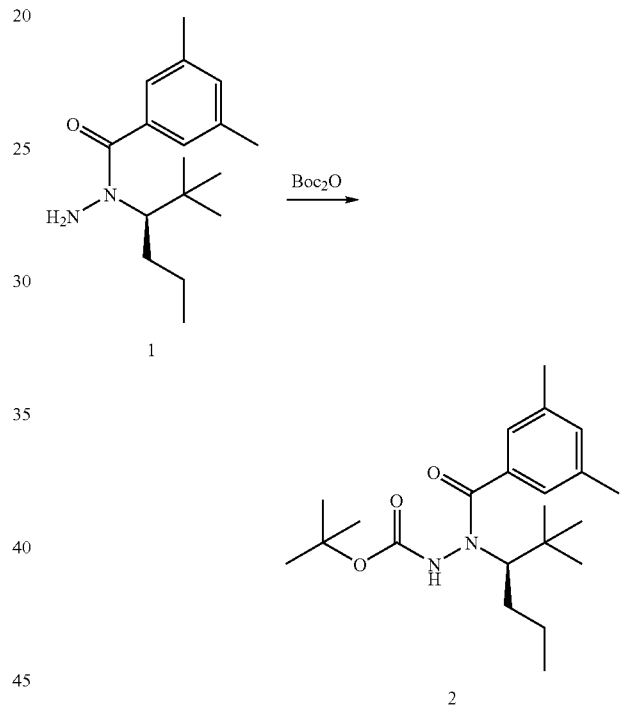

Compound 1: (R)—N'3,5-Dimethyl-benzoic acid N-(1-tert-butyl-but-3-enyl)-hydrazide was prepared as described in Example 1.

Compound 2 (title compound): To a solution of (R)-3,5-dimethyl-benzoic acid N-(1-tert-butyl-butyl)-hydrazide (400 mg, 1.44 mmol) in THF (10 mL) was added t-boc anhydride (629 mg, 2.88 mmol). The reaction was refluxed for 40 h, cooled, diluted with ether (20 mL), washed with $H_2O$, and dried over anhydrous $Na_2SO_4$. The solvent was evaporated in vacuo and the residue was purified by flash chromatography and thin layer chromatography to give (R)—N'-(1-tert-butyl-butyl)-N'-(3,5-dimethyl-benzoyl)-hydrazinecarboxylic acid tert-butyl ester (45.7 mg, yield 4.1%) as a white solid. $R_f$=0.39 (1:3 EtOAc:n-Hexane); $[\alpha]^{25}_{589}$ +26.25 (c 2.09, $CH_3OH$), $^1$H NMR (400 MHz, $CDCl_3$) δ 7.15-7.03 (m, 3H), 6.07+6.00 (2d, 1H), 4.59+4.50 (2 dd, 1H), 2.37+2.34 (2 s, 6H), 1.85-0.89 (m, 25H) ppm; HRMS (ESI) m/z calcd for $C_{22}H_{37}N_2O_3$ $[M+H]^+$ 377.2804, found 377.2795, calcd for $C_{22}H_{36}N_2NaO_3$ $[M+Na]^+$ 399.2624, found 399.2618.

Example 50

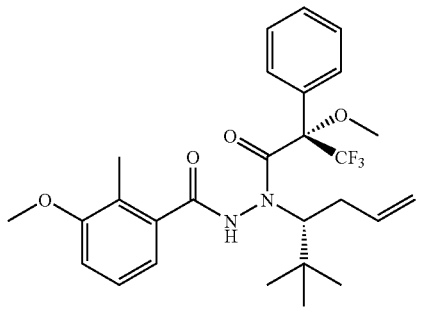

(R)-3-Methoxy-2-methyl-benzoic acid N'-(1-tert-butyl-but-3-enyl)-
N'-((S)-3,3,3-trifluoro-2-methoxy-2-phenyl-propionyl)-hydrazide Synthesis

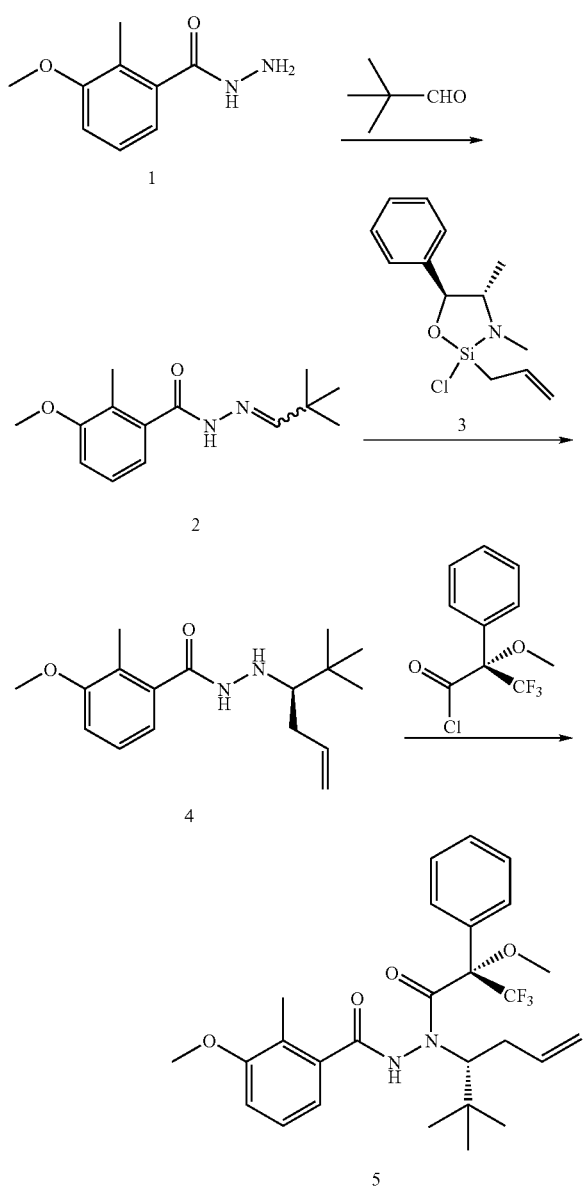

Compound 1: 3-Methoxy-2-methyl-benzoic acid hydrazide was prepared using methodology described in US 2005/0209283 A1.

Compound 2: Pivaldehyde (13.45 g, 156 mmoles) was dissolved in 300 mL methanol in a round bottom flask. 3-methoxy-2-methyl-benzoic acid hydrazide (26.6 g, 147.6 mmoles) and 150 drops glacial acetic acid were added, and the mixture was heated at reflux for ca. 8 hours, while monitoring by TLC. Upon completion of the reaction, the solvent was removed in vacuo, and the product was slurried in cold hexanes and filtered on a Büchner funnel to provide 24.4 g (66%) of 3-methoxy-2-methyl-benzoic acid (2,2-dimethyl-propylidene)-hydrazide. $R_f$=0.19, (2:1 hexanes:ethyl acetate); $^1$H NMR (400 MHz, DMSO-$d_6$) δ 7.42+7.41 (3 s, 1H), 7.1 (t, 1H), 6.9 (d, 1H), 6.82 (d, 1H), 3.78 (s, 3H), 2.2+2.1 (2 s, 3H), 1.07+1.0 (3 s, 9H), multiple conformations, possibly E/Z mixture.

Compound 3: (S,S)-2-Allyl-2-chloro-3,4-dimethyl-5-phenyl-[1,3,2]oxazasilolidine was prepared as described in Example 1.

Compound 4: 3-methoxy-2-methyl-benzoic acid (2,2-dimethyl-propylidene)-hydrazide (10.84 g, 43.31 mmol) was charged to a dried, 1 L round bottom flask kept under a nitrogen atmosphere. 350 mL anhydrous methylene chloride was added by catheter. The flask was cooled to about 5° C. in an ice bath. (S,S)-Allyl-2-chloro-3,4-dimethyl-5-phenyl-[1,3,2]oxazasilolidine (17.4 g, 65 mmol) was added by syringe. Within minutes, the originally light mixture turned a dark transparent yellow, and was left to stir under nitrogen at ca. 5° C. After 4 hr, TLC indicated a complete reaction. The reaction was quenched by adding ca. 25 mL methanol with gentle mixing. The dark color dissipated. The solution was concentrated and the residue was diluted with ethyl acetate (100 mL) and water (100 mL). The phases were separated and the aqueous layer was extracted with ethyl acetate (2×100 mL). The combined organic phases were washed once with brine, dried over MgSO$_4$, decanted, and concentrated to yield a deep yellow oil that crystallized upon standing (13.66 g, 72.4% yield). The crude material was crystallized from 4:1 hexanes:ethyl acetate, while separating from an insoluble powdery residue, possibly pseudoephedrine. After one crystallization, the purified material indicated an e.e of ca. 80%, favoring the R-isomer, as determined by Mosher analysis. After 3 crystallizations, 6.65 g of (R)-3-methoxy-2-methyl-benzoic acid N'-(1-tert-butyl-but-3-enyl)-hydrazide (35.2%), was recovered as a crystalline solid, but without further improvement in ee $R_f$=0.38 (2:1 hexanes:ethyl acetate); $^1$H NMR (400 MHz, CDCl$_3$) δ 7.22 (t, 1H), 7.11 (br s, 1H), 6.95 (d, 1H), 6.15 (m, 1H), 5.2 (d, 1H), 5.15 (d, 1H), 3.89 (s, 3H), 2.80 (d, 1H), 2.50 (dm, 1H), 2.33 (s, 3H), 2.2 (dt, 1H), 1.08 (s, 9H).

Compound 5 (title compound): (R)-3-methoxy-2-methyl-benzoic acid N'-(1-tert-butyl-but-3-enyl)-hydrazide (100 mg, 0.344 mmoles) and (R)-(+)-alpha-methyl-alpha-(trifluoromethyl)-phenylacetyl chloride (104 mg, 0.413 mmoles) were dissolved in 1.5 mL methylene chloride in a vial. A solution of K$_2$CO$_3$ (95 mg, 0.69 mmoles) in ca. 0.5 mL water was added, and the reaction mixture was stirred at room temperature overnight, and monitored by TLC. The phases were separated, adding additional methylene chloride and/or water as needed to aid manipulation. The methylene chloride layer was dried over MgSO$_4$ or Na$_2$SO$_4$, and solvent was removed in vacuo to provide crude product as an oily solid. This residue was triturated with hexanes/ether, whereupon crystallization commenced. Crystallization was allowed to proceed without further disturbance. Isolation from the mother liquor provided 83 mg (16.4%) crystalline (R)-3-methoxy-2-methyl-benzoic acid N'-(1-tert-butyl-but-3-enyl)-N'-((S)-3, 3,3-trifluoro-2-methoxy-2-phenyl-propionyl)-hydrazide from which was obtained an X-ray crystal structure. Mp=128-129° C.; [α]$^{25}_{589}$ +66.40 (c 2.00, CH$_3$OH); $^1$H NMR (400 MHz, CDCl$_3$) δ 7.5 (d, 2H), 7.2-7.3 (m, 4H), 7.07 (m, 1H), 6.9 (d, 1H), 6.6+6.2 (br, 1H), 5.2 (d, 1H), 5.1 (d, 1H), 4.8 (1H, br), 3.85 (s, 3H), 3.8 (s, 3H), 2.55 (br, 1H), 2.35 (br, 2H), 1.5 (3H), 1.05 (br s, 9H); $^{13}$C NMR (100 MHz, CDCl$_3$) δ 168.1, 158.3, 138.7, 134.0, 129.4, 128.0, 126.5, 126.4, 126.3, 124.9, 122.1, 118.0, 117.0, 112.2, 57.3, 55.7, 35.8, 32.0, 28.1, 12.3; HRMS (ESI) m/z calcd for C$_{27}$H$_{34}$F$_3$N$_2$O$_4$ [M+H]$^+$ 507.2471, found 507.2463, m/z calcd for C$_{27}$H$_{33}$F$_3$N$_2$NaO$_4$ [+Na]$^+$ 529.2290, found 529.2284. Anal. Calcd for C$_{27}$H$_{33}$F$_3$N$_2$O$_4$: C, 64.02; H, 6.57; F, 11.25; N, 5.53; O, 12.63. Found: C, 63.87; H, 6.71; N, 5.52.

In order to determine the stereochemical course of the asymmetric allylation reaction in Example 50, the x-ray crystal structure of (R)-3-methoxy-2-methyl-benzoic acid N'-(1-tert-butyl-but-3-enyl)-N'-((S)-3,3,3-trifluoro-2-methoxy-2-phenyl-propionyl)-hydrazide was determined. This experiment established the absolute configuration of the carbon bearing the tert-butyl group and n-propyl group is R.

Example 51

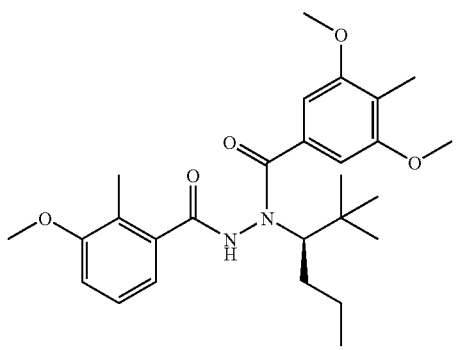

(R)-3,5-Dimethoxy-4-methyl-benzoic acid N-(1-tert-butyl-butyl)-N'-(3-methoxy-2-methyl-benzoyl)-hydrazide Synthesis

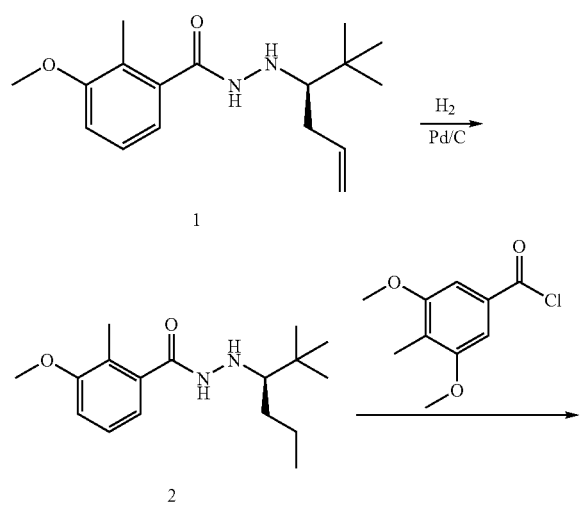

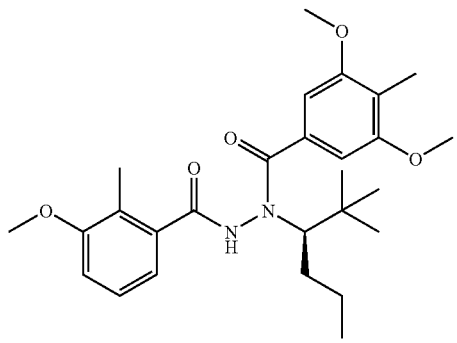

Compound 1: (R)-3-methoxy-2-methyl-benzoic acid N'-(1-tert-butyl-but-3-enyl)-hydrazide was prepared as described in Example 50.

Compound 2: (R)-3-methoxy-2-methyl-benzoic acid N'-(1-tert-butyl-but-3-enyl)-hydrazide (3.05 g, 10.5 mmol) was dissolved in 100 mL methanol. Palladium on charcoal (1%, 240 mg) was carefully added, and the mixture was shaken on a Parr hydrogenator for 2.5 hours at a starting pressure of 55 psi. Decrease in pressure was monitored as a measure of the reaction progress; after 1.5 hours, hydrogen uptake ceased. The mixture was filtered through a pad of Celite, and solvent was removed in vacuo. Analysis by TLC using several solvents was largely unsuccessful in distinguishing between the two hydrazide spots, although 3:1 hexanes:ethyl acetate (R$_f$=0.28) was marginally successful. The crude product was crystallized twice from 2:1 pentane:hexanes to provide >0.6 g of (R)-3-methoxy-2-methyl-benzoic acid N'-(1-tert-butyl-butyl)-hydrazide. $^1$H NMR (400 MHz, CDCl$_3$) δ 7.05 (t, 1H), 6.79 (d, 1H), 6.76 (d, 1H), 3.7 (s, 3H), 2.37 (m, 1H), 2.12 (s, 3H), 1.7-1.1 (m, 4H), 0.90 (s, 9H), 0.82 (t, 3H).

Compound 3 (title compound): (R)-3-methoxy-2-methyl-benzoic acid N'-(1-tert-butyl-butyl)-hydrazide (100 mg, 0.34 mmol) and 3,5-dimethoxy-4-methyl-benzoyl chloride (90 mg, 0.41 mmol) were dissolved in 1 mL methylene chloride. 1.5 eq. of ca. 25% K$_2$CO$_3$ was added, and the reaction mixture was stirred at room temperature and monitored by TLC. Upon completion, the phases were separated, adding additional CH$_2$Cl$_2$ and/or water as needed to aid manipulation. The CH$_2$Cl$_2$ phase was dried over MgSO$_4$ or Na$_2$SO$_4$, and solvent was removed in vacuo to provide an oily solid. This was triturated with 1:1 hexane:ether and allowed to dry in air to yield (R)-3,5-Dimethoxy-4-methyl-benzoic acid N-(1-tert-butyl-butyl)-N'-(3-methoxy-2-methyl-benzoyl)-hydrazide. R$_f$=0.29 (2:1 hexanes:ethyl acetate); $^1$H NMR (400 MHz, CDCl$_3$) δ 7.1 (t, 1H), 7.0 (s, NH 1H), 6.9 (d, 1H), 6.7 (s, 2H), 6.3 (d, 1H), 4.78 (m, 1H), 3.95 (s, 3H), 3.85 (2 s, 6H), 2.2 (s, 3H), 2.05 (m, 1H), 1.95 (s, 3H), 1.8 (m, 1H), 1.6 (m, 2H), 1.2+1.1+1.05 (3 s, 9H), 1.05 (m, 3H); HRMS (ESI) m/z calcd for C$_{27}$H$_{39}$N$_2$O$_5$ [M+H]$^+$ 471.2859, found 471.2850, calcd for C$_{27}$H$_{38}$NaN$_2$O$_5$ [M+Na]$^+$ 493.2670, found 493.2678.

Example 52

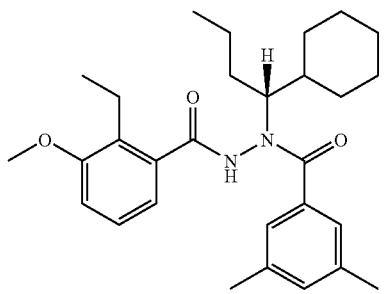

(R)-3,5-Dimethyl-benzoic acid N-(1-cyclohexyl-butyl)-N'-(2-ethyl-3-methoxy-benzoyl)-hydrazide Synthesis

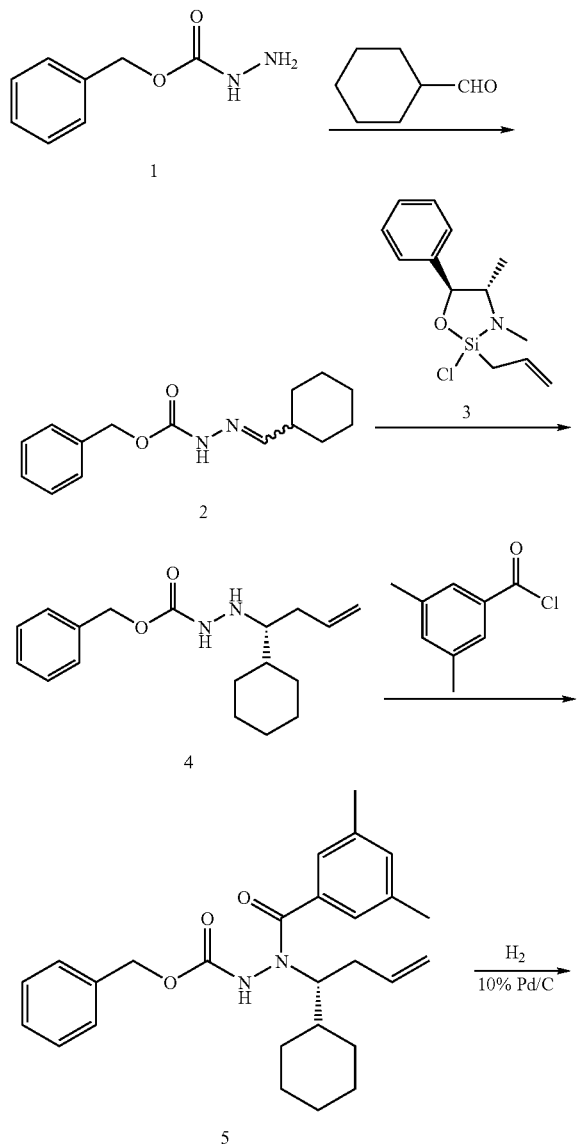

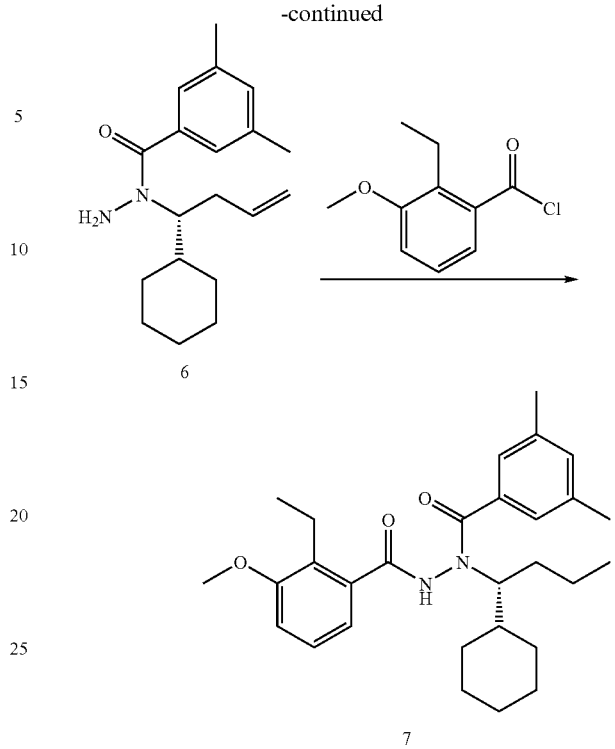

Compound 1: Benzyl carbazate is commercially available.

Compound 2: Benzyl carbazate (25 g, 150.44 mmoles) was dissolved in 200 mL ethanol under a nitrogen atmosphere in a round bottom flask equipped with magnetic stirring. Cyclohexanecarbaldehyde (17.7 g, 158 mmoles) and acetic acid (1 mL) were added to the solution and the mixture was stirred at room temperature for 8 h. The resultant solid precipitate was filtered, washed with hexanes, crystallized from ethyl acetate, and dried overnight on the open bench to provide 28.87 g (73.7% yield) white crystalline N'-cyclohexylmethylene-hydrazinecarboxylic acid benzyl ester. $R_f$=0.67 (1:3 hexanes: ethyl acetate), $^1$H NMR (400 MHz, CDCl$_3$) δ 7.8 (1H, br s), 7.4 (5H, m), 7.1 (1H, br s), 5.3 (2H, s), 2.4 (1H, m), 1.7-1.9 (4H, m), 1.3 (6H, m); HRMS (ESI) m/z calcd for $C_{15}H_{21}N_2O_2$ [M+H]$^+$ 261.1603, found 261.1592, calcd for $C_{15}H_{20}NaN_2O_2$ [M+Na]$^+$ 283.1426, found 283.1417.

Compound 3: (S,S)-2-Allyl-2-chloro-3,4-dimethyl-5-phenyl-[1,3,2]oxazasilolidine was prepared as described in Example 1.

Compound 4: A round bottom flask with magnetic stirrer and N$_2$ atmosphere was charged with 5 g (19.21 mmoles) N'-cyclohexylmethylene-hydrazinecarboxylic acid benzyl ester in 75 mL anhydrous CHCl$_3$. The mixture was chilled to 0° C., and (S,S)-oxazasilolidine (5.66 g, 21.1 mmoles) was added to the solution using a syringe. The ice bath was removed after ca. 30 minutes and the reaction was stirred at room temperature overnight. The reaction was quenched with aq. Na$_2$CO$_3$. The organic layer was removed, and the aqueous phase extracted with CHCl$_3$. The combined organic phases were backwashed several times with water, dried over anhydrous Na$_2$SO$_4$, and freed of solvent using a rotary evaporator. The resultant crude product was purified by column chromatography to provide (R)—N'-(1-cyclohexyl-but-3-enyl)-hydrazinecarboxylic acid benzyl ester as a light yellow viscous oil in 2.31 g, 39.8% yield. $R_f$=0.41 (3:1 hexanes:ethyl acetate); $^1$H NMR (400 MHz, CDCl$_3$) δ 7.4 (5H, m), 6.3 (1H, br), 5.9 (1H, br s), 5.25 (2H, s), 5.2 (2H, br s), 2.95 (1H, br s), 2.35 (1H, br d), 2.17 (1H, br m), 1.8 (2H, br m), 1.75 (2H, br d), 1.55 (1H, br t), 1.0-1.4 (6H, m) ppm; HRMS (ESI) m/z calcd for $C_{18}H_{27}N_2O_2$ [M+H]$^+$ 303.2072, found 303.2079, calcd for $C_{18}H_{26}NaN_2O_2$ [M+Na]$^+$ 325.1892, found 325.1899.

Compound 5: R—N'-(1-cyclohexyl-but-3-enyl)-hydrazinecarboxylic acid benzyl ester (2.20 g, 7.27 mmoles) was dissolved in 2 mL methylene chloride in a vial with a magnetic stirrer. Aqueous $K_2CO_3$ solution (1.51 g, 10.91 mmoles in 4 mL) was added and the mixture was cooled on ice. The neat acid chloride was slowly added and ca. 1 mL methylene chloride was used to chase and rinse. The mixture was stirred overnight, first on ice then at room temperature, while monitoring by TLC. Water and/or $CH_2Cl_2$ was added to the reaction mixture to aid manipulation, and the organic layer was collected. The aqueous layer was extracted once with $CH_2Cl_2$, and the organic layers were combined and dried over solid $Na_2SO_4$. Solvent was removed in vacuo, and the residue was triturated with 2:1 hexanes:ether to yield 2.93 g (92.7%) of (R)—N'-(1-cyclohexyl-but-3-enyl)-N'-(3,5-dimethyl-benzoyl)-hydrazinecarboxylic acid benzyl ester as a white solid. $R_f$=0.33 (3:1 hexanes:ethyl acetate); $^1$H NMR (400 MHz, DMSO-d$_6$) δ 9.8+9.65 (0.5H, NH, 2 s), 7.1-7.5 (3.5H, m), 6.9-7.1 (5H, m), 6.05 (0.5H, m), 5.9 (0.5H, m), 5.2 (1H, m), 5.0 (2H, m), 4.8 (1H, m), 4.35 (1H, m), 2.35 (2H, br m), 2.25 (6H, s), 0.8-2.0 (11H, m); HMS (ESI) m/z calcd for $C_{27}H_{35}N_2O_3$ [M+H]$^+$ 435.2647, found 435.2659, calcd for $C_{27}H_{34}NaN_2O_3$ [M+Na]$^+$ 457.2467, found 457.2470.

Compound 6: (R)—N'-(1-Cyclohexyl-but-3-enyl)-N'-(3,5-dimethyl-benzoyl)-hydrazine carboxylic acid benzyl ester (2.91 g, 6.7 mmoles) was suspended in ca. 50 mL glacial acetic acid. 102 mg 10% palladium on charcoal was added as a slurry in several mL of acetic acid. The mixture was diluted with acetic acid to 75 mL, and shaken on a Parr hydrogenator for 90 minutes at 20-30 psi. The suspension was allowed to stand for two days to allow the carbon to settle out. The supernatant was filtered through a 0.45 micron syringe filter into a recrystallizing dish and solvent was evaporated to leave 2.06 g (102% mass balance) of (R)-3,5-dimethyl-benzoic acid N-(1-cyclohexyl-butyl)-hydrazide as a reddish brown viscous oil. $R_f$=0.24 (2:1 hexanes:ethyl acetate); $^1$H NMR (400 MHz, CDCl$_3$) δ 7.05 (1H, s), 7.0 (2H, s), 4.55+3.35 (1H, 2 t), 2.4 (6H, s), 0.8-1.9 (15H, m), 0.9 (3H, t); HRMS (ESI) m/z calcd for $C_{19}H_{31}N_2O$ [M+H]$^+$ 303.2436, found 303.2441, calcd for $C_{19}H_{30}N_2NaO$ [M+Na]$^+$ 325.2256, found 325.2262.

Compound 7 (title compound): (R)-3,5-Dimethyl-benzoic acid N-(1-cyclohexyl-butyl)-hydrazide (0.14 g, 0.46 mmoles) was dissolved in 1 mL of methylene chloride in a vial with a magnetic stirrer. Aqueous $K_2CO_3$ solution (0.1 g, 0.69 mmoles, 2.77 mL) was added. The flask was cooled on ice, and neat acid chloride was added. Ca. 0.8 mL additional methylene chloride was used to chase and rinse. The mixture was stirred overnight, first on ice and then at room temperature, while monitoring the reaction by TLC. Water and $CH_2Cl_2$ were added to the reaction mixture to aid manipulation, and the aqueous layer was extracted once with $CH_2Cl_2$. The organic layers were combined and dried over solid $Na_2SO_4$. Solvent was removed in vacuo, and the crude product was purified by chromatography to yield 143 mg (67.9% yield) (R)-3,5-dimethyl-benzoic acid N-(1-cyclohexyl-butyl)-N'-(2-ethyl-3-methoxy-benzoyl)-hydrazide as a reddish brown viscous oil. $^1$H NMR (400 MHz, DMSO-d$_6$) δ 10.4 (1H, 2 s), 7.0-7.25 (5H, m), 6.2 (1H, m), 4.45 (1H, m), 3.8 (3H, s), 2.35 (6H, s), 2.0-2.2 (2H, m), 0.9-2.0 (15H, m), 0.9 (6H, m).

Examples 53 to 55 were prepared using methodology described in Example 52. The percent enantiomeric excess (ee) was determined by chiral HPLC.

| Example | Structure | % ee | Name |
|---|---|---|---|
| 53 | 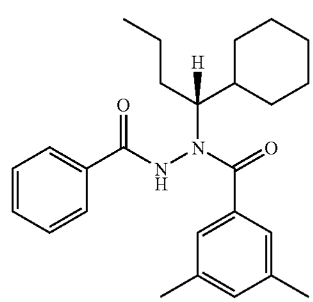 | 62.4 | (R)-3,5-Dimethyl-benzoic acid N'-benzoyl-N-(1-cyclohexyl-butyl)-hydrazide |
| 54 | 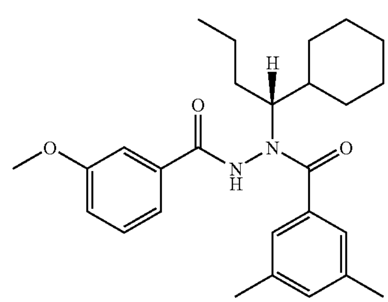 | 59.1 | (R)-3,5-Dimethyl-benzoic acid N-(1-cyclohexyl-butyl)-N'-(3-methoxy-benzoyl)-hydrazide |

-continued

| Example | Structure | % ee | Name |
|---|---|---|---|
| 55 | 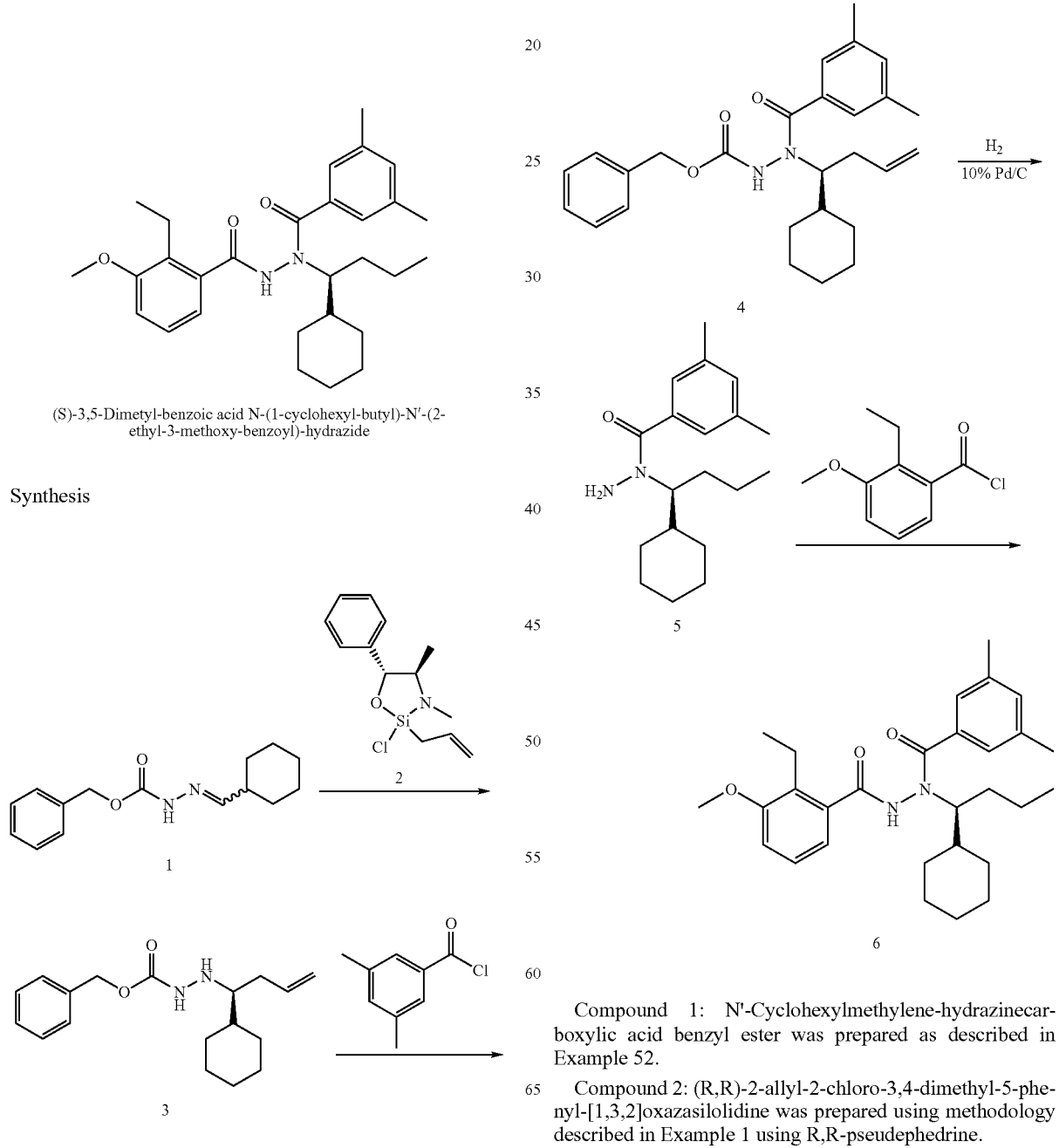 | 58.1 | (R)-3,5-Dimethyl-benzoic acid N-(1-cyclohexyl-butyl)-N'-(4-ethyl-benzoyl)-hydrazide |

Example 56

(S)-3,5-Dimetyl-benzoic acid N-(1-cyclohexyl-butyl)-N'-(2-ethyl-3-methoxy-benzoyl)-hydrazide Synthesis Compound 1: N'-Cyclohexylmethylene-hydrazinecarboxylic acid benzyl ester was prepared as described in Example 52.

Compound 2: (R,R)-2-allyl-2-chloro-3,4-dimethyl-5-phenyl-[1,3,2]oxazasilolidine was prepared using methodology described in Example 1 using R,R-pseudephedrine.

Compound 3: (S)—N'-(1-cyclohexyl-but-3-enyl)-hydrazinecarboxylic acid benzyl ester was prepared in 69% yield as a light yellow viscous oil using methodology described in Example 52. Analytical data: $R_f$=0.41 (3:1 hexanes:ethyl acetate); $^1$H NMR (400 MHz, DMSO-d6) δ 8.65 (1H, br s), 7.4 (5H, m), 5.85 (1H, br), 5.1 (4H, m), 4.2 (1H, s), 2.7 (1H, br s), 2.1 (1H, br m), 2.0 (1H, br m), 1.8 (2H, br m), 1.65 (2H, br m), 1.45 (1H, br m) 1.0-1.2 (6H, br m); $^1$H NMR (400 MHz, CDCl$_3$) δ 7.4 (5H, m), 6.3 (1H, br), 5.9 (1H, br s), 5.25 (2H, s), 5.2 (2H, br s), 2.95 (1H, br s), 2.35 (1H, br d), 2.17 (1H, br m), 1.8 (2H, br m), 1.75 (2H, br d), 1.55 (1H, br t), 1.0-1.4 (6H, m); HRMS (ESI) m/z calcd for C$_{18}$H$_{27}$N$_2$O$_2$ [M+H]$^+$ 303.2072, found 303.2057, calcd for C$_{18}$H$_{26}$NaN$_2$O$_2$ [M+Na]$^+$ 325.1892, found 325.1873.

Compound 4: (S)—N'-(1-cyclohexyl-but-3-enyl)-N'-(3,5-dimethyl-benzoyl)-hydrazine carboxylic acid benzyl ester was prepared in 84.8% yield as a white solid using methodology described in Example 52. Analytical data: ee≧80%. $R_f$=0.34 (3:1 hexanes:ethyl acetate); $^1$H NMR (400 MHz, DMSO-d$_6$) δ 9.8+9.65 (0.5H, NH, 2 s), 7.1-7.5 (3.5H, m), 6.9-7.1 (5H, m), 6.05 (0.5H, m), 5.9 (0.5H, m), 5.2 (1H, m), 5.0 (2H, m), 4.8 (1H, m), 4.35 (1H, m), 2.35 (2H, br m), 2.25 (6H, s), 0.8-2.0 (11H, m); HRMS (ESI) m/z calcd for C$_{27}$H$_{35}$N$_2$O$_3$ [M+H]$^+$ 435.2647, found 435.2655, calcd for C$_{27}$H$_{34}$NaN$_2$O$_3$ [M+Na]$^+$ 457.2467, found 457.2469.

Compound 5: (S)-3,5-dimethyl-benzoic acid N-(1-cyclohexyl-butyl)-hydrazide was prepared using methodology described in example 52. Analytical data: $R_f$=0.24 (2:1 hexanes:ethyl acetate); $^1$H NMR (400 MHz, DMSO-d$_6$) δ 7.05+6.95 (1H, s), 7.0+6.85 (2H, 2 s), 4.55+4.05 (2H, 2 s), 4.3+3.15 (1H, 2 t), 2.3 (6H, 2 s), 0.6-1.9 (15H, m), 0.9+0.8 (3H, 2 t); (400 MHz, CDCl$_3$) δ 7.05 (1H, s), 7.0 (2H, s), 4.55+3.35 (1H, 2 t), 2.4 (6H, s), 0.8-1.9 (15H, m), 0.9 (3H, t); HRMS (ESI) m/z calcd for C$_{19}$H$_{31}$N$_2$O [M+H]$^+$ 303.2436, found 303.2440, calcd for C$_{19}$H$_{30}$N$_2$NaO [M+Na]$^+$ 325.2256, found 325.2260.

Compound 6 (title compound): (S)-3,5-Dimethyl-benzoic acid N-(1-cyclohexyl-butyl)-N'-(2-ethyl-3-methoxy-benzoyl)-hydrazide was prepared using methodology described in Example 52 in 37% ee.

Examples 57 to 59 were prepared using methodology described in Example 56. The percent enantiomeric excess (ee) was determined by chiral HPLC. Table 3 provides analytical data for examples 57 to 59.

| Example | Structure | % ee | name |
|---|---|---|---|
| 57 | 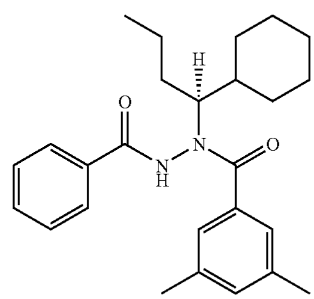 | 87.7 | (S)-3,5-Dimethyl-benzoic acid N'-benzoyl-N-(1-cyclohexyl-butyl)-hydrazide |
| 58 | 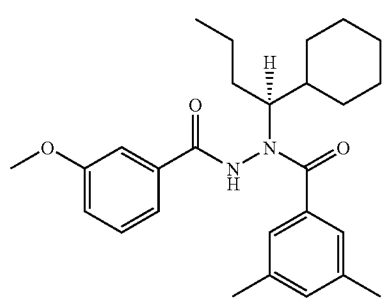 | 86.7 | (S)-3,5-Dimethyl-benzoic acid N-(1-cyclohexyl-butyl)-N'-(3-methoxy-bnezoyl)-hydrazide |
| 59 | 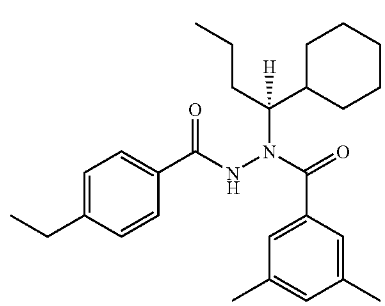 | 99 | (S)-3,5-Dimethyl-benzoic acid N-(1-cyclohexyl-butyl)-N'-(4-ethyl-benzoyl)-hydrazide |

TABLE 3

Analytical Data

| Example | $^1$H NMR (solvent) | MS |
|---|---|---|
| 57 | (CDCl$_3$) δ 8.0 (1H, NH, br s), 7.0-7.8 (8H, m), 4.6 + 3.6 (1H, 2 br s), 2.3-2.4 (6H, 2 br s), 1.4-2.0 (10H, br m), 1.1-1.4 (4H, 2 br s), 0.9-1.1 (4H, 2 br s) ppm | [M + H$^+$] 407.2695 [M + Na$^+$] 429.2513 |
| 58 | (CDCl$_3$) δ 6.9-7.6 (7H + 1NH, m), 4.6 + 3.65 (1H, 2 br s), 3.85 (3H, 2 br s), 2.4 (6H, 2 br s), 1.4-2.0 (10H, br m), 1.1-1.4 (4H, br m), 0.9-1.3 (4H, 2 br s) ppm | [M + H$^+$] 437.2799 [M + Na$^+$] 459.2616 |
| 59 | (CDCl$_3$) δ 7.9 (1H, NH, br s), 6.9-7.6 (7H, m), 3.6 + 4.6 (1H, 2 br s), 2.75 (2H, br s), 2.4 (6H, 2 br s), 1.5-2.0 (9H, br m), 1.1-1.4 (8H, br m), 1.0 (4H, 2 br s) ppm | [M + H$^+$] 435.3016 [M + Na$^+$] 457.2827 |

Example 60

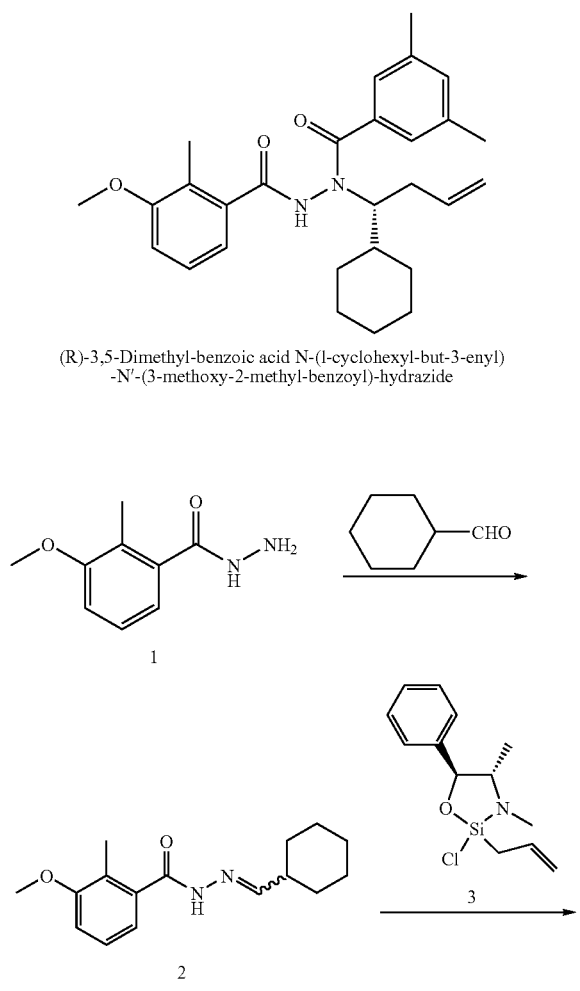

(R)-3,5-Dimethyl-benzoic acid N-(1-cyclohexyl-but-3-enyl)-N'-(3-methoxy-2-methyl-benzoyl)-hydrazide

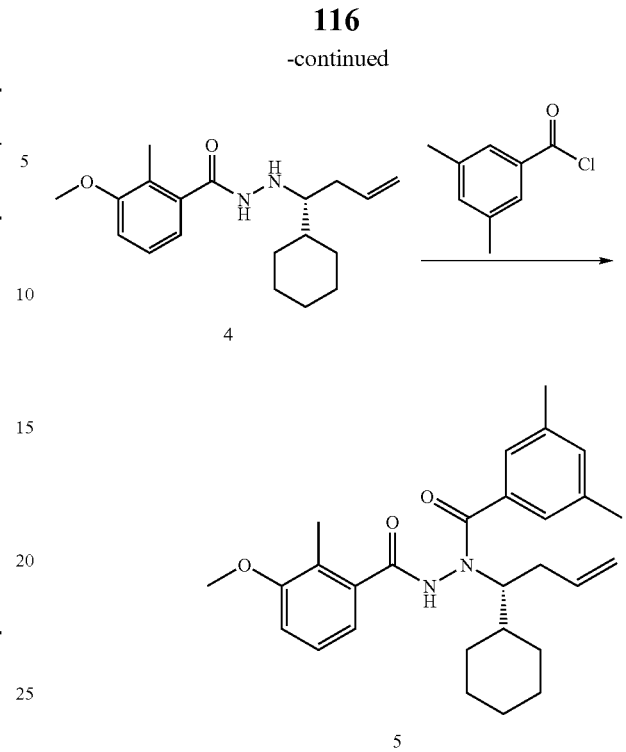

Compound 1: 3-Methoxy-2-methyl-benzoic acid hydrazide was prepared as described in Example 50.

Compound 2: 10.0 g (55.5 mmol) of 3-methoxy-2-methyl-benzoic acid hydrazide was dissolved in 200 mL of absolute ethyl alcohol. Cyclohexanecarbaldehyde (6.85 g, 61.0 mmol) and glacial acetic acid (3 mL) were added, and the reaction mixture was stirred for 18 h while monitoring by TLC. The precipitate was collected by filtration and washed with hexane. Product 3-methoxy-2-methyl-benzoic acid cyclohexyl-methylene-hydrazide was obtained as a white solid (9.36 g, yield 61%): R$_f$=0.20 (3:1 EtOAc:n-Hexane); $^1$H NMR (400 MHz, CDCl$_3$) δ 11.17 (s, 1H), 7.91 (s, 1H), 7.50 (d, J=4.8 Hz, 1H), 7.25 (t, J=6.4 Hz, 1H), 6.99 (t, J=5.6 Hz, 1H), 3.89 (s, 3H), 2.28 (s, 3H), 1.92-1.62 (m, 5H), 1.38-1.14 (m, 6H); HRMS (ESI) m/z calcd for C$_{16}$H$_{23}$N$_2$O$_2$ [M+H]$^+$ 275.1760, found 275.1752, calcd for C$_{16}$H$_{22}$N$_2$NaO$_2$ [M+Na]$^+$ 297.1579, found 297.1568.

Compound 3: (S,S)-2-Allyl-2-chloro-3,4-dimethyl-5-phenyl-[1,3,2]oxazasilolidine was prepared as described in Example 1.

Compound 4: To a round bottom flask with a stirrer and a nitrogen inlet was added 3-methoxy-2-methyl-benzoic acid cyclohexylmethylene-hydrazide (2.8 g, 10.2 mmol) and dry CHCl$_3$ (50 mL). (S,S)-Oxazasilolidine (3.28 g, 12.20 mmol) was added dropwise. The reaction was stirred at 50° C. for 6 h, then at room temperature for 18 h. Saturated NaHCO$_3$ solution (30 mL) was added to quench the reaction. The CHCl$_3$ layer was separated and the aqueous layer was extracted with CHCl$_3$ (2×30 mL). The CHCl$_3$ solution was combined and dried over anhydrous Na$_2$SO$_4$. The solvent was evaporated in vacuo, and the crude mixture was purified by flash chromatography to obtain (R)-3-methoxy-2-methyl-benzoic acid N'-(1-cyclohexyl-but-3-enyl)-hydrazide as a white solid (1.74 g, 54% yield). $^1$H NMR (400 MHz, CDCl$_3$) δ 9.69 (s, 1H), 7.24 (t, J=8.0 Hz, 1H), 7.05 (d, J=8.0 Hz, 1H), 6.88 (d, J=7.6 Hz, 1H), 5.92 (m, 1H), 5.15 (dd, J=1.6, 17.2 Hz, 1H), 5.08 (dd, J=1.6, 10.4 Hz, 1H), 4.91 (dd, J=3.6, 6.8 Hz, 1H), 3.83 (s, 3H), 2.75 (m, 1H), 2.26-2.22 (m, 1H), 2.16 (s, 3H), 2.14-2.08 (m, 1H), 1.81-1.08 (m, 11H); HRMS (ESI) m/z calcd for $C_{19}H_{29}N_2O_2$ [M+H]$^+$ 317.2229, found 317.2221, m/z calcd for $C_{19}H_{29}N_2O_2$ [M+Na]$^+$ $C_{19}H_2N_2NaO_2$ 339.2048, found 339.2037.

Compound 5 (title compound): To a solution of (R)-3-methoxy-2-methyl-benzoic acid N'-(1-cyclohexyl-but-3-enyl)-hydrazide (1.3 g, 4.11 mmol) in $CH_2Cl_2$ (5 mL), was added $K_2CO_3$ (2.27 g, 16.44 mmol), $H_2O$ (5 mL), and finally 3,5-dimethylbenzoyl chloride (727 mg, 4.31 mmol). The reaction was stirred at room temperature for 24 h. Additional $CH_2Cl_2$ and $H_2O$ were added to aid manipulation, the $CH_2Cl_2$ layer was separated, and the aqueous layer was extracted with $CH_2Cl_2$. The $CH_2Cl_2$ solutions were combined and dried over anhydrous $Na_2SO_4$. The solvent was evaporated in vacuo and the residue was purified by flash chromatography to provide (R)-3,5-dimethyl-benzoic acid N-(1-cyclohexyl-but-3-enyl)-N'-(3-methoxy-2-methyl-benzoyl)-hydrazide as a white solid (1.45 g, 78% yield). $R_f$=0.21 (3:1 EtOAc:n-Hexane); $^1$H NMR (400 MHz, DMSO-d$_6$) δ 10.47+10.39 (2 s, 1H), 7.20-7.01 (m, 5H), 6.37 (d, J=7.2 Hz, 1H), 6.22-5.89 (m, 1H), 5.18 (dd, 1H), 5.02 (dd, 1H), 4.46 (m, 1H), 3.79 (s, 3H), 2.44-2.34 (m, 2H), 2.29 (s, 3H), 2.02-1.53 (m, 8H), 1.26-1.02 (m, 3H); HRMS (ESI) m/z calcd for $C_{28}H_{37}N_2O_3$ [M+H]$^+$ 449.2804, found 449.2793, calcd for $C_{28}H_{36}N_2NaO_3$ [M+Na]$^+$ 471.2624, found 471.2615.

Example 61

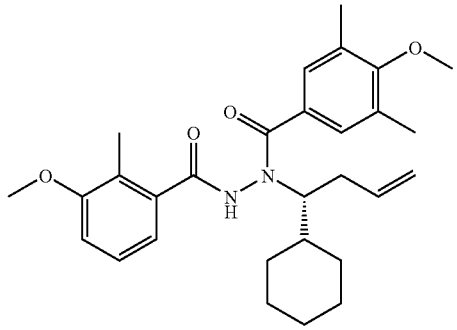

(R)-4-Methoxy-3,5-dimetyl-benzoic acid N-(1-cyclohexyl-but-3-enyl)-N'-(3-methoxy-2-methyl-benzoyl)-hydrazide Synthesis (R)-4-Methoxy-3,5-dimethyl-benzoic acid N-(1-cyclohexyl-but-3-enyl)-N'-(3-methoxy-2-methyl-benzoyl)-hydrazide was prepared in 71% yield using methodology described in Example 60. Analytical data: $R_f$=0.14 (1:3 EtOAc:n-Hexane); $^1$H NMR (400 MHz, DMSO-d$_6$) δ 10.46+ 10.38 (2 s, 1H), 7.21-6.42 (m, 5H), 6.16-5.93 (m, 1H), 5.23 (dd, 1H), 5.01 (dd, 1H), 4.45 (m, 1H), 3.79 (s, 3H), 3.77 (s, 6H), 2.42-2.28 (m, 2H), 2.04 (s, 3H), 1.88-1.05 (m, 14H); HRMS (ESI) m/z calcd for $C_{29}H_{38}N_2O_5$ [M+H]$^+$ 495.2859, found 495.2848, calcd for $C_{29}H_{38}N_2NaO_5$ [M+Na]$^+$ 517.2678, found 517.2667.

Example 62

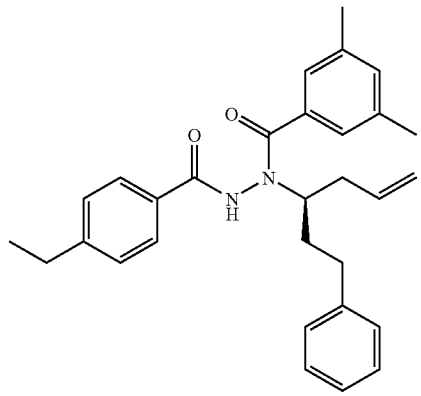

(R)-3,5-Dimethyl-benzoic acid N'-(4-ethyl-benzoyl)-N-(l-phenethyl-but-3-enyl)-hydrazide Synthesis

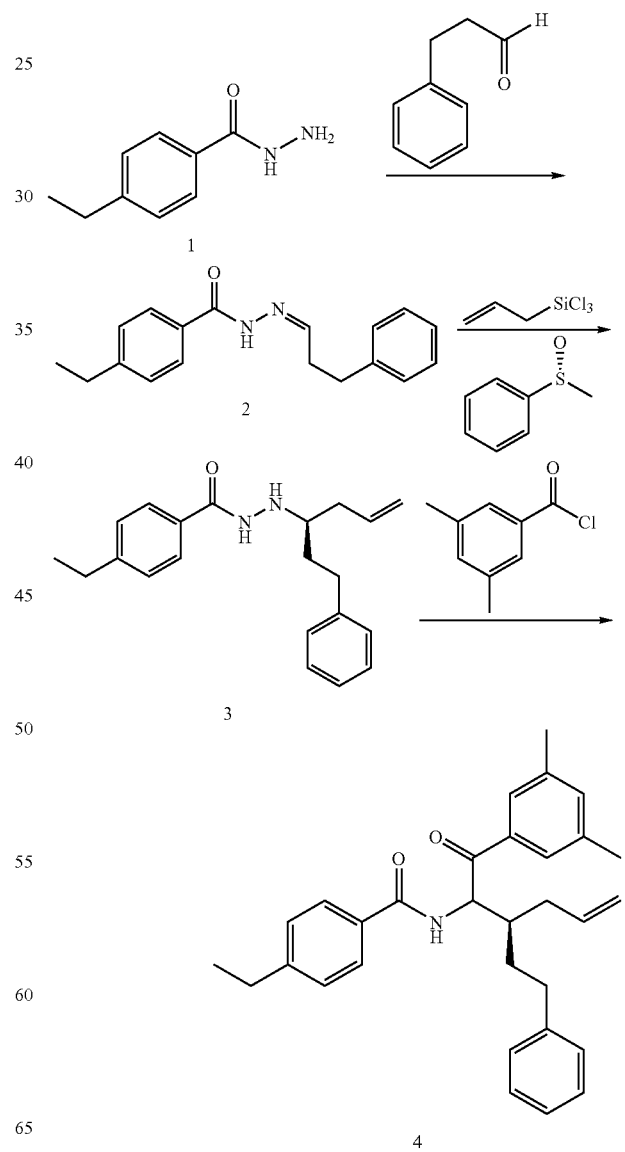

Compound 1: 4-ethyl-benzoic acid hydrazide is commercially available.

Compound 2: 4-ethyl-benzoic acid hydrazide (10 g, 60.9 mmoles) was dissolved in 32 mL of methanol. Acetic acid (1 mL) was added, the mixture was brought to reflux, and hydrocinnamaldehyde (5.77 g, 67 mmoles) was then slowly added. The reaction mixture was refluxed for 10 h and monitored by TLC. The precipitates were collected via filtration and washed with hexanes. 4-Ethyl-benzoic acid (3-phenyl-propylidene)-hydrazide was obtained as a white solid (9.34 g, 54.7% yield). $R_f$=0.36 (1:1 EtOAc:n-hexane); $^1$H NMR (400 MHz, CDCl$_3$) δ 8.87 (s, 1H), 7.72-7.24 (m, 10H), 2.87 (t, J=15.2 Hz, 2H), 2.79-2.57 (m, 4H), 1.24 (t, J=8 Hz, 3H).

Compound 3: (R)-(+)-methyl p-tolyl sulfoxide (0.5 g, 3.21 mmoles) and tetrabutylammonium triphenyl-difluorosilicate (TBAT) (0.12 g, 0.214 mmoles) were dissolved in 0.038 mL of 2-methyl-2-butene and 2.4 mL of anhydrous methylene chloride under nitrogen and with magnetic stirring. Allyltrichlorosilane (0.23 mL, 1.61 mmoles) was added at −78° C. and the reaction was stirred for 15 minutes. 4-ethyl-benzoic acid (1-methyl-3-phenyl-propylidene)hydrazide (0.3 g, 1.07 mmoles) was dissolved in 11.6 mL of anhydrous methylene chloride and added to the reaction over a period of 30 minutes. The reaction mixture was stirred for 5 hours under nitrogen and maintained at −78° C. to −70° C., with TLC monitoring. The reaction was quenched with 1.5 mL triethylamine and 3 mL anhydrous methanol at −78° C. Brine was then added and the mixture was allowed to warm to room temperature. The organic layer was removed, combined with three methylene chloride extractions, and dried over sodium sulfate. The solvent was evaporated, and the crude mixture was purified by flash chromatography using a step gradient of 2:1 and 1:1 pentane:ethyl acetate. Purified (R)-4-ethyl-benzoic acid N'-(1-phenethyl-but-3-enyl)-hydrazide was obtained as a clear oil (0.145 g, 41.4% yield, 57.6% ee by chiral HPLC on Chiralcel ADH). $R_f$=0.50 (1:1 EtOAc:n-hexane); $^1$H NMR (400 MHz, CDCl$_3$) δ 7.64-7.13 (m, 9H), 5.91 (m, 1H), 5.15 (t, J=28.0 Hz, 2H), 3.12 (m, 1H), 2.76-2.63 (m, 4H), 2.38-2.24 (m, 2H), 1.88-1.74 (m, 2H), 1.23 (t, J=8.0 Hz, 3H).

Compound 4 (title compound): (R)-4-ethyl-benzoic acid N'-(1-phenethyl-but-3-enyl)-hydrazide (0.1 g, 0.31 mmoles) was dissolved in 0.47 mL of methylene chloride with magnetic stirring. Potassium bicarbonate (0.064 g, 0.37 mmoles) in 0.7 mL of deionized water and 3,5-dimethylbenzoyl chloride (0.063 g, 0.37 mmoles) were added to the mixture. The reaction mixture was first stirred on ice and then allowed to warm to room temperature over the weekend while monitoring by TLC. The organic layer was removed and the aqueous layer was extracted with methylene chloride three times and dried over sodium sulfate. The solvent was evaporated, and the crude mixture was purified by flash chromatography, using 2:1 hexanes:ethyl acetate as eluant. Purified (R)-3,5-dimethyl-benzoic acid N-(4-ethyl-benzoyl)-N-(1-phenethyl-but-3-enyl)-hydrazide was obtained as a yellow oil (0.102 g, yield 72.9%, 51.2% ee by chiral HPLC on Chiralcel ADH). $R_f$=0.34 (2:1 hexane:EtOAc); $^1$H NMR (400 MHz, CDCl$_3$) δ 7.8-7.02 (m, 12H), 5.99 (br, 1H), 5.22 (d, J=24.0 Hz, 2H), 2.73 (d, J=8 Hz, 2H), 2.31 (s, 6H), 2.12-2.03 (m, 2H), 1.87 (s, 1H), 1.61 (s, 2H), 1.29 (t, J=8.0 Hz, 3H); HRMS (ESI) m/z calcd for $C_{30}H_{35}N_2O_2$ [M+H]$^+$ 455.2699, found 455.2685, calcd for $C_{30}H_{34}N_2NaO_2$ [M+Na]$^+$ 477.2518, found 477.2505.

Example 63

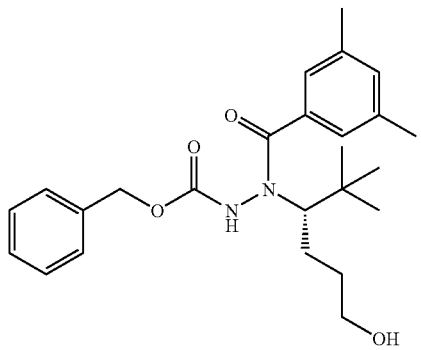

(S)-N'-(1-tert-Butyl-4-hydroxy-butyl)-N'-(3,5-dimethyl-benzoyl)-hydrazine carboxylic acid benzyl ester Synthesis

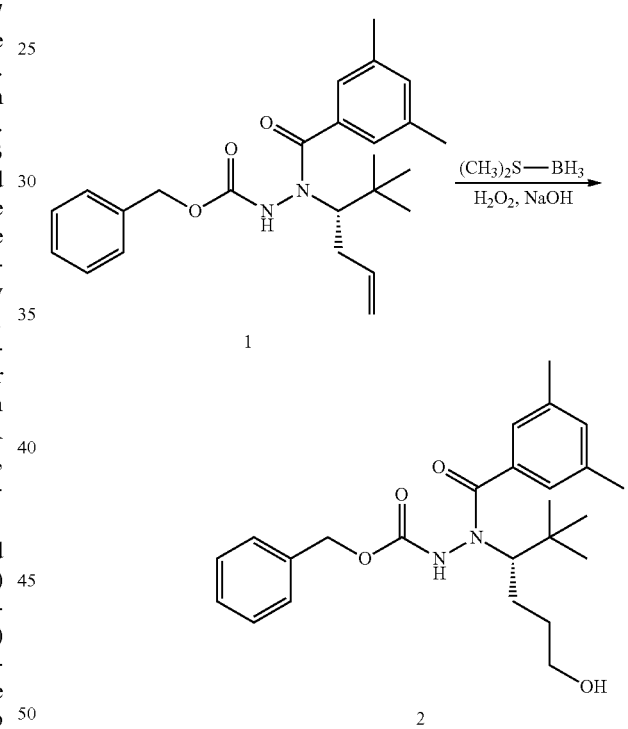

Compound 1: Compound 1 was prepared as described in Example 31.

Compound 2 (title compound): To a solution of (S)—N'-(1-tert-butyl-but-3-enyl)-N'-(3,5-dimethyl-benzoyl)-hydrazinecarboxylic acid benzyl ester (200 mg, 0.49 mmol) in THF (3 mL), was added borane dimethyl sulfide (2 M in THF, 125 μL, 0.25 mmol) at 0° C. The mixture was stirred at room temperature for 16 h. Excess borane and THF was removed in vacuo, and additional THF (3 mL), followed by H$_2$O$_2$ (61 microliters, 0.54 mmol) and 3N NaOH (90 microliters, 0.27 mmol) were added. After stirring at 50-55° C. for 1 h, more water was added, the mixture was extracted with ether, and the ether layer was dried over anhydrous Na$_2$SO$_4$. The solvent was removed in vacuo and the residue was purified by flash chromatography to give (S)—N'-(1-tert-butyl-4-hydroxy-butyl)-N'-(3,5-dimethyl-benzoyl)-hydrazinecarboxylic acid benzyl ester as a white solid (128 mg, yield 61%). $R_f$=0.30 (1:1 EtOAc:n-hexane). $^1$H NMR (400 MHz, DMSO-$d_6$) δ 9.71+9.63 (2 s, 1H), 7.44-6.88 (m, 8H), 5.06 (dd, J=3.6, 12.8 Hz, 1H), 4.79 (dd, J=12.4, 25.2 Hz, 1H), 4.43 (d, J=10.8 Hz, 1H), 4.28 (t, J=5.2 Hz, 1H), 3.47 (m, 2H), 2.27 (s, 6H), 1.86-1.21 (m, 4H), 1.01 (s, 9H); HRMS (ESI) m/z calcd for $C_{25}H_{35}N_2O_4$ [M+H]$^+$ 427.2597, found 427.2587, calcd for $C_{25}H_{34}N_2NaO_4$ [M+Na]$^+$ 449.2416, found 449.2407.

Example 64

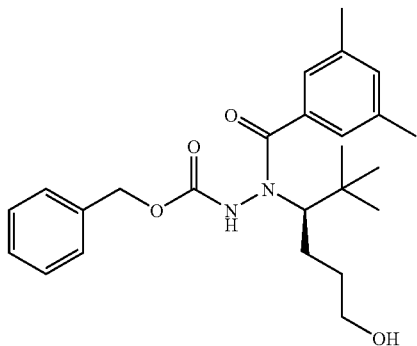

(R)-N'-(1-tert-Butyl-4-hydroxy-butyl)-N'-(3,5-dimethyl-benzoyl)-hydrazine carboxylic acid benzyl ester Synthesis (R)—N'-(1-tert-Butyl-4-hydroxy-butyl)-N'-(3,5-dimethyl-benzoyl)-hydrazine carboxylic acid benzyl ester was prepared in >99% ee using methodology described in Example 63.

Example 65

This example illustrates the analytical method used to determine the enantiomeric excess (ee) of compounds of the invention.

Figure 2A:
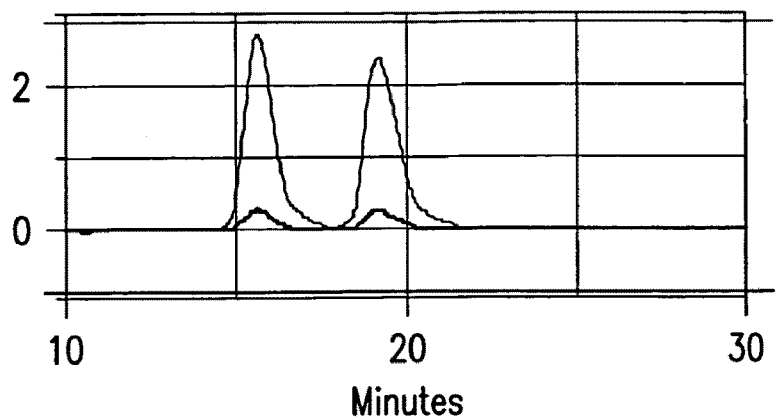
FIGS. 2A-2C: Chiral HPLC comparison of (A) rac-, (B) (R)- and (C) (S)-3,5-dimethyl-benzoic acid N-(1-tert-butyl-butyl)-N'-(2,6-dichloro-benzoyl)-hydrazide.
Figure 2B:
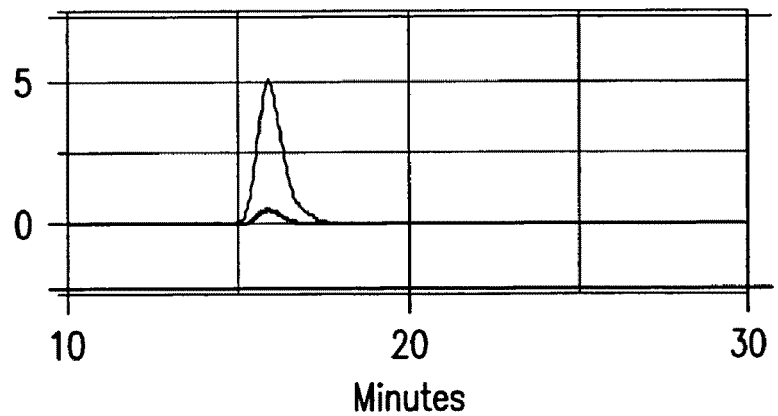
Figure 2C:
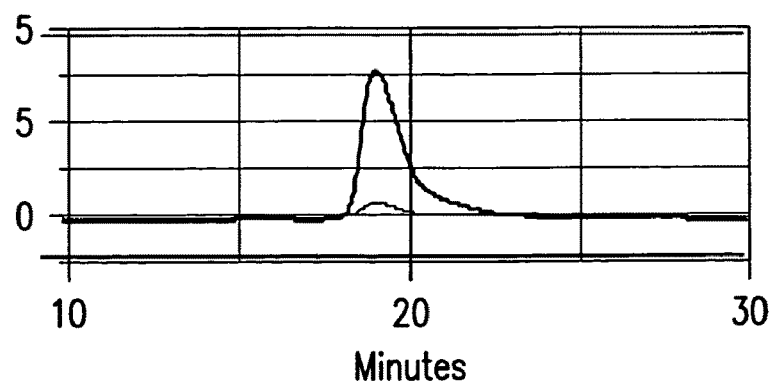

As shown in FIG. 2A-C, the chiral HPCL chromatograms for rac-3,5-dimethyl-benzoic acid N-(1-tert-butyl-butyl)-N'-(2,6-dichloro-benzoyl)-hydrazide (Example 16), (R)-3,5-dimethyl-benzoic acid N-(1-tert-butyl-butyl)-N'-(2,6-dichloro-benzoyl)-hydrazide and (S)-3,5-dimethyl-benzoic acid N-(1-tert-butyl-butyl)-N'-(2,6-dichloro-benzoyl)-hydrazide (Example 41) illustrates the method used to determine enantiomeric excess. rac-3,5-Dimethyl-benzoic acid N-(1-tert-butyl-butyl)-N'-(2,6-dichloro-benzoyl)-hydrazide contains 50% of the R-isomer (peak 1 at approx. 16 minutes) and 50% of the S-isomer (peak 2 at approx. 19 minutes). The enantiomerically enriched sample of (R)-3,5-dimethyl-benzoic acid N-(1-tert-butyl-butyl)-N'-(2,6-dichloro-benzoyl)-hydrazide is substantially free of the S-isomer with an ee of >99%. The enantiomerically enriched sample of (S)-3,5-dimethyl-benzoic acid N-(1-tert-butyl-butyl)-N'-(2,6-dichloro-benzoyl)-hydrazide is substantially free of the R-isomer with an ee of >99%. In this experiment, data were generated using a 4.6 mm×25 cm Regis Rexchrom (S,S) ULMO column at a flow rate of 2.0 mL/min using 2% methanol in hexane as the solvent and an injection volume of 20 µL. The enantiomeric excess of other compounds of Formula II or III were determined in similar fashion, unless otherwise noted.

Example 66

This example illustrates in vitro testing of compounds of the invention.

Gene Expression Cassette

GAL4 DBD (1-147)-CfEcR(DEF)/VP16AD-βRXREF-LmUSPEF: The wild-type D, E, and F domains from spruce budworm *Choristoneura fumiferana* EcR ("CfEcR-DEF"; SEQ ID NO: 1) were fused to a GAL4 DNA binding domain ("Gal4 DBD1-147"; SEQ ID NO: 2) and placed under the control of a phosphoglycerate kinase promoter ("PGK"; SEQ ID NO: 3). Helices 1 through 8 of the EF domains from *Homo sapiens* RXRβ ("HsRXRβ-EF"; nucleotides 1-465 of SEQ ID NO: 4) and helices 9 through 12 of the EF domains of *Locusta migratoria* Ultraspiracle Protein ("LmUSP-EF"; nucleotides 403-630 of SEQ ID NO: 5) were fused to the transactivation domain from VP16 ("VP16AD"; SEQ ID NO: 6) and placed under the control of an elongation factor-1α: promoter ("EF-1α"; SEQ ID NO: 7). Five consensus GAL4 response element binding sites ("5XGAL4RE"; comprising 5 copies of a GAL4RE comprising SEQ ID NO: 8) were fused to a synthetic TATA minimal promoter (SEQ ID NO: 9) and placed upstream of the luciferase reporter gene (SEQ ID NO: 10).

Stable Cell Line

CHO cells were transiently transfected with transcription cassettes for GAL4 DBD (1-147) CfEcR(DEF) and for VP16AD βRXREF-LmUSPEF controlled by ubiquitously active cellular promoters (PGK and EF-1α, respectively) on a single plasmid. Stably transfected cells were selected by Zeocin resistance. Individually isolated CHO cell clones were transiently transfected with a GAL4 RE-luciferase reporter (pFR Luc). 27-63 clone was selected using Hygromycin.

Treatment with Chiral Diacylhydrazine Ligand

Cells were trypsinized and diluted to a concentration of 2.5×10$^4$ cells mL. 100 µL of cell suspension was placed in each well of a 96 well plate and incubated at 37° C. under 5% CO$_2$ for 24 h. Ligand stock solutions were prepared in DMSO and diluted 300 fold for all treatments. Dose response testing consisted of 8 concentrations ranging from 33 µM to 0.0 µM.

Reporter Gene Assay

Luciferase reporter gene expression was measured 48 h after cell treatment using Bright-Glo™ Luciferase Assay System from Promega (E2650). Luminescence was detected at room temperature using a Dynex MLX microtiter plate luminometer.

Stable Cell Line

A population of stably transformed cells containing CVBE and 6XEcRE as described in Suhr et al., *Proc. Natl. Acad. Sci. USA* 95:7999-804 (1998) were obtained. Human 293 kidney cells, also referred to as HEK-293 cells, were sequentially infected with retroviral vectors encoding first the switch construct CVBE, and subsequently the reporter construct 6XEcRE Lac Z. The switch construct contained the coding sequence for amino acids 26-546 from *Bombyx mori* EcR (BE) (Iatrou) inserted in frame and downstream of the VP16 transactivation domain (VBE). A synthetic ATG start codon was placed under the control of cytomegalovirus (CVBE) immediate early promoter and flanked by long terminal repeats (LTR). The reporter construct contained six copies of the ecdysone response element (EcRE) binding site placed upstream of LacZ and flanked on both sides with LTR sequences (6XEcRE).

Dilution cloning was used to isolate individual clones. Clones were selected using 450 ug/mL G418 and 100 ng/mL puromycin. Individual clones were evaluated based on their response in the presence and absence of test ligands. Clone Z3 was selected for screening and SAR purposes.

Human 293 kidney cells stably transformed with CVBE and 6XEcRE LacZ were maintained in Minimum Essential Medium (Mediates, 10-010-CV) containing 10% FBS (Life Technologies, 26140-087), 450 gum G418 (Mediates, 30-234-CR), and 100 gnome promising (Sigma, P-7255), at 37° C. in an atmosphere containing 5% $CO_2$ and were subculture when they reached 75% confluence.

Treatment with Chiral Diacylhydrazine Ligand

Z3 cells were seeded into 96-well tissue culture plates at a concentration of $2.5\times10^3$ cells per well and incubated at 37° C. in 5% $CO_2$ for twenty-four hours. Stock solutions of ligands were prepared in DMSO. Ligand stock solutions were diluted 100 fold in media and 50 µL of this diluted ligand solution (33 µM) was added to cells. The final concentration of DMSO was maintained at 0.03% in both controls and treatments.

Reporter Gene Assays

Reporter gene expression was evaluated 48 hours after treatment of cells. β-galactosidase activity was measured using Gal Screen™ bioluminescent reporter gene assay system from Tropix (GSY1000). Fold induction activities were calculated by dividing relative light units ("RLU") in ligand treated cells with RLU in DMSO treated cells. Luminescence was detected at room temperature using a Dynex MLX microtiter plate luminometer.

A schematic of switch construct CVBE, and the reporter construct 6XEcRE Lac Z is shown in FIG. 1. Flanking both constructs are long terminal repeats, G418 and puromycin are selectable markers, CMV is the cytomegalovirus promoter, VBE is coding sequence for amino acids 26-546 from *Bombyx mori* EcR inserted downstream of the VP16 transactivation domain, 6× EcRE is six copies of the ecdysone response element, lacZ encodes for the reporter enzyme β-galactosidase.

Gene Expression Cassette

GAL4 DBD-CfEcR(DEF)/VP16AD-MmRXRE: The wild-type D, E, and F domains from spruce budworm *Choristoneura fumiferana* EcR ("CfEcR-DEF"; SEQ ID NO: 1) were fused to a GAL4 DNA binding domain ("Gal4 DBD1-147"; SEQ ID NO: 2) and placed under the control of the SV40e promoter of pM vector (PT3119-5, Clontech, Palo Alto, Calif.). The D and E domains from *Mus Musculus* RXR ("MmRXR-DE"; SEQ ID NO: 11) were fused to the transactivation domain from VP16 ("VP16AD"; SEQ ID NO: 6) and placed under the control of the SV40e promoter of the pVP16 vector (PT3127-5, Clontech, Palo Alto, Calif.).

Stable Cell Line

CHO cells were transiently transfected with transcription cassettes for GAL4 DBD-CfEcR(DEF) and for VP16AD-MmRXRE controlled by SV40e promoters. Stably transfected cells were selected using Hygromycin. Individually isolated CHO cell clones were transiently transfected with a GAL4 RE-luciferase reporter (pFR-Luc, Stratagene, La Jolla, Calif.). The 13B3 clone was selected using Zeocin.

Treatment with Chiral Diacylhydrazine Ligand

Cells were trypsinized and diluted to a concentration of $2.5\times10^4$ cells mL. 100 µL of cell suspension was placed in each well of a 96 well plate and incubated at 37° C. under 5% $CO_2$ for 24 h. Ligand stock solutions were prepared in DMSO and diluted 300 fold for all treatments. Dose response testing consisted of 8 concentrations ranging from 33 µM to 0.01 µM.

Gene Switch Assay—Engineered EcR:USP/PXR systems

Cellular gene switch assays were performed by transiently transfecting the following constructs in mouse embryonic fibroblast cells (NIH3T3). The wild-type D, E and F domains from *Choristoneura fumiferana* EcR or its V390I/Y410E/E274V mutant were fused to GAL4-DBD and placed under the control of the CMV promoter in the pBIND vector (Promega Corporation, Madison, Wis., USA). The DEF domains of EcRs shown were amplified using primers designed based on 20-25 nt sequences at the 5' and 3' ends. Restriction enzyme sites EcoR I/BamH I and Xba I were added to 5' and 3' primers respectively. The PCR products were digested with appropriate restriction enzymes and cloned into pBIND vector. The EcR LBDs cloned into pBIND vector were verified by sequencing. A chimeric RXR from *Homo sapiens* RXRβ and *Locusta migratoria* RXR, fused to VP16-AD and placed under the control of an SV40e promoter, was constructed as previously described (Kumar P & Katakam A in *Gene Transfer*, Friedmann T and Rossi J, eds, pp. 643-651 (2007), Cold Spring Harbor Laboratory Press, Cold Spring Harbor, N.Y.). The inducible luciferase reporter plasmid pFRLuc (Stratagene Cloning Systems, La Jolla, Calif., USA), contains five copies of the GAL4 response element and a synthetic minimal promoter.

NIH3T3 cells were maintained at 37° C. and 5% $CO_2$ in Dulbecco's modified Eagle's medium (DMEM) supplemented with 10% bovine calf serum, both obtained from Mediatech Inc., Manassas, Va. Cells were planted in a 96-well plate at a density of 2,500 cells/well in 50 µL of growth medium. The following day cells were first treated with 35 µL of serum-free DMEM containing dimethyl sulfoxide (DMSO; control) or a DMSO solution containing ligand. Cells were then transfected with 15 µl of serum-free DMEM containing 0.04 µg of EcR construct, 0.04 ug of RXR construct, and 0.16 µg of luciferase reporter construct per well, using SuperFect™ transfection reagent (Qiagen Inc., Valencia, Calif., USA) according to the manufacturer's instructions. Ligands were tested at 8 doses from 0.01-33 µM and the final DMSO concentration was 0.33% in both control and treatment wells. After a 48 hour post-treatment and transfection incubation, the cells were assayed for luciferase activity using the Bright-Glo™ Luciferase Assay System (Promega Corporation, Madison, Wis., USA) following the manufacturer's instructions. $EC_{50}$ values were measured minimally in duplicate.

Reporter Gene Assay

Luciferase reporter gene expression was measured 48 h after cell treatment using Bright-Glo™ Luciferase Assay System from Promega (E2650). Luminescence was detected at room temperature using a Dynex MLX microtiter plate luminometer.

Each assay was conducted in two separate wells, and the two values were averaged. Fold inductions were calculated by dividing relative light units ("RLU") in ligand treated cells with RLU in DMSO treated cells. $EC_{50}$s were calculated from dose response data using a three-parameter logistic model. Relative Max FI was determined as the maximum fold induction of the tested ligand (an embodiment of the invention) observed at any concentration relative to the maximum fold induction of GS™-E ligand (3,5-dimethyl-benzoic acid N-tert-butyl-N'-(2-ethyl-3-methoxy-benzoyl)-hydrazide) observed at any concentration.

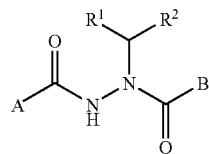

| Example(s) | A | B | R¹ | R² | rac EC$_{50}$ (nM) | RMFI[a] | R EC$_{50}$ (nM) | RMFI | S EC$_{50}$ (nM) | RMFI |
|---|---|---|---|---|---|---|---|---|---|---|
| 1.5[b]; 31.4[c] | PhCH$_2$O— | 3,5-di-CH$_3$-Ph- | CH$_2$=CHCH$_2$— | (CH$_3$)$_3$C— | | | >10,000 | 0.01 | >10,000 | 0.00 |
| 48; 49 | (CH$_3$)$_3$CO— | 3,5-di-CH$_3$-Ph- | CH$_3$CH$_2$CH$_2$— | (CH$_3$)$_3$C— | >33,000 | 0.02 | 15118 | 0.15 | >33,000 | 0.03 |
| 2; 32 | Ph- | 3,5-di-CH$_3$-Ph- | CH$_3$CH$_2$CH$_2$— | (CH$_3$)$_3$C— | ~100 | 0.60 | ~30 | 0.74 | ~3,300 | 0.19 |
| 3; 33 | 2-CH$_3$-Ph- | 3,5-di-CH$_3$-Ph- | CH$_3$CH$_2$CH$_2$— | (CH$_3$)$_3$C— | 100 | 0.70 | 90.0 | 0.75 | ~3,300 | 0.20 |
| 4 | 2-CH$_3$O-Ph- | 3,5-di-CH$_3$-Ph- | CH$_3$CH$_2$CH$_2$— | (CH$_3$)$_3$C— | ~2,000 | 0.32 | 993 | 0.38 | | |
| 5; 34 | 2-F-Ph- | 3,5-di-CH$_3$-Ph- | CH$_3$CH$_2$CH$_2$— | (CH$_3$)$_3$C— | 81 | 0.59 | ~40 | 0.68 | 529 | 0.41 |
| 6; 35 | 2-Cl-Ph- | 3,5-di-CH$_3$-Ph- | CH$_3$CH$_2$CH$_2$— | (CH$_3$)$_3$C— | 59 | 0.72 | ~20 | 0.88 | ~1,000 | 0.44 |
| 7; 36 | 2-Br-Ph- | 3,5-di-CH$_3$-Ph- | CH$_3$CH$_2$CH$_2$— | (CH$_3$)$_3$C— | 86 | 0.63 | 78.7 | 0.58 | ~3,300 | 0.11 |
| 8; 37 | 3-CH$_3$-Ph- | 3,5-di-CH$_3$-Ph- | CH$_3$CH$_2$CH$_2$— | (CH$_3$)$_3$C— | 193 | 0.88 | ~30 | 0.86 | ~3,300 | 0.22 |
| 9 | 3-CH$_3$O-Ph- | 3,5-di-CH$_3$-Ph- | CH$_3$CH$_2$CH$_2$— | (CH$_3$)$_3$C— | 304 | 0.84 | 100.7 | 0.81 | | |
| 10 | 3-Cl-Ph- | 3,5-di-CH$_3$-Ph- | CH$_3$CH$_2$CH$_2$— | (CH$_3$)$_3$C— | ~100 | 0.50 | 94.5 | 0.87 | | |
| 11; 38 | 4-CH$_3$-Ph- | 3,5-di-CH$_3$-Ph- | CH$_3$CH$_2$CH$_2$— | (CH$_3$)$_3$C— | 89 | 0.66 | ~20 | 0.74 | 2168 | 0.25 |
| 12; 39 | 4-CH$_3$CH$_2$-Ph- | 3,5-di-CH$_3$-Ph- | CH$_3$CH$_2$CH$_2$— | (CH$_3$)$_3$C— | ~20 | 0.79 | 23.6 | 0.78 | 418 | 0.29 |
| 13 | 4-CH$_3$O-Ph- | 3,5-di-CH$_3$-Ph- | CH$_3$CH$_2$CH$_2$— | (CH$_3$)$_3$C— | ~100 | 0.54 | 42.3 | 0.73 | | |
| 14 | 4-Cl-Ph- | 3,5-di-CH$_3$-Ph- | CH$_3$CH$_2$CH$_2$— | (CH$_3$)$_3$C— | ~200 | 0.46 | 140 | 0.74 | | |
| 15; 40 | 2,6-di-F-Ph- | 3,5-di-CH$_3$-Ph- | CH$_3$CH$_2$CH$_2$— | (CH$_3$)$_3$C— | 94 | 0.68 | 66.2 | 0.82 | ~1,000 | 0.39 |
| 16; 41 | 2,6-di-Cl-Ph | 3,5-di-CH$_3$-Ph- | CH$_3$CH$_2$CH$_2$— | (CH$_3$)$_3$C— | ~300 | 0.43 | ~300 | 0.53 | ~3,300 | 0.10 |
| 29; 47 | 2-CH$_3$-3-CH$_3$O-Ph- | 3,5-di-CH$_3$-Ph- | CH$_3$CH$_2$CH$_2$— | (CH$_3$)$_3$C— | 3.88 | 0.98 | ~1 | 1.08 | ~200 | 0.49 |
| 1; 31 | CH$_3$CH$_2$-3-CH$_3$O-Ph- | 3,5-di-CH$_3$-Ph- | CH$_3$CH$_2$CH$_2$— | (CH$_3$)$_3$C— | 1.63 | 1.05 | 2.23 | 0.97 | 136 | 0.52 |
| 17 | 3,4-di-CH$_3$O-Ph- | 3,5-di-CH$_3$-Ph- | CH$_3$CH$_2$CH$_2$— | (CH$_3$)$_3$C— | 4134 | 0.25 | ~4,000 | 0.27 | | |
| 18 | 3,5-di-F-Ph- | 3,5-di-CH$_3$-Ph- | CH$_3$CH$_2$CH$_2$— | (CH$_3$)$_3$C— | 30.5 | 0.26 | 140.6 | 0.52 | | |
| 19; 42 | 3,5-di-CH$_3$O-4-CH$_3$-Ph- | 3,5-di-CH$_3$-Ph- | CH$_3$CH$_2$CH$_2$— | (CH$_3$)$_3$C— | >10,000 | 0.00 | ~5,000 | 0.09 | >10,000 | 0.00 |
| 20 | 2-CH$_3$-3,4-(OCH$_2$O)-Ph- | 3,5-di-CH$_3$-Ph- | CH$_3$CH$_2$CH$_2$— | (CH$_3$)$_3$C— | 99.3 | 0.90 | 7.60 | 1.02 | | |
| 21 | 2-CH$_3$-3,4-(OCH$_2$CH$_2$O)-Ph- | 3,5-di-CH$_3$-Ph- | CH$_3$CH$_2$CH$_2$— | (CH$_3$)$_3$C— | 1.32 | 0.86 | 0.304 | 0.87 | | |
| 22 | 2-CH$_3$CH$_2$-3,4-(OCH$_2$CH$_2$O)-Ph- | 3,5-di-CH$_3$-Ph- | CH$_3$CH$_2$CH$_2$— | (CH$_3$)$_3$C— | 0.499 | 0.88 | 0.266 | 0.78 | | |
| 23 | 1-naphthyl- | 3,5-di-CH$_3$-Ph- | CH$_3$CH$_2$CH$_2$— | (CH$_3$)$_3$C— | 521 | 0.60 | 111 | 0.69 | | |
| 24 | 2-naphthyl- | 3,5-di-CH$_3$-Ph- | CH$_3$CH$_2$CH$_2$— | (CH$_3$)$_3$C— | ~500 | 0.44 | ~200 | 0.46 | | |
| 25; 43 | 2-thienyl- | 3,5-di-CH$_3$-Ph- | CH$_3$CH$_2$CH$_2$— | (CH$_3$)$_3$C— | 3163 | 0.52 | 432 | 0.42 | 5385 | 0.13 |
| 26; 44 | 2,5-di-CH$_3$-3-furanyl- | 3,5-di-CH$_3$-Ph- | CH$_3$CH$_2$CH$_2$— | (CH$_3$)$_3$C— | 2145 | 0.76 | ~1,000 | 1.16 | ~10,000 | 0.07 |
| 27; 45 | 2-Cl-3-pyridyl- | 3,5-di-CH$_3$-Ph- | CH$_3$CH$_2$CH$_2$— | (CH$_3$)$_3$C— | | | 95.2 | 0.70 | 7059 | 0.32 |
| 28; 46 | 6-Cl-3-pyridyl- | 3,5-di-CH$_3$-Ph- | CH$_3$CH$_2$CH$_2$— | (CH$_3$)$_3$C— | 470 | 0.70 | 243 | 0.38 | ~20,000 | 0.05 |
| 51 | 2-CH$_3$-3-CH$_3$O-Ph- | 3,5-di-CH$_3$O-4-CH$_3$-Ph- | CH$_3$CH$_2$CH$_2$— | (CH$_3$)$_3$C— | 80.2 | 0.82 | ~70 | 1.00 | | |
| 60 | 2-CH$_3$-3-CH$_3$O-Ph- | 3,5-di-CH$_3$-Ph- | CH$_2$=CHCH$_2$— | cyclohexyl | ~1000 | 0.49 | ~2,000 | 0.62 | | |
| 61 | 2-CH$_3$-3-CH$_3$O-Ph- | 3,5-di-CH$_3$O-4-CH$_3$-Ph- | CH$_2$=CHCH$_2$— | cyclohexyl | ~3,300 | 0.31 | ~3,300 | 0.33 | | |
| 53; 57 | Ph- | 3,5-di-CH$_3$-Ph- | CH$_3$CH$_2$CH$_2$— | cyclohexyl | | | ~3,300 | 0.30 | 2755 | 0.32 |
| 54; 58 | 3-CH$_3$O-Ph- | 3,5-di-CH$_3$-Ph- | CH$_3$CH$_2$CH$_2$— | cyclohexyl | | | ~3,300 | 0.19 | ~3,300 | 0.25 |
| 55; 59 | 4-CH$_3$CH$_2$-Ph- | 3,5-di-CH$_3$-Ph- | CH$_3$CH$_2$CH$_2$— | cyclohexyl | | | ~2,000 | 0.26 | ~1,000 | 0.28 |
| 52; 56 | 2-CH$_3$CH$_2$-3-CH$_3$O-Ph- | 3,5-di-CH$_3$-Ph- | CH$_3$CH$_2$CH$_2$— | cyclohexyl | | | 220 | 0.38 | 159 | 0.37 |
| 62 | 4-CH$_3$CH$_2$-Ph- | 3,5-di-CH$_3$-Ph- | CH$_2$=CHCH$_2$— | PhCH$_2$CH$_2$— | ~5,000 | 0.06 | 3093 | 0.14 | | |
| 63; 64 | PhCH$_2$O— | 3,5-di-CH$_3$-Ph- | HO(CH$_2$)$_3$C— | (CH$_3$)$_3$C— | | | >33,000 | 0.02 | >10,000 | 0.00 |

[a]RMFI = relative maximum fold induction; [b]"1.5" denotes Compound 5 of Example 1; [c]"31.4" denotes Compound 4 of Example 31.

| Example(s) | A | B | R¹ | R² | rac EC$_{50}$ (nM) | RMFI$^a$ | R EC$_{50}$ (nM) | RMFI | S EC$_{50}$ (nM) | RMFI |
|---|---|---|---|---|---|---|---|---|---|---|
| 1.5$^b$; 31.4$^c$ | PhCH$_2$O— | 3,5-di-CH$_3$-Ph- | CH$_2$=CHCH$_2$— | (CH$_3$)$_3$C— | | | ~2000 | 0.36 | >10,000 | 0.00 |
| 48; 49 | (CH$_3$)$_3$CO— | 3,5-di-CH$_3$-Ph- | CH$_3$CH$_2$CH$_2$— | (CH$_3$)$_3$C— | ~4000 | 0.50 | 2749 | 0.59 | 6605 | 0.20 |
| 2; 32 | Ph- | 3,5-di-CH$_3$-Ph- | CH$_3$CH$_2$CH$_2$— | (CH$_3$)$_3$C— | 3.9 | 0.85 | 2.2 | 0.91 | 267 | 0.38 |
| 3; 33 | 2-CH$_3$-Ph- | 3,5-di-CH$_3$-Ph- | CH$_3$CH$_2$CH$_2$— | (CH$_3$)$_3$C— | 12.2 | 0.97 | 1.1 | 0.69 | ~400 | 0.48 |
| 4 | 2-CH$_3$O-Ph- | 3,5-di-CH$_3$-Ph- | CH$_3$CH$_2$CH$_2$— | (CH$_3$)$_3$C— | ~300 | 0.72 | 99 | 0.52 | | |
| 5; 34 | 2-F-Ph- | 3,5-di-CH$_3$-Ph- | CH$_3$CH$_2$CH$_2$— | (CH$_3$)$_3$C— | 1.1 | 0.67 | ~0.8 | 1.16 | 86 | 0.64 |
| 6; 35 | 2-Cl-Ph- | 3,5-di-CH$_3$-Ph- | CH$_3$CH$_2$CH$_2$— | (CH$_3$)$_3$C— | 1.2 | 0.95 | 0.63 | 1.01 | ~20 | 0.77 |
| 7; 36 | 2-Br-Ph- | 3,5-di-CH$_3$-Ph- | CH$_3$CH$_2$CH$_2$— | (CH$_3$)$_3$C— | ~3 | 1.28 | 1.4 | 0.90 | 433 | 0.36 |
| 8; 37 | 3-CH$_3$-Ph- | 3,5-di-CH$_3$-Ph- | CH$_3$CH$_2$CH$_2$— | (CH$_3$)$_3$C— | 16.2 | 0.86 | 1.2 | 0.92 | 292 | 0.47 |
| 9 | 3-CH$_3$O-Ph- | 3,5-di-CH$_3$-Ph- | CH$_3$CH$_2$CH$_2$— | (CH$_3$)$_3$C— | 7.1 | 0.63 | 1.4 | 0.70 | | |
| 10 | 3-Cl-Ph- | 3,5-di-CH$_3$-Ph- | CH$_3$CH$_2$CH$_2$— | (CH$_3$)$_3$C— | 23.9 | 0.86 | ~3 | 0.76 | | |
| 11; 38 | 4-CH$_3$-Ph- | 3,5-di-CH$_3$-Ph- | CH$_3$CH$_2$CH$_2$— | (CH$_3$)$_3$C— | 6.3 | 0.73 | ~1 | 0.90 | 341 | 0.44 |
| 12; 39 | 4-CH$_3$CH$_2$-Ph- | 3,5-di-CH$_3$-Ph- | CH$_3$CH$_2$CH$_2$— | (CH$_3$)$_3$C— | ~0.6 | 0.96 | 0.56 | 0.82 | ~20 | 0.70 |
| 13 | 4-CH$_3$O-Ph- | 3,5-di-CH$_3$-Ph- | CH$_3$CH$_2$CH$_2$— | (CH$_3$)$_3$C— | ~5 | 0.71 | 1.4 | 0.68 | | |
| 14 | 4-Cl-Ph- | 3,5-di-CH$_3$-Ph- | CH$_3$CH$_2$CH$_2$— | (CH$_3$)$_3$C— | ~20 | 0.83 | 51 | 0.74 | | |
| 15; 40 | 2,6-di-F-Ph- | 3,5-di-CH$_3$-Ph- | CH$_3$CH$_2$CH$_2$— | (CH$_3$)$_3$C— | ~1 | 0.92 | 0.54 | 0.79 | ~20 | 0.69 |
| 16; 41 | 2,6-di-Cl-Ph- | 3,5-di-CH$_3$-Ph- | CH$_3$CH$_2$CH$_2$— | (CH$_3$)$_3$C— | ~30 | 0.73 | 51.2 | 0.83 | ~700 | 0.62 |
| 29; 47 | 2-CH$_3$-3-CH$_3$O-Ph- | 3,5-di-CH$_3$-Ph- | CH$_3$CH$_2$CH$_2$— | (CH$_3$)$_3$C— | 0.15 | 0.77 | 0.078 | 1.05 | 56.3 | 0.57 |
| 1; 31 | 2-CH$_3$CH$_2$-3-CH$_3$O-Ph- | 3,5-di-CH$_3$-Ph- | CH$_3$CH$_2$CH$_2$— | (CH$_3$)$_3$C— | 0.14 | 1.05 | 0.13 | 0.82 | ~30 | 0.57 |
| 17 | 3,4-di-CH$_3$O-Ph- | 3,5-di-CH$_3$-Ph- | CH$_3$CH$_2$CH$_2$— | (CH$_3$)$_3$C— | 720 | 0.51 | ~300 | 0.53 | | |
| 18 | 3,5-di-F-Ph- | 3,5-di-CH$_3$-Ph- | CH$_3$CH$_2$CH$_2$— | (CH$_3$)$_3$C— | ~3 | 1.00 | ~10 | 0.79 | | |
| 19; 42 | 3,5-di-CH$_3$O-4-CH$_3$-Ph- | 3,5-di-CH$_3$-Ph- | CH$_3$CH$_2$CH$_2$— | (CH$_3$)$_3$C— | 3928 | 0.15 | ~2000 | 0.37 | ~7000 | 0.08 |
| 20 | 2-CH$_3$-3,4-(OCH$_2$O)-Ph- | 3,5-di-CH$_3$-Ph- | CH$_3$CH$_2$CH$_2$— | (CH$_3$)$_3$C— | 12.1 | 0.92 | 0.26 | 1.01 | | |
| 21 | 2-CH$_3$-3,4-(OCH$_2$CH$_2$O)-Ph- | 3,5-di-CH$_3$-Ph- | CH$_3$CH$_2$CH$_2$— | (CH$_3$)$_3$C— | ~0.1 | 0.85 | ~0.04 | 1.14 | | |
| 22 | 2-CH$_3$CH$_2$-3,4-(OCH$_2$CH$_2$O)-Ph- | 3,5-di-CH$_3$-Ph- | CH$_3$CH$_2$CH$_2$— | (CH$_3$)$_3$C— | 0.059 | 0.79 | 0.064 | 0.77 | | |
| 23 | 1-naphthyl- | 3,5-di-CH$_3$-Ph- | CH$_3$CH$_2$CH$_2$— | (CH$_3$)$_3$C— | 66 | 0.84 | ~10 | 0.73 | | |
| 24 | 2-naphthyl- | 3,5-di-CH$_3$-Ph- | CH$_3$CH$_2$CH$_2$— | (CH$_3$)$_3$C— | 61 | 0.62 | ~20 | 0.80 | | |
| 25; 43 | 2-thienyl- | 3,5-di-CH$_3$-Ph- | CH$_3$CH$_2$CH$_2$— | (CH$_3$)$_3$C— | 172 | 0.89 | ~20 | 0.72 | 1065 | 0.52 |
| 26; 44 | 2,5-di-CH$_3$-3-furanyl- | 3,5-di-CH$_3$-Ph- | CH$_3$CH$_2$CH$_2$— | (CH$_3$)$_3$C— | 84 | 0.97 | 99.4 | 0.95 | ~2000 | 0.49 |
| 27; 45 | 2-Cl-3-pyridyl- | 3,5-di-CH$_3$-Ph- | CH$_3$CH$_2$CH$_2$— | (CH$_3$)$_3$C— | | | 7.0 | 0.73 | 1469 | 0.80 |
| 28; 46 | 6-Cl-3-pyridyl- | 3,5-di-CH$_3$-Ph- | CH$_3$CH$_2$CH$_2$— | (CH$_3$)$_3$C— | 47 | 0.68 | ~20 | 0.78 | 3995 | 0.42 |

-continued

| | | | | | [V390I/Y410E/E274V]-CfEcR, 3T3 Cells | | | | | |
|---|---|---|---|---|---|---|---|---|---|---|
| | | | | | rac | | R | | S | |
| Example(s) | A | B | R¹ | R² | EC$_{50}$ (nM) | RMFI$^a$ | EC$_{50}$ (nM) | RMFI | EC$_{50}$ (nM) | RMFI |
| 51 | 2-CH$_3$-3-CH$_3$O-Ph- | 3,5-di-CH$_3$O-4-CH$_3$-Ph- | CH$_3$CH$_2$CH$_2$— | (CH$_3$)$_3$C— | 15 | 0.81 | 0.56 | 0.81 | | |
| 60 | 2-CH$_3$-3-CH$_3$O-Ph- | 3,5-di-CH$_3$-Ph- | CH$_2$=CHCH$_2$— | cyclohexyl | ~200 | 0.73 | 746 | 0.78 | | |
| 61 | 2-CH$_3$-3-CH$_3$O-Ph- | 3,5-di-CH$_3$O-4-CH$_3$-Ph- | CH$_2$=CHCH$_2$— | cyclohexyl | 521 | 0.39 | 1016 | 0.67 | | |
| 53; 57 | Ph- | 3,5-di-CH$_3$-Ph- | CH$_3$CH$_2$CH$_2$— | cyclohexyl | | | 629 | 0.62 | 769 | 0.50 |
| 54; 58 | 3-CH$_3$O-Ph- | 3,5-di-CH$_3$-Ph- | CH$_3$CH$_2$CH$_2$— | cyclohexyl | | | 474 | 0.44 | 121 | 0.42 |
| 55; 59 | 4-CH$_3$CH$_2$-Ph- | 3,5-di-CH$_3$-Ph- | CH$_3$CH$_2$CH$_2$— | cyclohexyl | | | ~70 | 0.42 | ~30 | 0.35 |
| 52; 56 | 2-CH$_3$CH$_2$-3-CH$_3$O-Ph- | 3,5-di-CH$_3$-Ph- | CH$_3$CH$_2$CH$_2$— | cyclohexyl | | | ~200 | 0.64 | 107 | 0.52 |
| 62 | 4-CH$_3$CH$_2$-Ph- | 3,5-di-CH$_3$-Ph- | CH$_2$=CHCH$_2$— | PhCH$_2$CH$_2$— | 2106 | 0.67 | 1991 | 0.54 | | |
| 63; 64 | PhCH$_2$O— | 3,5-di-CH$_3$-Ph- | HO(CH$_2$)$_3$— | (CH$_3$)$_3$C— | | | ~8000 | 0.33 | >10,000 | 0.00 |

$^a$RMFI = relative maximum fold induction;
$^b$"1.5" denotes Compound 5 of Example 1;
$^c$"31.4" denotes Compound 4 of Example 31.

Example 67

This example illustrates in vivo testing of compounds of the invention. In vivo induction of a reporter enzyme with chiral diacylhydrazine ligands of the present invention was evaluated in a C57BL/6 mouse model system containing a gene switch.

Gene Expression Cassettes

The wild-type D, E, and F domains from spruce budworm *Choristoneura fumiferana* EcR ("CfEcR-DEF"; SEQ ID NO: 1) were mutated [V107 (gtt)→I107 (att) and Y127 (tac)→E127 (gag)] and fused to a GAL4 DNA binding domain ("Gal4 DBD1-147"; SEQ ID NO: 2). Helices 1 through 8 of the EF domains from *Homo sapiens* RXRβ ("HsRXRβ-EF"; nucleotides 1-465 of SEQ ID NO: 4) and helices 9 through 12 of the EF domains of *Locusta migratoria* Ultraspiracle Protein ("LmUSP-EF"; nucleotides 403-630 of SEQ ID NO: 5) were fused to the transactivation domain from VP16 ("VP16AD"; SEQ ID NO: 6), which regulates a reporter gene human secreted alkaline phosphatase ("SEAP", SEQ ID NO: 12) that was placed under the control of a 6×GAL4 response element (SEQ ID NO: 13) and a transthyretin promoter (SEQ ID NO: 14). Each element of the gene switch was on a separate plasmid. Receptor expression was under the control of a CMV promoter (SEQ ID NO: 15). Induction was evaluated by the amount of reporter protein expressed in the presence of ligand.

Electroporation of Gene Switch

SEAP expression in serum of mice was evaluated after electroporation of the gene switch into mouse quadriceps. Mice were anesthetized with 2 μL/g of a mixture of ketamine (100 mg/mL) and xylazine (20 mg/mL). Animals were then shaved, DNA vectors injected into the muscle in a volume of 2×50 μL polyglutamic acid (12 mg/mL water), electrode conductivity gel applied, and an electrode caliber (1 cm×1 cm; model 384) was placed on hind leg. The muscle was electroporated with 200 V/cm, 8 times, for 20 msec/pulse, at 1 sec time intervals. The transverse electrical field direction was reversed after the animals received half of the pulses. Electroporation was performed with an ECM 830 electroporator from BTX Molecular Delivery Systems.

Treatment with Chiral Diacylhydrazine Ligand

In some experiments mice received an intraperitoneal injection (IP) of 2.6 μmol of ligand in 50 μL of DMSO 3 days after electroporation of the gene switch. In other experiments the concentration of ligand was decreased to 26 nmol/50 μL of DMSO/mouse. SEAP expression was evaluated 2-11 days after ligand administration. In other experiments ligand was administered in rodent chow. The chow was prepared by dissolving 2 g of ligand in 20 mL of acetone and adding it to 1 kg of LabDiet 5010 autoclavable chow from Purina Mills. This was thoroughly mixed in a Hobart mixer and then mixed for an additional 15 min in a Cross Blend mixer. Animals received chow ad libitum for 1, 2, or 3 days. All values are the average from four animals. Background SEAP in sera from animals treated with vector alone without ligand addition was 0-11 ng/mL serum.

Reporter Assay

Mouse serum was obtained by centrifugation of blood acquired by retroorbital bleeding with a small glass capillary tube. SEAP quantification was determined using a Clontech Great Escape chemiluminescence kit and by comparison with the Clontech SEAP standard.

To evaluate the relative in vivo effectiveness of (R)-2-ethyl-3-methoxy-benzoic acid N'-(1-tert-butyl-butyl)-N'-(3,5-dimethyl-benzoyl)-hydrazide (Example 1) to induce RheoSwitch® Therapeutic System (RTS) gene expression, twelve C57BL6 mice were electroporated with the following plasmids: pCMV/GEVY(DEF), pCMV/VP16-Hs-LmRXR and p6XGAL4RE-TTR-SEAP. The plasmid pCMV/GEVY (DEF) consists of the D, E and F domains from *Choristoneura fumiferana* EcR carrying the mutations V390I/Y410E/

Figure 3:
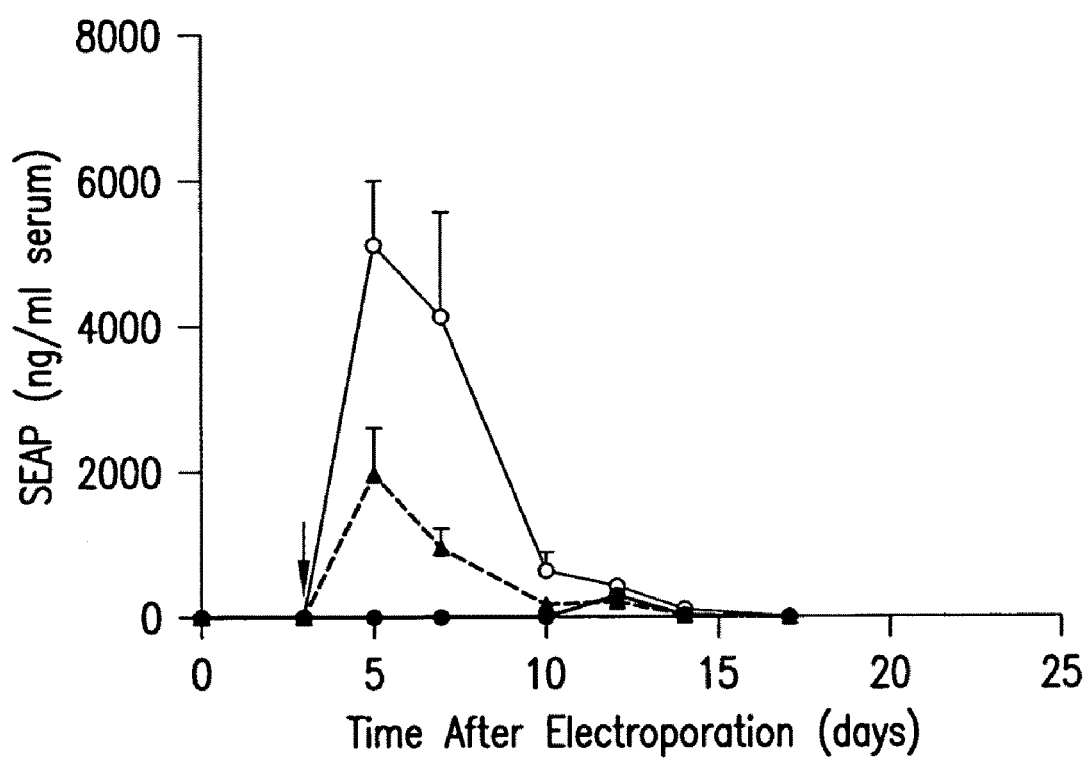
FIG. 3: Graph showing in vivo comparison of rac-, (R)- and (S)-2-ethyl-3-methoxy-benzoic acid N'-(1-tert-butyl-butyl)-N'-(3,5-dimethyl-benzoyl)-hydrazide on induction of RheoSwitch® Therapeutic System gene expression in mice. Solid circles are the S enantiomer, solid triangles are the Racemate, and open circles are the R enantiomer.
Figure 20:
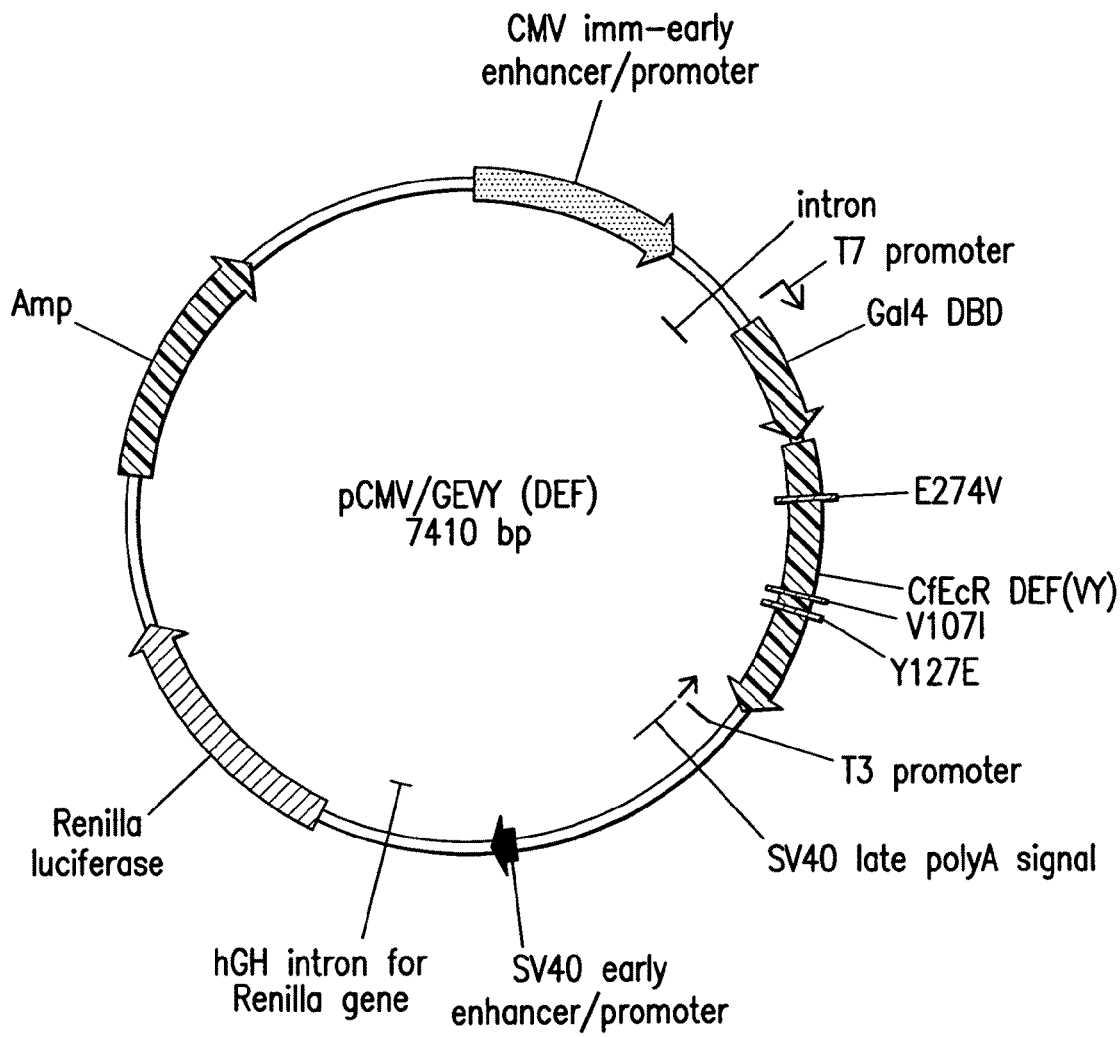
FIG. 20: Diagrammatic representation of pCMV/GEVY (DEF) plasmid. The plasmid pCMV/GEVY(DEF) consists of the D, E and F domains from *Choristoneura fumiferana* EcR carrying the mutations V390I/Y410E/E274V fused downstream of the yeast GAL4-DBD (aa 1-147) and placed under the control of the CMV promoter and a downstream SV40 polyadenylation signal in the pBIND vector (Promega Corporation, Madison, Wis., USA). The DEF domains of EcRs shown were amplified using primers designed based on 20-25 nt sequences at the 5' and 3' ends. Restriction enzyme sites B In another embodiment, the present invention pertains to enantiomerically enriched compounds of Formula II
Figure 21:
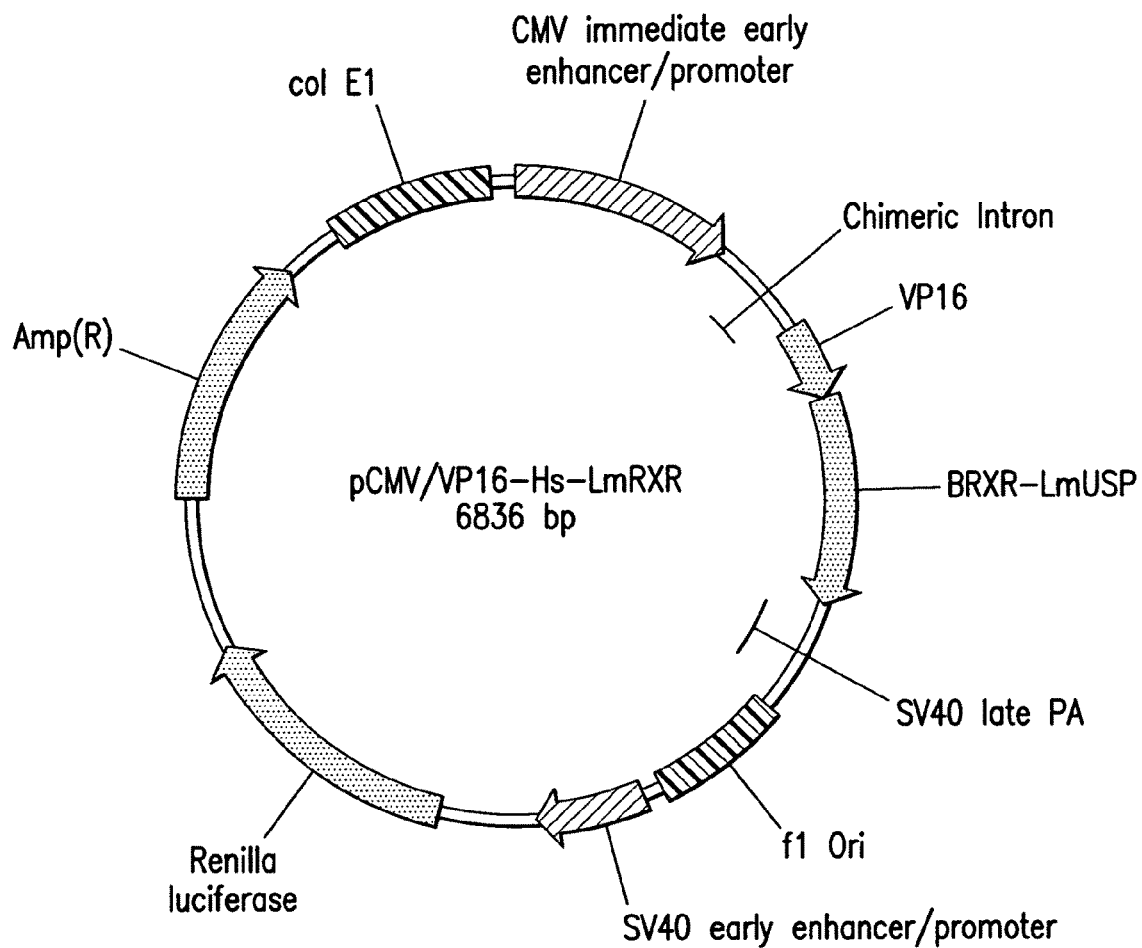
Figure 22:
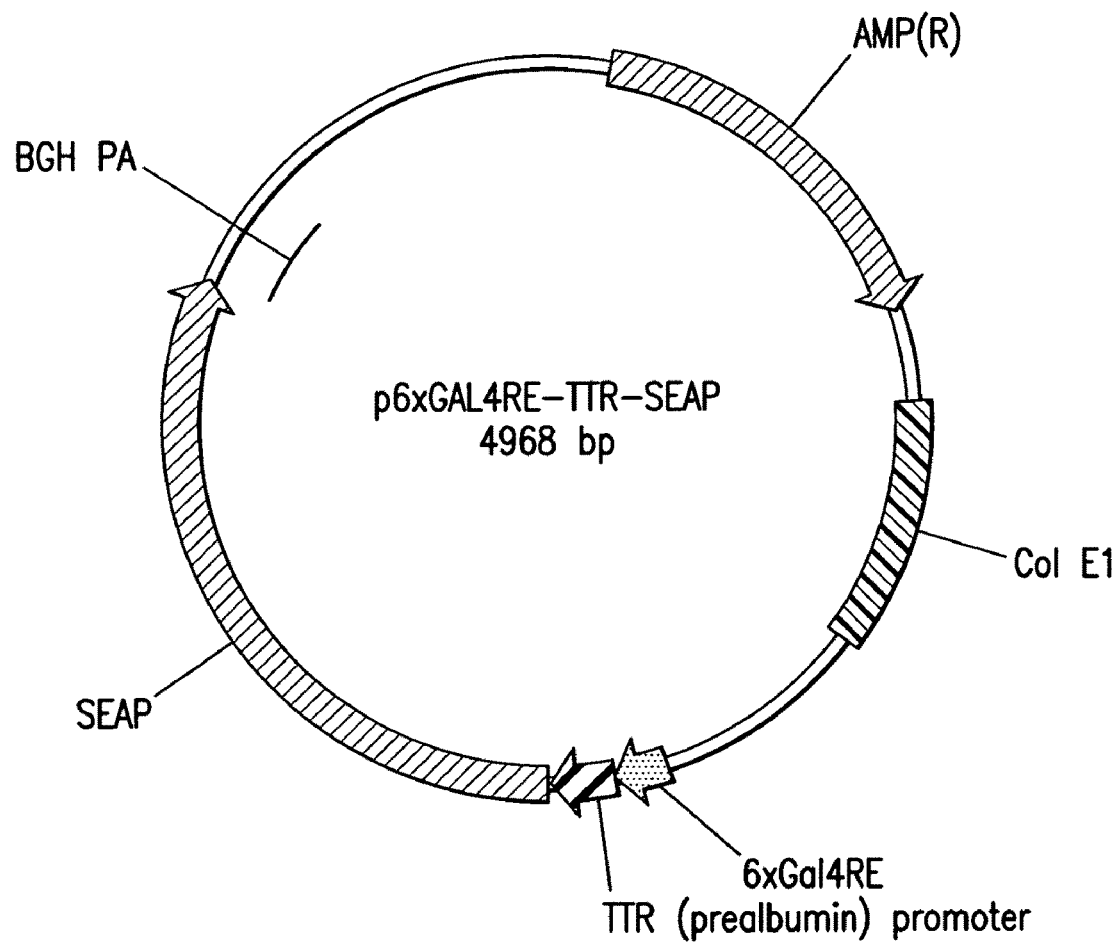

E274V fused downstream of the yeast GAL4-DBD (aa 1-147) and placed under the control of the CMV promoter and a downstream SV40 polyadenylation signal in the pBIND vector (Promega Corporation, Madison, Wis., USA). The DEF domains of EcRs shown were amplified using primers designed based on 20-25 nt sequences at the 5' and 3' ends. Restriction enzyme sites BamH I and Xba I were added to 5' and 3' primers respectively. The PCR products were digested with appropriate restriction enzymes and cloned into pBIND vector (FIG. 20). The vector pCMV/VP16-Hs-LmRXR contains a chimeric RXR from *Homo sapiens* RXRβ (helix 1-8 of E domain) and *Locusta migratoria* RXR (helix 9-12 of E domain), fused downstream of VP16-activation domain and placed under the control of the CMV promoter in the pBIND vector (FIG. 21). The inducible SEAP reporter vector p6xGAL4RE-TTR-SEAP contains the human secreted alkaline phosphatase reporter gene placed under the control of the inducible promoter consisting of 6 copies of the Gal4 response element upstream of the transthyretin (TTR) promoter (FIG. 22). Three days after electroporation of plasmid DNA into the quadriceps of mice, the three ligand preparations were administered to mice by intraperitoneal injection at a rate of 26 nmol/mouse (11.4 µg/mouse, approximately 570 µg/kg). Human secreted alkaline phosphatase (SEAP) expression in mouse serum was subsequently monitored for seventeen days after ligand administration. The relative in vivo effectiveness of (S)-2-ethyl-3-methoxy-benzoic acid N'-(1-tert-butyl-butyl)-N'-(3,5-dimethyl-benzoyl)-hydrazide (Example 31) and rac-2-ethyl-3-methoxy-benzoic acid N'-(1-tert-butyl-butyl)-N'-(3,5-dimethyl-benzoyl)-hydrazide was evaluated for comparison. As shown in FIG. 3, (S)-2-ethyl-3-methoxy-benzoic acid N'-(1-tert-butyl-butyl)-N'-(3,5-dimethyl-benzoyl)-hydrazide (●-●) does not induce RTS gene reporter expression. rac-2-Ethyl-3-methoxy-benzoic acid N'-(1-tert-butyl-butyl)-N'-(3,5-dimethyl-benzoyl)-hydrazide induces modest RTS gene reporter expression (▲-▲). (R)-2-Ethyl-3-methoxy-benzoic acid N'-(1-tert-butyl-butyl)-N'-(3,5-dimethyl-benzoyl)-hydrazide (○-○) induces substantial RTS gene reporter expression.

Example 68

Physical Properties of the R Enantiomer and Racemate of 2-Ethyl-3-methoxy-benzoic Acid N'-(1-tert-butyl-butyl)-N'-(3,5-dimethyl-benzoyl)-hydrazide Morphic Form: The solid sample lots are reported in FIG. 4. With respect to the R enantiomer, samples obtained by rapid crystallization/precipitation from either methanol/water or toluene/heptane yield the same powder X-ray diffraction pattern (data not shown), and have essentially the same melting point ([toluene/heptane]166.2-167.1° C., [CH$_3$OH/H$_2$O]166.5-167.4° C.) as compared to each other and as compared to a standard obtained from CH$_3$OH crystallization (165.1-166.5° C.). With respect to the racemate, two separate preparations obtained by methanol evaporation gave the same melting point (170-171° C., 169-170° C.) within experimental error and slight variations in purity. The morphic forms of the racemate and R enantiomer of 2-Ethyl-3-methoxy-benzoic acid N'-(1-tert-butyl-butyl)-N'-(3,5-dimethyl-benzoyl)-hydrazide appear to be the most typical.

Micronization and Particle Size: To normalize for particle size, each of the R enantiomer and racemate of 2-Ethyl-3-methoxy-benzoic acid N'-(1-tert-butyl-butyl)-N'-(3,5-dimethyl-benzoyl)-hydrazide were pre-screened through 20 mesh and micronized. Particle size was determined by weighing out about 20 mg of the test substance into a 15 mL Falcon tube. 10 mL of deionized water were added into the powder. The suspension was mixed, sonicated for 20 minutes, and then immediately analyzed for particle size by laser light diffraction using a Malvern Mastersizer device. The size distributions appear in FIGS. 5 and 6. Although the racemate appears to have a slightly larger overall particle size than the R enantiomer, the two samples are quite similar.

Bulk and tapped density analysis: Bulk densities of micronized R enantiomer and racemate of 2-Ethyl-3-methoxy-benzoic acid N'-(1-tert-butyl-butyl)-N'-(3,5-dimethyl-benzoyl)-hydrazide were calculated using the measured weight and volume in a 10 mL a graduated cylinder. Tapped density of micronized material was calculated using the material weight and tapped volume. The tapped volume was measured using tap density analyzer (model: Stampfvolumeter, STAV2003 by JEL), the tapped volume was recorded when it became constant (FIG. 7). The R enantiomer has a slightly lower bulk density and tapped density. Both materials are flocculent (low bulk density).

Thermal gravimetric analysis/Differential Thermal Analysis (TGA/DTA) Analysis: Micronized R enantiomer and racemate of 2-Ethyl-3-methoxy-benzoic acid N'-(1-tert-butyl-butyl)-N'-(3,5-dimethyl-benzoyl)-hydrazide were analyzed by thermal gravimetric analysis/differential thermal analysis. The thermal gravimetry plot appears in FIG. 8. Both materials showed an endothermal event on the DTA profile. The onset temperature for the R enantiomer (163.6° C.) was significantly lower than that of the racemate (171.2° C.). Heat of fusion for the R enantiomer (59.8 uv·s/mg) was also significantly lower than that of the racemate (80.8 uv·s/mg). This illustrates the two materials are different crystalline forms. The lower melting point and lower heat of fusion of the R enantiomer are reflected in differing solubility properties.

Figure 8:
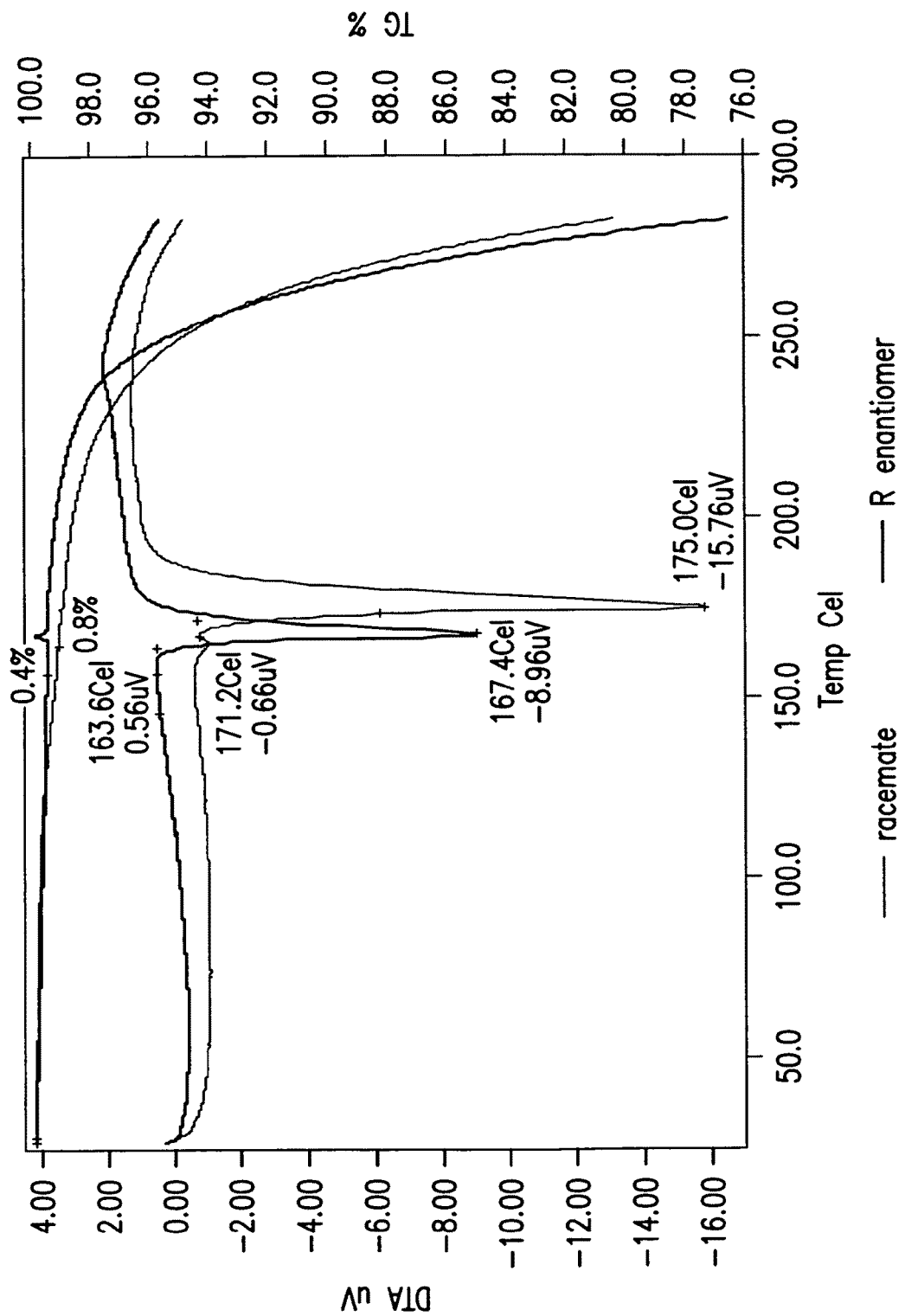
FIG. 8: Thermal gravimetric analysis/Differential Thermal Analysis (TGA/DTA) analysis (thermal plot) of micronized racemate and R enantiomer of 2-ethyl-3-methoxy-benzoic acid N'-(1-tert-butyl-butyl)-N'-(3,5-dimethyl-benzoyl)-hydrazide demonstrates different crystalline forms. Lot Nos: REH-28-9-1 and REH-28-4-2; sample weight 7.71994 mg. Signal output in units of uV per mg of sample (uV/mg); thermal gravimetry—percentage weight change of the sample (TG %). Both materials showed an endothermal event on the DTA profile. The onset temperature for the R enantiomer (163.6° C.) was significantly lower than that of the racemate (171.2° C.). Heat of fusion for the R enantiomer (59.8 uv·s/mg) was also significantly lower than that of the racemate (80.8 uv·s/mg).

Upon heating to above 150° C., R enantiomer lost 0.4% of total weight and the racemate lost 0.8% of total weight (FIG. 8). The moisture content (heat-removable moisture) in the two materials is slightly different.

Dynamic Vapor Sorption Analysis: When exposed to a desiccant condition (20% RH), the racemate did not show any significant weight loss, whereas the R enantiomer lost 0.9% of total weight (data not shown) which may correspond to loosely associated moisture acquired during sample transfer or storage. After dehydration under dessicant conditions, the two materials showed comparable weight gains upon exposing to low (30-40% RH), medium (50-60% RH) and high (70-80% RH) humidity. At 70% RH, the weight gain is 6.3% for the R enantiomer and 6.2% for the racemate (data not shown), indicating moderate hygroscopicity for both materials.

Solubility in Pharmaceutical Excipients: Assay 1: The solubility of micronized R enantiomer and racemate of 2-Ethyl-3-methoxy-benzoic acid N'-(1-tert-butyl-butyl)-N'-(3,5-dimethyl-benzoyl)-hydrazide was assessed qualitatively in commercially-available excipients (FIG. 9). Initial solutions/suspensions of 10 mg/g (test article/excipient) in glass vials were prepared by sonication at room temperature for 15 minutes with swirling for 30 seconds at 5 minute intervals, followed by heating in an aluminum block at 50° C. for 12 minutes with swirling for 30 seconds at 3 minute intervals. Based on the appearance of this initial 10 mg/g excipient sample, a 2-4 point concentration continuum was scanned by up or down sampling at several of the following points: 5, 10, 15, 20, 30, 50 mg/g (test article/excipient). The R enantiomer was more soluble than racemate in all the tested pharmaceutical excipients except for neat polysorbate 80, in which the R enantiomer and the racemate appear comparably soluble (see FIG. 9). No change in color was observed for any of the samples. Photos of several of the preparations in clear glass vials were taken (not shown).

Assay 2: For each excipient, the lowest concentration at which R enantiomer or racemate of 2-Ethyl-3-methoxy-benzoic acid N'-(1-tert-butyl-butyl)-N'-(3,5-dimethyl-benzoyl)-hydrazide is insoluble in the FIG. 9 assay was identified. Suspensions of both materials at this same concentration were prepared in vials. Each sample was stirred at room temperature for ≦2.5 hr (treatment 1). As a separate experiment, test article/excipient combinations were heated in an aluminum block at 90° C. for 5 minutes, or longer as needed; indicated in FIG. 10, and allow to cool to room temperature, and seeded with a tiny amount of the same micronized substance. (treatment 2). The physical appearance was recorded at 72 hr or the indicated time (FIG. 10). In all cases, no change in color was observed. This solubility assay operates from a fully dissolved condition in which initial particle size and morphic form are irrelevant. The observation of precipitation/crystallization upon seeding supersaturated 2-Ethyl-3-methoxy-benzoic acid N'-(1-tert-butyl-butyl)-N'-(3,5-dimethyl-benzoyl)-hydrazide racemate solutions with any morphic form of crystalline racemate, while R enantiomer remains fully dissolved (especially without heating) indicates a solubility differential between the racemate and the R enantiomer at the tested concentration. Photos were taken of preparations in clear glass vials (R enantiomer under the conditions of assay 1 without heating to 90° C., and racemate after 90° C. treatment, cooling and seeding, not shown).

Assay 3: R enantiomer and racemate of 2-ethyl-3-methoxy-benzoic acid N'-(1-tert-butyl-butyl)-N'-(3,5-dimethyl-benzoyl)-hydrazide were mixed with 20% PEG 1000 in distilled water, pH 7.0 at 1-2 mg of powder per mL The mixture was incubated at 37° C., vortexed at room temperature for ca. 2 hours, and allowed to stand for another 12 hours at room temperature. The solution was filtered or centrifuged, and concentrations were quantified by duplicate LC/MS/MS injections, using a generic LC/MS/MS method with a minimum 4 point calibration curve (FIG. 11). See Löbenberg R, et al., Solubility as a limiting factor to drug absorption, In: Oral Drug Absorption, J. B. Dressman (Ed), Marcel Dekker, NY, 2000 and Mader W J, Grady L T, Determination of solubility, Chapter 5 in Techniques of Chemistry, Physical Methods in Chemistry, Vol. 1, Part V, Weissberger, V. A., Rossiter, B. W., Eds., Wiley, New York, 1971.

Assay 4: Equilibrium solubility in formulation excipients and biological fluids influences drug bioavailability, although kinetics of dissolution may also be a limiting factor in determining bioavailability. The solubilities of R enantiomer and racemate of 2-ethyl-3-methoxy-benzoic acid N'-(1-tert-butyl-butyl)-N'-(3,5-dimethyl-benzoyl)-hydrazide were established quantitatively in aqueous preparations of the pharmaceutical surfactant polysorbate 80 and then the intrinsic dissolution rate of compacted test substance was observed. Mixtures of racemate and R enantiomer in 0.5%, 1%, and 1.5% polysorbate 80 solutions were prepared by addition of 20+/−1 mg test substance in a 2 mL Eppendorf vial, followed by 500 mg polysorbate solution. The mixture was bead-beaten for 120 second, shaken at 25° C. for 16 to 24 hours, and filtered using a Spin-X (0.2 µM). The pH of the filtrate was recorded. The concentration of test substance in the filtrate was measured by quantitative HPLC analysis (FIG. 12). The R enantiomer is 2-3× more soluble in 1.0 and 1.5% polysorbate 80 solutions. In deionized water and 0.5% polysorbate 80, the solubility of racemate and R enantiomer are comparable.

Next, the intrinsic dissolution profiles of R enantiomer and racemate of 2-ethyl-3-methoxy-benzoic acid N'-(1-tert-butyl-butyl)-N'-(3,5-dimethyl-benzoyl)-hydrazide were determined using compressed pellets (7 mm diameter, 100 mg) in 1% Polysorbate 80 in Di-water at 37° C., according to the following test conditions:

Vessel: 1000 mL
Medium: 1% Polysorbate 80 in di-water (vacuum filtered thru a 0.8 µM filter)
Medium volume: 1000 mL
Speed: 100 RPM
Temp: 37° C.
Sampling points: 15, 30, 45, 60, 90 and 120 min
Sampling volume: 1 mL (filtered thru 30 micron)
Analysis: HPLC (prepare standard solutions from each lot)
Sample size: n=2 pellets/test substance The release of racemate and R enantiomer was under the detection limit by HPLC up to 120 minutes. After 120 minutes, it was observed that the pellets for both substances remained intact in the medium.

Example 69

Cellular Membrane Permeability Properties of the R Enantiomer and Racemate of 2-Ethyl-3-methoxy-benzoic acid N'-(1-tert-butyl-butyl)-N'-(3,5-dimethyl-benzoyl)-hydrazide Bidirectional Permeability Through Caco-2 Cell Monolayers (see Sambuy Y, et al., The Caco-2 cell line as a model of the intestinal barrier: influence of cell and culture-related factors on Caco-2 cell functional characteristics. Cell Biol Toxicol. 2005 January; 21(1):1-26 and Artursson P, et al., Caco-2 monolayers in experimental and theoretical predictions of drug transport. Adv Drug Deliv Rev. 2001 Mar. 1; 46(1-3):27-43):

Data is shown in FIG. 13. The test compounds were prepared as 5 µM in HBSSg with a maximum DMSO concentration ≦1%. Confluent monolayers of Caco-2 cells, 21 to 28 days old were prepared. The receiver well was prepared with 1% BSA in modified Hanks buffer HBSSg, and the apical and basolateral sides of Caco-2 cell were maintained at pH 7.4±0.2. Two monolayers were dosed in each direction (N=2): the apical side was dosed for (A→B) assessment and the basolateral side was dosed for (B→A) assessment. The test compound concentration was measured for both apical and basolateral sides at a time point of 120 minutes using a generic LC/MS/MS method with a minimum 4 point calibration curve. The values in FIG. 13 are: the percent recovery of the test compound from Transwell® wells containing Caco-2 cell monolayers; apparent permeability (Papp) in both directions; efflux ratio (Papp B→A)/(Papp A→B); absorption potential of a test compound classified as either Low or High; efflux classification is significant when efflux ≧3.0 and Papp (B→A)≧1.0×10-6 cm/s. The R enantiomer is more permeable than the racemate in both directions. Also, the efflux rate for the R enantiomer is lower.

Blood Brain Barrier Penetration Potential Determination Using MDR1-MDCK Cells (see Taub M E, et al., Functional assessment of multiple P-glycoprotein (P-gp) probe substrates: Influence of cell line and modulator concentration on P-gp activity. Drug Metab Dispos. 2005 November; 33(11): 1679-87 and Wang Q, et al., Evaluation of the MDR-MDCK cell line as a permeability screen for the blood-brain barrier. Int J Pharm. 2005 Jan. 20; 288(2):349-59. (revised from Absorption Systems Inc. bulletin):

Data is shown in FIG. 14. The test compounds were prepared as a 5 μM solution in HBSSg with a maximum DMSO concentration ≦1%. Confluent monolayers of MDR1-MDCK cells, 7 to 11 days old were prepared. The receiver well was prepared with 1% BSA in modified Hanks buffer (HBSSg), and the apical and basolateral sides were maintained at pH 7.4±0.2. Two monolayers were dosed in each direction (N=2): the apical side was dosed for (A→B) assessment and the basolateral side was dosed for (B→A) assessment. Test compound concentration was measured for both apical and basolateral sides at a time point of 120 minutes using a generic LC/MS/MS method with a minimum 4 point calibration curve. The reported values in FIG. 14: the percent recovery of the test compound from the Transwell® wells containing MDR1-MDCK cell monolayers; apparent permeability (Papp) in both directions; efflux ratio (Papp B→A)/(Papp A→B); and the blood-brain barrier penetration potential classification. R enantiomer of 2-ethyl-3-methoxy-benzoic acid N'-(1-tert-butyl-butyl)-N'-(3,5-dimethyl-benzoyl)-hydrazide is more permeable than racemate in both A→B and B→A directions in MDR1-MDCK cells. Also, R enantiomer experiences less efflux. The R enantiomer is classified as moderately penetrating through the blood-brain barrier, whereas reacemate is classified as low. Higher blood-brain barrier penetration is a significant advantage for medical indications where central nervous system (CNS) penetration is required.

Example 70

Microsomal Metabolism of the R Enantiomer and Racemate of 2-Ethyl-3-methoxy-benzoic Acid N'-(1-tert-butyl-butyl)-N'-(3,5-dimethyl-benzoyl)-hydrazide (see Jeffrey P, et al., Utility of Metabolic Stability Screening: Comparison of In Vitro and In Vivo Clearance. Xenobiotica. 2001 August-September; 31(8-9):591-8 and Lin J H, et al., Role of Pharmacokinetics and Metabolism in Drug Discovery and Development. Pharmacol Rev. 1997 December; 49(4):403-49)

The test compounds were prepared as 5 μM solutions in DMSO (concentration less than 0.25%), methanol, or acetonitrile. Mixed gender human liver microsomes were pooled from ≧10 donors, and incubated with 1 mM NADPH. The test compound was incubated at 37° C. in buffer containing 1.0 mg/mL of microsomal protein with 1 mM NADPH. At 0 and 60 minutes, the mixture was sampled and monitored by LC/MS/MS for the peak area corresponding to the test compound, with the range of 10-100%. The assay was run in duplicate (N=2 separate incubations). The data reported in FIG. 15 is percent remaining of testosterone standard and percent remaining of the test compound. R enantiomer is slightly more stable to metabolism in human liver microsomes than is the racemate.

Example 71

Bioavailability of the R Enantiomer and Racemate of 2-Ethyl-3-methoxy-benzoic Acid N'-(1-tert-butyl-butyl)-N'-(3,5-dimethyl-benzoyl)-hydrazide Compounds in Labrasol were administered to C57BL/6N:Crl (wild-type) mice (Charles River Laboratories) by oral gavage, the intended route of administration in humans. Dosage was set at 3, 10, 30, or 50 mg/kg/day and 2.5 mL/kg/dose (FIG. 16). Doses were administered for 9 days (first 18 females/group) or 12 days (second 18 females/group) (FIG. 16). Blood was withdrawn at 9-day and 12-day time points. Concentrations were quantified by reverse-phase HPLC.

For each concentration, the samples were prepared by adding Labrasol to solid R enantiomer or racemate in a beaker, sonicating to break up visible aggregates, and magnetic stirring until a uniform appearance was attained. The mixtures were transferred to a graduated cylinder and topped off to the requisite volume using a Labrasol rinse of the beaker. The contents of the cylinder were mixed by inversion and stirred magnetically until dosing.

These Labrasol dosing preparations utilized micronized R enantiomer, but non-micronized racemate. To address the possibility that the non-micronized racemate specimen might bias its dissolution rate in Labrasol, an independent experiment was performed. In this experiment, the solubility and appearance of 20 mg/mL preparations of micronized and non-micronized racemate were examined. Micronized racemate (lot REH-28-9-1/PYAP-2-8-2-2M), non-micronized racemate (lot #PYAP-2-8-2-2), and micronized R enantiomer (lot #REH-28-4-2) were each suspended in Labrasol, swirled by hand, and then sonicated in a Branson 2100 table top sonicator at 25-28° C. for 3×5 min intervals and a 1×10 min interval, interspersed with swirling by hand. The R enantiomer readily dissolved while both the micronized and non-micronized racemate mixtures remained cloudy with suspended fine particles (photos not shown). By visual inspection, the quantity of undissolved material in micronized and non-micronized racemate samples was substantially the same. Microscopy (FIG. 17) revealed that most particles in both micronized and non-micronized racemate suspensions were below 25 microns (FIG. 17). Some larger crystal fragments remained in the non-micronized sample. Since both micronized and non-micronized samples of racemate result in similar amounts of undissolved material, it appears that the major difference between R enantiomer and racemate Labrasol preparations is the intrinsic solubility rather than the starting particle size of the solute.

Figure 18:
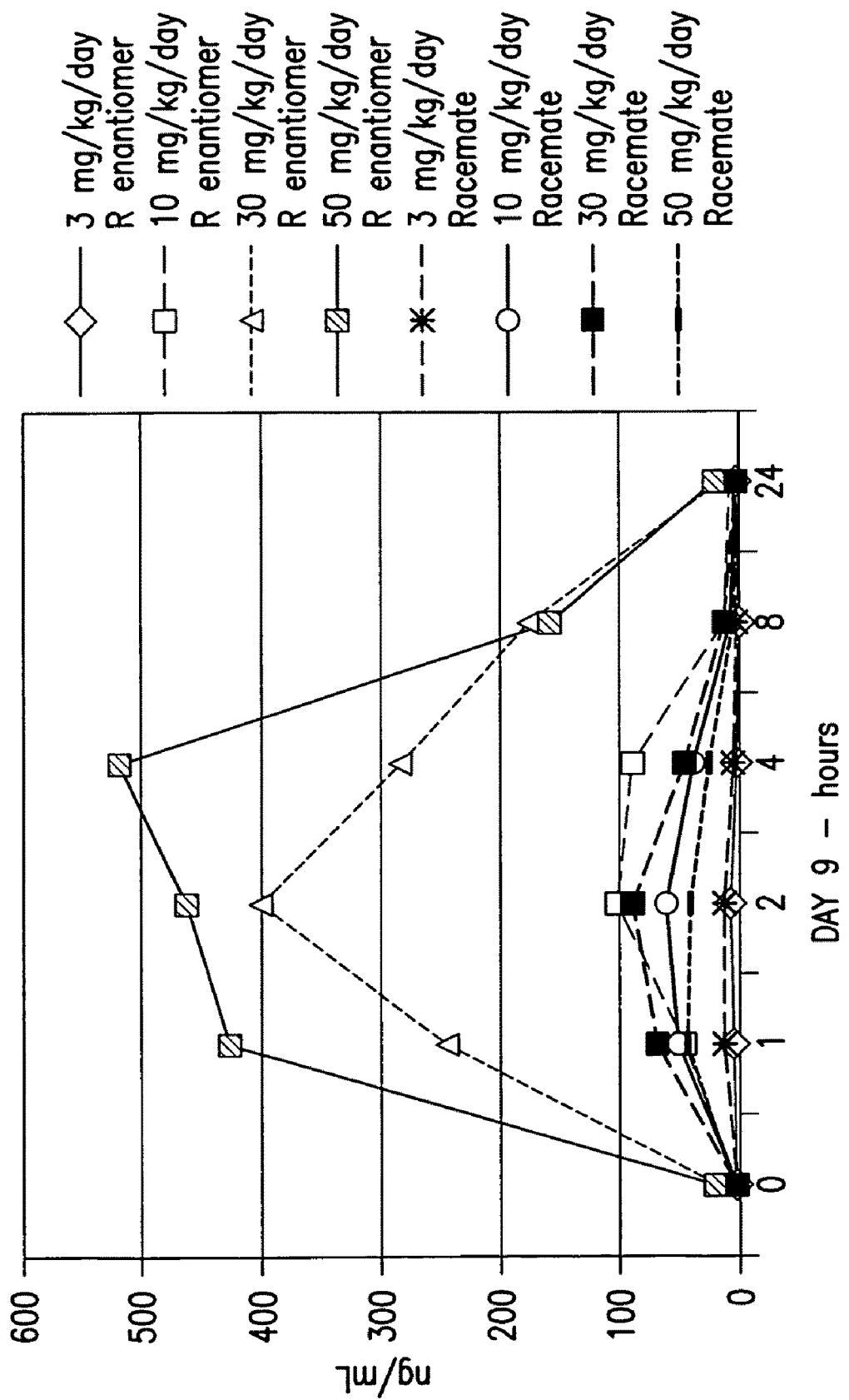
FIG. 18: Table showing blood serum levels of racemate and R enantiomer of 2-ethyl-3-methoxy-benzoic acid N'-(1-tert-butyl-butyl)-N'-(3,5-dimethyl-benzoyl)-hydrazide administered in Labrasol at 4 dosage levels (3, 10, 30 and 50 mg/kg/day) after 9 days of drug administration and hours after the daily dose.
Figure 19:
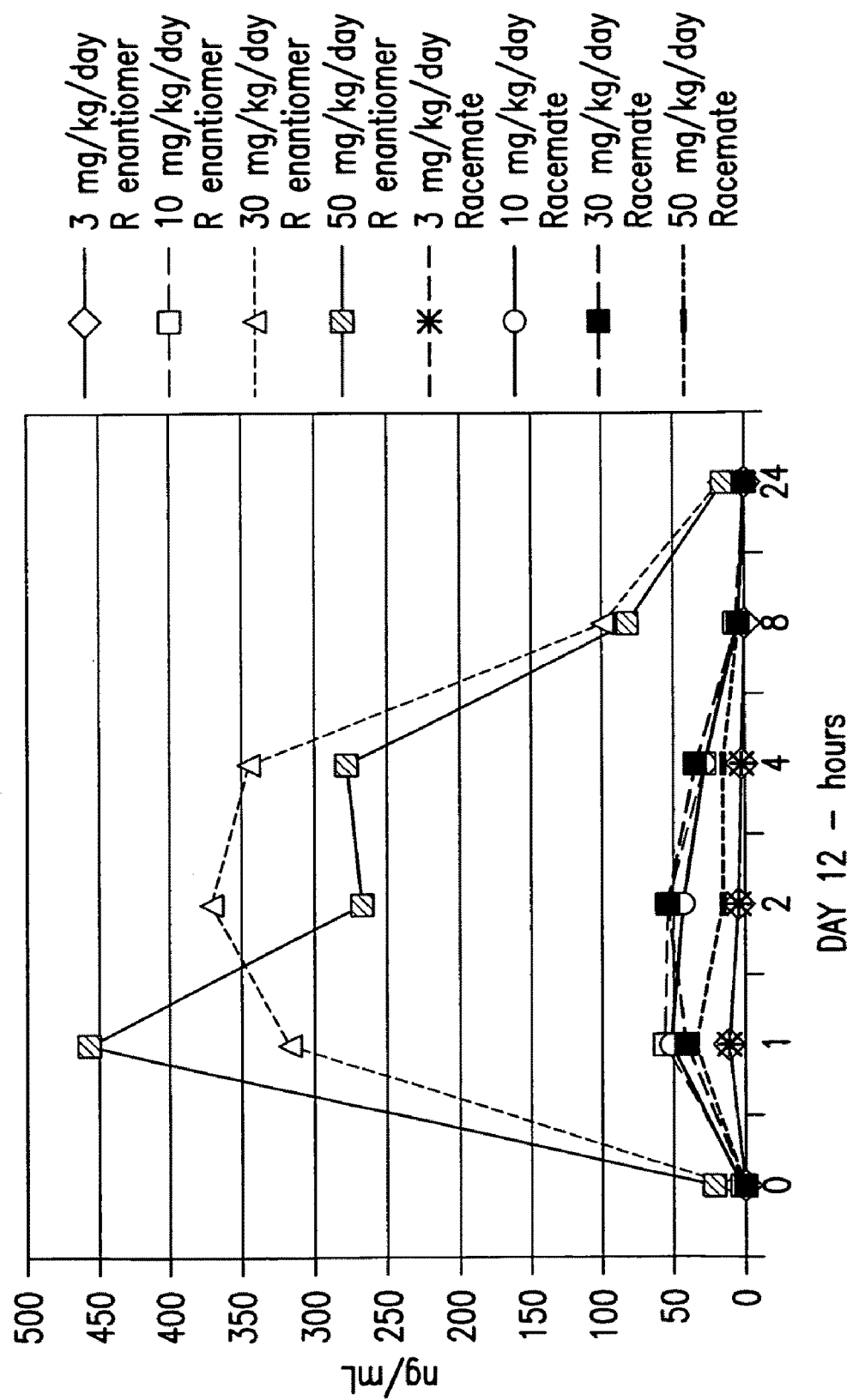
FIG. 19: Table showing blood serum levels of racemate and R enantiomer of 2-ethyl-3-methoxy-benzoic acid N'-(1-tert-butyl-butyl)-N'-(3,5-dimethyl-benzoyl)-hydrazide administered in Labrasol at 4 dosage levels (3, 10, 30 and 50 mg/kg/day) after 12 days of drug administration and hours after the daily dose.

Mouse blood serum levels as a function of time were measured by quantitative HPLC. The R enantiomer in Labrasol attains significantly higher blood serum levels at the higher doses of 30 and 50 mg/kg/day (12 and 20 mg/mL Labrasol administered). Racemate blood serum levels remain substantially lower (<4-5 fold AUC) (FIGS. 18 and 19). The initial particle size differences between racemate an R enantiomer may account for a portion of the serum level differences. Also, the greater intrinsic solubility of the R enantiomer over the racemate in Labrasol may account for a portion of the serum level differences. Furthermore, serum level differences may be due to differences in membrane permeability (per Caco-2 cell and MDCK cell experiments; FIGS. 13 and 14), absorption, distribution, or excretion.

Example 72

Comparison of the R Enantiomer and Racemate of 2-Ethyl-3-methoxy-benzoic Acid N'-(1-tert-butyl-butyl)-N'-(3,5-dimethyl-benzoyl)-hydrazide for In Vivo Induction of Transgene IL-12 Production from Gene-Modified Tumor Cells The transgene tested in this example was murine IL-12 under the control of the RTS. Mouse melanoma cells (B16) were transduced with an adenoviral vector Ad-RTS-mIL-12 that carries the murine IL-12 transgene under the control of RTS. These cells were injected subcutaneously (s.c.) into the C57BL/6 mice (histocompatible with B16 cells) and the mice were treated with different doses of the R enantiomer and racemic 2-ethyl-3-methoxy-benzoic acid N'-(1-tert-butyl-butyl)-N'-(3,5-dimethyl-benzoyl)-hydrazide for three days. The control groups included the mice receiving untransduced B16 cells and the higher dose of ligand and another group receiving the transduced B16 cells and no ligand. To assess the transgene expression directly induced by the ligands, the tumors and serum were collected from half of the mice from each group 72 hours after the subcutaneous injection. Tumor extracts and serum were prepared and assayed for IL-12 by ELISA.

The remaining mice were used for testing the transgene turn-off when the ligand administration is discontinued for an additional 72 hours. The results indicate a difference in the transgene IL-12 expression in the tumor and the serum levels in the mice treated with the racemate and the R enantiomer of the ligand. The discontinuation of the ligand administration resulted in the transgene turn off in all the groups in a similar fashion.

Materials and Methods: B16 cells were infected with Ad.-RTS-mIL-12 (MOI=100) in vitro. After 48 h, $5 \times 10^5$ (B16, right flank) cells were injected s.c. into C57 BL/6 mice (10 mice/group). The R enantiomer and racemate ligands were dissolved in Labrasol by heating a 10 mg/mL mixture at 50° C. for 5 minutes. Both ligands were dissolved in Labrasol based on visual inspection. Activating ligands were provided via oral gavage at the following doses (0 mg/kg; 3 mg/kg; 10 mg/kg; 30 mg/kg and 50 mg/kg) daily for 3 days. Additional controls included B16-bearing mice receiving ligand only (50 mg/kg/day for 3 days and untreated tumor-bearing mice). Five mice/group were harvested for isolation of tumor lesions and peripheral blood. Tissue was homogenized in 1 ml total of phosphate-buffered saline. Lysate/serum was cryopreserved at −80° C. The alternate 5 mice/group were allowed to sit for an additional 72 h in the absence of further ligand administration. These latter 5 mice/group were harvested for isolation of tumor lesions and peripheral blood. Tissue was homogenized as above, and cryopreserved and lysate/serum was cryopreserved at −80° C. Specimens were thawed at 37° C. in water bath and analyzed for mIL-12p70 and also mIFN-γ, a corollary IL-12-dependent cytokine important for CTL trafficking into tumors, using specific ELISAs (BD-Pharmingen).

Figure 24:
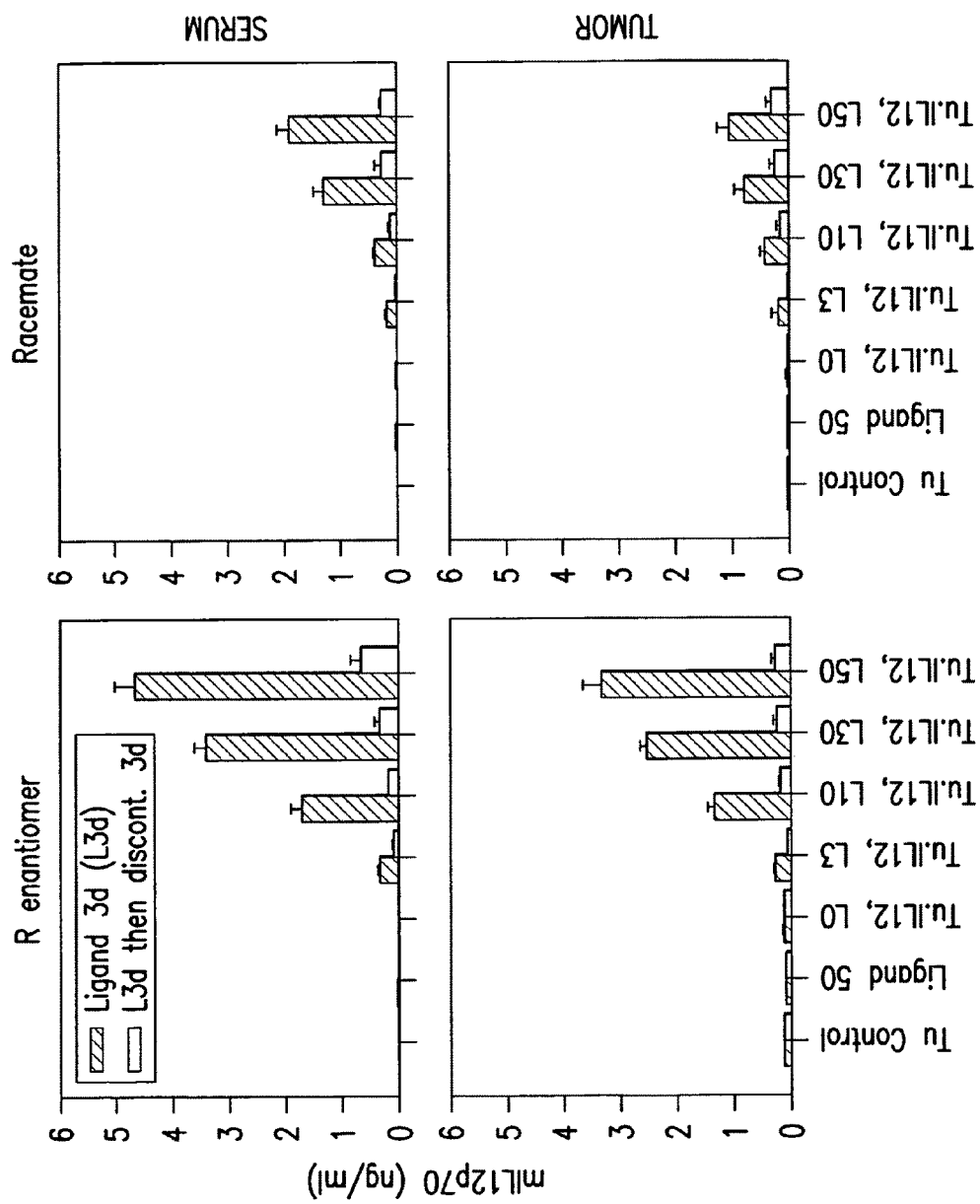
Figure 25:
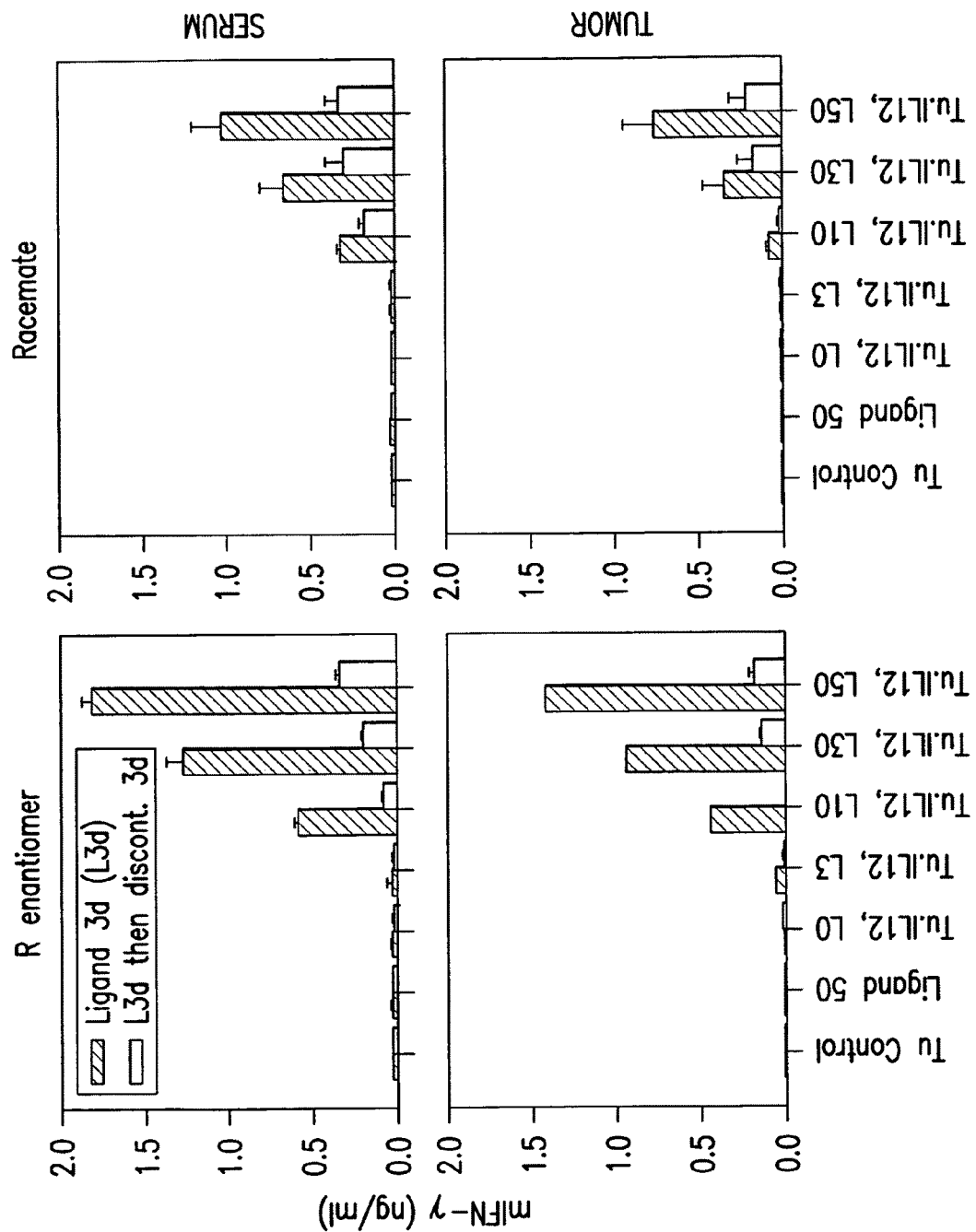

Results: The transgene IL-12 expression in the tumor as well as the serum levels followed a dose-dependent pattern for both the ligands (FIGS. 24 and 25). However, the expression levels were 2.5 to 3 fold higher in the mice treated with the R enantiomer of 2-ethyl-3-methoxy-benzoic acid N'-(1-tert-butyl-butyl)-N'-(3,5-dimethyl-benzoyl)-hydrazide. This pattern was observed in the tumor extracts and the serum. The control groups in which the mice received either the untransduced B16 cells plus the maximum dose of the ligand, or transduced B16 cells without ligand administration did not show any IL-12 expression. In the groups in which the ligand treatment was discontinued for 3 days, the expression levels dropped to similar proportions in all the treatment groups, indicating that the ligand is cleared and the RTS activation is reversible when the ligand is withdrawn. When the IFN-γ levels were assayed in the tumor and the serum, the R-enantiomer group clearly showed enhanced expression.

Example 73

Pharmaceutical Composition Comprising 2-Ethyl-3-methoxy-benzoic Acid N'-(1-tert-butyl-butyl)-N'-(3, 5-dimethyl-benzoyl)-hydrazide Table 1 shows a pharmaceutical composition comprising 2-ethyl-3-methoxy-benzoic acid N'-(1-tert-butyl-butyl)-N'-(3,5-dimethyl-benzoyl)-hydrazide, PL90G, vitamin E TPGS, BHT, and Miglyol 812N. PL90G is a highly purified phosphatidylcholine from soybean. The manufacturer of PL90G is PHOSPHOLIPID GmbH, a subsidiary of Lipoid. Vitamin E TPGS is a GRAS (Generally Recognized as Safe) compound and conforms to all requirements of the current National Formulary (NF) monograph. Miglyol 812N contains triglycerides of the fractionated plant $C_8$ and $C_{10}$ fatty acids. The fatty acids used for the production of Miglyol 812N are classified as GRAS and meet the requirements of the current NF and EP monographs for Medium-Chain Triglycerides. BHT [$MeC_6H_2(CMe_3)_2OH$] is an organic compound that is a lipophilic (fat-soluble) phenol which is widely used as an antioxidant food additive. The formulation was dispensed into hard gelatin capsules.

Example 74

Efficacy in Animal Models of Disease

Murine or human dendritic cells (DCs) transduced with adenoviral vector encoding for RTS and mIL-12 or hIL-12, respectively, express cytokine in vitro in the presence of (R)-2-ethyl-3-methoxy-benzoic acid N'-(1-tert-butyl-butyl)-N'-(3,5-dimethyl-benzoyl)-hydrazide in a dose dependent fashion. In the absence of (R)-2-ethyl-3-methoxy-benzoic acid N'-(1-tert-butyl-butyl)-N'-(3,5-dimethyl-benzoyl)-hydrazide, IL-12 expression is at a basal level.

A comparative analysis of various administration routes and doses of (R)-2-ethyl-3-methoxy-benzoic acid N'-(1-tert-butyl-butyl)-N'-(3,5-dimethyl-benzoyl)-hydrazide on the anti-tumor efficacy of intra-tumorally delivered DCs transduced with an adenoviral vector encoding murine interleukin-12 p70 (DC-SP1(IL-12p70)) were carried out in a B16 melanoma mouse model. Results indicated that anti-tumor efficacy was demonstrated with (DC-SP1(IL-12p70)) therapy in combination with (R)-2-ethyl-3-methoxy-benzoic acid N'-(1-tert-butyl-butyl)-N'-(3,5-dimethyl-benzoyl)-hydrazide administered by intraperitoneal (i.p.) injection, oral gavage or diet admix. Optimal anti-tumor effects occurred at ≧30 mg/kg (R)-2-ethyl-3-methoxy-benzoic acid N'-(1-tert-butyl-butyl)-N'-(3,5-dimethyl-benzoyl)-hydrazide dose administered with (DC-SP1 (IL-12p70)) therapy.

In a murine B16 melanoma model in which mice were inoculated with tumor prior to the initiation of treatment (C57/BL6 mice were given subcutaneous injections of B16 cells to form tumors), transduced AdDCs carrying murine IL-12 genes injected into the tumor mediated a complete regression of tumor and prolonged animal survival that was dependent upon systemic administration of (R)-2-ethyl-3-methoxy-benzoic acid N'-(1-tert-butyl-butyl)-N'-(3,5-dimethyl-benzoyl)-hydrazide within 48 hours following AdDCs injection. This drug dependent effect was associated with: transgene expression in the tumor and DLN; prolonged Ad-DCs survival in the tumor microenvironment; migration and persistence of AdDCs in the DLN; and induction of anti B16 CD8+ T cells.

In the above murine B16 melanoma model, intratumoral therapy consisting of an injection of $10^7$ AdDCs in combination with a 13 day treatment with (R)-2-ethyl-3-methoxy-benzoic acid N'-(1-tert-butyl-butyl)-N'-(3,5-dimethyl-benzoyl)-hydrazide showed protective immunity that was tumor-specific. When tumor-free animals were re-challenged, on day 50 (post-initial tumor inoculation), these animals were refractory to B16 melanoma, but not MC38 colon carcinoma, progression.

Example 75

Replication Incompetent Recombinant Adenovirus Harboring RTS and hIL-12

Figure 23:
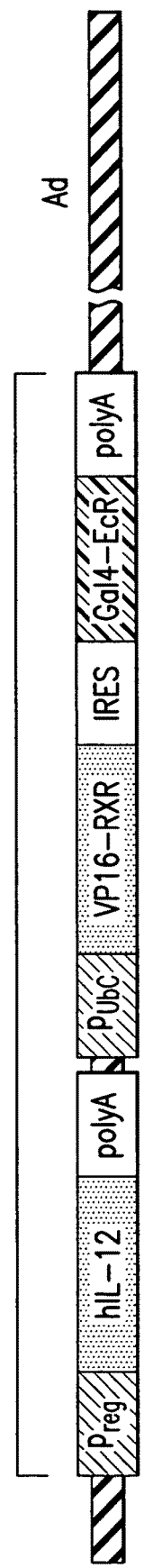

FIG. 23 is a diagrammatic representation of Ad-RTS-hIL-12 in which the E1 and E3 regions have been deleted and the RTS-IL12 components replace the E1 region (FIG. 23 is not drawn to scale). The terms used in FIG. 23 have the following meanings:

RTS-IL-12: Human IL-12 under the control of the RheoSwitch® Therapeutic System $P_{reg}$: Promoter driving the IL12 expression, regulated by the activated drug hIL-12: Coding sequences for the p40 and p35 subunits of human IL-12 separated by an IRES sequence polyA: Polyadenylation signal $P_{UbC}$: Ubiquitin C promoter VP16-RXR: Fusion between VP16 transcriptional activation domain and a chimeric RXR IRES: Internal Ribosome Entry Site Gal4-EcR: Fusion protein between Gal4 DNA binding domain and ecdysone receptor ligand binding domain Ad: Adenovirus-5 backbone containing E1 and E3 gene deletions.

The recombinant adenoviral vector Ad-RTS-hIL-12 is prepared as described by Anderson et al., *Gene Therapy*, 4: 1034-1038 (2000). The Ad-RTS-hIL-12 vector is produced in the following manner. The coding sequences for the receptor fusion proteins, VP16-RXR and Gal4-EcR separated by the EMCV-IRES (internal ribosome entry site), are inserted into the adenoviral shuttle vector under the control of the human ubiquitin C promoter (constitutive promoter). Subsequently, the coding sequences for the p40 and p35 subunits of hIL-12 separated by IRES, placed under the control of a synthetic inducible promoter, are inserted upstream of the ubiquitin C promoter and the receptor sequences. The shuttle vector contains the adenovirus serotype 5 sequences from the left end to mu16, from which the E1 sequences are deleted and replaced by the RTS and IL-12 sequences (RTS-hIL-12). The shuttle vector carrying the RTS-hIL-12 is tested by transient transfection in HT-1080 cells for ligand dependent IL-12 expression. The shuttle vector is then recombined with the E3-deleted adenoviral backbone by cotransfection into HEK 293 cells to obtain recombinant adenovirus Ad-RTS-hIL-12. The clinical grade adenoviral vector is produced in a cGMP facility.

Example 76

Transduction of Autologous Immature Dendritic Cells by Adenovirus Containing hIL-12 Transgene and Rheoswitch® Therapeutic System Harvesting of PBMC by leukapheresis: Subjects undergo a 90-120 minute leukapheresis at the Hillman outpatient CTRC. The leukapheresis procedure involves the removal of blood from a vein in one arm; the passage of blood through a centrifuge (cell separator), where its components are separated and one or more components are removed; and the return of the remaining components to the subject's vein in the same or other arm. No more than 15% of the subject's total blood volume is withdrawn at any one time as blood is processed through the cell separator device. In the cell separator, blood is separated into plasma, platelets, white cells and red blood cells. White blood cells (WBC) are removed and all the other components are returned into the subject's circulation. Every attempt is made to use two peripheral IV lines for this procedure. If that is not possible, a central line may be necessary. The subject has to be cleared by physician to undergo leukapheresis, and is routinely screened for vital signs (including blood pressure) prior to the procedure.

Processing: After collection, the leukapack is delivered by hand to the CPL, and is immediately processed by centrifugal elutriation in ELUTRA™. This is a closed system validated for clinical use. The monocyte fraction is recovered, and after the recovery and viability of cells are established, they are transferred to an Aastrom cartridge for 6-day culture in the presence of IL-4 and GM-CSF. All processing and washing procedures are performed under sterile conditions.

Initial plating: Monocytes recovered from a single leukapack are counted in the presence of a trypan blue dye to determine the number of viable cells. Monocytes are evaluated for purity by flow cytometry. Monocytes are resuspended in serum-free and antibiotic-free CellGenix medium, containing 1,000 IU/mL of IL-4 and 1,000 IU/mL of GM-CSF per SOP-CPL-0166, and placed in an Aastrom cartridge. A minimum loading volume of 50 ml and a minimum cell number are required for cassette inoculation.

Culture: The Aastrom cartridge is placed in the incubator in the Replicell System, a fully closed, cGMP-compatible automated culture device for immature DC generation.

Immature DC harvest: On day 6, the Aastrom cartridge is removed from the incubator and immature DCs are harvested. The cells are recovered by centrifugation at 1,500 rpm, washed in CellGenix medium, counted in the presence of a trypan blue dye and checked for morphologic and phenotypic characteristics.

Viability: This is determined by performing hemocytometer cell counts in the presence of trypan blue. Generally, >95% of harvested cells are viable, i.e., exclude a trypan blue dye. If viability is less than 70% the immature DCs will be discarded.

Phenotyping: The cells generated in culture are counted by microscopic observation on a hemocytometer, and a preliminary differential count (DC vs. lymphocytes) is obtained using a trypan blue dye. Confirmation of the differential count is made by flow cytometry, gating on DC vs. lymphocytes and using high forward and side scatter properties of immature DC as the criterion for their identification. Immature DCs routinely contain >80% of cells with dendritic cell morphology and have DC phenotype.

IL-12p70 potency assay: It has been established that mature DCs (mDCs) have the ability to produce IL-12p70 spontaneously or upon activation with CD40L with or without addition of innate immunity signals (e.g., LPS). A standardized IL-12p70 production assay was recently established and is applicable to small samples or large lots of DC vaccines generated under a variety of conditions. The current potency assay consists of two distinct steps, the first involving co-incubation of responder DCs with J588 lymphoma cells stably transfected with the human CD40 ligand gene as stimulators. The second step involves testing of supernatants from these co-cultures for levels of IL-12p70 secreted by DCs stimulated with J558/CD40L+/−LPS in the Luminex system. This potency assay has an inter-assay CV of 18.5% (n=30) and a broad dynamic range, which facilitates evaluation of various DC products characterized by vastly different levels of IL-12p70 production. The normal range for the assay established using DC products generated from monocytes of 13 normal donors was 8-999 pg/mL, with a mean of 270 pg/mL

Example 77

Adenovirus Transduction of Immature DCs

Immature DCs are harvested, counted and tested for viability. Approximately 6-7×10⁷ DCs are transduced with the adenoviral vector at the optimal multiplicity of infection (the optimal MOI, between 500 and 1000, to be finalized) for the optimal viral adsorption time (between 2 h and 4 h, to be finalized). After transduction, the cells are washed repeatedly to remove any unadsorbed viral particles. Aliquots are set aside for sterility, endotoxin, mycoplasma, DC Phenotype and IL-12 transgene induction assays. The target dose of 5×10⁷ cells is held at 4° C. in saline until release testing is complete.

The transduced DCs (AdDCs) which have passed all release testing are delivered to the clinic for patient administration as described below.

The in vitro testing of the IL-12 transgene induction by the transduced AdDCs takes a minimum of two days for the results to be available and therefore IL-12 production in response to (R)-2-ethyl-3-methoxy-benzoic acid N'-(1-tert-butyl-butyl)-N'-(3,5-dimethyl-benzoyl)-hydrazide will not be a release criterion for the intratumoral injection of the AdDCs. However, based on preliminary studies with AdDCs derived from three healthy volunteers, the induced IL-12 expression in response to (R)-2-ethyl-3-methoxy-benzoic acid N'-(1-tert-butyl-butyl)-N'-(3,5-dimethyl-benzoyl)-hydrazide has been achieved within a target range of 80 to 300 ng IL-12 per million cells in 24 hours (expression level of 80 ng/million cells/24 h was observed in 2 out of the 3 AdDC preparations). Therefore, the in vitro IL-12 induction results are used for analysis of the treatment outcome. As such, the transduced AdDCs are used for injection after viral transduction and washing. Any left-over untransduced and transduced DCs are cryopreserved for future analysis as necessary.

Administration of the AdDCs to patients: A single intratumoral injection of AdDCs in 0.9% saline solution that contains approximately 5×10⁷ cells per injection (or approximately 90% of the DC yield from the trial subject) in a volume of 150 microliters. Subjects should be dosed with the maximum feasible dose of AdDCs, not to exceed 5×10⁷ cells per injection.

Example 78

Administration to Humans of Adenovirally Transduced Autologous Dendritic Cells Engineered to Express hIL-12 Under Control of The RheoSwitch® Therapeutic System in Subjects with Stage III and IV Melanoma Cohort 1 will consist of 12 subjects and cohort 2 will consist of 28 subjects all who will receive a single intratumoral injection of transduced autologous AdDCs approximately 24 hours after the first dose of (R)-3,5-dimethyl-benzoic acid N-(1-tert-butyl-butyl)-N'-(2-ethyl-3-methoxy-benzoyl)-hydrazide. Cohort 1 subjects will be placed into 4 groups of 3 subjects each (A, B, C, D) to receive escalating doses of (R)-3,5-dimethyl-benzoic acid N-(1-tert-butyl-butyl)-N'-(2-ethyl-3-methoxy-benzoyl)-hydrazide. Cohort 2, subjects will receive the maximum tolerated oral dose of (R)-3,5-dimethyl-benzoic acid N-(1-tert-butyl-butyl)-N'-(2-ethyl-3-methoxy-benzoyl)-hydrazide (as determined from cohort 1). Immediately following the injection of AdDCs, subjects will be treated with thirteen additional daily doses of (R)-3,5-dimethyl-benzoic acid N-(1-tert-butyl-butyl)-N'-(2-ethyl-3-methoxy-benzoyl)-hydrazide. Safety, tolerance, and transgene function will be assessed for all subjects in each group of cohort 1 up to one month after injection of AdDCs before enrolling subjects to receive the next higher dose of (R)-3,5-dimethyl-benzoic acid N-(1-tert-butyl-butyl)-N'-(2-ethyl-3-methoxy-benzoyl)-hydrazide. Thirty days after cohort 1 has completed the inpatient treatment phase and at least six to eight weeks following the intratumoral injection of transduced autologous dendritic cells, if the subject desires retreatment and the subject meets the criteria for a retreatment, additional injection(s) of DCs with 14 consecutive daily doses of (R)-3,5-dimethyl-benzoic acid N-(1-tert-butyl-butyl)-N'-(2-ethyl-3-methoxy-benzoyl)-hydrazide may be administered. The dose of (R)-3,5-dimethyl-benzoic acid N-(1-tert-butyl-butyl)-N'-(2-ethyl-3-methoxy-benzoyl)-hydrazide (0.01 mg/kg, 0.1 mg/kg, 1.0 mg/kg or 10.0 mg/kg) will be the maximum tolerated dose from cohort 1.

Patients will be assessed by physical examinations (including ECOG performance status), vital signs, serum chemistry, urinalysis, hematology, adverse events, antibodies and cellular immune response to adenoviral vector and components of the RheoSwitch® Therapeutic System. Also assessed will be single dose and steady-state pharmacokinetics/ADME of oral (R)-3,5-dimethyl-benzoic acid N-(1-tert-butyl-butyl)-N'-(2-ethyl-3-methoxy-benzoyl)-hydrazide and its major metabolites, analysis of transgene function through measurement of hIL-12 levels in biopsies of the target tumor and/or draining lymph nodes, evaluation of the immunological effects by measurement of the cellular immune response (T cells) in biopsies of target tumor, draining lymph nodes and peripheral circulation, and a serum cytokine profile.

It is to be understood that the foregoing described embodiments and exemplifications are not intended to be limiting in any respect to the scope of the invention, and that the claims presented herein are intended to encompass all embodiments and exemplifications whether or not explicitly presented herein.

---

What is claimed is:

1. A compound selected from the group consisting of:
(R)-3,5-Dimethyl-benzoic acid N-(1-tert-butyl-butyl)-N'-(2-ethyl-3-methoxy-benzoyl)-hydrazide;
(R)-3,5-Dimethyl-benzoic acid N'-benzoyl-N-(1-tert-butyl-butyl)-hydrazide;
(R)-3,5-Dimethyl-benzoic acid N-(1-tert-butyl-butyl)-N'-(2-methyl-benzoyl)-hydrazide;
(R)-3,5-Dimethyl-benzoic acid N-(1-tert-butyl-butyl)-N'-(2-fluoro-benzoyl)-hydrazide;
(R)-3,5-Dimethyl-benzoic acid N'-(2-bromo-benzoyl)-N-(1-tert-butyl-butyl)-hydrazide;
(R)-3,5-Dimethyl-benzoic acid N-(1-tert-butyl-butyl)-N'-(3-methyl-benzoyl)-hydrazide;
(R)-3,5-Dimethyl-benzoic acid N-(1-tert-butyl-butyl)-N'-(4-methyl-benzoyl)-hydrazide;
(R)-3,5-Dimethyl-benzoic acid N-(1-tert-butyl-butyl)-N'-(2-chloro-pyridine-3-carbonyl)-hydrazide;
(R)-3,5-Dimethyl-benzoic acid N-(1-tert-butyl-butyl)-N'-(6-chloro-pyridine-3-carbonyl)-hydrazide; and
(R)-3,5-Dimethyl-benzoic acid N-(1-tert-butyl-butyl)-N'-(3-methoxy-2-methyl-benzoyl)-hydrazide.

2. (R)-3,5-Dimethyl-benzoic acid N-(1-tert-butyl-butyl)-N'-(2-ethyl-3-methoxy-benzoyl)-hydrazide having an enantiomeric excess of at least 95% or a pharmaceutically acceptable salt thereof.

3. (R)-3,5-Dimethyl-benzoic acid N-(1-tert-butyl-butyl)-N'-(2-ethyl-3-methoxy-benzoyl)-hydrazide having an enantiomeric excess of at least 99% or a pharmaceutically acceptable salt thereof.

4. A pharmaceutical composition comprising the compound of claim 1 and a pharmaceutically acceptable carrier.

5. A pharmaceutical composition comprising the compound of claim 2 or 3 and a pharmaceutically acceptable carrier.

* * * * *

SEQUENCE LISTING

<160> NUMBER OF SEQ ID NOS: 18

<210> SEQ ID NO 1
<211> LENGTH: 1054
<212> TYPE: DNA
<213> ORGANISM: Chorietoneura fumiferana

<400> SEQUENCE: 1
cctgagtgcg tagtacccga gactcagtgc gccatgaagc ggaaagagaa gaaagcacag      60

| | |
|---|---|
| aaggagaagg acaaactgcc tgtcagcacg acgacggtgg acgaccacat gccgcccatt | 120 |
| atgcagtgtg aacctccacc tcctgaagca gcaaggattc acgaagtggt cccaaggttt | 180 |
| ctctccgaca agctgttgga gacaaaccgg cagaaaaaca tcccccagtt gacagccaac | 240 |
| cagcagttcc ttatcgccag gctcatctgg taccaggacg ggtacgagca gccttctgat | 300 |
| gaagatttga gaggattac gcagacgtgg cagcaagcgg acgatgaaaa cgaagagtct | 360 |
| gacactccct tccgccagat cacagagatg actatcctca cggtccaact tatcgtggag | 420 |
| ttcgcgaagg gattgccagg gttcgccaag atctcgcagc tgatcaaat tacgctgctt | 480 |
| aaggcttgct caagtgaggt aatgatgctc cgagtcgcgc gacgatacga tgcggcctca | 540 |
| gacagtgttc tgttcgcgaa caaccaagcg tacactcgcg acaactaccg caaggctggc | 600 |
| atggcctacg tcatcgagga tctactgcac ttctgccggt gcatgtactc tatggcgttg | 660 |
| gacaacatcc attacgcgct gctcacggct gtcgtcatct tttctgaccg gccagggttg | 720 |
| gcgcagccgc aactggtgga agaaatccag cggtactacc tgaatacgct ccgcatctat | 780 |
| atcctgaacc agctgagcgg gtcggcgcgt tcgtccgtca tatacggcaa gatcctctca | 840 |
| atcctctctg agctacgcac gctcggcatg caaaactcca acatgtgcat ctccctcaag | 900 |
| ctcaagaaca gaaagctgcc gccttttcctc gaggagatct gggatgtggc ggacatgtcg | 960 |
| cacacccaac cgccgcctat cctcgagtcc ccacgaatc tctagcccct gcgcgcacgc | 1020 |
| atcgccgatg ccgcgtccgg ccgcgctgct ctga | 1054 |

<210> SEQ ID NO 2
<211> LENGTH: 441
<212> TYPE: DNA
<213> ORGANISM: Saccharomyces cerevisiae

<400> SEQUENCE: 2

| | |
|---|---|
| atgaagctac tgtcttctat cgaacaagca tgcgatattt gccgacttaa aaagctcaag | 60 |
| tgctccaaag aaaaaccgaa gtgcgccaag tgtctgaaga caactggga gtgtcgctac | 120 |
| tctcccaaaa ccaaaaggtc tccgctgact agggcacatc tgacagaagt ggaatcaagg | 180 |
| ctagaaagac tggaacagct atttctactg attttttcctc gagaagacct tgacatgatt | 240 |
| ttgaaaatgg attctttaca ggatataaaa gcattgttaa caggattatt tgtacaagat | 300 |
| aatgtgaata aagatgccgt cacagataga ttggcttcag tggagactga tatgcctcta | 360 |
| acattgagac agcatagaat aagtgcgaca tcatcatcgg aagagagtag taacaaaggt | 420 |
| caaagacagt tgactgtatc g | 441 |

<210> SEQ ID NO 3
<211> LENGTH: 538
<212> TYPE: DNA
<213> ORGANISM: Mus musculus

<400> SEQUENCE: 3

| | |
|---|---|
| tcgagggccc ctgcaggtca attctaccgg gtaggggagg cgcttttccc aaggcagtct | 60 |
| ggagcatgcg ctttagcagc cccgctggca cttggcgcta cacaagtggc ctctggcctc | 120 |
| gcacacattc cacatccacc ggtagcgcca accggctccg ttctttggtg gccccttcgc | 180 |
| gccaccttct actcctcccc tagtcaggaa gttcccccc gccccgcagc tcgcgtcgtg | 240 |
| caggacgtga caaatggaag tagcacgtct cactagtctc gtgcagatgg acagcaccgc | 300 |
| tgagcaatgg aagcgggtag gcctttgggg cagcggccaa tagcagcttt gctccttcgc | 360 |
| tttctgggct cagaggctgg gaaggggtgg gtccgggggc gggctcaggg gcgggctcag | 420 |

```
gggcggggcg ggcgcgaagg tcctcccgag gctcggcatt ctcgcacgct tcaaaagcgc    480
acgtctgccg cgctgttctc ctcttcctca tctccgggcc tttcgacctg cagccaat     538

<210> SEQ ID NO 4
<211> LENGTH: 720
<212> TYPE: DNA
<213> ORGANISM: Homo sapiens

<400> SEQUENCE: 4
gcccccgagg agatgcctgt ggacaggatc ctggaggcag agcttgctgt ggaacagaag     60
agtgaccagg gcgttgaggg tcctggggga accgggggta gcggcagcag cccaaatgac    120
cctgtgacta acatctgtca ggcagctgac aaacagctat tcacgcttgt tgagtgggcg    180
aagaggatcc cacactttc ctccttgcct ctggatgatc aggtcatatt gctgcgggca    240
ggctggaatg aactcctcat tgcctccttt tcacaccgat ccattgatgt tcgagatggc    300
atcctccttg ccacaggtct tcacgtgcac cgcaactcag cccattcagc aggagtagga    360
gccatctttg atcgggtgct gacagagcta gtgtccaaaa tgcgtgacat gaggatggac    420
aagacagagc ttggctgcct gagggcaatc attctgttta atccagatgc caagggcctc    480
tccaacccta gtgaggtgga ggtcctgcgg gagaaagtgt atgcatcact ggagacctac    540
tgcaaacaga gtaccctga gcagcaggga cggtttgcca agctgctgct acgtcttcct    600
gccctccggt tccattggcc taagtgtcta gagcatctgt ttttcttcaa gctcattggt    660 gtcccccca tcgacacctt cctcatggag atgcttgagg ctccccatca actggcctga    720

<210> SEQ ID NO 5
<211> LENGTH: 635
<212> TYPE: DNA
<213> ORGANISM: Locusta migratoria

<400> SEQUENCE: 5
tgcatacaga catgcctgtt gaacgcatac ttgaagctga aaaacgagtg gagtgcaaag     60
cagaaaacca gtggaatat gagctggtgg agtgggctaa acacatcccg cacttcacat    120
ccctacctct ggaggaccag gttctcctcc tcagagcagg ttggaatgaa ctgctaattg    180 cagcatttc acatcgatct gtagatgtta aagatggcat agtacttgcc actggtctca    240
cagtgcatcg aaattctgcc catcaagctg gagtcggcac aatatttgac agagttttga    300
cagaactggt agcaaagatg agagaaatga aaatggataa aactgaactt ggctgcttgc    360
gatctgttat tcttttcaat ccagaggtga ggggtttgaa atccgcccag gaagttgaac    420
ttctacgtga aaaagtatat gccgctttgg aagaatatac tagaacaaca catcccgatg    480
aaccaggaag atttgcaaaa cttttgcttc gtctgcctc tttacgttcc ataggcctta    540
agtgtttgga gcatttgttt ttctttcgcc ttattggaga tgttccaatt gatacgttcc    600
tgatggagat gcttgaatca ccttctgatt cataa                               635

<210> SEQ ID NO 6
<211> LENGTH: 271
<212> TYPE: DNA
<213> ORGANISM: herpes simplex virus 7

<400> SEQUENCE: 6
atgggcccta aaagaagcg taaagtcgcc ccccgaccg atgtcagcct gggggacgag      60
ctccacttag acggcgagga cgtggcgatg gcgcatgccg acgcgctaga cgatttcgat    120
ctggacatgt tgggggacgg ggattccccg gggccgggat ttaccccca cgactccgcc    180
```

```
cctacggcg ctctggatat ggccgacttc gagtttgagc agatgtttac cgatgccctt      240
ggaattgacg agtacggtgg ggaattcccg g                                     271

<210> SEQ ID NO 7
<211> LENGTH: 1167
<212> TYPE: DNA
<213> ORGANISM: Homo sapiens

<400> SEQUENCE: 7
tgaggctccg gtgcccgtca gtgggcagag cgcacatcgc ccacagtccc cgagaagttg       60
gggggagggg tcggcaattg aaccggtgcc tagagaaggt ggcgcggggt aaactgggaa     120
agtgatgtcg tgtactggct ccgccttttt cccgagggtg ggggagaacc gtatataagt     180
gcagtagtcg ccgtgaacgt tctttttcgc aacgggtttg ccgccagaac acaggtaagt     240
gccgtgtgtg gttcccgcgg gcctggcctc tttacgggtt atggcccttg cgtgccttga     300
attacttcca cctggctcca gtacgtgatt cttgatcccg agctggagcc aggggcgggc     360
cttgcgcttt aggagcccct tcgcctcgtg cttgagttga ggcctggcct gggcgctggg     420
gccgccgcgt gcgaatctgg tggcaccttc gcgcctgtct cgctgctttc gataagtctc     480
tagccattta aaatttttga tgacctgctg cgacgctttt tttctggcaa gatagtcttg     540
taaatgcggg ccaggatctg cacactggta tttcggtttt tgggcccgcg gccggcgacg     600
gggcccgtgc gtcccagcgc acatgttcgg cgaggcgggg cctgcgagcg cggccaccga     660
gaatcggacg ggggtagtct caagctgccg ggcctgctct ggtgcctggc ctcgcgccgc     720
cgtgtatcgc cccgccctgg gcggcaaggc tggcccggtc ggcaccagtt gcgtgagcgg     780
aaagctggcc gcttcccggc cctgctccag ggggctcaaa atggaggacg cggcgctcgg     840
gagagcgggc gggtgagtca cccacacaaa ggaaaagggc ctttccgtcc tcagccgtcg     900
cttcatgtga ctccacggag taccgggcgc cgtccaggca cctcgattag ttctggagct     960
tttggagtac gtcgtctttta ggttgggggg aggggtttta tgcgatggag tttccccaca    1020
ctgagtgggt ggagactgaa gttaggccag cttggcactt gatgtaattc tcgttggaat    1080
ttgccccttt tgagtttgga tcttggttca ttctcaagcc tcagacagtg gttcaaagtt    1140
tttttcttcc atttcaggtg tcgtgaa                                        1167

<210> SEQ ID NO 8
<211> LENGTH: 19
<212> TYPE: DNA
<213> ORGANISM: Artificial Sequence
<220> FEATURE:
<223> OTHER INFORMATION: Synthetic GAL4 response element

<400> SEQUENCE: 8
ggagtactgt cctccgagc                                                   19

<210> SEQ ID NO 9
<211> LENGTH: 6
<212> TYPE: DNA
<213> ORGANISM: Artificial Sequence
<220> FEATURE:
<223> OTHER INFORMATION: Synthetic promoter

<400> SEQUENCE: 9 tatata                                                                  6

<210> SEQ ID NO 10
<211> LENGTH: 1653
<212> TYPE: DNA
```

<213> ORGANISM: Artificial Sequence
<220> FEATURE:
<223> OTHER INFORMATION: Synthetic luciferase gene

<400> SEQUENCE: 10

| | | | | | |
|---|---|---|---|---|---|
| atggaagacg | ccaaaaacat | aaagaaaggc | ccggcgccat | tctatcctct | agaggatgga | 60 |
| accgctggag | agcaactgca | taaggctatg | aagagatacg | ccctggttcc | tggaacaatt | 120 |
| gcttttacag | atgcacatat | cgaggtgaac | atcacgtacg | cggaatactt | cgaaatgtcc | 180 |
| gttcggttgg | cagaagctat | gaaacgatat | gggctgaata | caaatcacag | aatcgtcgta | 240 |
| tgcagtgaaa | actctcttca | attctttatg | ccggtgttgg | gcgcgttatt | tatcggagtt | 300 |
| gcagttgcgc | ccgcgaacga | catttataat | gaacgtgaat | tgctcaacag | tatgaacatt | 360 |
| tcgcagccta | ccgtagtgtt | tgtttccaaa | aaggggttgc | aaaaaatttt | gaacgtgcaa | 420 |
| aaaaaattac | caataatcca | gaaaattatt | atcatggatt | ctaaaacgga | ttaccaggga | 480 |
| tttcagtcga | tgtacacgtt | cgtcacatct | catctacctc | ccggttttaa | tgaatacgat | 540 |
| tttgtaccag | agtcctttga | tcgtgacaaa | acaattgcac | tgataatgaa | ttcctctgga | 600 |
| tctactgggt | tacctaaggg | tgtggcccct | ccgcatagaa | ctgcctgcgt | cagattctcg | 660 |
| catgccagag | atcctatttt | tggcaatcaa | atcattccgg | atactgcgat | tttaagtgtt | 720 |
| gttccattcc | atcacggttt | tggaatgttt | actacactcg | gatatttgat | atgtggattt | 780 |
| cgagtcgtct | taatgtatag | atttgaagaa | gagctgtttt | tacgatccct | tcaggattac | 840 |
| aaaattcaaa | gtgcgttgct | agtaccaacc | ctattttcat | tcttcgccaa | aagcactctg | 900 |
| attgacaaat | acgatttatc | taatttacac | gaaattgctt | ctggggcgc | acctctttcg | 960 |
| aaagaagtcg | gggaagcggt | tgcaaaacgc | ttccatcttc | cagggatacg | acaaggatat | 1020 |
| gggctcactg | agactacatc | agctattctg | attacacccg | aggggatga | taaaccgggc | 1080 |
| gcggtcggta | agttgttcc | attttttgaa | gcgaaggttg | tggatctgga | taccgggaaa | 1140 |
| acgctgggcg | ttaatcagag | aggcgaatta | tgtgtcagag | gacctatgat | tatgtccggt | 1200 |
| tatgtaaaca | atccggaagc | gaccaacgcc | ttgattgaca | aggatggatg | gctacattct | 1260 |
| ggagacatag | cttactggga | cgaagacgaa | cacttcttca | tagttgaccg | cttgaagtct | 1320 |
| ttaattaaat | acaaaggata | tcaggtggcc | cccgctgaat | tggaatcgtt | attgttacaa | 1380 |
| cacccccaaca | tcttcgacgc | gggcgtggca | ggtcttcccg | acgatgacgc | cggtgaactt | 1440 |
| cccgccgccg | ttgttgtttt | ggagcacgga | aagacgatga | cggaaaaaga | gatcgtggat | 1500 |
| tacgtcccca | gtcaagtaac | aaccgcgaaa | agttgcgcg | gaggagttgt | gtttgtggac | 1560 |
| gaagtaccga | aaggtcttac | cggaaaactc | gacgcaagaa | aaatcagaga | gatcctcata | 1620 |
| aaggccaaga | agggcggaaa | gtccaaattg | taa | | | 1653 |

<210> SEQ ID NO 11
<211> LENGTH: 786
<212> TYPE: DNA
<213> ORGANISM: Mus musculus

<400> SEQUENCE: 11

| | | | | | |
|---|---|---|---|---|---|
| aagcgggaag | ctgtgcagga | ggagcggcag | cggggcaagg | accggaatga | gaacgaggtg | 60 |
| gagtccacca | gcagtgccaa | cgaggacatg | cctgtagaga | agattctgga | agccgagctt | 120 |
| gctgtcgagc | ccaagactga | gacatacgtg | gaggcaaaca | tggggctgaa | ccccagctca | 180 |
| ccaaatgacc | ctgttaccaa | catctgtcaa | gcagcagaca | agcagctctt | cactcttgtg | 240 |
| gagtgggcca | agaggatccc | acacttttct | gagctgcccc | tagacgacca | ggtcatcctg | 300 |

| | |
|---|---|
| ctacgggcag gctggaacga gctgctgatc gcctccttct cccaccgctc catagctgtg | 360 |
| aaagatggga ttctcctggc caccggcctg cacgtacacc ggaacagcgc tcacagtgct | 420 |
| ggggtgggcg ccatctttga cagggtgcta acagagctgg tgtctaagat gcgtgacatg | 480 |
| cagatggaca agacggagct gggctgcctg cgagccattg tcctgttcaa ccctgactct | 540 |
| aaggggctct caaaccctgc tgaggtggag gcgttgaggg agaaggtgta tgcgtcacta | 600 |
| gaagcgtact gcaaacacaa gtaccctgag cagccgggca ggtttgccaa gctgctgctc | 660 |
| cgcctgcctg cactgcgttc catcgggctc aagtgcctgg agcacctgtt cttcttcaag | 720 |
| ctcatcgggg acacgcccat cgacaccttc ctcatggaga tgctggaggc accacatcaa | 780 |
| gccacc | 786 |

```
<210> SEQ ID NO 12
<211> LENGTH: 1560
<212> TYPE: DNA
<213> ORGANISM: Homo sapiens

<400> SEQUENCE: 12
```

| | |
|---|---|
| atgctgctgc tgctgctgct gctgggcctg aggctacagc tctccctggg catcatccca | 60 |
| gttgaggagg agaacccgga cttctggaac cgggaggcag ccgaggccct gggtgccgcc | 120 |
| aagaagctgc agcctgcaca gacagccgcc aagaacctca tcatcttcct gggcgatggg | 180 |
| atggggtgt ctacggtgac agctgccagg atcctaaaag ggcagaagaa ggacaaactg | 240 |
| gggcctgaga taccctggc catggaccgc ttcccatatg tggctctgtc caagacatac | 300 |
| aatgtagaca aacatgtgcc agacagtgta gccacagcca cggcctacct gtgcggggtc | 360 |
| aagggcaact tccagaccat tggcttgagt gcagccgccc gctttaacca gtgcaacacg | 420 |
| acacgcggca acgaggtcat ctccgtgatg aatcgggcca agaaagcagg gaagtcagtg | 480 |
| ggagtggtaa ccaccacacg agtgcagcac gcctcgccag ccggcaccta cgcccacacg | 540 |
| gtgaaccgca actggtactc ggacgccgac gtgcctgcct cggcccgcca ggaggggtgc | 600 |
| caggacatag ctacgcagct catctccaac atggacattg acgtgatcct aggtggaggc | 660 |
| cgaaagtaca tgtttcgcat gggaacccca gaccctgagt accagatga ctacagccaa | 720 |
| ggtgggacca ggctggacgg gaagaatctg gtgcaggaat ggctggcgaa cgccagggt | 780 |
| gtccgttatg tgtggaaccg cactgagctc atgcaggctt ccctggaccc gtctgtgacc | 840 |
| catctcatgg gtctctttga gcctygagac atgaaatacg agatccaccg agactccaca | 900 |
| ctggacccct cctgatgga gatgacagag gctgccctgc cctgctgag caggaacccc | 960 |
| cgcggcttct tcctcttcgt ggagggtggt cgcatcgacc atggtcatca tgaaagcagg | 1020 |
| gcttaccggg cactgactga gacgatcatg ttcgacgacg ccattgagag ggcgggccag | 1080 |
| ctcaccagcg aggaggacac gctgagcctc gtgactgccg accactccca cgtcttctcc | 1140 |
| ttcggaggct accccctggg agggagctcc atcttcgggc tggcccctgg caaggcccgg | 1200 |
| gacaggaagg cctacacggt cctcctatac ggaaacggtc caggctatgt gctcaaggac | 1260 |
| ggcgcccgac cggatgttac cgagagcgag agcgggagcc ccgagtatcg gcagcagtca | 1320 |
| gcagtgcccc tggacgaaga gacccacgca ggcgaggacg tggcggtgtt cgcgcgcggc | 1380 |
| ccycaggcgc acctggttca cggcgtgcag gagcagacct tcatagcgca cgtcatggcc | 1440 |
| ttcgccgcct gcctggagcc ctacaccgcc tgcgacctgg cgcccccgc cggcaccacc | 1500 |
| gacgccgcgc acccgggtta ctctagagtc ggggcggccg ccgcttcga gcagacatga | 1560 |

```
<210> SEQ ID NO 13
```

```
<211> LENGTH: 117
<212> TYPE: DNA
<213> ORGANISM: Artificial Sequence
<220> FEATURE:
<223> OTHER INFORMATION: Synthetic response element

<400> SEQUENCE: 13
gcggagtact gtcctccgag cggagtactg tcctccgagc ggagtactgt cctccgagcg      60
gagtactgtc ctccgagcgg agtactgtcc tccgagcgga gtactgtcct ccgagcg       117

<210> SEQ ID NO 14
<211> LENGTH: 136
<212> TYPE: DNA
<213> ORGANISM: Mus musculus

<400> SEQUENCE: 14
cttttgttga ctaagtcaat aatcagaatc agcaggtttg gagtcagctt ggcagggatc      60
agcagcctgg gttggaagga gggggtataa aagccccttc accaggagaa gccgtcacac     120
agatccacaa gctcct                                                     136

<210> SEQ ID NO 15
<211> LENGTH: 659
<212> TYPE: DNA
<213> ORGANISM: Cytomegalovirus

<400> SEQUENCE: 15
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg acccccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg     480
gcagtacatc tacgtattag tcatcgctat taccatggtg atgaggtttt ggcagtacac     540
caatgggcgt ggatagcggt ttgactcacg gggatttcca gtctccacc ccattgacgt     600 caatgggagt ttgttttggc accaaaatca acgggacttt ccaaaatgtc gtaacaact     659

<210> SEQ ID NO 16
<211> LENGTH: 15
<212> TYPE: PRT
<213> ORGANISM: Artificial Sequence
<220> FEATURE:
<223> OTHER INFORMATION: Synthetic ecdysone receptor
<220> FEATURE:
<221> NAME/KEY: MISC_FEATURE
<222> LOCATION: (4)..(4)
<223> OTHER INFORMATION: X is Glycine or Threonine
<220> FEATURE:
<221> NAME/KEY: MISC_FEATURE
<222> LOCATION: (12)..(12)
<223> OTHER INFORMATION: X is Cysteine or Alanine

<400> SEQUENCE: 16

Arg Arg Gly Xaa Thr Cys Ala Asn Thr Gly Ala Xaa Cys Tyr Tyr
1               5                   10                  15

<210> SEQ ID NO 17
<211> LENGTH: 13
```

```
<212> TYPE: DNA
<213> ORGANISM: Artificial Sequence
<220> FEATURE:
<223> OTHER INFORMATION: Synthetic ecdysone receptor
<220> FEATURE:
<221> NAME/KEY: misc_feature
<222> LOCATION: (7)..(7)
<223> OTHER INFORMATION: n is any nucleotide

<400> SEQUENCE: 17
aggtcanagg tca                                                    13

<210> SEQ ID NO 18
<211> LENGTH: 15
<212> TYPE: DNA
<213> ORGANISM: Artificial Sequence
<220> FEATURE:
<223> OTHER INFORMATION: Synthetic ecdysone receptor

<400> SEQUENCE: 18
gggttgaatg aattt                                                  15
```